US010787487B2

(12) United States Patent
Kim et al.

(10) Patent No.: US 10,787,487 B2
(45) Date of Patent: Sep. 29, 2020

(54) CELL/TISSUE-SPECIFIC CELL-PENETRATING ANTIBODIES

(71) Applicant: ORUM THERAPEUTICS INC., Daejeon (KR)

(72) Inventors: Yong Sung Kim, Suwon (KR); Ji Sun Kim, Go-yang (KR); Jae Yeong Park, Suwon (KR); Seong Wook Park, Suwon (KR); Sei Yong Jun, Paju (KR); Dong-Ki Choi, Daejeon (KR)

(73) Assignee: ORUM THERAPEUTICS INC. (KR)

( * ) Notice: Subject to any disclaimer, the term of this patent is extended or adjusted under 35 U.S.C. 154(b) by 0 days.

(21) Appl. No.: 16/447,804

(22) Filed: Jun. 20, 2019

(65) Prior Publication Data

US 2019/0389910 A1 Dec. 26, 2019

Related U.S. Application Data

(60) Provisional application No. 62/688,339, filed on Jun. 21, 2018.

(51) Int. Cl.
*C07K 7/64* (2006.01)
*C07K 16/28* (2006.01)

(52) U.S. Cl.
CPC ................ *C07K 7/64* (2013.01); *C07K 16/28* (2013.01); *C07K 2317/92* (2013.01); *C07K 2319/035* (2013.01); *C07K 2319/30* (2013.01)

(58) Field of Classification Search
CPC ................ C07K 16/28; C07K 2317/92; C07K 2319/035; C07K 2319/30; C07K 7/64; C07K 16/00; C07K 16/2863; C07K 16/30; C07K 2317/565; C07K 2317/77; A61K 38/00; A61P 35/00
See application file for complete search history.

(56) References Cited

U.S. PATENT DOCUMENTS

| | | | | |
|---|---|---|---|---|
| 9,815,866 | B2 * | 11/2017 | Shiba ....................... | C07K 7/08 |
| 2005/0288492 | A1 | 12/2005 | Rabbitts et al. | |
| 2011/0189206 | A1 | 8/2011 | Barbas | |
| 2011/0263829 | A1 | 10/2011 | Kim et al. | |
| 2013/0266570 | A1 | 10/2013 | Weisbart et al. | |
| 2014/0179543 | A1 | 6/2014 | Rabbitts et al. | |
| 2015/0246945 | A1 * | 9/2015 | Shiba ....................... | C07K 7/08 435/5 |
| 2016/0229892 | A1 * | 8/2016 | Hazlehurst ............... | C07K 7/08 |
| 2017/0158777 | A1 | 6/2017 | Kim et al. | |
| 2017/0218084 | A1 | 8/2017 | Kim et al. | |
| 2019/0144566 | A1 | 5/2019 | Kim et al. | |
| 2019/0231872 | A1 * | 8/2019 | Kwon .................... | C07K 16/18 |

FOREIGN PATENT DOCUMENTS

| | | | |
|---|---|---|---|
| CN | 1241574 | A | 1/2000 |
| CN | 101402675 | A | 4/2009 |
| CN | 102209726 | A | 10/2011 |
| CN | 103874710 | A | 6/2014 |
| JP | H 8-511162 | A | 11/1996 |
| JP | 2006521088 | A | 9/2006 |
| JP | 2006523086 | A | 10/2006 |
| JP | 2011519370 | A | 7/2011 |
| KR | 10-2009-0008290 | A | 1/2009 |
| KR | 10-2010-0045683 | A | 5/2010 |
| KR | 10-2010-0053466 | A | 5/2010 |
| KR | 10-2016-0011598 | A | 2/2016 |
| KR | 10-1790669 | B1 | 10/2017 |
| KR | 10-2019-0056340 | A | 5/2019 |
| WO | WO 2003077945 | A1 | 9/2003 |
| WO | WO 2004046186 | A2 | 6/2004 |
| WO | WO 2004046186 | A3 | 6/2004 |
| WO | WO 2004046188 | A2 | 6/2004 |
| WO | WO 2004046188 | A3 | 6/2004 |
| WO | WO 2007133835 | A2 | 11/2007 |
| WO | WO 2007133835 | A3 | 11/2007 |
| WO | WO 2009134025 | A2 | 11/2009 |
| WO | WO 2009134025 | A3 | 11/2009 |
| WO | WO 2009134027 | A2 | 11/2009 |
| WO | WO 2009134027 | A3 | 11/2009 |
| WO | WO 2010056043 | A2 | 5/2010 |
| WO | WO 2010056043 | A3 | 5/2010 |
| WO | WO 2010056043 | A9 | 5/2010 |

(Continued)

OTHER PUBLICATIONS

Williams et al. Peptide ligands for targeting the extracellular domain of EGFR: Comparison between linear and cyclic peptides. Chem Biol Drug Des. Feb. 2018 vol. 91: pp. 605-619. (Year: 2018).*
Claro et al. Design and applications of cyclic peptides (Chapter 4) in Peptide Applications in Biomedicine, Biotechnology and Bioengineering (Woodhead Publishing Series in Biomaterials). Woodhead Publishing Series in Biomaterials. Nov. 27, 2017. ( Year: 2017).*
Al-Lazikani et al., 1997, "Standard conformations for the canonical structures of immunoglobulins," J Mol Biol, 273(4):927-948.
Altmann et al., 2017, "Identification of a Novel ITGαvβ6-Binding Peptide Using Protein Separation and Phage Display," Clin Cancer Res., 23(15):4170-4180.

(Continued)

*Primary Examiner* — Marcela M Cordero Garcia
(74) *Attorney, Agent, or Firm* — Jones Day

(57) ABSTRACT

Presented herein are cyclic peptides that specifically bind to a cell surface molecule, thereby allowing cell/tissue-specific targeting. The cyclic peptides can be attached to an agent, for example, a polypeptide such as an antibody, e.g., a cell-penetrating antibody. Cyclic peptide-containing cell/tissue-specific cell-penetrating antibodies described herein are capable of targeted delivery in a cell type-specific or tissue-specific (i.e., cell/tissue-specific) manner. The cell/tissue-specific cell-penetrating antibodies described herein can be used as an effective anticancer agent for cancer that overexpresses a cell membrane protein that specifically binds to the fused cyclic peptides.

8 Claims, 48 Drawing Sheets

Figure 1A:
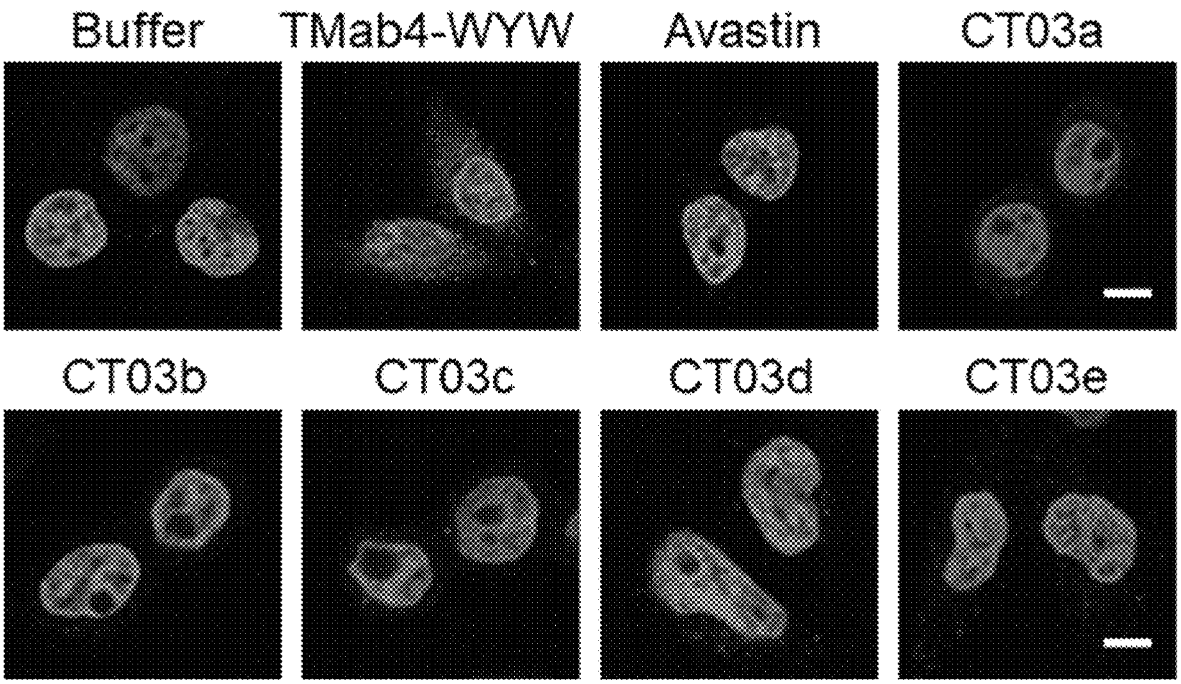

Specification includes a Sequence Listing.

(56) References Cited

FOREIGN PATENT DOCUMENTS

| | | | |
|---|---|---|---|
| WO | WO 2011026641 | A1 | 3/2011 |
| WO | WO 2011026641 | A9 | 3/2011 |
| WO | WO 2011140151 | A1 | 11/2011 |
| WO | WO 2012135831 | A1 | 10/2012 |
| WO | WO 2014042209 | A1 | 3/2014 |
| WO | WO 2016013870 | A1 | 1/2016 |
| WO | WO 2016013871 | A1 | 1/2016 |
| WO | WO 2016161390 | A1 | 10/2016 |
| WO | WO 2017204606 | A1 | 11/2017 |

OTHER PUBLICATIONS

Avrameas et al., 1998, "Polyreactive anti-DNA monoclonal antibodies and a derived peptide as vectors for the intracytoplasmic and intranuclear translocation of macromolecules," Proc Natl Acad Sci USA, 95(10):5601-5606.
Baek et al., 2014, "Construction of a large synthetic human Fab antibody library on yeast cell surface by optimized yeast mating," J Microbiol Biotechnol., 24(3):408-420.
Baek et al., 2014, "DNA Assembly Tools and Strategies for the Generation of Plasmids," Microbiol Spectr, 2(5), pp. 1-12.
Baek et al., 2015, "Humanization of a phosphothreonine peptide-specific chicken antibody by combinatorial library optimization of the phosphoepitope-binding motif," Biochem Biophys Res Commun., 463(3):414-420.
Barbas et al., 2007, "Quantitation of DNA and RNA," Cold Spring Harb. Protoc., retreived from Internet: http://cshprotocols.cshlp.org/content/2007/11/pdb.ip47.1ong on Nov. 1, 2019 (2 pages).
Barrette-Ng et al., 2013, "The structure of the SBP-Tag-streptavidin complex reveals a novel helical scaffold bridging binding pockets on separate subunits," Acta Crystallogr D Biol Crystallogr., 69(Pt 5):879-887.
Benatuil et al., 2010, "An improved yeast transformation method for the generation of very large human antibody libraries," Protein Eng Des Sel., 23(4):155-159.
Bissig et al., 2013, "Lipid sorting and multivesicular endosome biogenesis," Cold Spring Hath Perspect Biol., 5(10):a016816.
Blundell et al., 2006, "Structural biology and bioinformatics in drug design: opportunities and challenges for target identification and lead discovery," Philos Trans R Soc Lond B Biol Sci., 361(1467):413-423.
Bonvin et al., 2015, "De novo isolation of antibodies with pH-dependent binding properties," Mabs, 7(2):294-302.
Cabantous et al., 2005, "Protein tagging and detection with engineered self-assembling fragments of green fluorescent protein," Nat Biotechnol., 23(1):102-107.
Caldas et al., 2003, "Humanization of the anti-CD18 antibody 6.7: an unexpected effect of a framework residue in binding to antigen," Mol Immunol., 39(15):941-952.
Cao et al., 2008, "Enhancement of antitumor properties of TRAIL by targeted delivery to the tumor neovasculature," Mol Cancer Ther., 7(4):851-861.
Casset et al., 2003, "A peptide mimetic of an anti-CD4 monoclonal antibody by rational design," Biochem Biophys Res Commun., 307(1):198-205.
Chang et al., 2014, "Loop-sequence features and stability determinants in antibody variable domains by high-throughput experiments," Structure, 22(1):9-21.
Chauhan et al., 2007, "The taming of the cell penetrating domain of the HIV Tat: myths and realities," J Control Release, 117(2):148-162.
Chen et al., 1995, "Enhancement and destruction of antibody function by somatic mutation: unequal occurrence is controlled by V gene combinatorial associations," EMBO J., 14(12):2784-2794.
Chien et al., 1989, "Significant structural and functional change of an antigen-binding site by a distant amino acid substitution: proposal of a structural mechanism," Proc Natl Acad Sci USA, 86(14):5532-5536.
Choi et al., 2014, "A general strategy for generating intact, full-length IgG antibodies that penetrate into the cytosol of living cells," MAbs,6(6):1402-1414.
Colman, 1994, "Effects of amino acid sequence changes on antibody-antigen interactions," Res Immunol., 145(1):33-36.
Cross et al., 2001, "Mechanisms of Cell Entry by Influenza Virus," Expert Review in Molecular Medicine, Aug. 2001, pp. 1-18.
De Pascalis et al., 2002, "Grafting of "abbreviated" complementarity-determining regions containing specificity-determining residues essential for ligand contact to engineer a less immunogenic humanized monoclonal antibody," J Immunol., 169(6):3076-3084.
Devanaboyina et al., 2013, "The effect of pH dependence of antibody-antigen interactions on subcellular trafficking dynamics," Mabs, 5(6):851-859.
Di Paolo et al., 2003, "A recombinant immunotoxin derived from a humanized epithelial cell adhesion molecule-specific single-chain antibody fragment has potent and selective antitumor activity," Clin Cancer Res, 9(7):2837-2848.
Di Russo et al., 2012, "pH-Dependent conformational changes in proteins and their effect on experimental pK(a)s: the case of Nitrophorin 4," PLoS Comput Biol., 8(11):e1002761.
Dohi et al., 2001, "Elimination of colonic patches with lymphotoxin receptor-Ig prevents Th2 cell-type colitis," The Journal of Immunology, 167(5):2781-2790.
Du et al., 2011, "pK(a) coupling at the intein active site: implications for the coordination mechanism of protein splicing with a conserved aspartate," J Am Chem Soc., 133(26):10275-10282.
Dudgeon et al., 2012, "General strategy for the generation of human antibody variable domains with increased aggregation resistance," Proc Natl Acad Sci USA, 109(27):10879-10884.
Edman, 1959, "Chemistry of amino acids and peptides," Annu Rev Biochem, 28:69-96.
Ehrenstein et al., 1995, "Human IgG anti-DNA antibodies deposit in kidneys and induce proteinuria in SCID mice," Kidney Int., 48(3):705-711.
Ewert et al., 2004, "Stability improvement of antibodies for extracellular and intracellular applications: CDR grafting to stable frameworks and structure-based framework engineering," Methods, 34(2):184-199.
Extended European Search Report and Written Opinion of European Patent Application No. 15825418.5 dated Jan. 4, 2018 (8 pages).
Falnes et al., 2001, "Ability of the Tat basic domain and VP22 to mediate cell binding, but not membrane translocation of the diphtheria toxin A-fragment," Biochemistry, 40(14):4349-4358.
Fernandes et al., 2016, "Context-dependent roles for lymphotoxin-β receptor signaling in cancer development," Biochim Biophys Acta., 1865(2):204-219.
Garrigues et al., 1993, "Ley specific antibody with potent anti-tumor activity is internalized and degraded in lysosomes," Am J Pathol., 142(2):607-622.
Gerber et al., 2013, "The antibody-drug conjugate: an enabling modality for natural product-based cancer therapeutics," Nat Prod Rep., 30(5):625-639.
Gingis-Velitski et al., 2004, "Heparanase uptake is mediated by cell membrane heparan sulfate proteoglycans," J Biol Chem., 279(42):44084-44092.
Giusti et al., 1987, "Somatic diversification of S107 from an antiphosphocholine to an anti-DNA autoantibody is due to a single base change in its heavy chain variable region," Proc Natl Acad Sci USA, 84(9):2926-2930.
Gouttefangeas et al., 2014, "Flow Cytometry in Cancer Immunotherapy: Applications, Quality Assurance, and Future," N. Rezaei (ed.), Cancer Immunology: A Translational Medicine Context, Springer-Verlag Berlin Heidelberg, Chapter 25, pp. 471-490.
Guglielmi et al., 2011, "Selection for intrabody solubility in mammalian cells using GFP fusions," Protein Eng Des Sel., 24(12):873-881.
Guidotti et al., 2017, "Cell-Penetrating Peptides: From Basic Research to Clinics," Trends in Pharmacological Sciences, 38(4):406-424.
Guillard et al., 2015, "Engineering therapeutic proteins for cell entry: the natural approach," Trends in biotechnology, 33(3):163-171.

(56) References Cited

OTHER PUBLICATIONS

Gussow et al., 1991, "Humanization of monoclonal antibodies," Methods Enzymol., 203:99-121.
Herce et al., 2009, "Arginine-rich peptides destabilize the plasma membrane, consistent with a pore formation translocation mechanism of cell-penetrating peptides," Biophys J., 97(7):1917-1925.
Holig et al., 2004, "Novel RGD lipopeptides for the targeting of liposomes to integrin-expressing endothelial and melanoma cells," Prot Eng Des Sel, 17(5):433-441.
Hollingshead, 2008, "Antitumor efficacy testing in rodents," J Natl Cancer Inst., 100(21):1500-1510.
Holm et al., 2007, "Functional mapping and single chain construction of the anti-cytokeratin 8 monoclonal antibody TS1," Mol Immunol., 44(6):1075-1084.
Horth et al., 1991, "Theoretical and functional analysis of the SIV fusion peptide," EMBO J., 10(10):2747-2755.
Horton et al., 2002, "Exploring privileged structures: the combinatorial synthesis of cyclic peptides," J Comput Aided Mol Des., 16(5-6):415-430.
Hu et al., 2013, "Comparison of the inhibition mechanisms of adalimumab and infliximab in treating tumor necrosis factor α-associated diseases from a molecular view," J Biol Chem., 288(38):27059-27067.
Imai et al., 2006, "Comparing antibody and small-molecule therapies for cancer," Nat Rev Cancer, 6(9):714-727.
International Search Report and Written Opinion dated Oct. 11, 2019 of International Patent Application No. PCT/IB2019/055193 (14 pages).
International Search Report and Written Opinion dated Oct. 7, 2015 of International Patent Application No. PCT/KR2015/007626 (published as WO 2016013870) (12 pages).
International Search Report and Written Opinion dated Sep. 29, 2017 of International Patent Application No. PCT/KR2017/005559 (published as WO 2017204606) (10 pages).
International Search Report and Written Opinion dated Sep. 30, 2015 of International Patent Application No. PCT/KR2015/007627 (published as WO 2016013871) (12 pages).
Jang et al., 2009, "A nucleic acid-hydrolyzing antibody penetrates into cells via caveolae-mediated endocytosis, localizes in the cytosol and exhibits cytotoxicity," Cell Mol Life Sci., 66(11-12):1985-1997.
Jenssen et al., 2006, "Peptide antimicrobial agents," Clin Microbiol Rev., 19(3):491-511.
Kabat et al., 1991, "Sequences of Proteins of Immunological Interest," vol. 1 (24 pages).
Kamide et al. 2010, "Isolation of novel cell-penetrating peptides from a random peptide library using in vitro virus and their modifications," Int J Mol Med., 25(1):41-51.
Kim et al., 2005, "Antibody engineering for the development of therapeutic antibodies," Mol Cells, 20(1):17-29.
Kim et al., 2006, "Heavy and light chain variable single domains of an anti-DNA binding antibody hydrolyze both double- and single-stranded DNAs without sequence specificity," J Biol Chem., 281(22):15287-15295.
Kim et al., 2012, "Interfering transbody-mediated Her2 gene silencing induces apoptosis by G0/G1 cell cycle arrest in Her2-overexpressing SK-BR-3 breast cancer cells," Biotechnology and Bioprocess Engineering, 17(2):413-419.
Kim et al., 2015, "Quantitative assessment of cellular uptake and cytosolic access of antibody in living cells by an enhanced split GFP complementation assay," Biochem Biophys Res Commun., 467(4):771-777.
Kim et al., 2016, "Endosomal acidic pH-induced conformational changes of a cytosol-penetrating antibody mediate endosomal escape," J Control Release, 235:165-175.
Kim, 2014, "General Strategy for Generating Intact, full-lenght IgG antibodies that penetrate into the cytosol of living cells," KSBB, IP306, Oct. 5, 2014, XP002776743, retreived from the internet: URL:www.ksbb.or.kr/board/download.php?code=notice&num=1913&comm= [retrieved on Dec. 11, 2017].
Koivunen et al., 1995, "Phage libraries displaying cyclic peptides with different ring sizes: ligand specificities of the RGD-directed integrins," Biotechnology (NY), 13(3):265-270.
Korte et al., 1992, "ph-dependent hydrophobicity profile of hemagglutinin of influenza virus and its possible relevance in virus fusion," Biosci Rep., 12(5):397-406.
Kussie et al., 1994, "A single engineered amino acid substitution changes antibody fine specificity," J Immunol., 152(1):146-152.
Lee et al., 2010, "Gene silencing by cell-penetrating, sequence-selective and nucleic-acid hydrolyzing antibodies," Nucleic Acids Res., 38(5):1596-1609.
Lee et al., 2011, "Generation of bivalent and bispecific kringle single domains by loop grafting as potent agonists against death receptors 4 and 5," J Mol Biol., 411(1):201-219.
Lee et al., 2013, "Functional consequences of complementarity-determining region deactivation in a multifunctional anti-nucleic acid antibody," J Biol Chem., 288(50):35877-35885.
Leem et al., 2016, "ABodyBuilder: Automated antibody structure prediction with data-driven accuracy estimation," MAbs, 8(7):1259-1268.
Leshchiner et al., 2015, "Direct inhibition of oncogenic KRAS by hydrocarbon-stapled SOS1 helices," Proc Natl Acad Sci USA, 112(6):1761-1766.
Li et al., 2014, "pH-Controlled two-step uncoating of influenza virus," Biophys J., 106(7):1447-1456.
Lin et al., 2008, "Effect of chemical functionalities in poly(amido amine)s for non-viral gene transfection," J Control Release, 132(3):267-272.
Lonn et al 2016, "Enhancing Endosomal Escape for Intracellular Delivery of Macromolecular Biologic Therapeutics," Sci Rep., 6:32301.
Maccallum et al., 1996, "Antibody-antigen interactions: contact analysis and binding site topography," J Mol Biol., 262(5):732-745.
Madaio et al., 1996, "Spontaneously produced anti-DNA/DNase I autoantibodies modulate nuclear apoptosis in living cells," Eur J Immunol., 26(12):3035-3041.
Madgdelaine-Beuzelin et al., 2007, "Structure-function relationships of the variable domains of monoclonal antibodies approved for cancer treatment," Crit Rev Oncol Hematol., 64(3):210-225.
Manikandan et al., 2007, "Protein i: interference at protein level by intrabodies," Front Biosci., 12:1344-1352.
Marchisio et al., 1984, "Immunofluorescence localization of phosphotyrosine containing proteins in RSV-transformed mouse fibroblasts," Exp Cell Res., 154(1):112-124.
Mariuzza et al., 1987, "The structural basis of antigen-antibody recognition," Annu Rev Biophys Biophys Chem., 16:139-159.
Marschall et al., 2011, "Targeting antibodies to the cytoplasm," MAbs, 3(1):3-16.
Mauri et al., 1998, "LIGHT, a new member of the TNF superfamily, and lymphotoxin alpha are ligands," Immunity, 8(1):21-30.
Morita et al., 2011, "Lipid recognition propensities of amino acids in membrane proteins from atomic resolution data," BMC Biophys., 4:21 (12 pages).
Munyendo et al., 2012, "Cell penetrating peptides in the delivery of biopharmaceuticals," Biomolecules, 2(2):187-202.
Munz et al., 2009, "The emerging role of EpCAM in cancer and stem cell signaling," Cancer Res., 69(14):5627-5629.
Nakajima et al., 2004, "Method for delivering radiolabeled single-chain fv antibody to the brain," Journal of health science, 50(2):159-163.
NCBI, 2016, "Chain H, Heavy Chain of Fab Fragment Variable Region of Antibody D5," PDB: 3JAU_H, NCBI database, Feb. 10, 2016.
Patel et al., 2007, "Cell penetrating peptides: intracellular pathways and pharmaceutical perspectives," Pharm Res., 24(11):1977-1992.
Patgiri et al., 2011, "An orthosteric inhibitor of the Ras-Sos interaction," Nat Chem Biol, 7(9):585-587.
Perchiacca et al., 2011, "Mutational analysis of domain antibodies reveals aggregation hotspots within and near the complementarity determining regions," Proteins, 79(9):2637-2647.
Perrimon et al., 2000, "Specificities of heparan sulphate proteoglycans in developmental processes," Nature, 404(6779):725-728.

(56) References Cited

OTHER PUBLICATIONS

Pimenta et al., 2014, "Role of tertiary lymphoid structures (TLS) in antitumor immunity: Potential tumor-induced cytokines/chemokines that regulate TLS formation in epithelial-derived cancers," Cancer, 6(2):969-997.
Qin et al., 1999, "Functional implications of structural differences between variants A and B of bovine beta-lactoglobulin," Protein Sci., 8(1):75-83.
Quadir et al., 2014, "PEG-polypeptide block copolymers as pH-responsive endosome-solubilizing drug nanocarriers," Mol Pharm., 11(7):2420-2430.
Rezai et al., 2006, "Testing the conformational hypothesis of passive membrane permeability using synthetic cyclic peptide diastereomers," J Am Chem Soc., 128(8):2510-2511.
Rudikoff et al., 1982, "Single amino acid substitution altering antigen-binding specificity," Proc Natl Acad Sci USA, 79(6):1979-1983.
Sapra et al., 2002, "Internalizing antibodies are necessary for improved therapeutic efficacy of antibody-targeted liposomal drugs," Cancer Res., 62(24):7190-7194.
Scheffzek et al., 1997, "The Ras-RasGAP complex: structural basis for GTPase activation and its loss in oncogenic Ras mutants," Science, 277(5324):333-338.
Shin et al., 2017, "Antibody targeting intracellular oncogenic Ras mutants exerts anti-tumour effects after systemic administration," Nat Commun., 8:15090 (14 pages).
Simon et al., 2013, "Epithelial cell adhesion molecule-targeted drug delivery for cancer therapy, Expert opinion on drug delivery," Expert Opin Drug Deliv., 10(4):451-468.
Singh et al., 2016, "A New Triglycyl Peptide Linker for Antibody-Drug Conjugates (ADCs) with Improved Targeted Killing of Cancer Cells," Mol Cancer Ther., 15(6):1311-1320.
Stuible et al., 2014, "Mechanism and function of monoclonal antibodies targeting siglec-15 for therapeutic inhibition of osteoclastic bone resorption," J Biol Chem., 289(10):6498-6512.
Sudhamsu et al., 2013, "Dimerization of LTβR by LTα1β2 is necessary and sufficient for signal transduction," Proc Natl Acad Sci USA, 110(49):19896-19901.
Supplemental European Search Report and Written Opinion of European Patent Application No. 15825508.3 dated Feb. 8, 2018 (10 pages).
Tanaka et al., 2003, "Intrabodies based on intracellular capture frameworks that bind the RAS protein with high affinity and impair oncogenic transformation," EMBO J., 22(5):1025-1035.
Tanaka et al., 2003, "Single domain intracellular antibodies. A minimal fragment for direct in vivo selection of antigen-specific intrabodies," J Mol Biol., 331(5):1109-1120.
Tanaka et al., 2007, "Tumour prevention by a single antibody domain targeting the interaction of signal transduction proteins with RAS," EMBO J., 26(13):3250-3259.
Teicher, 2009, "In vivo/ex vivo and in situ assays used in cancer research: a brief review," Toxicol Pathol, 37(1):114-122.
Vajdos et al., 2002, "Comprehensive functional maps of the antigen-binding site of an anti-ErbB2 antibody obtained with shotgun scanning mutagenesis," J Mol Biol., 320(2):415-428.
Vargas-Madrazo et al., 2003, "An improved model of association for VH-VL immunoglobulin domains: asymmetries between VH and VL in the packing of some interface residues," J Mol Recognit, 16(3):113-120.
Wang et al., 2001, "The regulation of T cell homeostasis and autoimmunity by T cell-derived LIGHT," J Clin Invest, 108(12):1771-1780.
Weinstein, 2015, "Lymphotoxin Therapeutic Lymphoid Organogenesis in the Tumor Microenvironment," Adv Cancer Res., 128:197-233.
Weisbart et al., 2012, "A cell-penetrating bispecific antibody for therapeutic regulation of intracellular targets," Mol Cancer Ther., 11(10):2169-2173.
Went et al., 2006, "Frequent high-level expression of the immunotherapeutic target Ep-CAM in colon, stomach, prostate and lung cancers," Br J Cancer, 94(1):128-135.
Winkler et al., 2000, "Changing the antigen binding specificity by single point mutations of an anti-p24 (HIV-1) antibody," J Immunol., 165(8):4505-4514.
Wu et al., 1999, "Humanization of a murine monoclonal antibody by simultaneous optimization of framework and CDR residues," J Mol Biol., 294(1):151-162.
Xiong et al., 2002, "Crystal structure of the extracellular segment of integrin alpha Vbeta3 in complex with an Arg-Gly-Asp ligand," Science, 296(5565):151-155.
Yamaguchi et al., 2014, "Development of a sensitive screening method for selecting monoclonal antibodies to be internalized by cells," Biochem Biophys Res Commun., 454(4):600-603.
Yu et al., 2012, "Rationalization and design of the complementarity determining region sequences in an antibody-antigen recognition interface," PLoS One, 7(3):e33340 (15 pages).
Zack et al., 1996, "Mechanisms of cellular penetration and nuclear localization of an anti-double strand DNA autoantibody," J Immunol., 157(5):2082-2088.
Min et al., 2016, "Cell-free production and streamlined assay of cytosol-penetrating antibodies," Biotechnol Bioeng, 113(10):2107-2112.
Kim et al., 2009, "Generation of Humanized anti-DNA Hydrolyzing Catalytic Antibodies by Complementarily Determining Region Grafting," Biochem Biophys Res Commun., 379(2):314-318 (Epub 2008).
Paul, 1993, "Fundamental immunology—Third Edition," New York: Raven Press, pp. 292-295.

* cited by examiner

Library

| | | | | | | | | | | | |
|---|---|---|---|---|---|---|---|---|---|---|---|
| VRK | VRK | L | BNK | C | NNK | NNK | NNK | NNK | C | W | YCA |

| | Antigen | Washing | In-put | Out-put |
|---|---|---|---|---|
| 1st round | Integrin αVβ5 5μg | 3 | $4.2 \times 10^{11}$ | $8.1 \times 10^{7}$ |
| 2nd round | Integrin αVβ5 3μg | 5 | $4.2 \times 10^{11}$ | $1.3 \times 10^{7}$ |
| 3rd round | Integrin αVβ5 2μg | 10 | $7.0 \times 10^{10}$ | $5.1 \times 10^{7}$ |
| 4th round | Integrin αVβ5 1μg | 15 | $1.7 \times 10^{11}$ | $2.5 \times 10^{7}$ |
| 5th round | Integrin αVβ5 1μg | 25 | $8.5 \times 10^{10}$ | $2.7 \times 10^{7}$ |

FIG. 15B

| | | | | | | | | | | | | | | | | | | | |
|---|---|---|---|---|---|---|---|---|---|---|---|---|---|---|---|---|---|---|---|
| | | D | G | V | R | Q | C | R | G | D | C | F | D | G | P | L | | | in4 (SEQ ID NO: 53) |
| X | X | X | X | X | C | X | X | R | G | D | S | F | X | X | C | X | X | X | 5#1 Library (SEQ ID NO: 106) |
| X | X | X | X | X | C | X | X | R | G | D | T | F | X | X | C | X | X | X | 5#2 Library (SEQ ID NO: 107) |
| X | X | X | X | X | C | X | X | R | G | D | L | F | X | I/L | C | X | X | X | 6# Library (SEQ ID NO: 108) |

- X : NNK degenerate codon (20 amino acids)
- X : NHB degenerate codon (F, I, L, M, V, S, P, T, A, Y, H, Q, N, K, D, E)
- I/L : MTH degenerate codon (I, L)

SEQUENCE LISTING

```
<160> NUMBER OF SEQ ID NOS: 110

<210> SEQ ID NO 1
<211> LENGTH: 114
<212> TYPE: PRT
<213> ORGANISM: Artificial Sequence
<220> FEATURE:
<223> OTHER INFORMATION: hT4-WYW VL

<400> SEQUENCE: 1

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Trp Tyr Trp Met Tyr Thr Phe Gly Gln Gly Thr Lys Val Glu Ile
            100                 105                 110

Lys Arg


<210> SEQ ID NO 2
<211> LENGTH: 114
<212> TYPE: PRT
<213> ORGANISM: Artificial Sequence
<220> FEATURE:
<223> OTHER INFORMATION: CT03a VL (hT4-34 VL)

<400> SEQUENCE: 2

Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Thr Arg Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60
```

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Phe Cys Gln Gln
85 90 95

Tyr Trp Tyr Trp Met Tyr Thr Phe Gly Gln Gly Thr Lys Val Glu Ile
100 105 110

Lys Arg

<210> SEQ ID NO 3
<211> LENGTH: 114
<212> TYPE: PRT
<213> ORGANISM: Artificial Sequence
<220> FEATURE:
<223> OTHER INFORMATION: CT03b VL (hT4-35 VL)

<400> SEQUENCE: 3

Asp Leu Val Met Thr Gln Ser Pro Ser Ser Leu Ser Ala Ser Val Gly
1 5 10 15

Asp Arg Val Thr Ile Thr Cys Lys Ser Ser Gln Ser Leu Leu Asn Ser
20 25 30

Arg Asp Gly Asn Thr Tyr Leu Ala Trp Tyr Gln Gln Lys Pro Gly Lys
35 40 45

Ala Pro Lys Leu Leu Ile Tyr Trp Leu Ser Tyr Arg Ala Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Phe Cys Gln Gln
85 90 95

Tyr Trp Tyr Trp Met Tyr Thr Phe Gly Gln Gly Thr Lys Val Glu Ile
100 105 110

Lys Arg

<210> SEQ ID NO 4
<211> LENGTH: 114
<212> TYPE: PRT
<213> ORGANISM: Artificial Sequence
<220> FEATURE:
<223> OTHER INFORMATION: CT03c VL (hT4-36 VL)

<400> SEQUENCE: 4

Asp Leu Val Met Thr Gln Ser Pro Ser Ser Leu Ser Ala Ser Val Gly
1 5 10 15

Asp Arg Val Thr Ile Thr Cys Lys Ser Ser Gln Ser Leu Leu Asn Ser
20 25 30

Asp Asp Arg Asn Thr Tyr Leu Ala Trp Tyr Gln Gln Lys Pro Gly Lys
35 40 45

Ala Pro Lys Leu Leu Ile Tyr Trp Leu Ser Tyr Arg Ala Ser Gly Val
50 55 60

Pro Ser Arg Phe Ser Gly Ser Gly Ser Gly Thr Asp Phe Thr Leu Thr
65 70 75 80

Ile Ser Ser Leu Gln Pro Glu Asp Phe Ala Thr Tyr Phe Cys Gln Gln
85 90 95

Tyr Trp Tyr Trp Met Tyr Thr Phe Gly Gln Gly Thr Lys Val Glu Ile
100 105 110

Lys Arg

<210> SEQ ID NO 5
<211> LENGTH: 114
<212> TYPE: PRT
<213> ORGANISM: Artificial Sequence
<220> FEATURE:
<223> OTHER INFORMATION: CT03d VL (hT4-38 VL)

<400> SEQUENCE: 5

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Thr Gly Lys Thr Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Met Tyr Thr Phe Gly Gln Gly Thr Lys Val Glu Ile
            100                 105                 110

Lys Arg
```

<210> SEQ ID NO 6
<211> LENGTH: 114
<212> TYPE: PRT
<213> ORGANISM: Artificial Sequence
<220> FEATURE:
<223> OTHER INFORMATION: CT03e VL (hT4-39 VL)

<400> SEQUENCE: 6

```
Asp Leu Val Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Asp Gly Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Phe Cys Gln Gln
                85                  90                  95

Tyr Trp Tyr Trp Met Tyr Thr Phe Gly Gln Gly Thr Lys Val Glu Ile
            100                 105                 110

Lys Arg
```

<210> SEQ ID NO 7
<211> LENGTH: 108
<212> TYPE: PRT
<213> ORGANISM: Artificial Sequence
<220> FEATURE:
<223> OTHER INFORMATION: Panitumumab -WYW VL

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
```

```
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Trp Tyr Trp Met Tyr
                85                  90                  95

Thr Phe Gly Gly Gly Thr Lys Val Glu Ile Lys Arg
            100                 105


<210> SEQ ID NO 8
<211> LENGTH: 114
<212> TYPE: PRT
<213> ORGANISM: Artificial Sequence
<220> FEATURE:
<223> OTHER INFORMATION: CT05 VL

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Arg Asp Gly Lys Asn Tyr Leu Ala Trp Tyr Gln Gln Lys Pro Gly Lys
        35                  40                  45

Ala Pro Lys Leu Leu Ile Tyr Asp Ala Ser Asn Leu Glu Thr Gly Val
    50                  55                  60

Pro Ser Arg Phe Ser Gly Ser Gly Ser Gly Thr Asp Phe Thr Phe Thr
65                  70                  75                  80

Ile Ser Ser Leu Gln Pro Glu Asp Ile Ala Thr Tyr Phe Cys Gln Gln
                85                  90                  95

Tyr Trp Tyr Trp Met Tyr Thr Phe Gly Gly Gly Thr Lys Val Glu Ile
            100                 105                 110

Lys Arg


<210> SEQ ID NO 9
<211> LENGTH: 136
<212> TYPE: PRT
<213> ORGANISM: Artificial Sequence
<220> FEATURE:
<223> OTHER INFORMATION: epCT05 (G4S)2 VL

<400> SEQUENCE: 9

Glu His Leu His Cys Leu Gly Ser Leu Cys Trp Pro Gly Gly Gly Gly
1               5                   10                  15

Ser Gly Gly Gly Gly Ser Asp Ile Gln Met Thr Gln Ser Pro Ser Ser
            20                  25                  30

Leu Ser Ala Ser Val Gly Asp Arg Val Thr Ile Thr Cys Lys Ser Ser
        35                  40                  45

Gln Ser Leu Leu Asn Ser Arg Asp Gly Lys Asn Tyr Leu Ala Trp Tyr
    50                  55                  60

Gln Gln Lys Pro Gly Lys Ala Pro Lys Leu Leu Ile Tyr Asp Ala Ser
65                  70                  75                  80

Asn Leu Glu Thr Gly Val Pro Ser Arg Phe Ser Gly Ser Gly Ser Gly
                85                  90                  95

Thr Asp Phe Thr Phe Thr Ile Ser Ser Leu Gln Pro Glu Asp Ile Ala
```

```
            100                 105                 110

Thr Tyr Phe Cys Gln Gln Tyr Trp Tyr Trp Met Tyr Thr Phe Gly Gly
        115                 120                 125

Gly Thr Lys Val Glu Ile Lys Arg
    130                 135


<210> SEQ ID NO 10
<211> LENGTH: 120
<212> TYPE: PRT
<213> ORGANISM: Artificial Sequence
<220> FEATURE:
<223> OTHER INFORMATION: HT0 VH

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Tyr Lys Arg Gly Tyr Ala Met Asp Tyr Trp Gly Gln
            100                 105                 110

Gly Thr Thr Val Thr Val Ser Ser
        115                 120


<210> SEQ ID NO 11
<211> LENGTH: 116
<212> TYPE: PRT
<213> ORGANISM: Artificial Sequence
<220> FEATURE:
<223> OTHER INFORMATION: CT01 VH (HT0-01 VH)

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Val Met His Trp Val Arg Gln Ala Pro Gly Lys Gly Leu Glu Trp Val
        35                  40                  45

Ser Ala Ile Asn Pro Tyr Asn Asp Gly Asn Tyr Tyr Ala Asp Ser Val
    50                  55                  60

Lys Gly Arg Phe Thr Ile Ser Arg Asp Asn Ser Arg Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Met Asp Leu Trp Gly Gln Gly Thr Thr Val
            100                 105                 110

Thr Val Ser Ser
        115


<210> SEQ ID NO 12
<211> LENGTH: 116
```

<212> TYPE: PRT
<213> ORGANISM: Artificial Sequence
<220> FEATURE:
<223> OTHER INFORMATION: CT60 VH (CT10 VH)

<400> SEQUENCE: 12

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Phe
            20                  25                  30

Ser Met Ser Trp Val Arg Gln Ala Pro Gly Lys Gly Leu Glu Trp Val
        35                  40                  45

Ser Tyr Ile Ser Arg Thr Ser His Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Trp Met Asp Leu Trp Gly Gln Gly Thr Leu Val
            100                 105                 110

Thr Val Ser Ser
        115
```

<210> SEQ ID NO 13
<211> LENGTH: 12
<212> TYPE: PRT
<213> ORGANISM: Artificial Sequence
<220> FEATURE:
<223> OTHER INFORMATION: EP133 of EpCAM

<400> SEQUENCE: 13

```
Glu His Leu His Cys Leu Gly Ser Leu Cys Trp Pro
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: 3-27 of EpCAM

<400> SEQUENCE: 14

```
Arg Gly Leu Arg Cys Leu Gly Arg Leu Cys Trp Pro
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: 4-8 of EpCAM

<400> SEQUENCE: 15

```
Arg Asn Leu Leu Cys Ile Gly Asn Leu Cys Trp Pro
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: 4-12 of EpCAM

<400> SEQUENCE: 16

Arg Asn Leu Leu Cys Leu Arg Arg Ile Cys Trp Pro
1 5 10

<210> SEQ ID NO 17
<211> LENGTH: 12
<212> TYPE: PRT
<213> ORGANISM: Artificial Sequence
<220> FEATURE:
<223> OTHER INFORMATION: 4-13 of EpCAM

<400> SEQUENCE: 17

Arg Asn Leu Gln Cys Ile Arg Asn Ile Cys Trp Ser
1 5 10

<210> SEQ ID NO 18
<211> LENGTH: 12
<212> TYPE: PRT
<213> ORGANISM: Artificial Sequence
<220> FEATURE:
<223> OTHER INFORMATION: 4-14 of EpCAM

<400> SEQUENCE: 18

Arg Asn Leu His Cys Ile Gly Asn Leu Cys Trp Pro
1 5 10

<210> SEQ ID NO 19
<211> LENGTH: 12
<212> TYPE: PRT
<213> ORGANISM: Artificial Sequence
<220> FEATURE:
<223> OTHER INFORMATION: 4-19 of EpCAM

<400> SEQUENCE: 19

Arg Asn Leu Arg Cys Ile Gly Asn Ile Cys Trp Ser
1 5 10

<210> SEQ ID NO 20
<211> LENGTH: 12
<212> TYPE: PRT
<213> ORGANISM: Artificial Sequence
<220> FEATURE:
<223> OTHER INFORMATION: 4-27 of EpCAM

<400> SEQUENCE: 20

Arg His Leu Trp Cys Leu Gly Arg Leu Cys Trp Pro
1 5 10

<210> SEQ ID NO 21
<211> LENGTH: 132
<212> TYPE: PRT
<213> ORGANISM: Artificial Sequence
<220> FEATURE:
<223> OTHER INFORMATION: hT4-ep59 MG VL

<400> SEQUENCE: 21

Glu His Leu His Cys Leu Gly Ser Leu Cys Trp Pro Met Gly Ser Ser
1 5 10 15

Ser Asn Asp Ile Gln Met Thr Gln Ser Pro Ser Ser Leu Ser Ala Ser
20 25 30

Val Gly Asp Arg Val Thr Ile Thr Cys Lys Ser Ser Gln Ser Leu Leu
35 40 45

Asn Ser Arg Asp Gly Lys Asn Tyr Leu Ala Trp Tyr Gln Gln Lys Pro
50 55 60

Gly Lys Ala Pro Lys Leu Leu Ile Tyr Trp Ala Ser Thr Arg Glu Ser

-continued

```
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 22
<211> LENGTH: 132
<212> TYPE: PRT
<213> ORGANISM: Artificial Sequence
<220> FEATURE:
<223> OTHER INFORMATION: hT4-ep59 (3-27) MG VL

<400> SEQUENCE: 22

Arg Gly Leu Arg Cys Leu Gly Arg Leu Cys Trp Pro Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 23
<211> LENGTH: 132
<212> TYPE: PRT
<213> ORGANISM: Artificial Sequence
<220> FEATURE:
<223> OTHER INFORMATION: hT4-ep59 (4-8) MG VL

<400> SEQUENCE: 23

Arg Asn Leu Leu Cys Ile Gly Asn Leu Cys Trp Pro Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95
```

```
Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 24
<211> LENGTH: 132
<212> TYPE: PRT
<213> ORGANISM: Artificial Sequence
<220> FEATURE:
<223> OTHER INFORMATION: hT4-ep59 (4-12) MG VL

<400> SEQUENCE: 24

Arg Asn Leu Leu Cys Leu Arg Arg Ile Cys Trp Pro Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 25
<211> LENGTH: 132
<212> TYPE: PRT
<213> ORGANISM: Artificial Sequence
<220> FEATURE:
<223> OTHER INFORMATION: hT4-ep59 (4-13) MG VL

<400> SEQUENCE: 25

Arg Asn Leu Gln Cys Ile Arg Asn Ile Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125
```

```
Glu Ile Lys Arg
    130


<210> SEQ ID NO 26
<211> LENGTH: 132
<212> TYPE: PRT
<213> ORGANISM: Artificial Sequence
<220> FEATURE:
<223> OTHER INFORMATION: hT4-ep59 (4-14) MG VL

<400> SEQUENCE: 26

Arg Asn Leu His Cys Ile Gly Asn Leu Cys Trp Pro Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 27
<211> LENGTH: 132
<212> TYPE: PRT
<213> ORGANISM: Artificial Sequence
<220> FEATURE:
<223> OTHER INFORMATION: hT4-ep59 (4-19) MG VL

<400> SEQUENCE: 27

Arg Asn Leu Arg Cys Ile Gly Asn Ile Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130
```

<210> SEQ ID NO 28
<211> LENGTH: 132
<212> TYPE: PRT
<213> ORGANISM: Artificial Sequence
<220> FEATURE:
<223> OTHER INFORMATION: hT4-ep59 (4-27) MG VL

<400> SEQUENCE: 28

```
Arg His Leu Trp Cys Leu Gly Arg Leu Cys Trp Pro Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130
```

<210> SEQ ID NO 29
<211> LENGTH: 12
<212> TYPE: PRT
<213> ORGANISM: Artificial Sequence
<220> FEATURE:
<223> OTHER INFORMATION: Ep1 of EpCAM

<400> SEQUENCE: 29

```
Glu Asn Leu Leu Cys Ile Gly Asn Leu Cys Trp Ser
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: Ep2 of EpCAM

<400> SEQUENCE: 30

```
Glu His Leu Leu Cys Ile Gly Asn Leu Cys Trp Ser
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: Ep3 of EpCAM

<400> SEQUENCE: 31

```
Glu Asn Leu Gln Cys Ile Gly Asn Leu Cys Trp Ser
1               5                   10
```

<210> SEQ ID NO 32
<211> LENGTH: 12
<212> TYPE: PRT

<213> ORGANISM: Artificial Sequence
<220> FEATURE:
<223> OTHER INFORMATION: Ep4 of EpCAM

<400> SEQUENCE: 32

Glu His Leu His Cys Leu Gly Ser Leu Cys Trp Ser
1 5 10

<210> SEQ ID NO 33
<211> LENGTH: 12
<212> TYPE: PRT
<213> ORGANISM: Artificial Sequence
<220> FEATURE:
<223> OTHER INFORMATION: Ep5 of EpCAM

<400> SEQUENCE: 33

His Asn Leu Arg Cys Ile Gly Asn Ile Cys Trp Ser
1 5 10

<210> SEQ ID NO 34
<211> LENGTH: 12
<212> TYPE: PRT
<213> ORGANISM: Artificial Sequence
<220> FEATURE:
<223> OTHER INFORMATION: Ep6 of EpCAM

<400> SEQUENCE: 34

Asn Asn Leu Arg Cys Ile Gly Asn Ile Cys Trp Ser
1 5 10

<210> SEQ ID NO 35
<211> LENGTH: 12
<212> TYPE: PRT
<213> ORGANISM: Artificial Sequence
<220> FEATURE:
<223> OTHER INFORMATION: Ep7 of EpCAM

<400> SEQUENCE: 35

Asp Asn Leu Arg Cys Ile Gly Asn Ile Cys Trp Ser
1 5 10

<210> SEQ ID NO 36
<211> LENGTH: 12
<212> TYPE: PRT
<213> ORGANISM: Artificial Sequence
<220> FEATURE:
<223> OTHER INFORMATION: Ep8 of EpCAM

<400> SEQUENCE: 36

Glu Asn Leu Arg Cys Ile Gly Asn Ile Cys Trp Ser
1 5 10

<210> SEQ ID NO 37
<211> LENGTH: 12
<212> TYPE: PRT
<213> ORGANISM: Artificial Sequence
<220> FEATURE:
<223> OTHER INFORMATION: Ep9 of EpCAM

<400> SEQUENCE: 37

Lys Asn Leu Arg Cys Ile Gly Asn Ile Cys Trp Ser
1 5 10

<210> SEQ ID NO 38
<211> LENGTH: 132
<212> TYPE: PRT
<213> ORGANISM: Artificial Sequence
<220> FEATURE:
<223> OTHER INFORMATION: hT4-ep59 (ep1) MG VL

<400> SEQUENCE: 38

Glu Asn Leu Leu Cys Ile Gly Asn Leu Cys Trp Ser Met Gly Ser Ser
1 5 10 15

Ser Asn Asp Ile Gln Met Thr Gln Ser Pro Ser Ser Leu Ser Ala Ser
20 25 30

Val Gly Asp Arg Val Thr Ile Thr Cys Lys Ser Ser Gln Ser Leu Leu
35 40 45

Asn Ser Arg Asp Gly Lys Asn Tyr Leu Ala Trp Tyr Gln Gln Lys Pro
50 55 60

Gly Lys Ala Pro Lys Leu Leu Ile Tyr Trp Ala Ser Thr Arg Glu Ser
65 70 75 80

Gly Val Pro Ser Arg Phe Ser Gly Ser Gly Ser Gly Thr Asp Phe Thr
85 90 95

Leu Thr Ile Ser Ser Leu Gln Pro Glu Asp Phe Ala Thr Tyr Phe Cys
100 105 110

Gln Gln Tyr Trp Tyr Trp Met Tyr Thr Phe Gly Gln Gly Thr Lys Val
115 120 125

Glu Ile Lys Arg
130

<210> SEQ ID NO 39
<211> LENGTH: 132
<212> TYPE: PRT
<213> ORGANISM: Artificial Sequence
<220> FEATURE:
<223> OTHER INFORMATION: hT4-ep59 (ep2) MG VL

<400> SEQUENCE: 39

Glu His Leu Leu Cys Ile Gly Asn Leu Cys Trp Ser Met Gly Ser Ser
1 5 10 15

Ser Asn Asp Ile Gln Met Thr Gln Ser Pro Ser Ser Leu Ser Ala Ser
20 25 30

Val Gly Asp Arg Val Thr Ile Thr Cys Lys Ser Ser Gln Ser Leu Leu
35 40 45

Asn Ser Arg Asp Gly Lys Asn Tyr Leu Ala Trp Tyr Gln Gln Lys Pro
50 55 60

Gly Lys Ala Pro Lys Leu Leu Ile Tyr Trp Ala Ser Thr Arg Glu Ser
65 70 75 80

Gly Val Pro Ser Arg Phe Ser Gly Ser Gly Ser Gly Thr Asp Phe Thr
85 90 95

Leu Thr Ile Ser Ser Leu Gln Pro Glu Asp Phe Ala Thr Tyr Phe Cys
100 105 110

Gln Gln Tyr Trp Tyr Trp Met Tyr Thr Phe Gly Gln Gly Thr Lys Val
115 120 125

Glu Ile Lys Arg
130

<210> SEQ ID NO 40
<211> LENGTH: 132
<212> TYPE: PRT
<213> ORGANISM: Artificial Sequence
<220> FEATURE:
<223> OTHER INFORMATION: hT4-ep59 (ep3) MG VL

<400> SEQUENCE: 40

```
Glu Asn Leu Gln Cys Ile Gly Asn Leu Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 41
<211> LENGTH: 132
<212> TYPE: PRT
<213> ORGANISM: Artificial Sequence
<220> FEATURE:
<223> OTHER INFORMATION: hT4-ep59 (ep4) MG VL

<400> SEQUENCE: 41

Glu His Leu His Cys Leu Gly Ser Leu Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 42
<211> LENGTH: 132
<212> TYPE: PRT
<213> ORGANISM: Artificial Sequence
<220> FEATURE:
<223> OTHER INFORMATION: hT4-ep59 (ep5) MG VL

<400> SEQUENCE: 42

His Asn Leu Arg Cys Ile Gly Asn Ile Cys Trp Ser Met Gly Ser Ser
1               5                   10                  15

Ser Asn Asp Ile Gln Met Thr Gln Ser Pro Ser Ser Leu Ser Ala Ser
            20                  25                  30
```

Val Gly Asp Arg Val Thr Ile Thr Cys Lys Ser Ser Gln Ser Leu Leu
35 40 45

Asn Ser Arg Asp Gly Lys Asn Tyr Leu Ala Trp Tyr Gln Gln Lys Pro
50 55 60

Gly Lys Ala Pro Lys Leu Leu Ile Tyr Trp Ala Ser Thr Arg Glu Ser
65 70 75 80

Gly Val Pro Ser Arg Phe Ser Gly Ser Gly Ser Gly Thr Asp Phe Thr
85 90 95

Leu Thr Ile Ser Ser Leu Gln Pro Glu Asp Phe Ala Thr Tyr Phe Cys
100 105 110

Gln Gln Tyr Trp Tyr Trp Met Tyr Thr Phe Gly Gln Gly Thr Lys Val
115 120 125

Glu Ile Lys Arg
130

<210> SEQ ID NO 43
<211> LENGTH: 132
<212> TYPE: PRT
<213> ORGANISM: Artificial Sequence
<220> FEATURE:
<223> OTHER INFORMATION: hT4-ep59 (ep6) MG VL

<400> SEQUENCE: 43

Asn Asn Leu Arg Cys Ile Gly Asn Ile Cys Trp Ser Met Gly Ser Ser
1 5 10 15

Ser Asn Asp Ile Gln Met Thr Gln Ser Pro Ser Ser Leu Ser Ala Ser
20 25 30

Val Gly Asp Arg Val Thr Ile Thr Cys Lys Ser Ser Gln Ser Leu Leu
35 40 45

Asn Ser Arg Asp Gly Lys Asn Tyr Leu Ala Trp Tyr Gln Gln Lys Pro
50 55 60

Gly Lys Ala Pro Lys Leu Leu Ile Tyr Trp Ala Ser Thr Arg Glu Ser
65 70 75 80

Gly Val Pro Ser Arg Phe Ser Gly Ser Gly Ser Gly Thr Asp Phe Thr
85 90 95

Leu Thr Ile Ser Ser Leu Gln Pro Glu Asp Phe Ala Thr Tyr Phe Cys
100 105 110

Gln Gln Tyr Trp Tyr Trp Met Tyr Thr Phe Gly Gln Gly Thr Lys Val
115 120 125

Glu Ile Lys Arg
130

<210> SEQ ID NO 44
<211> LENGTH: 132
<212> TYPE: PRT
<213> ORGANISM: Artificial Sequence
<220> FEATURE:
<223> OTHER INFORMATION: hT4-ep59 (ep7) MG VL

<400> SEQUENCE: 44

Asp Asn Leu Arg Cys Ile Gly Asn Ile Cys Trp Ser Met Gly Ser Ser
1 5 10 15

Ser Asn Asp Ile Gln Met Thr Gln Ser Pro Ser Ser Leu Ser Ala Ser
20 25 30

Val Gly Asp Arg Val Thr Ile Thr Cys Lys Ser Ser Gln Ser Leu Leu
35 40 45

Asn Ser Arg Asp Gly Lys Asn Tyr Leu Ala Trp Tyr Gln Gln Lys Pro

-continued

```
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 45
<211> LENGTH: 132
<212> TYPE: PRT
<213> ORGANISM: Artificial Sequence
<220> FEATURE:
<223> OTHER INFORMATION: hT4-ep59 (ep8) MG VL

<400> SEQUENCE: 45

Glu Asn Leu Arg Cys Ile Gly Asn Ile Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 46
<211> LENGTH: 132
<212> TYPE: PRT
<213> ORGANISM: Artificial Sequence
<220> FEATURE:
<223> OTHER INFORMATION: hT4-ep59 (ep9) MG VL

<400> SEQUENCE: 46

Lys Asn Leu Arg Cys Ile Gly Asn Ile Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Trp Ala Ser Thr Arg Glu Ser
65                  70                  75                  80
```

```
Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Phe Cys
            100                 105                 110

Gln Gln Tyr Trp Tyr Trp Met Tyr Thr Phe Gly Gln Gly Thr Lys Val
        115                 120                 125

Glu Ile Lys Arg
    130


<210> SEQ ID NO 47
<211> LENGTH: 132
<212> TYPE: PRT
<213> ORGANISM: Artificial Sequence
<220> FEATURE:
<223> OTHER INFORMATION: ep6-CT05 MG VL

<400> SEQUENCE: 47

Asn Asn Leu Arg Cys Ile Gly Asn Ile Cys Trp Ser Met Gly Ser Ser
1               5                   10                  15

Ser Asn Asp Ile Gln Met Thr Gln Ser Pro Ser Ser Leu Ser Ala Ser
            20                  25                  30

Val Gly Asp Arg Val Thr Ile Thr Cys Lys Ser Ser Gln Ser Leu Leu
        35                  40                  45

Asn Ser Arg Asp Gly Lys Asn Tyr Leu Ala Trp Tyr Gln Gln Lys Pro
    50                  55                  60

Gly Lys Ala Pro Lys Leu Leu Ile Tyr Asp Ala Ser Asn Leu Glu Thr
65                  70                  75                  80

Gly Val Pro Ser Arg Phe Ser Gly Ser Gly Ser Gly Thr Asp Phe Thr
                85                  90                  95

Phe Thr Ile Ser Ser Leu Gln Pro Glu Asp Ile Ala Thr Tyr Phe Cys
            100                 105                 110

Gln Gln Tyr Trp Tyr Trp Met Tyr Thr Phe Gly Gly Gly Thr Lys Val
        115                 120                 125

Glu Ile Lys Arg
    130


<210> SEQ ID NO 48
<211> LENGTH: 136
<212> TYPE: PRT
<213> ORGANISM: Artificial Sequence
<220> FEATURE:
<223> OTHER INFORMATION: ep6-CT05 (G4S)2 VL

<400> SEQUENCE: 48

Asn Asn Leu Arg Cys Ile Gly Asn Ile Cys Trp Ser Gly Gly Gly Gly
1               5                   10                  15

Ser Gly Gly Gly Gly Ser Asp Ile Gln Met Thr Gln Ser Pro Ser Ser
            20                  25                  30

Leu Ser Ala Ser Val Gly Asp Arg Val Thr Ile Thr Cys Lys Ser Ser
        35                  40                  45

Gln Ser Leu Leu Asn Ser Arg Asp Gly Lys Asn Tyr Leu Ala Trp Tyr
    50                  55                  60

Gln Gln Lys Pro Gly Lys Ala Pro Lys Leu Leu Ile Tyr Asp Ala Ser
65                  70                  75                  80

Asn Leu Glu Thr Gly Val Pro Ser Arg Phe Ser Gly Ser Gly Ser Gly
                85                  90                  95

Thr Asp Phe Thr Phe Thr Ile Ser Ser Leu Gln Pro Glu Asp Ile Ala
            100                 105                 110
```

```
Thr Tyr Phe Cys Gln Gln Tyr Trp Tyr Trp Met Tyr Thr Phe Gly Gly
        115                 120                 125

Gly Thr Lys Val Glu Ile Lys Arg
    130                 135


<210> SEQ ID NO 49
<211> LENGTH: 13
<212> TYPE: PRT
<213> ORGANISM: Artificial Sequence
<220> FEATURE:
<223> OTHER INFORMATION: RGD10 of Integrin alphaVbeta3, Integrin
      alphaVbeta5

<400> SEQUENCE: 49

Asp Gly Ala Arg Tyr Cys Arg Gly Asp Cys Phe Asp Gly
1               5                   10


<210> SEQ ID NO 50
<211> LENGTH: 15
<212> TYPE: PRT
<213> ORGANISM: Artificial Sequence
<220> FEATURE:
<223> OTHER INFORMATION: in1 of Integrin alphaVbeta3, Integrin
      alphaVbeta5

<400> SEQUENCE: 50

Asp Gly Glu Lys Asn Cys Arg Gly Asp Cys Ile Glu Asp Gln Pro
1               5                   10                  15


<210> SEQ ID NO 51
<211> LENGTH: 15
<212> TYPE: PRT
<213> ORGANISM: Artificial Sequence
<220> FEATURE:
<223> OTHER INFORMATION: in2 of Integrin alphaVbeta3, Integrin
      alphaVbeta5

<400> SEQUENCE: 51

Asp Gly Glu Lys Ser Cys Arg Gly Asp Cys Phe Asp Pro Ser Gln
1               5                   10                  15


<210> SEQ ID NO 52
<211> LENGTH: 15
<212> TYPE: PRT
<213> ORGANISM: Artificial Sequence
<220> FEATURE:
<223> OTHER INFORMATION: in3 of Integrin alphaVbeta3, Integrin
      alphaVbeta5

<400> SEQUENCE: 52

Asp Gly Val Arg Ala Cys Arg Gly Asp Cys Phe Asp Val Gln Asp
1               5                   10                  15


<210> SEQ ID NO 53
<211> LENGTH: 15
<212> TYPE: PRT
<213> ORGANISM: Artificial Sequence
<220> FEATURE:
<223> OTHER INFORMATION: in4 of Integrin alphaVbeta3, Integrin
      alphaVbeta5

<400> SEQUENCE: 53

Asp Gly Val Arg Gln Cys Arg Gly Asp Cys Phe Asp Gly Pro Leu
1               5                   10                  15


<210> SEQ ID NO 54
```

<211> LENGTH: 15
<212> TYPE: PRT
<213> ORGANISM: Artificial Sequence
<220> FEATURE:
<223> OTHER INFORMATION: in5 of Integrin alphaVbeta3, Integrin alphaVbeta5

<400> SEQUENCE: 54

Asp Gly Gly Arg Leu Cys Arg Gly Asp Cys Phe Asp Ala Gln Gln
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: in6 of Integrin alphaVbeta3, Integrin alphaVbeta5

<400> SEQUENCE: 55

Asp Gly Glu Arg Gln Cys Arg Gly Asp Cys Phe Asp Ala Pro Val
1 5 10 15

<210> SEQ ID NO 56
<211> LENGTH: 15
<212> TYPE: PRT
<213> ORGANISM: Artificial Sequence
<220> FEATURE:
<223> OTHER INFORMATION: in7 of Integrin alphaVbeta3, Integrin alphaVbeta5

<400> SEQUENCE: 56

Asp Gly Gln Arg Thr Cys Arg Gly Asp Cys Phe Asp Pro Pro Ser
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: in8 of Integrin alphaVbeta3, Integrin alphaVbeta5

<400> SEQUENCE: 57

Asp Gly Asp Lys Gln Cys Arg Gly Asp Cys Phe Asp Pro Ala Pro
1 5 10 15

<210> SEQ ID NO 58
<211> LENGTH: 133
<212> TYPE: PRT
<213> ORGANISM: Artificial Sequence
<220> FEATURE:
<223> OTHER INFORMATION: hT4-i59 MG VL

<400> SEQUENCE: 58

Asp Gly Ala Arg Tyr Cys Arg Gly Asp Cys Phe Asp Gly Met Gly Ser
1 5 10 15

Ser Ser Asn Asp Ile Gln Met Thr Gln Ser Pro Ser Ser Leu Ser Ala
20 25 30

Ser Val Gly Asp Arg Val Thr Ile Thr Cys Lys Ser Ser Gln Ser Leu
35 40 45

Leu Asn Ser Arg Asp Gly Lys Asn Tyr Leu Ala Trp Tyr Gln Gln Lys
50 55 60

Pro Gly Lys Ala Pro Lys Leu Leu Ile Tyr Trp Ala Ser Thr Arg Glu
65 70 75 80

```
Ser Gly Val Pro Ser Arg Phe Ser Gly Ser Gly Ser Gly Thr Asp Phe
                85                  90                  95

Thr Leu Thr Ile Ser Ser Leu Gln Pro Glu Asp Phe Ala Thr Tyr Phe
            100                 105                 110

Cys Gln Gln Tyr Trp Tyr Trp Met Tyr Thr Phe Gly Gln Gly Thr Lys
        115                 120                 125

Val Glu Ile Lys Arg
    130


<210> SEQ ID NO 59
<211> LENGTH: 135
<212> TYPE: PRT
<213> ORGANISM: Artificial Sequence
<220> FEATURE:
<223> OTHER INFORMATION: hT4-i59 (in1) MG VL

<400> SEQUENCE: 59

Asp Gly Glu Lys Asn Cys Arg Gly Asp Cys Ile Glu Asp Gln Pro Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
    130                 135


<210> SEQ ID NO 60
<211> LENGTH: 135
<212> TYPE: PRT
<213> ORGANISM: Artificial Sequence
<220> FEATURE:
<223> OTHER INFORMATION: hT4-i59 (in2) MG VL

<400> SEQUENCE: 60

Asp Gly Glu Lys Ser Cys Arg Gly Asp Cys Phe Asp Pro Ser Gln Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110
```

```
Tyr Phe Cys Gln Gln Tyr Trp Tyr Trp Met Tyr Thr Phe Gly Gln Gly
        115                 120                 125

Thr Lys Val Glu Ile Lys Arg
    130                 135


<210> SEQ ID NO 61
<211> LENGTH: 135
<212> TYPE: PRT
<213> ORGANISM: Artificial Sequence
<220> FEATURE:
<223> OTHER INFORMATION: hT4-i59 (in3) MG VL

<400> SEQUENCE: 61

Asp Gly Val Arg Ala Cys Arg Gly Asp Cys Phe Asp Val Gln Asp Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
    130                 135


<210> SEQ ID NO 62
<211> LENGTH: 135
<212> TYPE: PRT
<213> ORGANISM: Artificial Sequence
<220> FEATURE:
<223> OTHER INFORMATION: hT4-i59 (in4) MG VL

<400> SEQUENCE: 62

Asp Gly Val Arg Gln Cys Arg Gly Asp Cys Phe Asp Gly Pro Leu Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
```

```
    130                 135


<210> SEQ ID NO 63
<211> LENGTH: 135
<212> TYPE: PRT
<213> ORGANISM: Artificial Sequence
<220> FEATURE:
<223> OTHER INFORMATION: hT4-i59 (in5) MG VL

<400> SEQUENCE: 63

Asp Gly Gly Arg Leu Cys Arg Gly Asp Cys Phe Asp Ala Gln Gln Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
    130                 135


<210> SEQ ID NO 64
<211> LENGTH: 135
<212> TYPE: PRT
<213> ORGANISM: Artificial Sequence
<220> FEATURE:
<223> OTHER INFORMATION: hT4-i59 (in6) MG VL

<400> SEQUENCE: 64

Asp Gly Glu Arg Gln Cys Arg Gly Asp Cys Phe Asp Ala Pro Val Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
    130                 135


<210> SEQ ID NO 65
<211> LENGTH: 135
```

<212> TYPE: PRT
<213> ORGANISM: Artificial Sequence
<220> FEATURE:
<223> OTHER INFORMATION: hT4-i59 (in7) MG VL

<400> SEQUENCE: 65

```
Asp Gly Gln Arg Thr Cys Arg Gly Asp Cys Phe Asp Pro Pro Ser Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
    130                 135
```

<210> SEQ ID NO 66
<211> LENGTH: 135
<212> TYPE: PRT
<213> ORGANISM: Artificial Sequence
<220> FEATURE:
<223> OTHER INFORMATION: hT4-i59 (in8) MG VL

<400> SEQUENCE: 66

```
Asp Gly Asp Lys Gln Cys Arg Gly Asp Cys Phe Asp Pro Ala Pro Met
1               5                   10                  15

Gly Ser Ser Ser Asn Asp Ile Gln Met Thr Gln Ser Pro Ser Ser Leu
            20                  25                  30

Ser Ala Ser Val Gly Asp Arg Val Thr Ile Thr Cys Lys Ser Ser Gln
        35                  40                  45

Ser Leu Leu Asn Ser Arg Asp Gly Lys Asn Tyr Leu Ala Trp Tyr Gln
    50                  55                  60

Gln Lys Pro Gly Lys Ala Pro Lys Leu Leu Ile Tyr Trp Ala Ser Thr
65                  70                  75                  80

Arg Glu Ser Gly Val Pro Ser Arg Phe Ser Gly Ser Gly Ser Gly Thr
                85                  90                  95

Asp Phe Thr Leu Thr Ile Ser Ser Leu Gln Pro Glu Asp Phe Ala Thr
            100                 105                 110

Tyr Phe Cys Gln Gln Tyr Trp Tyr Trp Met Tyr Thr Phe Gly Gln Gly
        115                 120                 125

Thr Lys Val Glu Ile Lys Arg
    130                 135
```

<210> SEQ ID NO 67
<211> LENGTH: 133
<212> TYPE: PRT
<213> ORGANISM: Artificial Sequence
<220> FEATURE:
<223> OTHER INFORMATION: inCT05 MG VL

<400> SEQUENCE: 67

Asp Gly Ala Arg Tyr Cys Arg Gly Asp Cys Phe Asp Gly Met Gly Ser
1 5 10 15

Ser Ser Asn Asp Ile Gln Met Thr Gln Ser Pro Ser Ser Leu Ser Ala
20 25 30

Ser Val Gly Asp Arg Val Thr Ile Thr Cys Lys Ser Ser Gln Ser Leu
35 40 45

Leu Asn Ser Arg Asp Gly Lys Asn Tyr Leu Ala Trp Tyr Gln Gln Lys
50 55 60

Pro Gly Lys Ala Pro Lys Leu Leu Ile Tyr Asp Ala Ser Asn Leu Glu
65 70 75 80

Thr Gly Val Pro Ser Arg Phe Ser Gly Ser Gly Ser Gly Thr Asp Phe
85 90 95

Thr Phe Thr Ile Ser Ser Leu Gln Pro Glu Asp Ile Ala Thr Tyr Phe
100 105 110

Cys Gln Gln Tyr Trp Tyr Trp Met Tyr Thr Phe Gly Gly Gly Thr Lys
115 120 125

Val Glu Ile Lys Arg
130

<210> SEQ ID NO 68
<211> LENGTH: 135
<212> TYPE: PRT
<213> ORGANISM: Artificial Sequence
<220> FEATURE:
<223> OTHER INFORMATION: in4-CT05 MG VL

<400> SEQUENCE: 68

Asp Gly Val Arg Gln Cys Arg Gly Asp Cys Phe Asp Gly Pro Leu Met
1 5 10 15

Gly Ser Ser Ser Asn Asp Ile Gln Met Thr Gln Ser Pro Ser Ser Leu
20 25 30

Ser Ala Ser Val Gly Asp Arg Val Thr Ile Thr Cys Lys Ser Ser Gln
35 40 45

Ser Leu Leu Asn Ser Arg Asp Gly Lys Asn Tyr Leu Ala Trp Tyr Gln
50 55 60

Gln Lys Pro Gly Lys Ala Pro Lys Leu Leu Ile Tyr Asp Ala Ser Asn
65 70 75 80

Leu Glu Thr Gly Val Pro Ser Arg Phe Ser Gly Ser Gly Ser Gly Thr
85 90 95

Asp Phe Thr Phe Thr Ile Ser Ser Leu Gln Pro Glu Asp Ile Ala Thr
100 105 110

Tyr Phe Cys Gln Gln Tyr Trp Tyr Trp Met Tyr Thr Phe Gly Gly Gly
115 120 125

Thr Lys Val Glu Ile Lys Arg
130 135

<210> SEQ ID NO 69
<211> LENGTH: 4
<212> TYPE: PRT
<213> ORGANISM: Artificial Sequence
<220> FEATURE:
<223> OTHER INFORMATION: Endosomal Escape Motif
<220> FEATURE:
<221> NAME/KEY: MISC_FEATURE
<222> LOCATION: (4)..(4)
<223> OTHER INFORMATION: Xaa is any one of M, I and L

<400> SEQUENCE: 69

```
Trp Tyr Trp Xaa
1


<210> SEQ ID NO 70
<211> LENGTH: 1014
<212> TYPE: PRT
<213> ORGANISM: Artificial Sequence
<220> FEATURE:
<223> OTHER INFORMATION: Integrin alphaV Extra-cellular domain-Acidic
      Leucine zipper-His x 6

<400> SEQUENCE: 70

Phe Asn Leu Asp Val Asp Ser Pro Ala Glu Tyr Ser Gly Pro Glu Gly
1               5                   10                  15

Ser Tyr Phe Gly Phe Ala Val Asp Phe Phe Val Pro Ser Ala Ser Ser
            20                  25                  30

Arg Met Phe Leu Leu Val Gly Ala Pro Lys Ala Asn Thr Thr Gln Pro
        35                  40                  45

Gly Ile Val Glu Gly Gly Gln Val Leu Lys Cys Asp Trp Ser Ser Thr
    50                  55                  60

Arg Arg Cys Gln Pro Ile Glu Phe Asp Ala Thr Gly Asn Arg Asp Tyr
65                  70                  75                  80

Ala Lys Asp Asp Pro Leu Glu Phe Lys Ser His Gln Trp Phe Gly Ala
                85                  90                  95

Ser Val Arg Ser Lys Gln Asp Lys Ile Leu Ala Cys Ala Pro Leu Tyr
            100                 105                 110

His Trp Arg Thr Glu Met Lys Gln Glu Arg Glu Pro Val Gly Thr Cys
        115                 120                 125

Phe Leu Gln Asp Gly Thr Lys Thr Val Glu Tyr Ala Pro Cys Arg Ser
    130                 135                 140

Gln Asp Ile Asp Ala Asp Gly Gln Gly Phe Cys Gln Gly Gly Phe Ser
145                 150                 155                 160

Ile Asp Phe Thr Lys Ala Asp Arg Val Leu Leu Gly Gly Pro Gly Ser
                165                 170                 175

Phe Tyr Trp Gln Gly Gln Leu Ile Ser Asp Gln Val Ala Glu Ile Val
            180                 185                 190

Ser Lys Tyr Asp Pro Asn Val Tyr Ser Ile Lys Tyr Asn Asn Gln Leu
        195                 200                 205

Ala Thr Arg Thr Ala Gln Ala Ile Phe Asp Asp Ser Tyr Leu Gly Tyr
    210                 215                 220

Ser Val Ala Val Gly Asp Phe Asn Gly Asp Gly Ile Asp Asp Phe Val
225                 230                 235                 240

Ser Gly Val Pro Arg Ala Ala Arg Thr Leu Gly Met Val Tyr Ile Tyr
                245                 250                 255

Asp Gly Lys Asn Met Ser Ser Leu Tyr Asn Phe Thr Gly Glu Gln Met
            260                 265                 270

Ala Ala Tyr Phe Gly Phe Ser Val Ala Ala Thr Asp Ile Asn Gly Asp
        275                 280                 285

Asp Tyr Ala Asp Val Phe Ile Gly Ala Pro Leu Phe Met Asp Arg Gly
    290                 295                 300

Ser Asp Gly Lys Leu Gln Glu Val Gly Gln Val Ser Val Ser Leu Gln
305                 310                 315                 320

Arg Ala Ser Gly Asp Phe Gln Thr Thr Lys Leu Asn Gly Phe Glu Val
                325                 330                 335

Phe Ala Arg Phe Gly Ser Ala Ile Ala Pro Leu Gly Asp Leu Asp Gln
```

```
            340                 345                 350

Asp Gly Phe Asn Asp Ile Ala Ile Ala Ala Pro Tyr Gly Gly Glu Asp
        355                 360                 365

Lys Lys Gly Ile Val Tyr Ile Phe Asn Gly Arg Ser Thr Gly Leu Asn
    370                 375                 380

Ala Val Pro Ser Gln Ile Leu Glu Gly Gln Trp Ala Ala Arg Ser Met
385                 390                 395                 400

Pro Pro Ser Phe Gly Tyr Ser Met Lys Gly Ala Thr Asp Ile Asp Lys
                405                 410                 415

Asn Gly Tyr Pro Asp Leu Ile Val Gly Ala Phe Gly Val Asp Arg Ala
            420                 425                 430

Ile Leu Tyr Arg Ala Arg Pro Val Ile Thr Val Asn Ala Gly Leu Glu
        435                 440                 445

Val Tyr Pro Ser Ile Leu Asn Gln Asp Asn Lys Thr Cys Ser Leu Pro
    450                 455                 460

Gly Thr Ala Leu Lys Val Ser Cys Phe Asn Val Arg Phe Cys Leu Lys
465                 470                 475                 480

Ala Asp Gly Lys Gly Val Leu Pro Arg Lys Leu Asn Phe Gln Val Glu
                485                 490                 495

Leu Leu Leu Asp Lys Leu Lys Gln Lys Gly Ala Ile Arg Arg Ala Leu
            500                 505                 510

Phe Leu Tyr Ser Arg Ser Pro Ser His Ser Lys Asn Met Thr Ile Ser
        515                 520                 525

Arg Gly Gly Leu Met Gln Cys Glu Glu Leu Ile Ala Tyr Leu Arg Asp
    530                 535                 540

Glu Ser Glu Phe Arg Asp Lys Leu Thr Pro Ile Thr Ile Phe Met Glu
545                 550                 555                 560

Tyr Arg Leu Asp Tyr Arg Thr Ala Ala Asp Thr Thr Gly Leu Gln Pro
                565                 570                 575

Ile Leu Asn Gln Phe Thr Pro Ala Asn Ile Ser Arg Gln Ala His Ile
            580                 585                 590

Leu Leu Asp Cys Gly Glu Asp Asn Val Cys Lys Pro Lys Leu Glu Val
        595                 600                 605

Ser Val Asp Ser Asp Gln Lys Lys Ile Tyr Ile Gly Asp Asp Asn Pro
    610                 615                 620

Leu Thr Leu Ile Val Lys Ala Gln Asn Gln Gly Glu Gly Ala Tyr Glu
625                 630                 635                 640

Ala Glu Leu Ile Val Ser Ile Pro Leu Gln Ala Asp Phe Ile Gly Val
                645                 650                 655

Val Arg Asn Asn Glu Ala Leu Ala Arg Leu Ser Cys Ala Phe Lys Thr
            660                 665                 670

Glu Asn Gln Thr Arg Gln Val Val Cys Asp Leu Gly Asn Pro Met Lys
        675                 680                 685

Ala Gly Thr Gln Leu Leu Ala Gly Leu Arg Phe Ser Val His Gln Gln
    690                 695                 700

Ser Glu Met Asp Thr Ser Val Lys Phe Asp Leu Gln Ile Gln Ser Ser
705                 710                 715                 720

Asn Leu Phe Asp Lys Val Ser Pro Val Val Ser His Lys Val Asp Leu
                725                 730                 735

Ala Val Leu Ala Ala Val Glu Ile Arg Gly Val Ser Ser Pro Asp His
            740                 745                 750

Val Phe Leu Pro Ile Pro Asn Trp Glu His Lys Glu Asn Pro Glu Thr
        755                 760                 765
```

```
Glu Glu Asp Val Gly Pro Val Val Gln His Ile Tyr Glu Leu Arg Asn
    770                 775                 780

Asn Gly Pro Ser Ser Phe Ser Lys Ala Met Leu His Leu Gln Trp Pro
785                 790                 795                 800

Tyr Lys Tyr Asn Asn Asn Thr Leu Leu Tyr Ile Leu His Tyr Asp Ile
                805                 810                 815

Asp Gly Pro Met Asn Cys Thr Ser Asp Met Glu Ile Asn Pro Leu Arg
            820                 825                 830

Ile Lys Ile Ser Ser Leu Gln Thr Thr Glu Lys Asn Asp Thr Val Ala
        835                 840                 845

Gly Gln Gly Glu Arg Asp His Leu Ile Thr Lys Arg Asp Leu Ala Leu
    850                 855                 860

Ser Glu Gly Asp Ile His Thr Leu Gly Cys Gly Val Ala Gln Cys Leu
865                 870                 875                 880

Lys Ile Val Cys Gln Val Gly Arg Leu Asp Arg Gly Lys Ser Ala Ile
                885                 890                 895

Leu Tyr Val Lys Ser Leu Leu Trp Thr Glu Thr Phe Met Asn Lys Glu
            900                 905                 910

Asn Gln Asn His Ser Tyr Ser Leu Lys Ser Ser Ala Ser Phe Asn Val
        915                 920                 925

Ile Glu Phe Pro Tyr Lys Asn Leu Pro Ile Glu Asp Ile Thr Asn Ser
    930                 935                 940

Thr Leu Val Thr Thr Asn Val Thr Trp Gly Ile Gln Pro Ala Pro Met
945                 950                 955                 960

Pro Val His Pro Gly Gly Gly Ser Gly Gly Gly Ser Gly Gly Ser Ala
                965                 970                 975

Gln Leu Glu Lys Glu Leu Gln Ala Leu Glu Lys Glu Asn Ala Gln Leu
            980                 985                 990

Glu Trp Glu Leu Gln Ala Leu Glu  Lys Glu Leu Ala Gln  Gly Ala Thr
        995                 1000                1005

His His  His His His His
    1010


<210> SEQ ID NO 71
<211> LENGTH: 742
<212> TYPE: PRT
<213> ORGANISM: Artificial Sequence
<220> FEATURE:
<223> OTHER INFORMATION: Integrin beta5 Extra-cellular domain-Basic
      Leucine zipper

<400> SEQUENCE: 71

Gly Leu Asn Ile Cys Thr Ser Gly Ser Ala Thr Ser Cys Glu Glu Cys
1               5                   10                  15

Leu Leu Ile His Pro Lys Cys Ala Trp Cys Ser Lys Glu Asp Phe Gly
            20                  25                  30

Ser Pro Arg Ser Ile Thr Ser Arg Cys Asp Leu Arg Ala Asn Leu Val
        35                  40                  45

Lys Asn Gly Cys Gly Gly Glu Ile Glu Ser Pro Ala Ser Ser Phe His
    50                  55                  60

Val Leu Arg Ser Leu Pro Leu Ser Ser Lys Gly Ser Gly Ser Ala Gly
65                  70                  75                  80

Trp Asp Val Ile Gln Met Thr Pro Gln Glu Ile Ala Val Asn Leu Arg
                85                  90                  95

Pro Gly Asp Lys Thr Thr Phe Gln Leu Gln Val Arg Gln Val Glu Asp
```

-continued

```
            100                 105                 110

Tyr Pro Val Asp Leu Tyr Tyr Leu Met Asp Leu Ser Leu Ser Met Lys
        115                 120                 125

Asp Asp Leu Asp Asn Ile Arg Ser Leu Gly Thr Lys Leu Ala Glu Glu
    130                 135                 140

Met Arg Lys Leu Thr Ser Asn Phe Arg Leu Gly Phe Gly Ser Phe Val
145                 150                 155                 160

Asp Lys Asp Ile Ser Pro Phe Ser Tyr Thr Ala Pro Arg Tyr Gln Thr
                165                 170                 175

Asn Pro Cys Ile Gly Tyr Lys Leu Phe Pro Asn Cys Val Pro Ser Phe
            180                 185                 190

Gly Phe Arg His Leu Leu Pro Leu Thr Asp Arg Val Asp Ser Phe Asn
        195                 200                 205

Glu Glu Val Arg Lys Gln Arg Val Ser Arg Asn Arg Asp Ala Pro Glu
    210                 215                 220

Gly Gly Phe Asp Ala Val Leu Gln Ala Ala Val Cys Lys Glu Lys Ile
225                 230                 235                 240

Gly Trp Arg Lys Asp Ala Leu His Leu Leu Val Phe Thr Thr Asp Asp
                245                 250                 255

Val Pro His Ile Ala Leu Asp Gly Lys Leu Gly Gly Leu Val Gln Pro
            260                 265                 270

His Asp Gly Gln Cys His Leu Asn Glu Ala Asn Glu Tyr Thr Ala Ser
        275                 280                 285

Asn Gln Met Asp Tyr Pro Ser Leu Ala Leu Leu Gly Glu Lys Leu Ala
    290                 295                 300

Glu Asn Asn Ile Asn Leu Ile Phe Ala Val Thr Lys Asn His Tyr Met
305                 310                 315                 320

Leu Tyr Lys Asn Phe Thr Ala Leu Ile Pro Gly Thr Thr Val Glu Ile
                325                 330                 335

Leu Asp Gly Asp Ser Lys Asn Ile Ile Gln Leu Ile Ile Asn Ala Tyr
            340                 345                 350

Asn Ser Ile Arg Ser Lys Val Glu Leu Ser Val Trp Asp Gln Pro Glu
        355                 360                 365

Asp Leu Asn Leu Phe Phe Thr Ala Thr Cys Gln Asp Gly Val Ser Tyr
    370                 375                 380

Pro Gly Gln Arg Lys Cys Glu Gly Leu Lys Ile Gly Asp Thr Ala Ser
385                 390                 395                 400

Phe Glu Val Ser Leu Glu Ala Arg Ser Cys Pro Ser Arg His Thr Glu
                405                 410                 415

His Val Phe Ala Leu Arg Pro Val Gly Phe Arg Asp Ser Leu Glu Val
            420                 425                 430

Gly Val Thr Tyr Asn Cys Thr Cys Gly Cys Ser Val Gly Leu Glu Pro
        435                 440                 445

Asn Ser Ala Arg Cys Asn Gly Ser Gly Thr Tyr Val Cys Gly Leu Cys
    450                 455                 460

Glu Cys Ser Pro Gly Tyr Leu Gly Thr Arg Cys Glu Cys Gln Asp Gly
465                 470                 475                 480

Glu Asn Gln Ser Val Tyr Gln Asn Leu Cys Arg Glu Ala Glu Gly Lys
                485                 490                 495

Pro Leu Cys Ser Gly Arg Gly Asp Cys Ser Cys Asn Gln Cys Ser Cys
            500                 505                 510

Phe Glu Ser Glu Phe Gly Lys Ile Tyr Gly Pro Phe Cys Glu Cys Asp
        515                 520                 525
```

Asn Phe Ser Cys Ala Arg Asn Lys Gly Val Leu Cys Ser Gly His Gly
    530                 535                 540

Glu Cys His Cys Gly Glu Cys Lys Cys His Ala Gly Tyr Ile Gly Asp
545                 550                 555                 560

Asn Cys Asn Cys Ser Thr Asp Ile Ser Thr Cys Arg Gly Arg Asp Gly
                565                 570                 575

Gln Ile Cys Ser Glu Arg Gly His Cys Leu Cys Gly Gln Cys Gln Cys
            580                 585                 590

Thr Glu Pro Gly Ala Phe Gly Glu Met Cys Glu Lys Cys Pro Thr Cys
        595                 600                 605

Pro Asp Ala Cys Ser Thr Lys Arg Asp Cys Val Glu Cys Leu Leu Leu
    610                 615                 620

His Ser Gly Lys Pro Asp Asn Gln Thr Cys His Ser Leu Cys Arg Asp
625                 630                 635                 640

Glu Val Ile Thr Trp Val Asp Thr Ile Val Lys Asp Asp Gln Glu Ala
                645                 650                 655

Val Leu Cys Phe Tyr Lys Thr Ala Lys Asp Cys Val Met Met Phe Thr
            660                 665                 670

Tyr Val Glu Leu Pro Ser Gly Lys Ser Asn Leu Thr Val Leu Arg Glu
        675                 680                 685

Pro Glu Cys Gly Asn Thr Pro Asn His Pro Gly Gly Gly Ser Gly Gly
    690                 695                 700

Gly Ser Gly Gly Ser Ala Gln Leu Lys Lys Lys Leu Gln Ala Leu Lys
705                 710                 715                 720

Lys Lys Asn Ala Gln Leu Lys Trp Lys Leu Gln Ala Leu Lys Lys Lys
                725                 730                 735

Leu Ala Gln Gly Ala Thr
            740

<210> SEQ ID NO 72
<211> LENGTH: 734
<212> TYPE: PRT
<213> ORGANISM: Artificial Sequence
<220> FEATURE:
<223> OTHER INFORMATION: Integrin beta6 Extra-cellular domain-Basic
      Leucine zipper

<400> SEQUENCE: 72

Gly Cys Ala Leu Gly Gly Ala Glu Thr Cys Glu Asp Cys Leu Leu Ile
1               5                   10                  15

Gly Pro Gln Cys Ala Trp Cys Ala Gln Glu Asn Phe Thr His Pro Ser
            20                  25                  30

Gly Val Gly Glu Arg Cys Asp Thr Pro Ala Asn Leu Leu Ala Lys Gly
        35                  40                  45

Cys Gln Leu Asn Phe Ile Glu Asn Pro Val Ser Gln Val Glu Ile Leu
    50                  55                  60

Lys Asn Lys Pro Leu Ser Val Gly Arg Gln Lys Asn Ser Ser Asp Ile
65                  70                  75                  80

Val Gln Ile Ala Pro Gln Ser Leu Ile Leu Lys Leu Arg Pro Gly Gly
                85                  90                  95

Ala Gln Thr Leu Gln Val His Val Arg Gln Thr Glu Asp Tyr Pro Val
            100                 105                 110

Asp Leu Tyr Tyr Leu Met Asp Leu Ser Ala Ser Met Asp Asp Asp Leu
        115                 120                 125

Asn Thr Ile Lys Glu Leu Gly Ser Arg Leu Ser Lys Glu Met Ser Lys

-continued

```
    130                 135                 140

Leu Thr Ser Asn Phe Arg Leu Gly Phe Gly Ser Phe Val Glu Lys Pro
145                 150                 155                 160

Val Ser Pro Phe Val Lys Thr Thr Pro Glu Glu Ile Ala Asn Pro Cys
                165                 170                 175

Ser Ser Ile Pro Tyr Phe Cys Leu Pro Thr Phe Gly Phe Lys His Ile
            180                 185                 190

Leu Pro Leu Thr Asn Asp Ala Glu Arg Phe Asn Glu Ile Val Lys Asn
        195                 200                 205

Gln Lys Ile Ser Ala Asn Ile Asp Thr Pro Glu Gly Gly Phe Asp Ala
    210                 215                 220

Ile Met Gln Ala Ala Val Cys Lys Glu Lys Ile Gly Trp Arg Asn Asp
225                 230                 235                 240

Ser Leu His Leu Leu Val Phe Val Ser Asp Ala Asp Ser His Phe Gly
                245                 250                 255

Met Asp Ser Lys Leu Ala Gly Ile Val Ile Pro Asn Asp Gly Leu Cys
            260                 265                 270

His Leu Asp Ser Lys Asn Glu Tyr Ser Met Ser Thr Val Leu Glu Tyr
        275                 280                 285

Pro Thr Ile Gly Gln Leu Ile Asp Lys Leu Val Gln Asn Asn Val Leu
    290                 295                 300

Leu Ile Phe Ala Val Thr Gln Glu Gln Val His Leu Tyr Glu Asn Tyr
305                 310                 315                 320

Ala Lys Leu Ile Pro Gly Ala Thr Val Gly Leu Leu Gln Lys Asp Ser
                325                 330                 335

Gly Asn Ile Leu Gln Leu Ile Ile Ser Ala Tyr Glu Glu Leu Arg Ser
            340                 345                 350

Glu Val Glu Leu Glu Val Leu Gly Asp Thr Glu Gly Leu Asn Leu Ser
        355                 360                 365

Phe Thr Ala Ile Cys Asn Asn Gly Thr Leu Phe Gln His Gln Lys Lys
    370                 375                 380

Cys Ser His Met Lys Val Gly Asp Thr Ala Ser Phe Ser Val Thr Val
385                 390                 395                 400

Asn Ile Pro His Cys Glu Arg Arg Ser Arg His Ile Ile Ile Lys Pro
                405                 410                 415

Val Gly Leu Gly Asp Ala Leu Glu Leu Leu Val Ser Pro Glu Cys Asn
            420                 425                 430

Cys Asp Cys Gln Lys Glu Val Glu Val Asn Ser Ser Lys Cys His His
        435                 440                 445

Gly Asn Gly Ser Phe Gln Cys Gly Val Cys Ala Cys His Pro Gly His
    450                 455                 460

Met Gly Pro Arg Cys Glu Cys Gly Glu Asp Met Leu Ser Thr Asp Ser
465                 470                 475                 480

Cys Lys Glu Ala Pro Asp His Pro Ser Cys Ser Gly Arg Gly Asp Cys
                485                 490                 495

Tyr Cys Gly Gln Cys Ile Cys His Leu Ser Pro Tyr Gly Asn Ile Tyr
            500                 505                 510

Gly Pro Tyr Cys Gln Cys Asp Asn Phe Ser Cys Val Arg His Lys Gly
        515                 520                 525

Leu Leu Cys Gly Gly Asn Gly Asp Cys Asp Cys Gly Glu Cys Val Cys
    530                 535                 540

Arg Ser Gly Trp Thr Gly Glu Tyr Cys Asn Cys Thr Thr Ser Thr Asp
545                 550                 555                 560
```

-continued

```
Ser Cys Val Ser Glu Asp Gly Val Leu Cys Ser Gly Arg Gly Asp Cys
                565                 570                 575

Val Cys Gly Lys Cys Val Cys Thr Asn Pro Gly Ala Ser Gly Pro Thr
            580                 585                 590

Cys Glu Arg Cys Pro Thr Cys Gly Asp Pro Cys Asn Ser Lys Arg Ser
        595                 600                 605

Cys Ile Glu Cys His Leu Ser Ala Ala Gly Gln Ala Arg Glu Glu Cys
    610                 615                 620

Val Asp Lys Cys Lys Leu Ala Gly Ala Thr Ile Ser Glu Glu Glu Asp
625                 630                 635                 640

Phe Ser Lys Asp Gly Ser Val Ser Cys Ser Leu Gln Gly Glu Asn Glu
                645                 650                 655

Cys Leu Ile Thr Phe Leu Ile Thr Thr Asp Asn Glu Gly Lys Thr Ile
            660                 665                 670

Ile His Ser Ile Asn Glu Lys Asp Cys Pro Lys Pro Pro Asn Ile Pro
        675                 680                 685

His Pro Gly Gly Gly Ser Gly Gly Gly Ser Gly Gly Ser Ala Gln Leu
    690                 695                 700

Lys Lys Lys Leu Gln Ala Leu Lys Lys Lys Asn Ala Gln Leu Lys Trp
705                 710                 715                 720

Lys Leu Gln Ala Leu Lys Lys Lys Leu Ala Gln Gly Ala Thr
                725                 730


<210> SEQ ID NO 73
<211> LENGTH: 19
<212> TYPE: PRT
<213> ORGANISM: Artificial Sequence
<220> FEATURE:
<223> OTHER INFORMATION: 5#1 of Integrin alphavbeta5

<400> SEQUENCE: 73

Leu Pro Ser Gly Ala Cys Val Val Arg Gly Asp Thr Phe Gln Cys Val
1               5                   10                  15

Ser Val Gly


<210> SEQ ID NO 74
<211> LENGTH: 17
<212> TYPE: PRT
<213> ORGANISM: Artificial Sequence
<220> FEATURE:
<223> OTHER INFORMATION: 5#2 of Integrin alphavbeta5

<400> SEQUENCE: 74

Ala Ser Tyr Asn Asp Cys Gln Ser Arg Gly Asp Thr Phe Cys Val Ala
1               5                   10                  15

Asp


<210> SEQ ID NO 75
<211> LENGTH: 16
<212> TYPE: PRT
<213> ORGANISM: Artificial Sequence
<220> FEATURE:
<223> OTHER INFORMATION: 5#3 of Integrin alphavbeta5

<400> SEQUENCE: 75

Ser Arg Asp Glu Thr Cys Thr Pro Arg Gly Asp Thr Phe Ala Ile Cys
1               5                   10                  15


<210> SEQ ID NO 76
```

```
<211> LENGTH: 20
<212> TYPE: PRT
<213> ORGANISM: Artificial Sequence
<220> FEATURE:
<223> OTHER INFORMATION: 5#4 of Integrin alphavbeta5

<400> SEQUENCE: 76

Glu His Ala Thr Asn Cys Thr Thr Arg Gly Asp Thr Phe Val Val Leu
1               5                   10                  15

Cys Gly Leu Gly
            20


<210> SEQ ID NO 77
<211> LENGTH: 16
<212> TYPE: PRT
<213> ORGANISM: Artificial Sequence
<220> FEATURE:
<223> OTHER INFORMATION: SFITGv6 of Integrin alphavbeta6

<400> SEQUENCE: 77

Gly Arg Cys Thr Phe Arg Gly Asp Leu Met Gln Leu Cys Tyr Pro Asp
1               5                   10                  15


<210> SEQ ID NO 78
<211> LENGTH: 20
<212> TYPE: PRT
<213> ORGANISM: Artificial Sequence
<220> FEATURE:
<223> OTHER INFORMATION: 6#1 of Integrin alphavbeta6

<400> SEQUENCE: 78

Asn Glu Asn Pro Asp Cys Pro Arg Arg Gly Asp Leu Phe His Ile Cys
1               5                   10                  15

Leu Lys Trp Pro
            20


<210> SEQ ID NO 79
<211> LENGTH: 19
<212> TYPE: PRT
<213> ORGANISM: Artificial Sequence
<220> FEATURE:
<223> OTHER INFORMATION: 6#2 of Integrin alphavbeta6

<400> SEQUENCE: 79

His Val Glu Phe Pro Cys Thr Arg Arg Gly Asp Leu Phe Val Leu Cys
1               5                   10                  15

Glu Gly Ser


<210> SEQ ID NO 80
<211> LENGTH: 18
<212> TYPE: PRT
<213> ORGANISM: Artificial Sequence
<220> FEATURE:
<223> OTHER INFORMATION: 6#3 of Integrin alphavbeta6

<400> SEQUENCE: 80

Thr Ala Ile Glu Pro Cys Lys Asn Arg Gly Asp Leu Phe Met Leu Cys
1               5                   10                  15

Ser Ala


<210> SEQ ID NO 81
<211> LENGTH: 20
<212> TYPE: PRT
<213> ORGANISM: Artificial Sequence
<220> FEATURE:
```

<223> OTHER INFORMATION: 6#4 of Integrin alphavbeta6

<400> SEQUENCE: 81

```
Glu Ser Phe Arg Pro Cys Gln Tyr Arg Gly Asp Leu Phe Val Leu Cys
1               5                   10                  15

Phe Pro Ser Asp
            20
```

<210> SEQ ID NO 82
<211> LENGTH: 20
<212> TYPE: PRT
<213> ORGANISM: Artificial Sequence
<220> FEATURE:
<223> OTHER INFORMATION: 6#5 of Integrin alphavbeta6

<400> SEQUENCE: 82

```
Thr Leu Ile Lys Ala Cys His Arg Arg Gly Asp Thr Phe Val Leu Cys
1               5                   10                  15

Glu His Tyr Ser
            20
```

<210> SEQ ID NO 83
<211> LENGTH: 18
<212> TYPE: PRT
<213> ORGANISM: Artificial Sequence
<220> FEATURE:
<223> OTHER INFORMATION: 6#6 of Integrin alphavbeta6

<400> SEQUENCE: 83

```
Leu Gly Pro Leu Pro Cys Gln Thr Arg Gly Asp Leu Phe Ser Leu Cys
1               5                   10                  15

His Tyr
```

<210> SEQ ID NO 84
<211> LENGTH: 20
<212> TYPE: PRT
<213> ORGANISM: Artificial Sequence
<220> FEATURE:
<223> OTHER INFORMATION: 6#7 of Integrin alphavbeta6

<400> SEQUENCE: 84

```
Asp Arg Asp Arg His Cys Asn Lys Arg Gly Asp Leu Phe Ser Leu Cys
1               5                   10                  15

Ala Leu Arg Ser
            20
```

<210> SEQ ID NO 85
<211> LENGTH: 18
<212> TYPE: PRT
<213> ORGANISM: Artificial Sequence
<220> FEATURE:
<223> OTHER INFORMATION: 6#8 of Integrin alphavbeta6

<400> SEQUENCE: 85

```
Phe Pro Asn Asn Gln Cys Gln His Arg Gly Asp Leu Phe Ala Leu Cys
1               5                   10                  15

Ala Asp
```

<210> SEQ ID NO 86
<211> LENGTH: 139
<212> TYPE: PRT
<213> ORGANISM: Artificial Sequence
<220> FEATURE:
<223> OTHER INFORMATION: hT4-i59 (5#1) MG VL

<400> SEQUENCE: 86

Leu Pro Ser Gly Ala Cys Val Val Arg Gly Asp Thr Phe Gln Cys Val
1 5 10 15

Ser Val Gly Met Gly Ser Ser Ser Asn Asp Ile Gln Met Thr Gln Ser
20 25 30

Pro Ser Ser Leu Ser Ala Ser Val Gly Asp Arg Val Thr Ile Thr Cys
35 40 45

Lys Ser Ser Gln Ser Leu Leu Asn Ser Arg Asp Gly Lys Asn Tyr Leu
50 55 60

Ala Trp Tyr Gln Gln Lys Pro Gly Lys Ala Pro Lys Leu Leu Ile Tyr
65 70 75 80

Trp Ala Ser Thr Arg Glu Ser Gly Val Pro Ser Arg Phe Ser Gly Ser
85 90 95

Gly Ser Gly Thr Asp Phe Thr Leu Thr Ile Ser Ser Leu Gln Pro Glu
100 105 110

Asp Phe Ala Thr Tyr Phe Cys Gln Gln Tyr Trp Tyr Trp Met Tyr Thr
115 120 125

Phe Gly Gln Gly Thr Lys Val Glu Ile Lys Arg
130 135

<210> SEQ ID NO 87
<211> LENGTH: 137
<212> TYPE: PRT
<213> ORGANISM: Artificial Sequence
<220> FEATURE:
<223> OTHER INFORMATION: hT4-i59 (5#2) MG VL

<400> SEQUENCE: 87

Ala Ser Tyr Asn Asp Cys Gln Ser Arg Gly Asp Thr Phe Cys Val Ala
1 5 10 15

Asp Met Gly Ser Ser Ser Asn Asp Ile Gln Met Thr Gln Ser Pro Ser
20 25 30

Ser Leu Ser Ala Ser Val Gly Asp Arg Val Thr Ile Thr Cys Lys Ser
35 40 45

Ser Gln Ser Leu Leu Asn Ser Arg Asp Gly Lys Asn Tyr Leu Ala Trp
50 55 60

Tyr Gln Gln Lys Pro Gly Lys Ala Pro Lys Leu Leu Ile Tyr Trp Ala
65 70 75 80

Ser Thr Arg Glu Ser Gly Val Pro Ser Arg Phe Ser Gly Ser Gly Ser
85 90 95

Gly Thr Asp Phe Thr Leu Thr Ile Ser Ser Leu Gln Pro Glu Asp Phe
100 105 110

Ala Thr Tyr Phe Cys Gln Gln Tyr Trp Tyr Trp Met Tyr Thr Phe Gly
115 120 125

Gln Gly Thr Lys Val Glu Ile Lys Arg
130 135

<210> SEQ ID NO 88
<211> LENGTH: 136
<212> TYPE: PRT
<213> ORGANISM: Artificial Sequence
<220> FEATURE:
<223> OTHER INFORMATION: hT4-i59 (5#3) MG VL

<400> SEQUENCE: 88

Ser Arg Asp Glu Thr Cys Thr Pro Arg Gly Asp Thr Phe Ala Ile Cys
1 5 10 15

```
Met Gly Ser Ser Ser Asn Asp Ile Gln Met Thr Gln Ser Pro Ser Ser
            20                  25                  30

Leu Ser Ala Ser Val Gly Asp Arg Val Thr Ile Thr Cys Lys Ser Ser
        35                  40                  45

Gln Ser Leu Leu Asn Ser Arg Asp Gly Lys Asn Tyr Leu Ala Trp Tyr
    50                  55                  60

Gln Gln Lys Pro Gly Lys Ala Pro Lys Leu Leu Ile Tyr Trp Ala Ser
65                  70                  75                  80

Thr Arg Glu Ser Gly Val Pro Ser Arg Phe Ser Gly Ser Gly Ser Gly
                85                  90                  95

Thr Asp Phe Thr Leu Thr Ile Ser Ser Leu Gln Pro Glu Asp Phe Ala
            100                 105                 110

Thr Tyr Phe Cys Gln Gln Tyr Trp Tyr Trp Met Tyr Thr Phe Gly Gln
        115                 120                 125

Gly Thr Lys Val Glu Ile Lys Arg
    130                 135


<210> SEQ ID NO 89
<211> LENGTH: 140
<212> TYPE: PRT
<213> ORGANISM: Artificial Sequence
<220> FEATURE:
<223> OTHER INFORMATION: hT4-i59 (5#4) MG VL

<400> SEQUENCE: 89

Glu His Ala Thr Asn Cys Thr Thr Arg Gly Asp Thr Phe Val Val Leu
1               5                   10                  15

Cys Gly Leu Gly Met Gly Ser Ser Ser Asn Asp Ile Gln Met Thr Gln
            20                  25                  30

Ser Pro Ser Ser Leu Ser Ala Ser Val Gly Asp Arg Val Thr Ile Thr
        35                  40                  45

Cys Lys Ser Ser Gln Ser Leu Leu Asn Ser Arg Asp Gly Lys Asn Tyr
    50                  55                  60

Leu Ala Trp Tyr Gln Gln Lys Pro Gly Lys Ala Pro Lys Leu Leu Ile
65                  70                  75                  80

Tyr Trp Ala Ser Thr Arg Glu Ser Gly Val Pro Ser Arg Phe Ser Gly
                85                  90                  95

Ser Gly Ser Gly Thr Asp Phe Thr Leu Thr Ile Ser Ser Leu Gln Pro
            100                 105                 110

Glu Asp Phe Ala Thr Tyr Phe Cys Gln Gln Tyr Trp Tyr Trp Met Tyr
        115                 120                 125

Thr Phe Gly Gln Gly Thr Lys Val Glu Ile Lys Arg
    130                 135                 140


<210> SEQ ID NO 90
<211> LENGTH: 136
<212> TYPE: PRT
<213> ORGANISM: Artificial Sequence
<220> FEATURE:
<223> OTHER INFORMATION: hT4-i59 (SFITGv6) MG VL

<400> SEQUENCE: 90

Gly Arg Cys Thr Phe Arg Gly Asp Leu Met Gln Leu Cys Tyr Pro Asp
1               5                   10                  15

Met Gly Ser Ser Ser Asn Asp Ile Gln Met Thr Gln Ser Pro Ser Ser
            20                  25                  30

Leu Ser Ala Ser Val Gly Asp Arg Val Thr Ile Thr Cys Lys Ser Ser
```

```
        35                  40                  45

Gln Ser Leu Leu Asn Ser Arg Asp Gly Lys Asn Tyr Leu Ala Trp Tyr
    50                  55                  60

Gln Gln Lys Pro Gly Lys Ala Pro Lys Leu Leu Ile Tyr Trp Ala Ser
65                  70                  75                  80

Thr Arg Glu Ser Gly Val Pro Ser Arg Phe Ser Gly Ser Gly Ser Gly
                85                  90                  95

Thr Asp Phe Thr Leu Thr Ile Ser Ser Leu Gln Pro Glu Asp Phe Ala
            100                 105                 110

Thr Tyr Phe Cys Gln Gln Tyr Trp Tyr Trp Met Tyr Thr Phe Gly Gln
        115                 120                 125

Gly Thr Lys Val Glu Ile Lys Arg
    130                 135


<210> SEQ ID NO 91
<211> LENGTH: 140
<212> TYPE: PRT
<213> ORGANISM: Artificial Sequence
<220> FEATURE:
<223> OTHER INFORMATION: hT4-i59 (6#1) MG VL

<400> SEQUENCE: 91

Asn Glu Asn Pro Asp Cys Pro Arg Arg Gly Asp Leu Phe His Ile Cys
1               5                   10                  15

Leu Lys Trp Pro Met Gly Ser Ser Ser Asn Asp Ile Gln Met Thr Gln
            20                  25                  30

Ser Pro Ser Ser Leu Ser Ala Ser Val Gly Asp Arg Val Thr Ile Thr
        35                  40                  45

Cys Lys Ser Ser Gln Ser Leu Leu Asn Ser Arg Asp Gly Lys Asn Tyr
    50                  55                  60

Leu Ala Trp Tyr Gln Gln Lys Pro Gly Lys Ala Pro Lys Leu Leu Ile
65                  70                  75                  80

Tyr Trp Ala Ser Thr Arg Glu Ser Gly Val Pro Ser Arg Phe Ser Gly
                85                  90                  95

Ser Gly Ser Gly Thr Asp Phe Thr Leu Thr Ile Ser Ser Leu Gln Pro
            100                 105                 110

Glu Asp Phe Ala Thr Tyr Phe Cys Gln Gln Tyr Trp Tyr Trp Met Tyr
        115                 120                 125

Thr Phe Gly Gln Gly Thr Lys Val Glu Ile Lys Arg
    130                 135                 140


<210> SEQ ID NO 92
<211> LENGTH: 139
<212> TYPE: PRT
<213> ORGANISM: Artificial Sequence
<220> FEATURE:
<223> OTHER INFORMATION: hT4-i59 (6#2) MG VL

<400> SEQUENCE: 92

His Val Glu Phe Pro Cys Thr Arg Arg Gly Asp Leu Phe Val Leu Cys
1               5                   10                  15

Glu Gly Ser Met Gly Ser Ser Ser Asn Asp Ile Gln Met Thr Gln Ser
            20                  25                  30

Pro Ser Ser Leu Ser Ala Ser Val Gly Asp Arg Val Thr Ile Thr Cys
        35                  40                  45

Lys Ser Ser Gln Ser Leu Leu Asn Ser Arg Asp Gly Lys Asn Tyr Leu
    50                  55                  60
```

Ala Trp Tyr Gln Gln Lys Pro Gly Lys Ala Pro Lys Leu Leu Ile Tyr
65 70 75 80

Trp Ala Ser Thr Arg Glu Ser Gly Val Pro Ser Arg Phe Ser Gly Ser
85 90 95

Gly Ser Gly Thr Asp Phe Thr Leu Thr Ile Ser Ser Leu Gln Pro Glu
100 105 110

Asp Phe Ala Thr Tyr Phe Cys Gln Gln Tyr Trp Tyr Trp Met Tyr Thr
115 120 125

Phe Gly Gln Gly Thr Lys Val Glu Ile Lys Arg
130 135

<210> SEQ ID NO 93
<211> LENGTH: 138
<212> TYPE: PRT
<213> ORGANISM: Artificial Sequence
<220> FEATURE:
<223> OTHER INFORMATION: hT4-i59 (6#3) MG VL

<400> SEQUENCE: 93

Thr Ala Ile Glu Pro Cys Lys Asn Arg Gly Asp Leu Phe Met Leu Cys
1 5 10 15

Ser Ala Met Gly Ser Ser Ser Asn Asp Ile Gln Met Thr Gln Ser Pro
20 25 30

Ser Ser Leu Ser Ala Ser Val Gly Asp Arg Val Thr Ile Thr Cys Lys
35 40 45

Ser Ser Gln Ser Leu Leu Asn Ser Arg Asp Gly Lys Asn Tyr Leu Ala
50 55 60

Trp Tyr Gln Gln Lys Pro Gly Lys Ala Pro Lys Leu Leu Ile Tyr Trp
65 70 75 80

Ala Ser Thr Arg Glu Ser Gly Val Pro Ser Arg Phe Ser Gly Ser Gly
85 90 95

Ser Gly Thr Asp Phe Thr Leu Thr Ile Ser Ser Leu Gln Pro Glu Asp
100 105 110

Phe Ala Thr Tyr Phe Cys Gln Gln Tyr Trp Tyr Trp Met Tyr Thr Phe
115 120 125

Gly Gln Gly Thr Lys Val Glu Ile Lys Arg
130 135

<210> SEQ ID NO 94
<211> LENGTH: 140
<212> TYPE: PRT
<213> ORGANISM: Artificial Sequence
<220> FEATURE:
<223> OTHER INFORMATION: hT4-i59 (6#4) MG VL

<400> SEQUENCE: 94

Glu Ser Phe Arg Pro Cys Gln Tyr Arg Gly Asp Leu Phe Val Leu Cys
1 5 10 15

Phe Pro Ser Asp Met Gly Ser Ser Ser Asn Asp Ile Gln Met Thr Gln
20 25 30

Ser Pro Ser Ser Leu Ser Ala Ser Val Gly Asp Arg Val Thr Ile Thr
35 40 45

Cys Lys Ser Ser Gln Ser Leu Leu Asn Ser Arg Asp Gly Lys Asn Tyr
50 55 60

Leu Ala Trp Tyr Gln Gln Lys Pro Gly Lys Ala Pro Lys Leu Leu Ile
65 70 75 80

Tyr Trp Ala Ser Thr Arg Glu Ser Gly Val Pro Ser Arg Phe Ser Gly
85 90 95

```
Ser Gly Ser Gly Thr Asp Phe Thr Leu Thr Ile Ser Ser Leu Gln Pro
            100                 105                 110

Glu Asp Phe Ala Thr Tyr Phe Cys Gln Gln Tyr Trp Tyr Trp Met Tyr
        115                 120                 125

Thr Phe Gly Gln Gly Thr Lys Val Glu Ile Lys Arg
    130                 135                 140


<210> SEQ ID NO 95
<211> LENGTH: 140
<212> TYPE: PRT
<213> ORGANISM: Artificial Sequence
<220> FEATURE:
<223> OTHER INFORMATION: hT4-i59 (6#5) MG VL

<400> SEQUENCE: 95

Thr Leu Ile Lys Ala Cys His Arg Arg Gly Asp Thr Phe Val Leu Cys
1               5                   10                  15

Glu His Tyr Ser Met Gly Ser Ser Ser Asn Asp Ile Gln Met Thr Gln
            20                  25                  30

Ser Pro Ser Ser Leu Ser Ala Ser Val Gly Asp Arg Val Thr Ile Thr
        35                  40                  45

Cys Lys Ser Ser Gln Ser Leu Leu Asn Ser Arg Asp Gly Lys Asn Tyr
    50                  55                  60

Leu Ala Trp Tyr Gln Gln Lys Pro Gly Lys Ala Pro Lys Leu Leu Ile
65                  70                  75                  80

Tyr Trp Ala Ser Thr Arg Glu Ser Gly Val Pro Ser Arg Phe Ser Gly
                85                  90                  95

Ser Gly Ser Gly Thr Asp Phe Thr Leu Thr Ile Ser Ser Leu Gln Pro
            100                 105                 110

Glu Asp Phe Ala Thr Tyr Phe Cys Gln Gln Tyr Trp Tyr Trp Met Tyr
        115                 120                 125

Thr Phe Gly Gln Gly Thr Lys Val Glu Ile Lys Arg
    130                 135                 140


<210> SEQ ID NO 96
<211> LENGTH: 138
<212> TYPE: PRT
<213> ORGANISM: Artificial Sequence
<220> FEATURE:
<223> OTHER INFORMATION: hT4-i59 (6#6) MG VL

<400> SEQUENCE: 96

Leu Gly Pro Leu Pro Cys Gln Thr Arg Gly Asp Leu Phe Ser Leu Cys
1               5                   10                  15

His Tyr Met Gly Ser Ser Ser Asn Asp Ile Gln Met Thr Gln Ser Pro
            20                  25                  30

Ser Ser Leu Ser Ala Ser Val Gly Asp Arg Val Thr Ile Thr Cys Lys
        35                  40                  45

Ser Ser Gln Ser Leu Leu Asn Ser Arg Asp Gly Lys Asn Tyr Leu Ala
    50                  55                  60

Trp Tyr Gln Gln Lys Pro Gly Lys Ala Pro Lys Leu Leu Ile Tyr Trp
65                  70                  75                  80

Ala Ser Thr Arg Glu Ser Gly Val Pro Ser Arg Phe Ser Gly Ser Gly
                85                  90                  95

Ser Gly Thr Asp Phe Thr Leu Thr Ile Ser Ser Leu Gln Pro Glu Asp
            100                 105                 110

Phe Ala Thr Tyr Phe Cys Gln Gln Tyr Trp Tyr Trp Met Tyr Thr Phe
```

```
        115                 120                 125

Gly Gln Gly Thr Lys Val Glu Ile Lys Arg
    130                 135


<210> SEQ ID NO 97
<211> LENGTH: 140
<212> TYPE: PRT
<213> ORGANISM: Artificial Sequence
<220> FEATURE:
<223> OTHER INFORMATION: hT4-i59 (6#7) MG VL

<400> SEQUENCE: 97

Asp Arg Asp Arg His Cys Asn Lys Arg Gly Asp Leu Phe Ser Leu Cys
1               5                   10                  15

Ala Leu Arg Ser Met Gly Ser Ser Ser Asn Asp Ile Gln Met Thr Gln
            20                  25                  30

Ser Pro Ser Ser Leu Ser Ala Ser Val Gly Asp Arg Val Thr Ile Thr
        35                  40                  45

Cys Lys Ser Ser Gln Ser Leu Leu Asn Ser Arg Asp Gly Lys Asn Tyr
    50                  55                  60

Leu Ala Trp Tyr Gln Gln Lys Pro Gly Lys Ala Pro Lys Leu Leu Ile
65                  70                  75                  80

Tyr Trp Ala Ser Thr Arg Glu Ser Gly Val Pro Ser Arg Phe Ser Gly
                85                  90                  95

Ser Gly Ser Gly Thr Asp Phe Thr Leu Thr Ile Ser Ser Leu Gln Pro
            100                 105                 110

Glu Asp Phe Ala Thr Tyr Phe Cys Gln Gln Tyr Trp Tyr Trp Met Tyr
        115                 120                 125

Thr Phe Gly Gln Gly Thr Lys Val Glu Ile Lys Arg
    130                 135                 140


<210> SEQ ID NO 98
<211> LENGTH: 138
<212> TYPE: PRT
<213> ORGANISM: Artificial Sequence
<220> FEATURE:
<223> OTHER INFORMATION: hT4-i59 (6#8) MG VL

<400> SEQUENCE: 98

Phe Pro Asn Asn Gln Cys Gln His Arg Gly Asp Leu Phe Ala Leu Cys
1               5                   10                  15

Ala Asp Met Gly Ser Ser Ser Asn Asp Ile Gln Met Thr Gln Ser Pro
            20                  25                  30

Ser Ser Leu Ser Ala Ser Val Gly Asp Arg Val Thr Ile Thr Cys Lys
        35                  40                  45

Ser Ser Gln Ser Leu Leu Asn Ser Arg Asp Gly Lys Asn Tyr Leu Ala
    50                  55                  60

Trp Tyr Gln Gln Lys Pro Gly Lys Ala Pro Lys Leu Leu Ile Tyr Trp
65                  70                  75                  80

Ala Ser Thr Arg Glu Ser Gly Val Pro Ser Arg Phe Ser Gly Ser Gly
                85                  90                  95

Ser Gly Thr Asp Phe Thr Leu Thr Ile Ser Ser Leu Gln Pro Glu Asp
            100                 105                 110

Phe Ala Thr Tyr Phe Cys Gln Gln Tyr Trp Tyr Trp Met Tyr Thr Phe
        115                 120                 125

Gly Gln Gly Thr Lys Val Glu Ile Lys Arg
    130                 135
```

```
<210> SEQ ID NO 99
<211> LENGTH: 12
<212> TYPE: PRT
<213> ORGANISM: Artificial Sequence
<220> FEATURE:
<223> OTHER INFORMATION: cyclic peptide
<220> FEATURE:
<221> NAME/KEY: MISC_FEATURE
<222> LOCATION: (1)..(1)
<223> OTHER INFORMATION: Xaa is any one of E, H, D and K
<220> FEATURE:
<221> NAME/KEY: MISC_FEATURE
<222> LOCATION: (2)..(2)
<223> OTHER INFORMATION: Xaa is any one of H and N
<220> FEATURE:
<221> NAME/KEY: MISC_FEATURE
<222> LOCATION: (4)..(4)
<223> OTHER INFORMATION: Xaa is any one of H, L, Q and R
<220> FEATURE:
<221> NAME/KEY: MISC_FEATURE
<222> LOCATION: (6)..(6)
<223> OTHER INFORMATION: Xaa is any one of L and I
<220> FEATURE:
<221> NAME/KEY: MISC_FEATURE
<222> LOCATION: (8)..(8)
<223> OTHER INFORMATION: Xaa is any one of S and N
<220> FEATURE:
<221> NAME/KEY: MISC_FEATURE
<222> LOCATION: (9)..(9)
<223> OTHER INFORMATION: Xaa is any one of L and I

<400> SEQUENCE: 99

Xaa Xaa Leu Xaa Cys Xaa Gly Xaa Xaa Cys Trp Ser
1               5                   10


<210> SEQ ID NO 100
<211> LENGTH: 15
<212> TYPE: PRT
<213> ORGANISM: Artificial Sequence
<220> FEATURE:
<223> OTHER INFORMATION: cyclic peptide
<220> FEATURE:
<221> NAME/KEY: MISC_FEATURE
<222> LOCATION: (3)..(3)
<223> OTHER INFORMATION: Xaa is any one of E, V, G, Q and D
<220> FEATURE:
<221> NAME/KEY: MISC_FEATURE
<222> LOCATION: (4)..(4)
<223> OTHER INFORMATION: Xaa is any one of R and K
<220> FEATURE:
<221> NAME/KEY: MISC_FEATURE
<222> LOCATION: (5)..(5)
<223> OTHER INFORMATION: Xaa is any one of N, S, A, Q, L and T
<220> FEATURE:
<221> NAME/KEY: MISC_FEATURE
<222> LOCATION: (11)..(11)
<223> OTHER INFORMATION: Xaa is any one of I and F
<220> FEATURE:
<221> NAME/KEY: MISC_FEATURE
<222> LOCATION: (12)..(12)
<223> OTHER INFORMATION: Xaa is any one of D and E
<220> FEATURE:
<221> NAME/KEY: MISC_FEATURE
<222> LOCATION: (13)..(13)
<223> OTHER INFORMATION: Xaa is any one of G, D, P, V and A
<220> FEATURE:
<221> NAME/KEY: MISC_FEATURE
<222> LOCATION: (14)..(14)
<223> OTHER INFORMATION: Xaa is any one of Q, S, P and A
<220> FEATURE:
<221> NAME/KEY: MISC_FEATURE
<222> LOCATION: (15)..(15)
<223> OTHER INFORMATION: Xaa is any one of P, Q, D, L, V and S

<400> SEQUENCE: 100
```

Asp Gly Xaa Xaa Xaa Cys Arg Gly Asp Cys Xaa Xaa Xaa Xaa Xaa
1 5 10 15

<210> SEQ ID NO 101
<211> LENGTH: 10
<212> TYPE: PRT
<213> ORGANISM: Artificial Sequence
<220> FEATURE:
<223> OTHER INFORMATION: linker

<400> SEQUENCE: 101

Gly Gly Gly Gly Ser Gly Gly Gly Gly Ser
1 5 10

<210> SEQ ID NO 102
<211> LENGTH: 6
<212> TYPE: PRT
<213> ORGANISM: Artificial Sequence
<220> FEATURE:
<223> OTHER INFORMATION: linker

<400> SEQUENCE: 102

Met Gly Ser Ser Ser Asn
1 5

<210> SEQ ID NO 103
<211> LENGTH: 5
<212> TYPE: PRT
<213> ORGANISM: Artificial Sequence
<220> FEATURE:
<223> OTHER INFORMATION: linker

<400> SEQUENCE: 103

Gly Gly Gly Gly Ser
1 5

<210> SEQ ID NO 104
<211> LENGTH: 10
<212> TYPE: PRT
<213> ORGANISM: Artificial Sequence
<220> FEATURE:
<223> OTHER INFORMATION: linker

<400> SEQUENCE: 104

His Pro Gly Gly Gly Ser Gly Gly Gly Ser
1 5 10

<210> SEQ ID NO 105
<211> LENGTH: 15
<212> TYPE: PRT
<213> ORGANISM: Artificial Sequence
<220> FEATURE:
<223> OTHER INFORMATION: RGD Library
<220> FEATURE:
<221> NAME/KEY: misc_feature
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is any one of K and R
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: misc_feature
<222> LOCATION: (11)..(11)
<223> OTHER INFORMATION: Xaa is any amino acid
<220> FEATURE:

<221> NAME/KEY: MISC_FEATURE
<222> LOCATION: (12)..(12)
<223> OTHER INFORMATION: Xaa is any one of D and E
<220> FEATURE:
<221> NAME/KEY: misc_feature
<222> LOCATION: (13)..(15)
<223> OTHER INFORMATION: Xaa is any amino acid

<400> SEQUENCE: 105

Asp Gly Xaa Xaa Xaa Cys Arg Gly Asp Cys Xaa Xaa Xaa Xaa Xaa
1               5                   10                  15

<210> SEQ ID NO 106
<211> LENGTH: 19
<212> TYPE: PRT
<213> ORGANISM: Artificial Sequence
<220> FEATURE:
<223> OTHER INFORMATION: 5#1 Library
<220> FEATURE:
<221> NAME/KEY: MISC_FEATURE
<222> LOCATION: (1)..(1)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (7)..(8)
<223> OTHER INFORMATION: Xaa is any amino acid
<220> FEATURE:
<221> NAME/KEY: misc_feature
<222> LOCATION: (14)..(15)
<223> OTHER INFORMATION: Xaa is any amino acid
<220> FEATURE:
<221> NAME/KEY: misc_feature
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (19)..(19)
<223> OTHER INFORMATION: Xaa is any amino acid

<400> SEQUENCE: 106

Xaa Xaa Xaa Xaa Xaa Cys Xaa Xaa Arg Gly Asp Ser Phe Xaa Xaa Cys
1               5                   10                  15

Xaa Xaa Xaa

<210> SEQ ID NO 107
<211> LENGTH: 19
<212> TYPE: PRT
<213> ORGANISM: Artificial Sequence
<220> FEATURE:
<223> OTHER INFORMATION: 5#2 Library
<220> FEATURE:
<221> NAME/KEY: MISC_FEATURE
<222> LOCATION: (1)..(1)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (7)..(8)
<223> OTHER INFORMATION: Xaa is any amino acid
<220> FEATURE:
<221> NAME/KEY: misc_feature
<222> LOCATION: (14)..(15)
<223> OTHER INFORMATION: Xaa is any amino acid
<220> FEATURE:
<221> NAME/KEY: misc_feature
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (19)..(19)
<223> OTHER INFORMATION: Xaa is any amino acid

<400> SEQUENCE: 107

```
Xaa Xaa Xaa Xaa Xaa Cys Xaa Xaa Arg Gly Asp Thr Phe Xaa Xaa Cys
1               5                   10                  15

Xaa Xaa Xaa
```

<210> SEQ ID NO 108
<211> LENGTH: 19
<212> TYPE: PRT
<213> ORGANISM: Artificial Sequence
<220> FEATURE:
<223> OTHER INFORMATION: 6# Library
<220> FEATURE:
<221> NAME/KEY: MISC_FEATURE
<222> LOCATION: (1)..(1)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is any one of F, I, L, M, V, S, P, T, A, Y, H, Q, N, K, D and E
<220> FEATURE:
<221> NAME/KEY: misc_feature
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any one of F, I, L, M, V, S, P, T, A, Y,
      H, Q, N, K, D and E
<220> FEATURE:
<221> NAME/KEY: misc_feature
<222> LOCATION: (7)..(8)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is any amino acid
<220> FEATURE:
<221> NAME/KEY: MISC_FEATURE
<222> LOCATION: (15)..(15)
<223> OTHER INFORMATION: Xaa is any one of I and L
<220> FEATURE:
<221> NAME/KEY: misc_feature
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any one of F, I, L, M, V, S, P, T, A, Y,
      H, Q, N, K, D and E
<220> FEATURE:
<221> NAME/KEY: misc_feature
<222> LOCATION: (19)..(19)
<223> OTHER INFORMATION: Xaa is any amino acid

<400> SEQUENCE: 108

Xaa Xaa Xaa Xaa Xaa Cys Xaa Xaa Arg Gly Asp Leu Phe Xaa Xaa Cys
1               5                   10                  15

Xaa Xaa Xaa

<210> SEQ ID NO 109
<211> LENGTH: 4
<212> TYPE: PRT
<213> ORGANISM: Artificial Sequence
<220> FEATURE:
<223> OTHER INFORMATION: linker

<400> SEQUENCE: 109

Gly Gly Gly Ser
1

<210> SEQ ID NO 110
<211> LENGTH: 12
<212> TYPE: PRT
<213> ORGANISM: Artificial Sequence
<220> FEATURE:
<223> OTHER INFORMATION: cyclic peptide
<220> FEATURE:
<221> NAME/KEY: MISC_FEATURE
<222> LOCATION: (1)..(1)
<223> OTHER INFORMATION: Xaa is any one of E, H, D, K, N and R
<220> FEATURE:
<221> NAME/KEY: MISC_FEATURE
<222> LOCATION: (2)..(2)
<223> OTHER INFORMATION: Xaa is any one of H, N and G
<220> FEATURE:
<221> NAME/KEY: MISC_FEATURE
<222> LOCATION: (4)..(4)
<223> OTHER INFORMATION: Xaa is any one of H, L, Q, R and W
<220> FEATURE:
<221> NAME/KEY: MISC_FEATURE
<222> LOCATION: (6)..(6)
<223> OTHER INFORMATION: Xaa is any one of L and I
<220> FEATURE:
<221> NAME/KEY: MISC_FEATURE
<222> LOCATION: (8)..(8)
<223> OTHER INFORMATION: Xaa is any one of S, N and R
<220> FEATURE:
<221> NAME/KEY: MISC_FEATURE
<222> LOCATION: (9)..(9)

-continued

```
<223> OTHER INFORMATION: Xaa is any one of L and I
<220> FEATURE:
<221> NAME/KEY: MISC_FEATURE
<222> LOCATION: (12)..(12)
<223> OTHER INFORMATION: Xaa is any one of S and P

<400> SEQUENCE: 110

Xaa Xaa Leu Xaa Cys Xaa Gly Xaa Xaa Cys Trp Xaa
1               5                   10
```

CELL/TISSUE-SPECIFIC CELL-PENETRATING ANTIBODIES

CROSS-REFERENCE TO RELATED APPLICATIONS

This application claims the benefit of U.S. Provisional Patent Application 62/688,339, filed Jun. 21, 2018, the disclosure of which is incorporated by reference herein in its entirety.

SEQUENCE LISTING

This application incorporates by reference a Sequence Listing submitted with this application as an ASCII text file, entitled 14532-001-999_SEQ_LISTING.txt, created on Jun. 19, 2019, and is 107,458 bytes in size.

1. INTRODUCTION

Presented herein are cyclic peptides that specifically bind to a cell surface molecule, thereby allowing cell/tissue-specific targeting. The cyclic peptides can be attached to an agent, for example, a polypeptide such as an antibody, e.g., a cell-penetrating antibody. Cyclic peptide-containing cell/tissue-specific cell-penetrating antibodies described herein are capable of targeted delivery in a cell type-specific or tissue-specific (i.e., cell/tissue-specific) manner.

2. BACKGROUND

The two main classes of therapeutics for targeting protein-protein interactions are small molecules and protein therapeutics. Many critical biological process involve protein-ligand binding, and characterization of protein binding sites for small molecules is crucial to the development of small molecule therapeutics. The analysis of crystallographic structures has indicated that most small molecules require hydrophobic protein pockets. These hydrophobic pockets usually consist of deep concave pockets that can maximize favorable protein-ligand interactions. However, since only about 10% of all intracellular disease-related proteins have hydrophobic pockets, only 10% of proteins are amenable for small-molecule modulation. Thus, 90% of intracellular proteins that are involved in pathogenesis and malignancy are considered "undruggable" targets for small molecules, including tumors and immune-related diseases (Imai & Takaoka, 2006). On the other hand, protein therapeutics have poor cellular penetration and are often subject to proteolytic degradation.

In order to increase the structural stability, metabolic stability, and cellular permeability of peptides, "stapled" cyclic peptides have been developed. By linking two non-adjacent monomers with a hydrocarbon chain, cyclic peptides are locked in an alpha-helical conformation. The broad potential of maintaining the alpha helix in stapled peptides is derived from the fact that it is the most common protein structure at the interface of protein-protein interactions. These advantages have led to the development of cyclic peptides as potential therapeutics for targeting protein. However, there are limitations to this method; high doses of the peptides are required to produce their therapeutic effects, and they elicit nonspecific effects on wild-type cell lines as well as target cell lines (Leshchiner, et al., 2015) (Patgiri, Yadav, & Bar-Sagi, 2011).

Cyclic peptides show better biological activity compared to their linear counterparts due to their conformational rigidity (Edman, 1959) (Horton, Bourne, & Smythe, 2002). The rigidity of cyclic peptides decreases their conformational entropy, therefore allowing them to selectively bind to proteins. Another benefit of the cyclic structure is the resistance to hydrolysis by exopeptidases due to the lack of both amino and carboxyl termini. Cyclic peptides can be resistant even to endopeptidases, as the structure is less flexible than linear peptides. Some cyclic peptides, though not all, can cross the cell membrane. Cyclosporin A is a good example of a membrane permeable cyclic peptide. It has been suggested that cyclic peptides cross the membrane better than their linear counterparts (Rezai, Yu, Millhauser, Jacobson, & Lokey, 2006).

Indeed, many cyclic peptides occur in nature, including peptide hormones such as calcitonin, oxytocin, somatostatin, and vasopressin. Several cyclic peptides found in nature are currently used in the clinic. These include gramicidin and tyrocidine, which have bactericidal activity, and cyclosporin A, which has immunosuppressive activity.

Encouraged by natural cyclic peptides with biological activity, efforts have been made to rationally design cyclic peptides using both genetic and synthetic methods in order to selectively recognize and target specific proteins. Cyclic peptides are potent regulators of biological processes and are rapidly emerging as important potential therapeutic agents and biochemical tools.

3. SUMMARY

The present application relates to a cell/tissue-specific cell-penetrating antibody comprising a light chain comprising a light chain variable region ("VL"), a heavy chain comprising a heavy chain variable region ("VH"), and a cyclic peptide that specifically binds to a cell surface molecule. In some embodiments, the light chain and the heavy chain are separate molecules. In some embodiments, the light chain and the heavy chain are part of the same molecule. In certain embodiments, the cyclic peptide is fused to the antibody. In some embodiments, the cyclic peptide is directed fused to the antibody. In certain embodiments, the cyclic peptide is fused to the antibody via a peptide linker. In some embodiments, the cyclic peptide is conjugated to the antibody. In some embodiments, the cyclic peptide is directly conjugated to the antibody. In some embodiments, the cyclic peptide is conjugated to the antibody via a linker. In certain embodiments, the cyclic peptide is fused to the light chain or the heavy chain of the antibody. In certain embodiments, the cyclic peptide is fused to the N-terminus of the light chain or the heavy chain of the antibody. In a particular embodiment, the cyclic peptide is fused to the light chain of the antibody. In some embodiments, the cyclic peptide is fused to the N-terminus of the light chain of the antibody. In some embodiments, the cyclic peptide is fused to the C-terminus of the light chain of the antibody. In certain embodiments, the cyclic peptide is fused to the heavy chain of the antibody. In some embodiments, the cyclic peptide is fused to the N-terminus of the heavy chain of the antibody. In certain embodiments, the cyclic peptide is fused to the C-terminus of the heavy chain of the antibody.

In some aspects, the antibody comprises a cyclic peptide fused to the light chain and a cyclic peptide fused to the heavy chain of the antibody. In certain embodiments, the cyclic peptide is fused to the N-terminus of the light chain or the heavy chain of the antibody. In certain embodiments, the cyclic peptide is fused to the N-terminus of the light chain and the heavy chain of the antibody. In certain embodiments, the cyclic peptide is fused to the C-terminus of the light chain or the heavy chain of the antibody. In some embodiments, the cyclic peptide is fused to the C-terminus of the light chain and the heavy chain of the antibody.

In some embodiments, provided herein is an antibody, wherein the cyclic peptide is conjugated to the light chain or the heavy chain of the antibody. In certain embodiments, provided herein is an antibody wherein the cyclic peptide is conjugated to the N-terminus of the light chain or the heavy chain of the antibody. In some embodiments, provided herein is an antibody wherein the cyclic peptide is conjugated to the light chain of the antibody. In some embodiments, provided herein is an antibody wherein the cyclic peptide is conjugated to the N-terminus of the light chain of the antibody. In some embodiments, provided herein is an antibody wherein the cyclic peptide is conjugated to the C-terminus of the light chain of the antibody. In some embodiments, provided herein is an antibody wherein the cyclic peptide is conjugated to the heavy chain of the antibody. In some embodiments, provided herein is an antibody wherein the cyclic peptide is conjugated to the N-terminus of the heavy chain of the antibody. In some embodiments, provided herein is an antibody wherein the cyclic peptide is conjugated to the C-terminus of the heavy chain of the antibody. In some embodiments, provided herein is an antibody wherein antibody comprises a cyclic peptide conjugated to the light chain and a cyclic peptide conjugated to the heavy chain of the antibody. In some embodiments, provided herein is an antibody wherein the cyclic peptide is conjugated to the N-terminus of the light chain or the heavy chain of the antibody. In some embodiments, provided herein is an antibody wherein the cyclic peptide is conjugated to the N-terminus of the light chain and the heavy chain of the antibody. In some embodiments, provided herein is an antibody wherein the cyclic peptide is conjugated to the C-terminus of the light chain or the heavy chain of the antibody. In some embodiments, provided herein is an antibody wherein the cyclic peptide is conjugated to the C-terminus of the light chain and the heavy chain of the antibody. In some embodiments, provided herein is an antibody wherein the cell surface molecule is a membrane protein selectively expressed or overexpressed on the surface of a cell or tissue.

In some embodiments, provided herein is an antibody wherein the cell surface molecule is a membrane protein selectively expressed or overexpressed on the surface of a cell.

In some embodiments, provided herein is an antibody wherein the cell surface molecule is a membrane protein selectively expressed or overexpressed on the surface of a tissue.

In some aspects, provided herein is an antibody wherein the cell surface molecule is selected from the group consisting of cell membrane protein epithelial cell adhesion molecule (EpCAM), integrin αvβ5, integrin αvβ3, and epidermal growth factor receptor (EGFR). In some embodiments, provided herein is an antibody wherein the cyclic peptide comprises a disulfide bond.

In some embodiments, provided herein is an antibody wherein the amino acid sequence of the cyclic peptide comprises: X1-X2-Leu-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile. In certain aspects, the cyclic peptide comprises a disulfide bond between Cys5 and Cys10.

In some embodiments, provided herein is an antibody wherein the amino acid sequence of the cyclic peptide comprises: X1-X2-Leu-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser. In certain aspects, the cyclic peptide comprises a disulfide bond between Cys5 and Cys10.

In some embodiments, provided herein is an antibody, wherein the amino acid sequence of the cyclic peptide is selected from the group consisting of SEQ ID NOs: 29 to 37. In some embodiments, provided herein is an antibody, wherein the cyclic peptide fused or conjugated to the light chain comprises the amino acid sequence selected from the group consisting of SEQ ID NOs: 9, 21, and 38 to 48. In some embodiments, provided herein is an antibody wherein the amino acid sequence of the cyclic peptide comprises: Asp-Gly-X3-X4-X5-Cys6-Arg-Gly-Asp-Cys10-X11-X12-X13-X14-X15 (SEQ ID NO: 100); wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser.

In some embodiments, provided herein is an antibody wherein the cyclic peptide comprises a disulfide bond between Cys6 and Cys10. In some embodiments, provided herein is an antibody, wherein the amino acid sequence of the cyclic peptide is selected from the group consisting of SEQ ID NOs: 50 to 57. In some embodiments, provided herein is an antibody wherein the cyclic peptide fused or conjugated to the light chain comprises the amino acid sequence selected from the group consisting of SEQ ID NOs: 58 to 66. In some embodiments, provided herein is an antibody wherein the light chain comprises a light chain constant region (CL) and the heavy chain comprises a heavy chain constant region (CH).

In certain embodiments, the antibody is of IgG1 subtype. In some embodiments, the antibody is of IgG2 subtype. In certain embodiments, the antibody is of IgG3 subtype. In certain embodiments, the antibody is of IgG4 subtype. In certain embodiments, the light chain of an antibody disclosed herein is of lambda subtype. In certain embodiments, the light chain of an antibody disclosed herein the light chain is of kappa subtype.

In some aspects, an antibody disclosed herein is of full-length immunoglobulin format. In some embodiments, an antibody disclosed herein comprises an endosomal escape motif in the light chain variable region (VL) and/or the heavy chain variable region (VH) of the antibody, wherein the endosomal escape motif induces penetration of the antibody into the cytosol of the cell. In some embodiments, an antibody disclosed herein comprises an endosomal escape motif in the light chain variable region (VL) of the antibody. In some embodiments, an antibody disclosed herein comprises endosomal escape motif in the heavy chain variable region (VH) of the antibody. In some embodiments, an antibody disclosed herein comprises endosomal escape motif in the light chain variable region (VL) and the heavy chain variable region (VH) of the antibody.

In some embodiments, an antibody disclosed herein comprises a VL that comprises a complementarity determining region (CDR) 1, CDR2, and CDR3, and a VH that comprises a CDR1, CDR2, and CDR3, and wherein acid sequence of the endosomal escape motif comprises: 1) Trp-Tyr-Trp-X (SEQ ID NO: 69) CDR3 of VL and/or VH, wherein X is selected from the group consisting of methionine (Met), isoleucine (Ile), and leucine (Leu); and 2) aspartic acid (Asp) or glutamic acid (Glu) as the first amino acid VL and/or VH.

In some embodiments, further disclosed herein is an antibody, wherein the affinity of the antibody for heparan sulfate proteoglycan (HSPG) is reduced or abolished. In some embodiments, further disclosed herein is an antibody wherein the light chain variable region (VL) comprises an amino acid sequence selected from the group consisting of SEQ ID NOs: 2 to 8. In some embodiments, further disclosed herein is an antibody wherein the heavy chain variable region (VH) of the antibody comprises an amino acid sequence selected from the group consisting of SEQ ID NOs: 11 and 12. In some embodiments, further disclosed herein is an antibody wherein the light chain variable region (VL) of the antibody comprises an amino acid sequence represented by SEQ ID NO: 8, and the heavy chain variable region (VH) of the antibody comprises an amino acid sequence represented by SEQ ID NO: 12.

In further embodiments provided herein is a cyclic peptide comprising: X1-X2-Leu3-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile, wherein the cyclic peptide specifically binds to EpCAM.

In further embodiments provided herein is a cyclic peptide comprising: X1-X2-Leu3-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser, wherein the cyclic peptide specifically binds to EpCAM.

In some embodiments, a cyclic peptide disclosed herein comprises a disulfide bond between Cys5 and Cys10. In some embodiments, the amino acid sequence of a cyclic peptide disclosed is selected from the group consisting of SEQ ID NOs: 29 to 37.

In some embodiments, further provided herein is a cyclic peptide comprising: Asp-Gly-X3-X4-X5-Cys6-Arg-Gly-Asp-Cys10-X11-X12-X13-X14-X15 (SEQ ID NO: 100); wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the cyclic peptide specifically binds αvβ5/αvβ3 integrin.

In some embodiments, a cyclic peptide disclosed herein comprises a disulfide bond between Cys6 and Cys10. In some embodiments the amino acid sequence of the cyclic peptide is selected from the group consisting of SEQ ID NOs: 50 to 57.

In some embodiments, provided herein is a polypeptide comprising the cyclic peptide disclosed herein. In some embodiments, provided herein is a polypeptide, wherein the polypeptide is an antibody.

In certain aspects, further provided herein is a composition comprising the cyclic peptide disclosed herein. In some embodiments, provided herein is a polynucleotide encoding the cell/tissue-specific cell-penetrating antibody or the cyclic peptide disclosed herein. In another embodiments, provided herein is a vector comprising the polynucleotide disclosed herein. In certain embodiments, provided herein is a host cell comprising the vector disclosed herein.

In certain embodiments, further provided herein is a method of making a cell/tissue-specific cell-penetrating antibody comprising: introducing the vector into a host cell; expressing the vector in the host cell; and recovering the expressed antibody. In certain embodiments, further provided herein is a method of making a cell/tissue-specific cell-penetrating antibody comprising: culturing a host cell disclosed herein such that the antibody is expressed; and recovering the expressed antibody.

In certain embodiments, further provided herein is a method of making a cell/tissue-specific cell-penetrating antibody, comprising: introducing into a host cell a vector comprising a polynucleotide encoding a VL with reduced of abolished HSPG binding ability, a polynucleotide encoding a VH, and a polynucleotide encoding a cyclic peptide that specifically binds to a cell surface molecule, wherein the VL and/or the VH comprise an endosomal escape motif, and the cyclic peptide is fused to the N-terminus of the light chain variable region (VL) and/or the heavy chain variable region (VH); expressing the vector in the host cell such that the antibody is expressed; and recovering the expressed antibody.

In certain embodiments, further provided herein is a method of making a cell/tissue-specific cell-penetrating antibody, comprising: culturing a host cell comprising a vector that comprises a polynucleotide encoding a VL with reduced of abolished HSPG binding ability, a polynucleotide encoding a VH, and a polynucleotide encoding a cyclic peptide that specifically binds to a cell surface molecule, wherein the VL and/or the VH comprise an endosomal escape motif, and the cyclic peptide is fused to the N-terminus of the light chain variable region (VL) and/or the heavy chain variable region (VH) such that the antibody is expressed; and recovering the expressed antibody.

In another aspect, provided herein is a pharmaceutical composition comprising the cell/tissue-specific cell-penetrating antibody or the cyclic peptide disclosed herein as an active ingredient and a pharmaceutically acceptable carrier. In another aspect, provided herein is a pharmaceutical composition provided herein for use in treating a disease or condition in a subject. In another aspect, provided herein is a pharmaceutical composition provided herein for use in treating the disease or condition of cancer. In some embodiments, provided herein is a pharmaceutical composition disclosed herein for treating cancer, wherein the cancer is overexpressing at least one cell surface molecule selected from the group consisting of epithelial cell adhesion molecule (EpCAM), integrin αvβ5, integrin αvβ3, and epidermal growth factor receptor (EGFR). In another aspect, provided herein is a pharmaceutical composition for use in treating an immune disease. In another aspect, provided herein is a pharmaceutical composition for use in treating is a neurological disease.

In another aspect, provided herein is a method of preventing or treating a disease or condition in a subject comprising administering a therapeutically effective amount of the cell/tissue-specific cell-penetrating antibody or the cyclic peptide disclosed herein In another aspect, provided herein is a method of preventing or treating a disease or condition in a subject wherein the disease or condition is a cancer. In another aspect, provided herein is a method of preventing or treating a disease or wherein the cancer is overexpressing at least one cell surface molecule selected from the group consisting of epithelial cell adhesion molecule (EpCAM), integrin αvβ5, integrin αvβ3, and epidermal growth factor receptor (EGFR). In another aspect, the disease or condition is an immune disease. In some embodiments, the disease or condition is a neurological disease.

4. BRIEF DESCRIPTION OF THE DRAWINGS

Figure 1B:
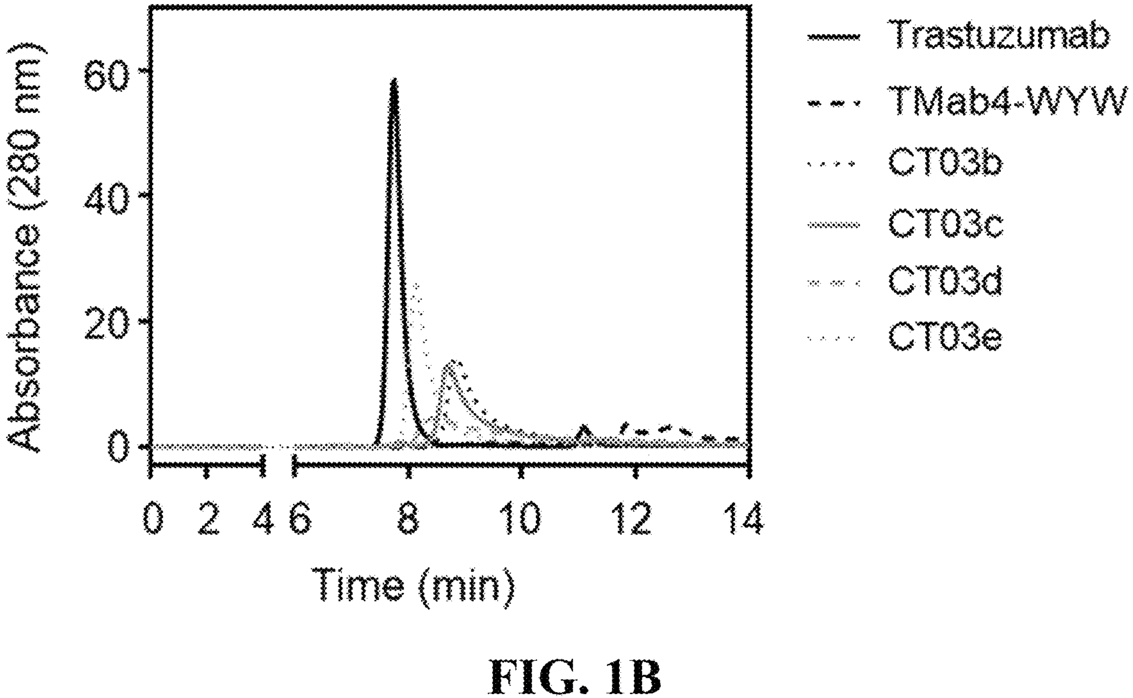

FIG. 1A: TMab4-WYW exhibits HSPG binding ability and cell-penetrating ability. TMab4-WYW variants CT03a, CT03b, CT03c, CT03d and CT03e displayed reduced HSPG binding. Negative controls are buffer and avastin. ability-reduced light chain variable region (VL) mutant is introduced into the antibody for the development of a tumor tissue-specific cell-penetrating antibody in which HeLa cells were treated with 1 μM of the antibody at 37° C. for 6 hours and observed by confocal microscopy;

FIG. 1B: SEC elution profiles of CT antibodies on a Zenix SEC-300 column. The clinically approved trastuzumab (Herceptin®) was included as a control. Absorbance is calculated at 280 nm.

Figure 2A:
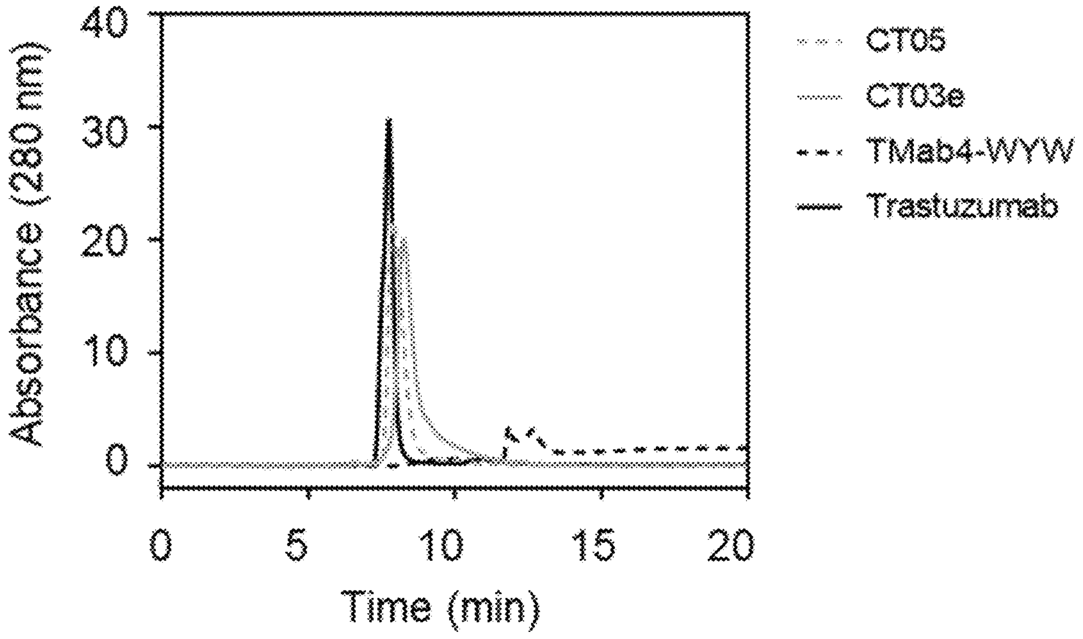

FIG. 2A: SEC elution profiles of CT antibodies on a Zenix SEC-300 column. The clinically approved trastuzumab (Herceptin®) was included as a control. Absorbance is calculated at 280 nm.

Figure 2B:
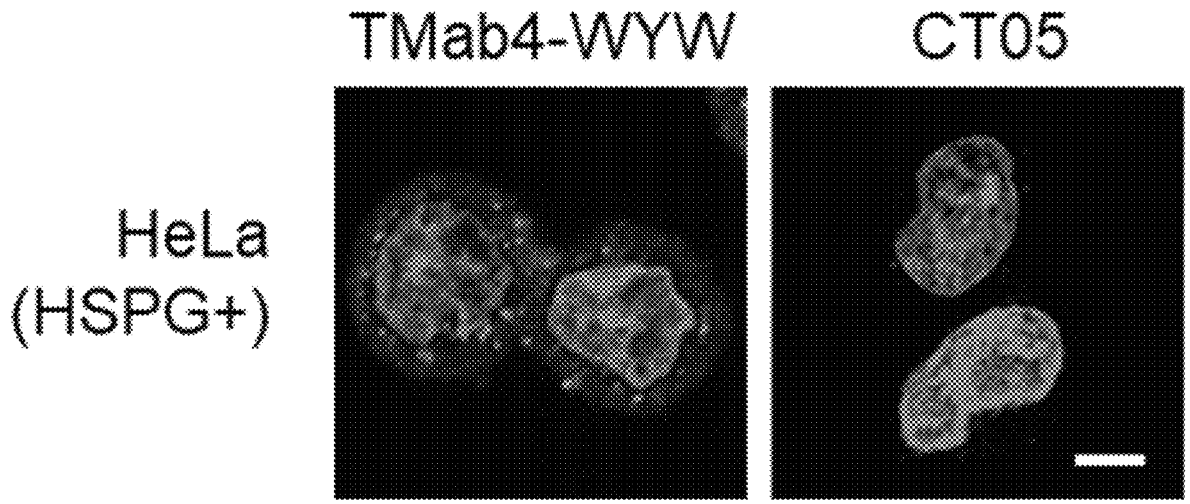

FIG. 2B: Comparison of cellular internalization and localization between TMab4-WYW and CT05 in HeLa cells treated with the CTs (1 μM) for 6 h at 37° C. Internalized CTs were visualized with an Alexa Fluor 488-conjugated anti-human IgG antibody (green) by confocal microscopy. The blue color represents Hoechst 33342-stained nuclei. Scale bar, 10 μm.

Figure 2C:
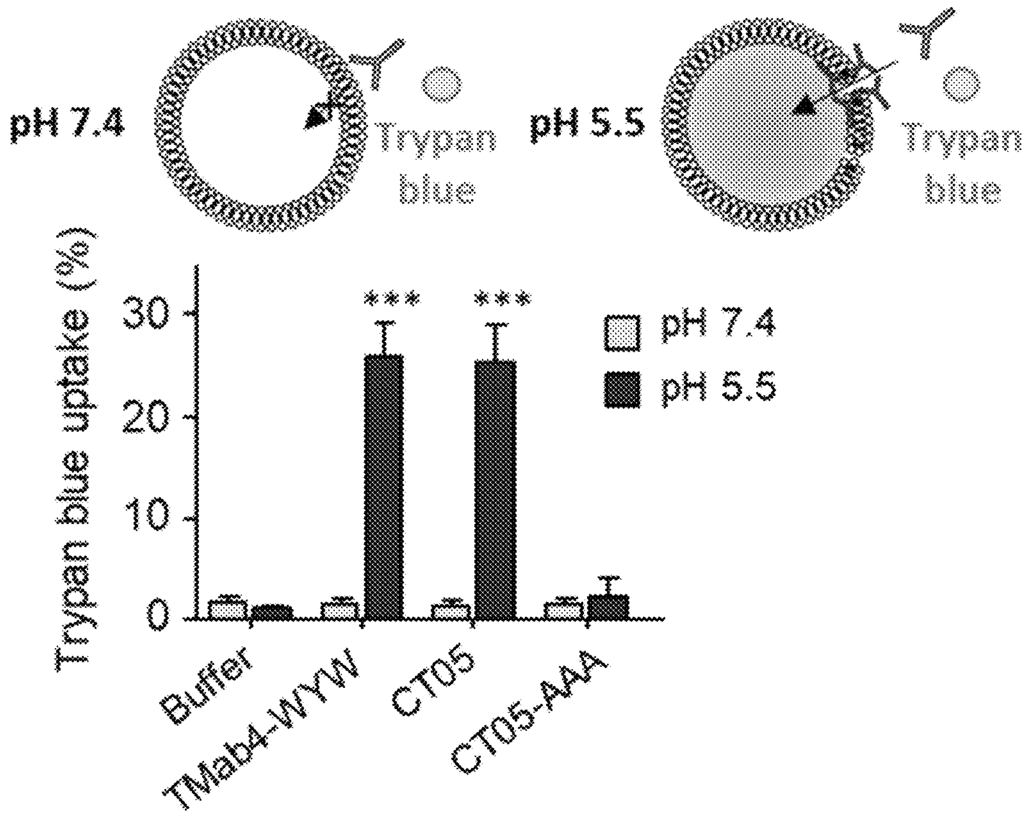

FIG. 2C: A trypan blue uptake assay in Ramos cells cotreated with trypan blue dye plus the indicated CTs (1 μM) for 2 h at 37° C. and pH 7.4 or 5.5. The lower panel shows the percentage of the trypan blue-stained cells out of all the incubated cells (n=400 cells per group) for Tmab4-WYW and CT05 at pH 7.4 or pH 5.5. ***P<0.001.

Figure 2D:
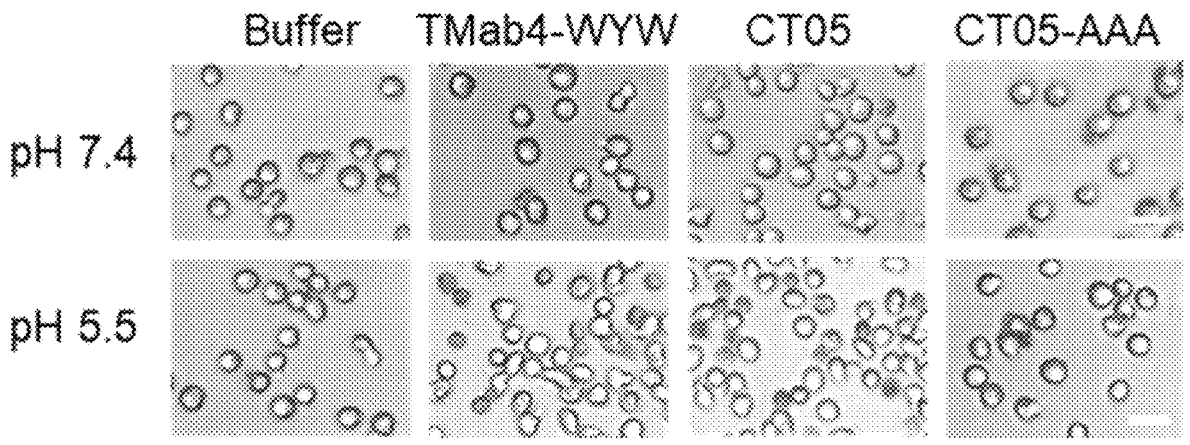

FIG. 2D: Representative microscopic images of Ramos cells in the trypan blue uptake assay. Cells that internalized trypan blue are stained.

Figure 3A:
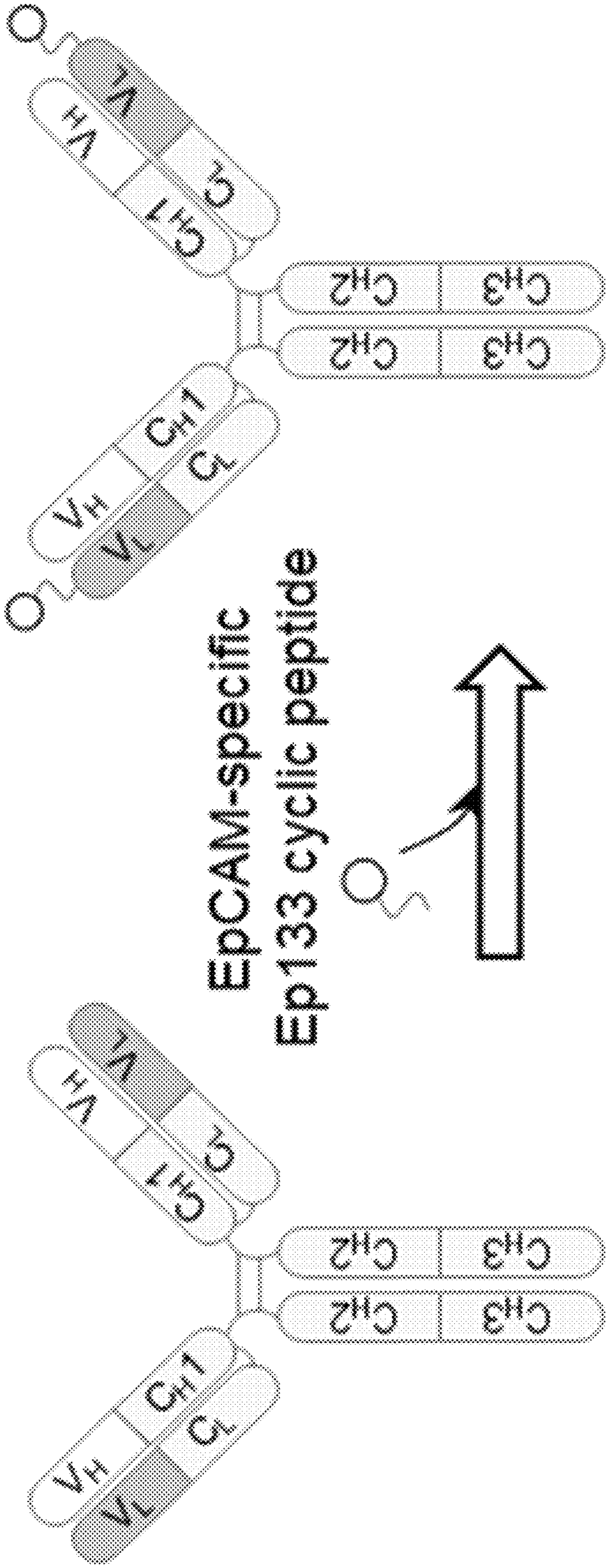

FIG. 3A: Schematic representation of epCT05 generated by genetic fusion of cyclic peptide Ep133 (specifically binding EpCAM) via the $(G_4S)_2$ linker (SEQ ID NO: 101) to the N terminus of CT05 LC.

Figure 3B:
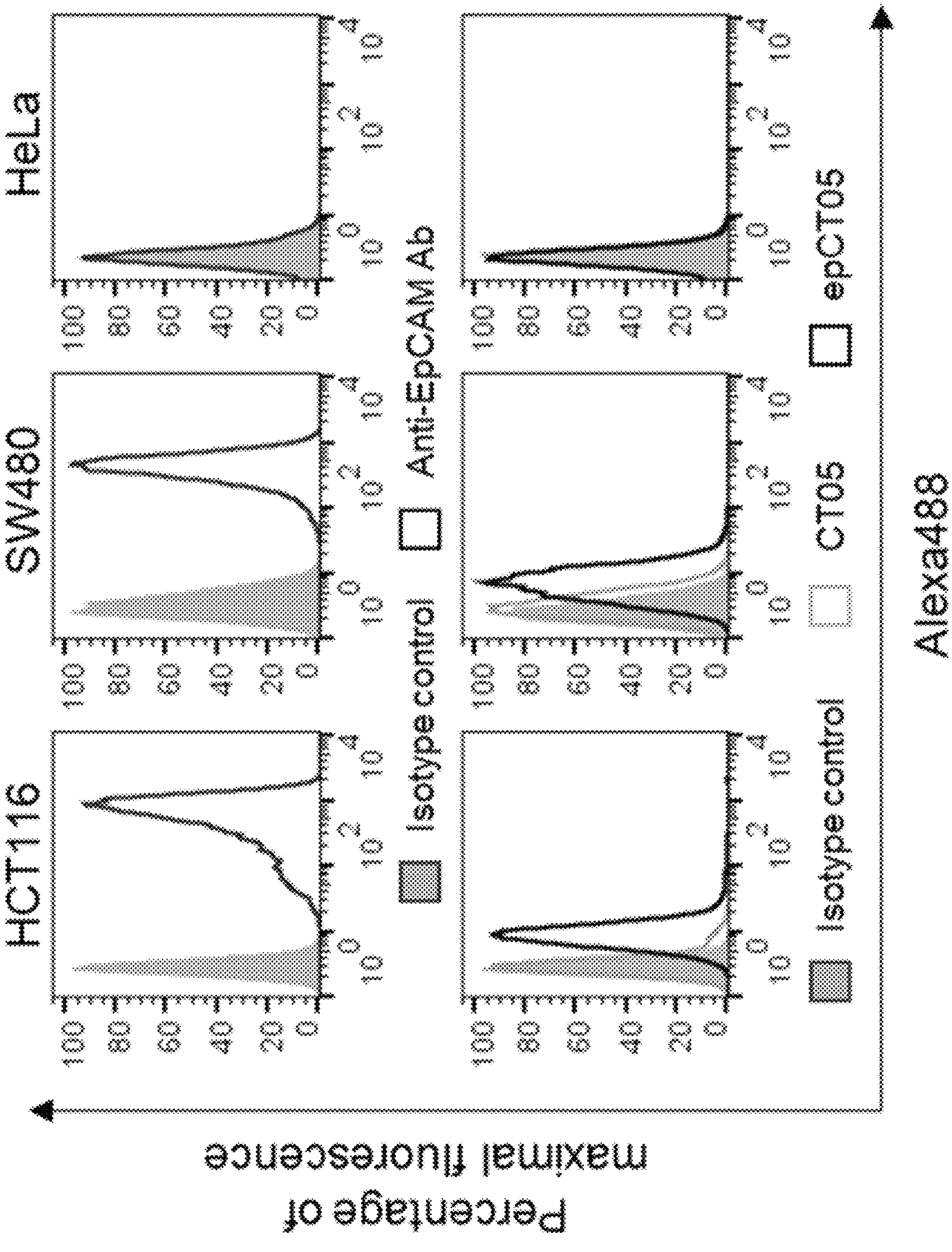

FIG. 3B: Flow cytometric analysis of the cell surface expression levels of EpCAM on human tumor cells (HCT116, SW480 and HeLa cells) analyzed by means of an Alexa Fluor 488-labeled anti-EpCAM antibody (upper panels). Cell surface-binding levels of the indicated CTs, coincubated at 100 nM with 300 IU/mL heparin for 1 h at 4° C. with the indicated cells before analysis (lower panels). An isotype control is used as a negative control.

Figure 4A:
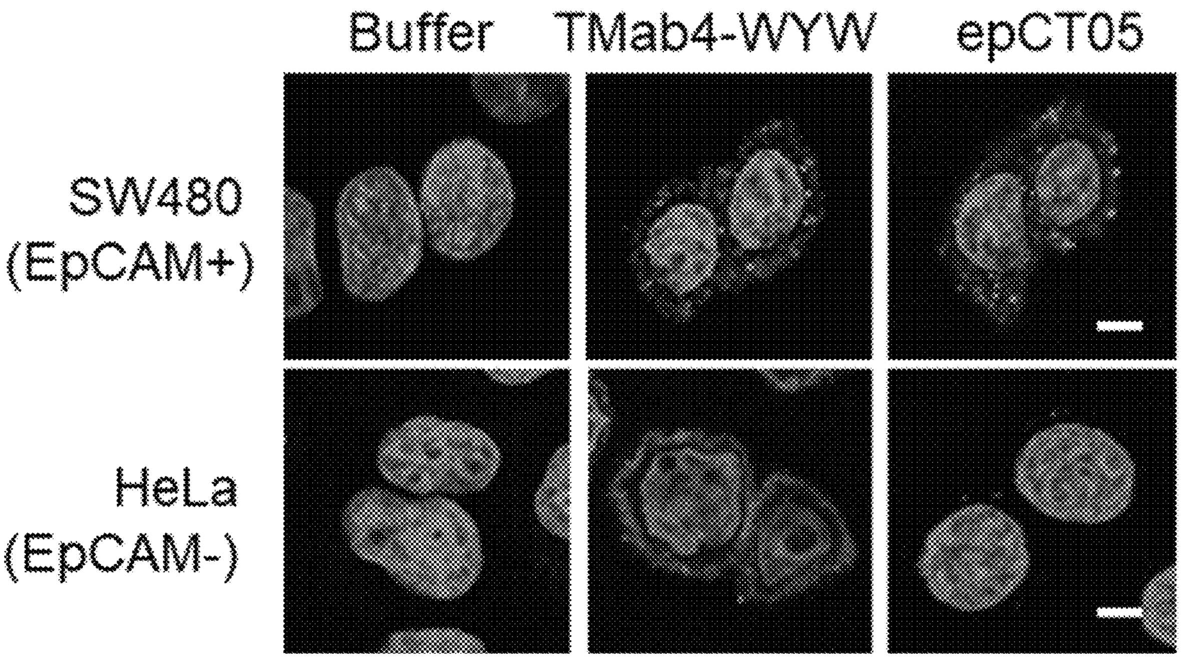

FIG. 4A: Cellular internalization and localization of the indicated CTs (green) in EpCAM-positive SW480 cells and EpCAM-negative HeLa cells, treated with antibodies (1 μM) for 6 h at 37° C. prior to confocal fluorescence microscopy. The blue color represents Hoechst 33342-stained nuclei.

Figure 4B:
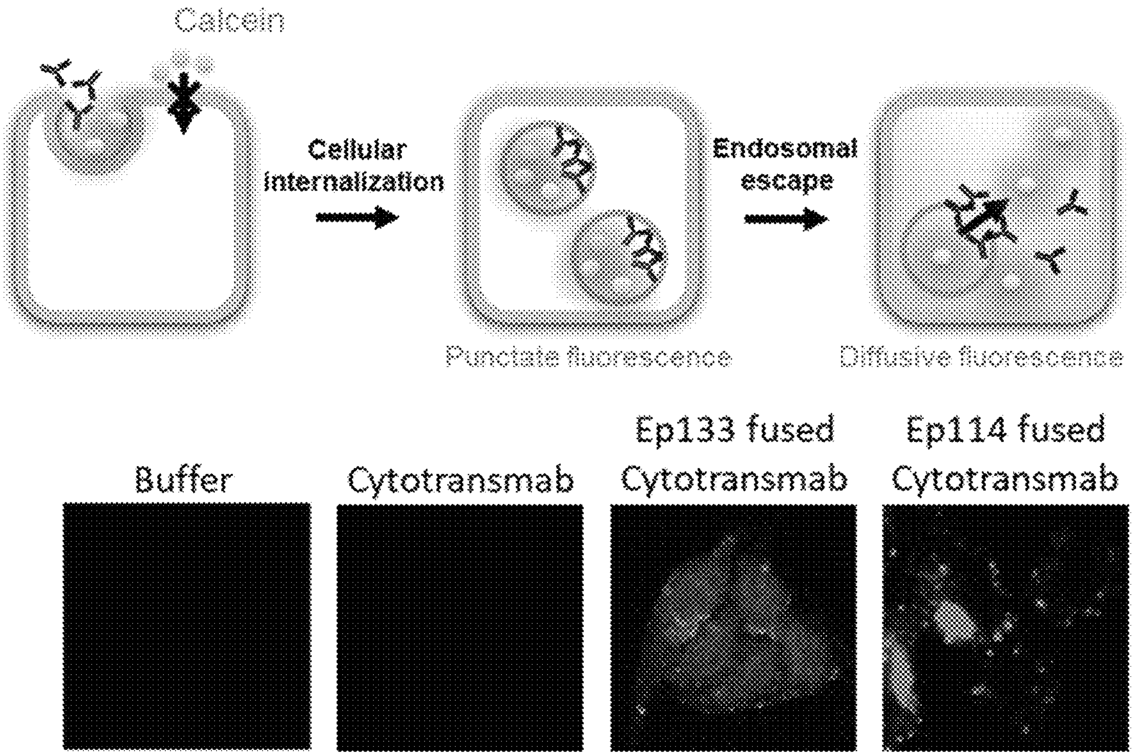

FIG. 4B: Confocal microscope image of a cytosolic calcein release assay to assess the endosomal escape ability of Ep133-fused CT and Ep144-fused CT.

Figure 4C:
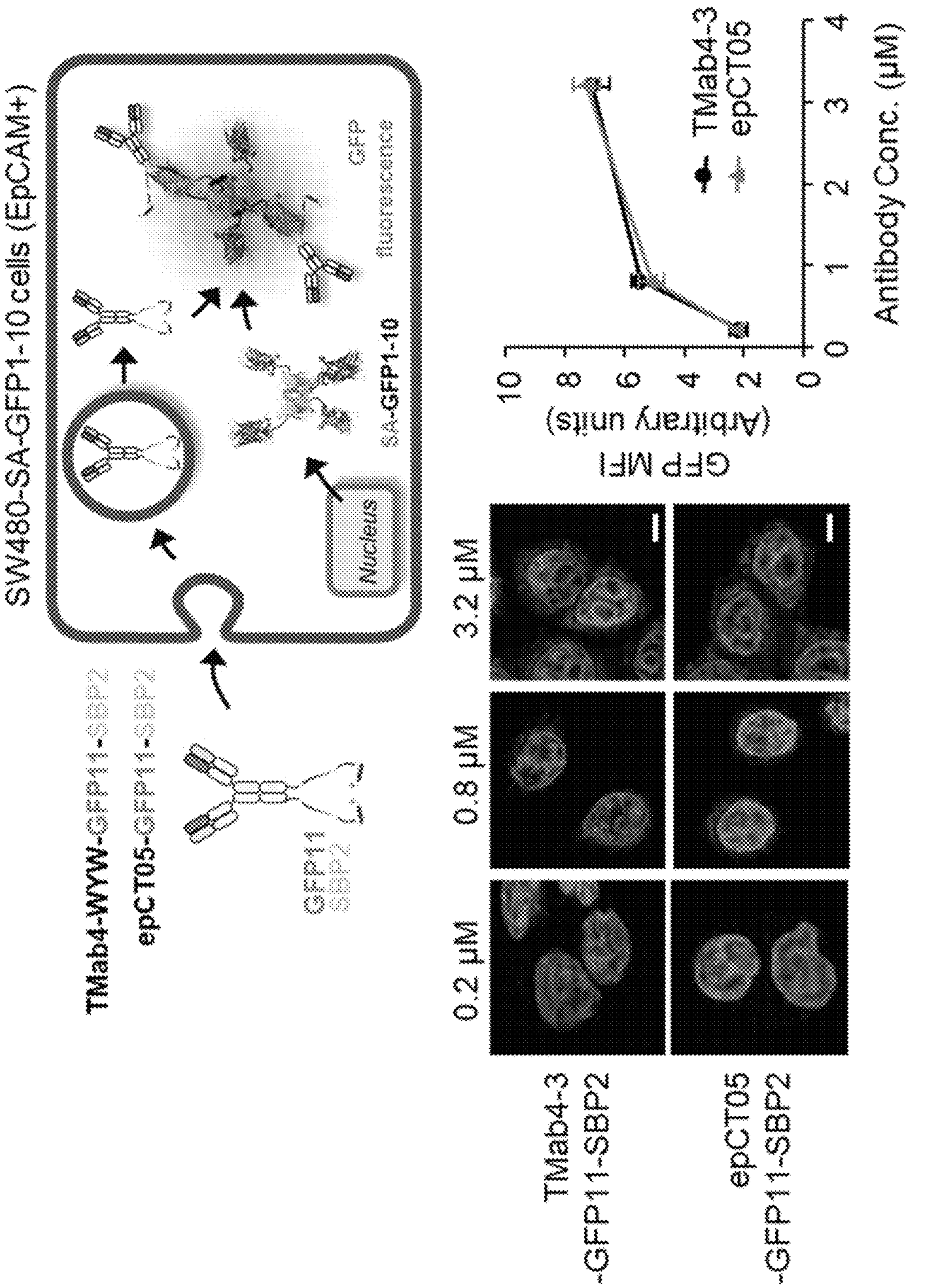

FIG. 4C: Schematic representation of the split-GFP complementation assay (top). Cellular internalization and cytosolic localization of GFP11-SBP2-fused antibodies epCT05 and TMab4-WYW, as assessed by confocal microscopy measuring complemented GFP signals (green) in SW480-SA-GFP1-10 cells after treatment with the indicated concentration of the antibodies for 6 h at 37° C. (bottom left). The blue color represents Hoechst 33342-stained nuclei. Graphical representation of the concentration-dependent endosomal escape efficiency of indicated CTs (bottom right).

Figure 5A:
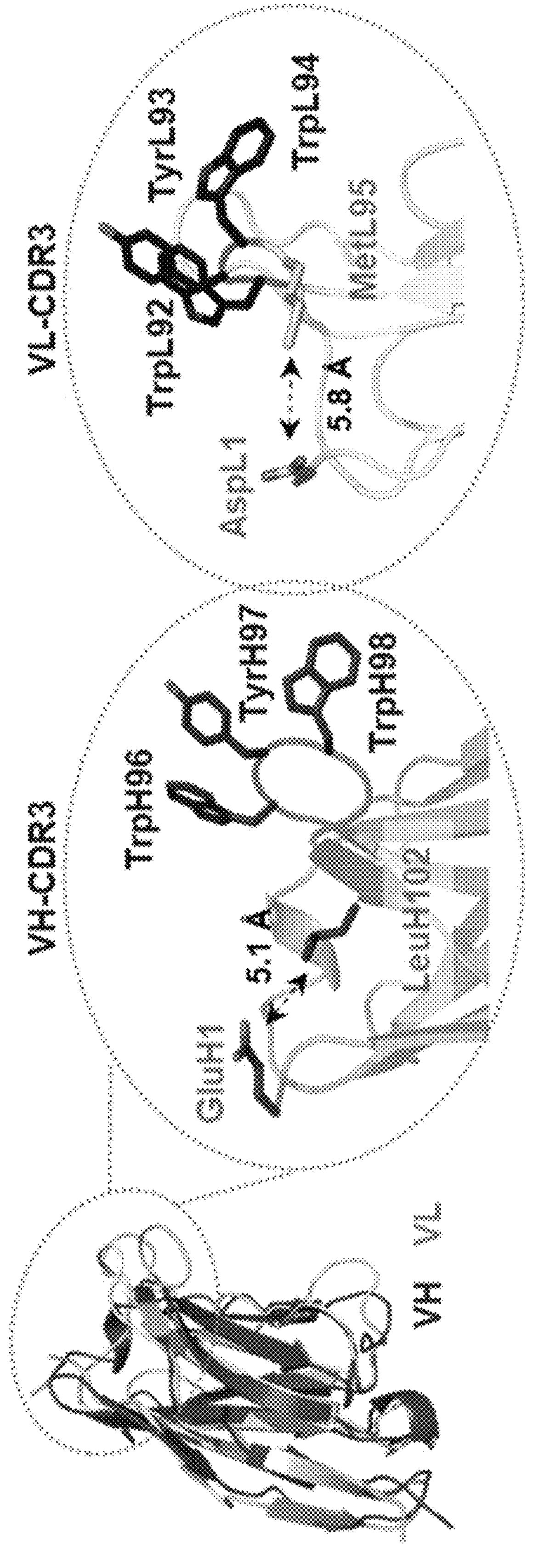

FIG. 5A: Superimposition of the homology-modeled structure of the CT60 VH (SEQ ID NO. 12) with that of CT05 VL, with highlighting of the pH-sensing pair and membrane-binding motif constituting the endosomal escape motif. The distance between the side chains of the residues of the pH-sensing pair is indicated. The homology-modeled structure was obtained by the Abodybuilder algorithm (Leem, Dunbar, Georges, Shi, & Deane, 2016). The images were generated in the PyMol software (DeLano Scientific LLC).

Figure 5B:
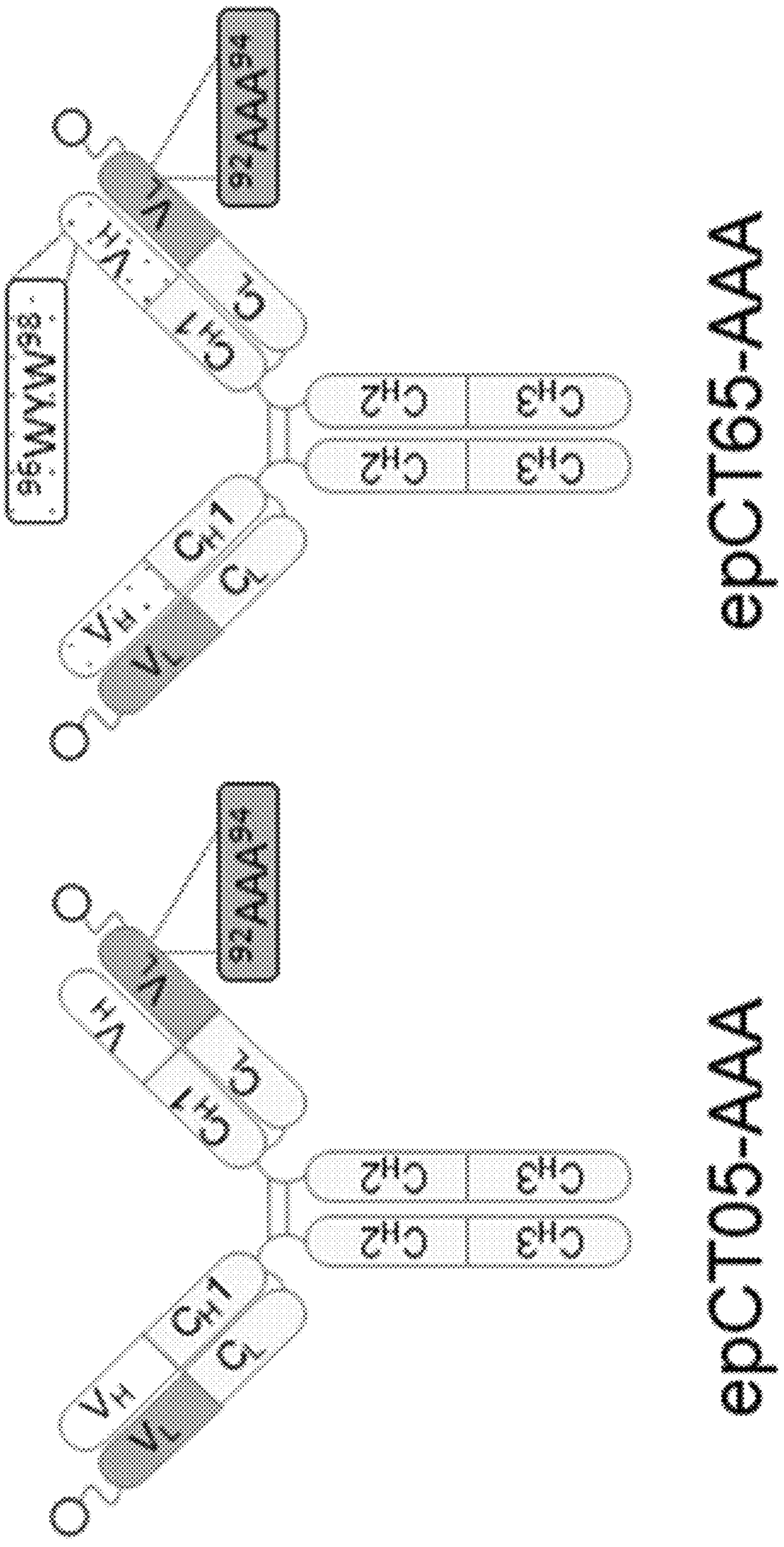

FIG. 5B: Schematic representation of epCT05-AAA and epCT65-AAA CTs. epCT05-AAA has no endosomal escape motif due to the replacement of $^{92}$WYW$^{94}$ with $^{92}$AAA$^{94}$ in the VL (left). epCT65-AAA has one endosomal escape motif imbedded in the VH (right).

Figure 6A:
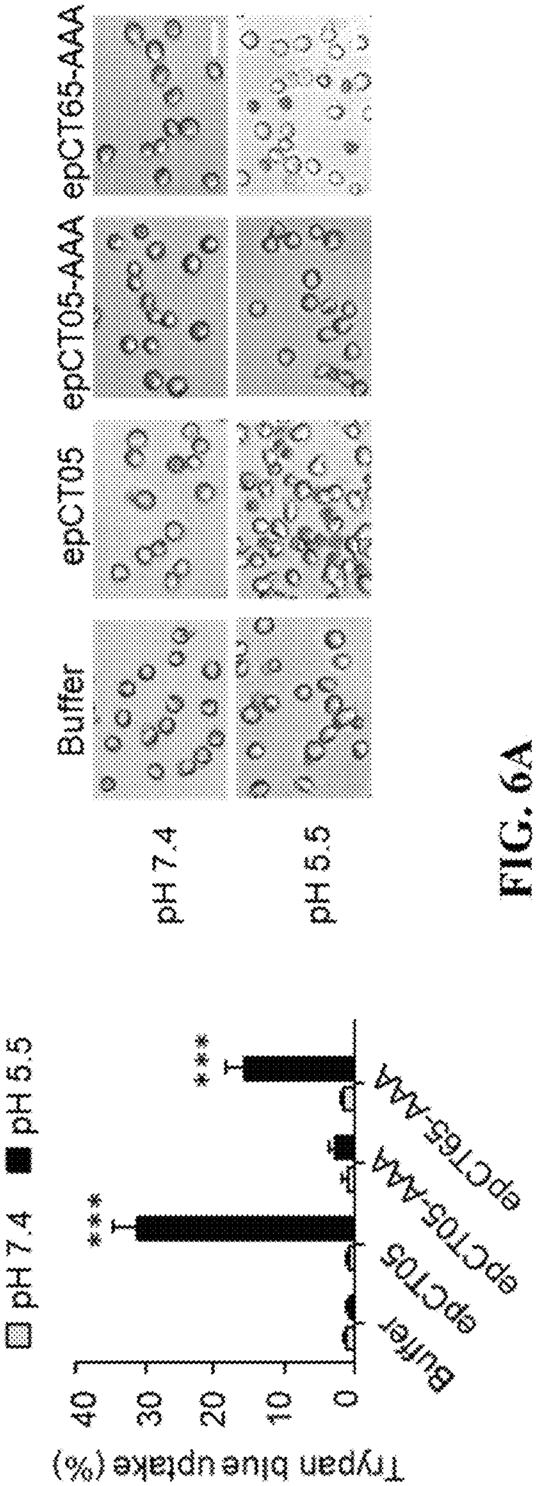

FIG. 6A: Graph showing the percentage of trypan blue-stained cells among the cells incubated with epCT05, epCT05-AAA, epCT65-AAA or buffer at pH 5.5 and pH 7.4 (left). Error bars denote SD (n=400 cells per group). Representative microscopic images showing uptake of the trypan blue dye by Ramos cells cotreated with the indicated antibodies (1 μM) for 2 h at 37° C. and pH 7.4 or 5.5 (right). Scale bar, 10 μm.

Figure 6B:
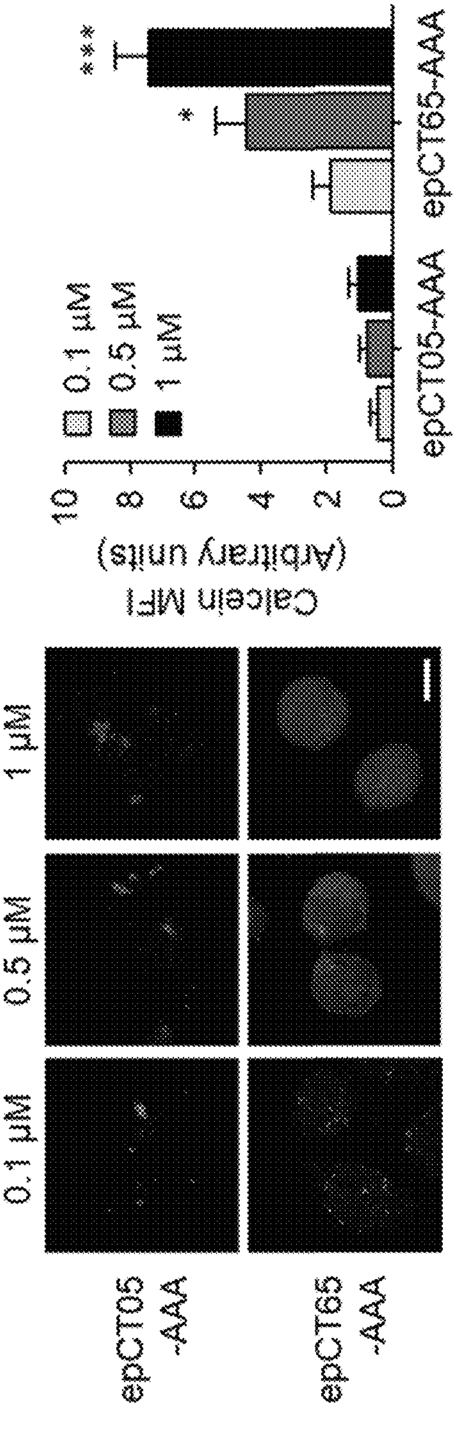

FIG. 6B: Confocal microscope image of a cytosolic calcein release assay to assess the endosomal escape ability of epCT05-AAA and epCT65-AAA in SW480 cells (left). Graph of mean fluorescence intensity (MFI) of calcein in cytoplasmic regions of cells (right).

Figure 6C:
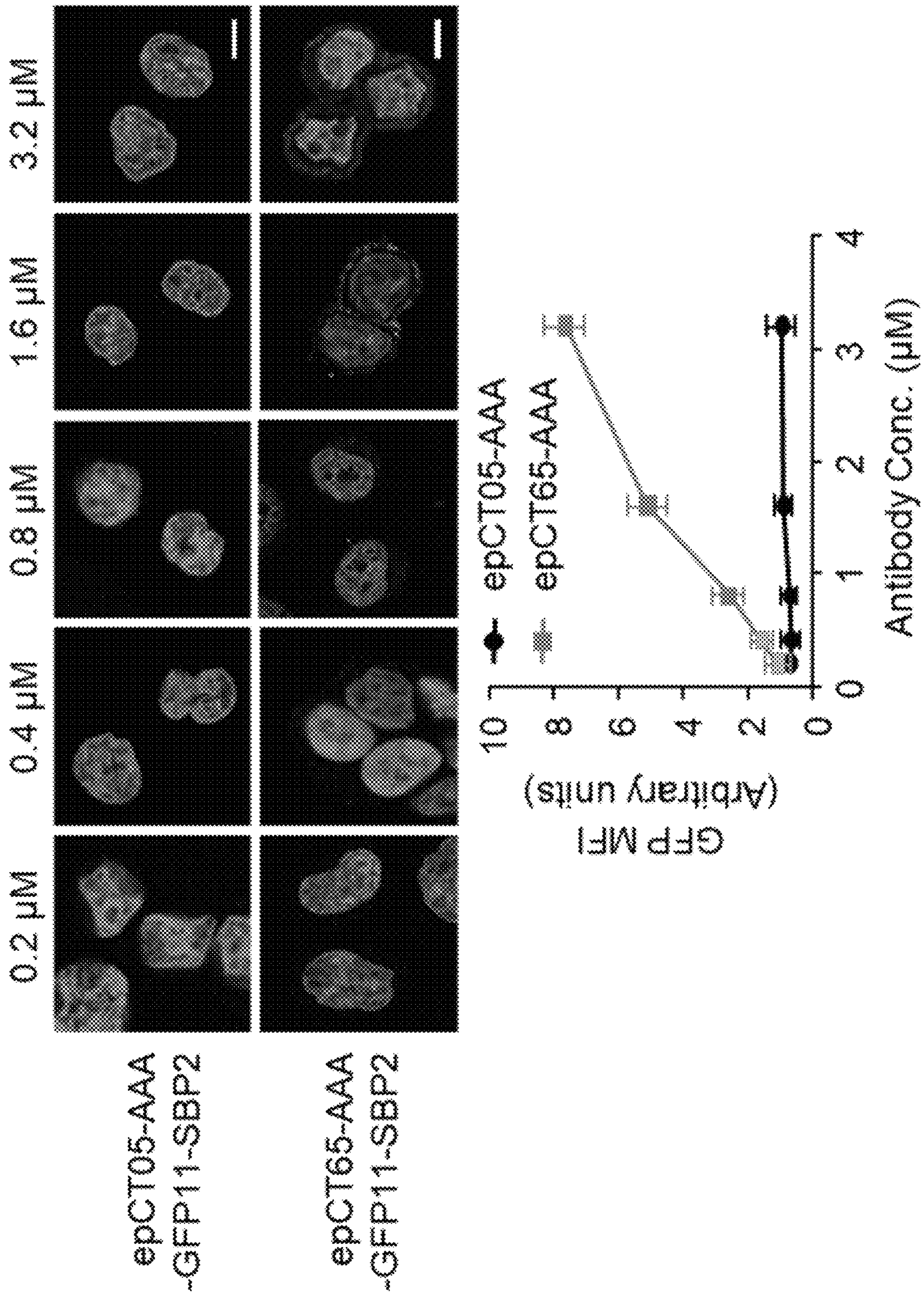

FIG. 6C: Confocal microscopic analysis of complemented GFP signals in SW480-SA-GFP1-10 cells, which were treated for 6 h at 37° C. with the indicated concentrations of epCT05-AAA-GFP11-SBP2 or epCT65-AAA-GFP11-SBP2 (top). The blue color represents Hoechst 33342-stained nuclei. The scale bar is 10 μm. Graph of mean fluorescence intensity (MFI) of GFP in cytoplasmic regions of cells compared with that in the PBS-treated control (bottom). Error bars denote SD (n=20 cells per group).

Figure 7A:
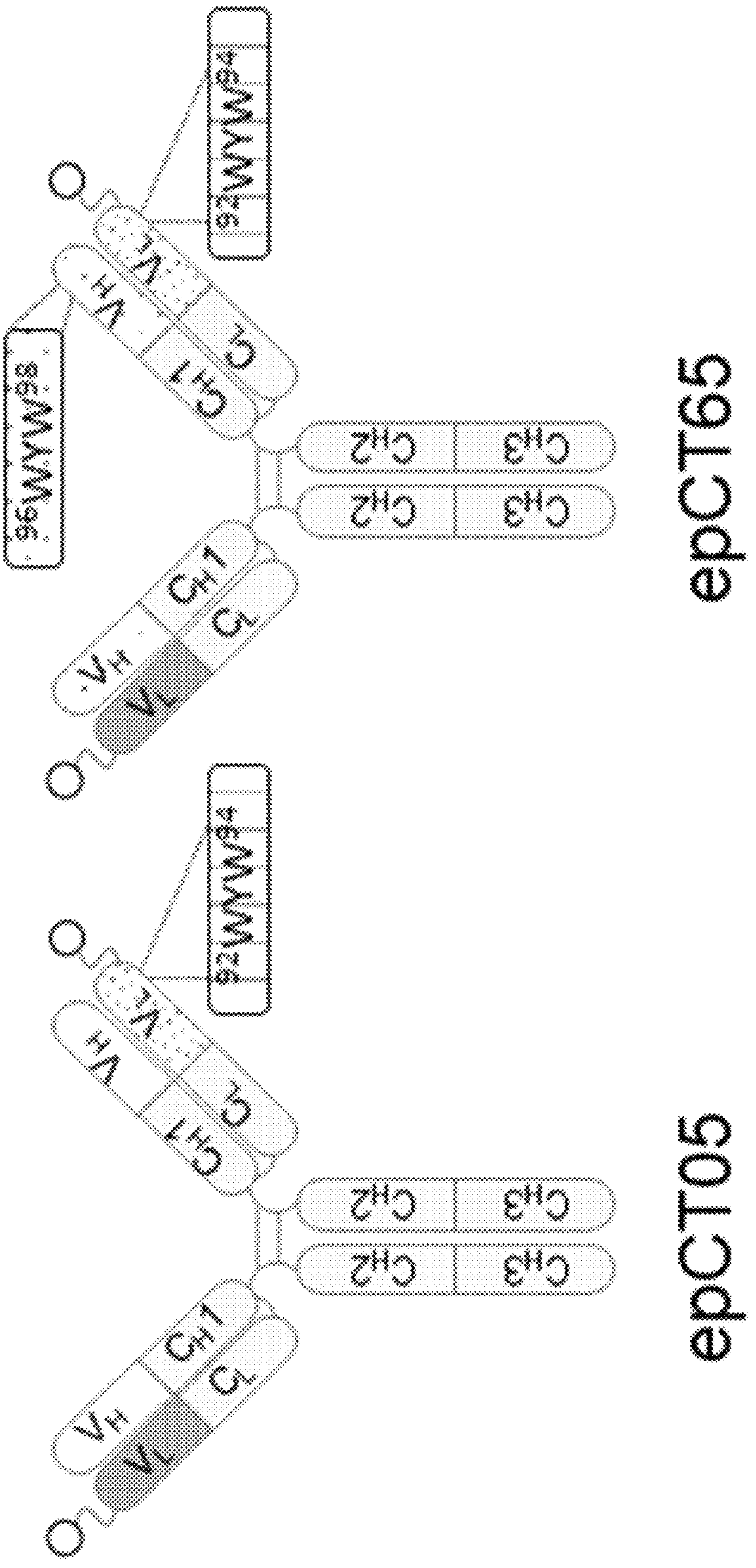

FIG. 7A: Schematic representation of epCT05 and epCT65 CTs. epCT05 has one endosomal escape motif in VL (left), while epCT65 has endosomal escape motifs in both the VH and VL (right).

Figure 7B:
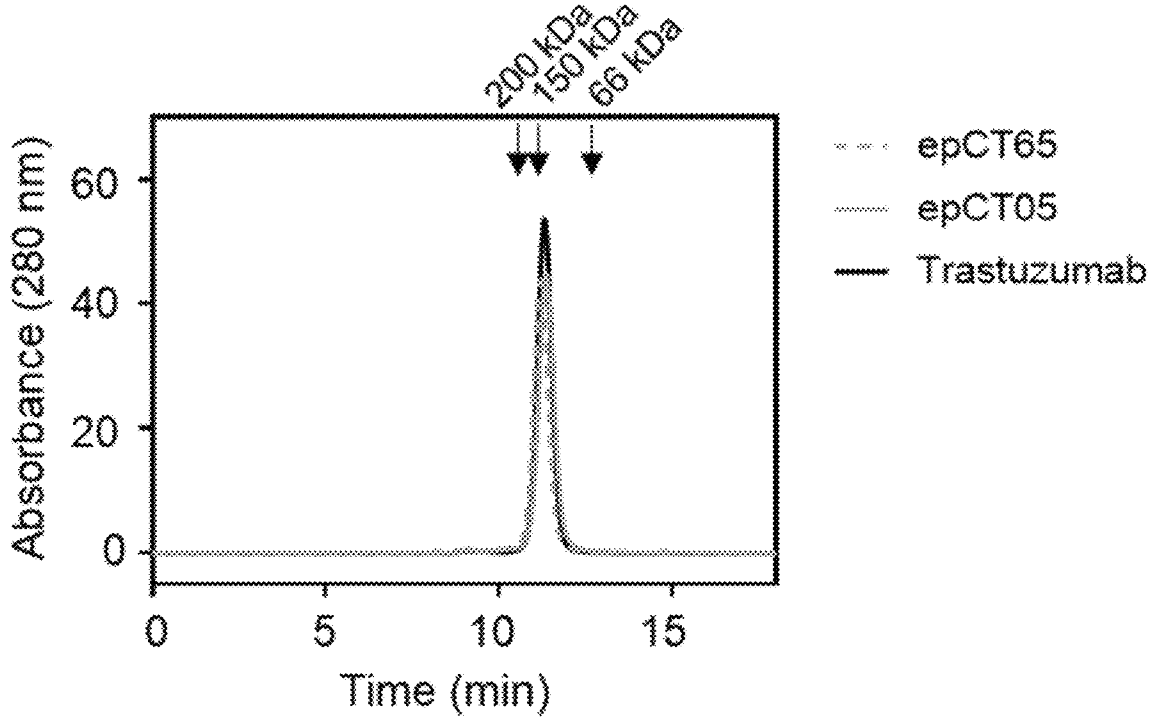

FIG. 7B: SEC elution profiles of Trastuzumab, epCT05 and epCT65 on a Superdex column to confirm the presence of a monomer. The purified CTs were injected at 1.0 mg/mL and 30 μL sample volume and were monitored at 280 nm. Arrows indicate the elution positions of molecular weight standards.

Figure 7C:
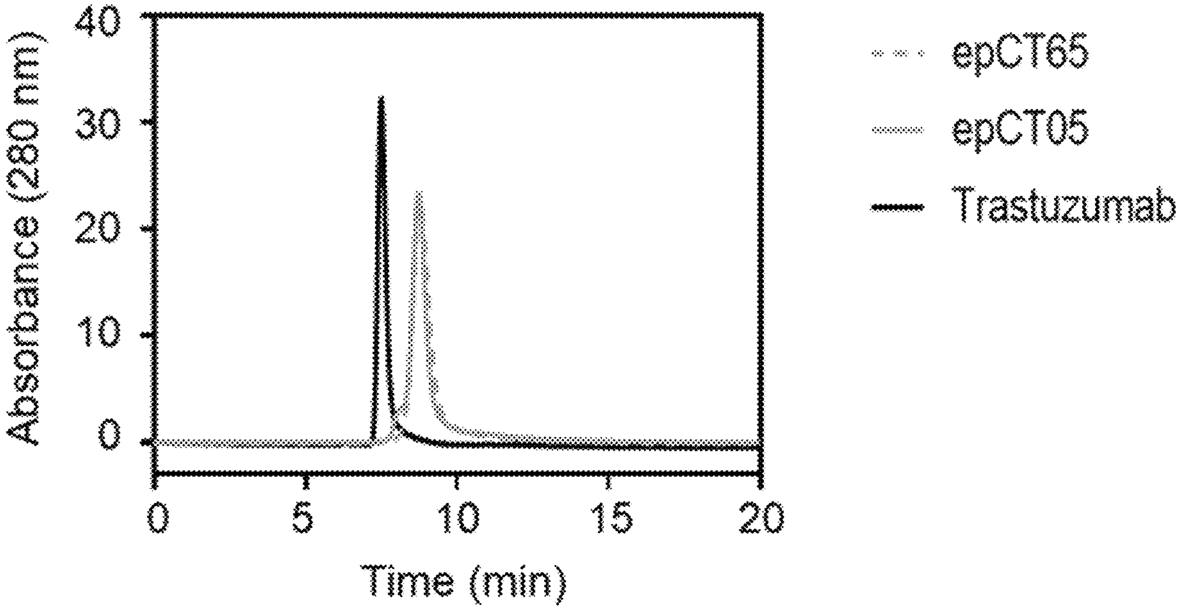

FIG. 7C: Elution profiles of Trastuzumab, epCT05 and epCT65 on a Zenix SEC-300 column to evaluate the protein hydrophobicity using a high performance liquid chromatography. The purified CTs were injected at 1.0 mg/mL and 30 μL sample volume and were monitored at 280 nm.

Figure 8A:
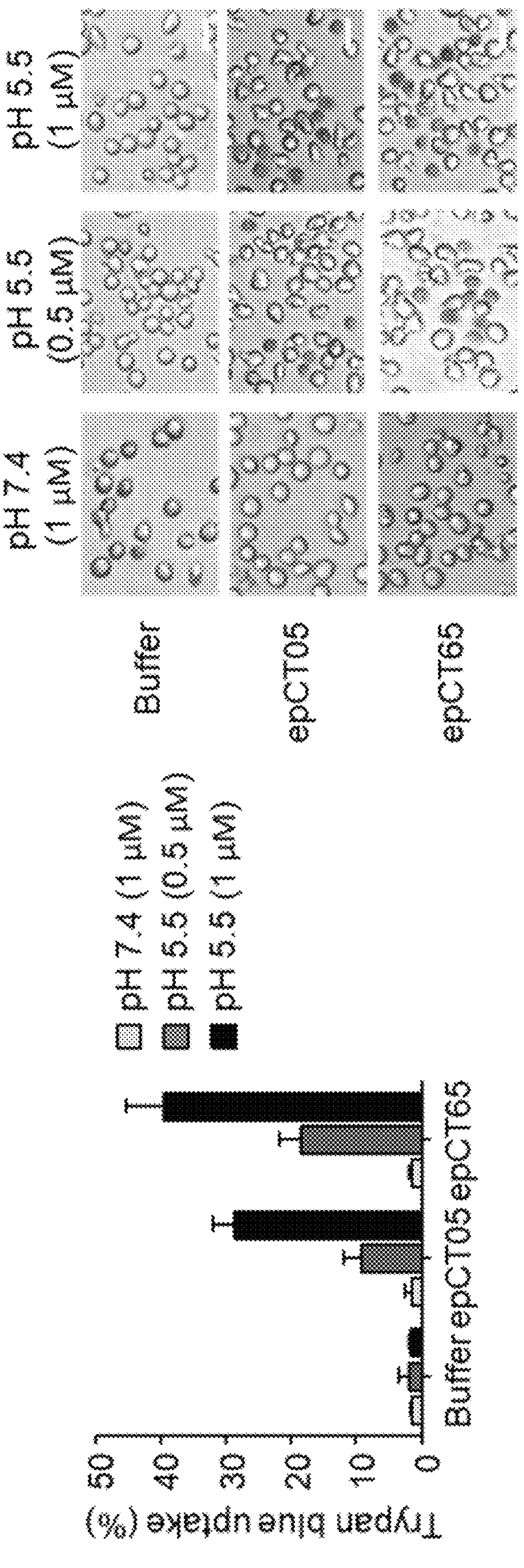

FIG. 8A: Graph showing the percentage of trypan blue-stained cells among the cells incubated with indicated CTs at indicated concentrations (left). Error bars indicate SD (n=400 cells per group). Representative microscopic images showing uptake of the trypan blue dye by Ramos cells cotreated with the indicated concentrations of CTs (0.5 or 1 μM) for 2 h at 37° C. and pH 7.4 or 5.5 (right). Scale bar, 10 μm.

Figure 8B:
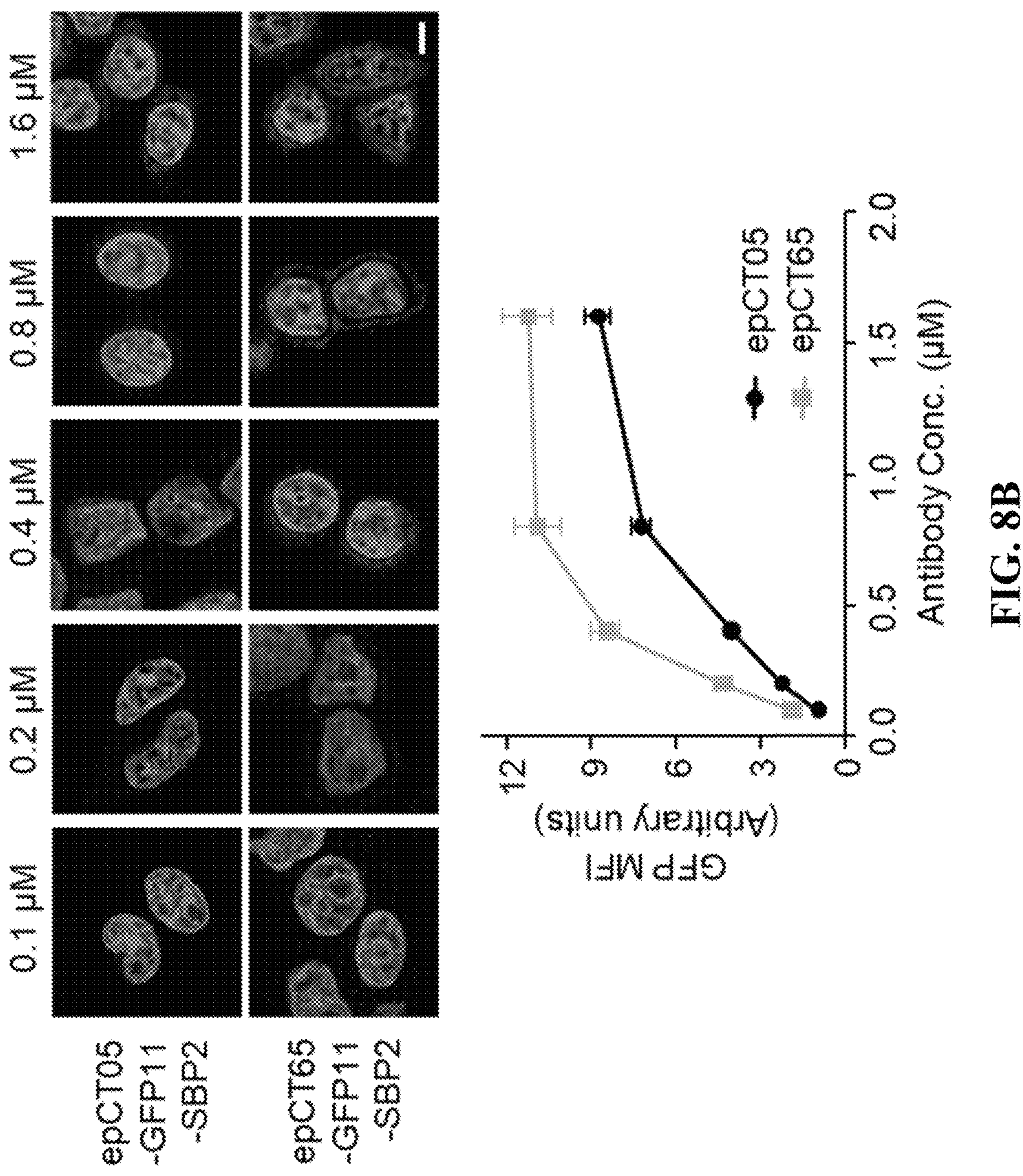

FIG. 8B: Confocal microscopic analysis of GFP complemented signals in SW480-SA-GFP1-10 cells, which were treated for 6 h at 37° C. with the indicated concentrations of epCT05-GFP11-SBP2 or epCT65-GFP11-SBP2 (left). The blue color represents Hoechst 33342-stained nuclei. The scale bar is 10 μm. The right-hand panel shows the MFI of GFP in cytoplasmic regions of cells compared with that in PBS-treated control. Error bars denote SD (n=20 cells per group).

Figure 9A:
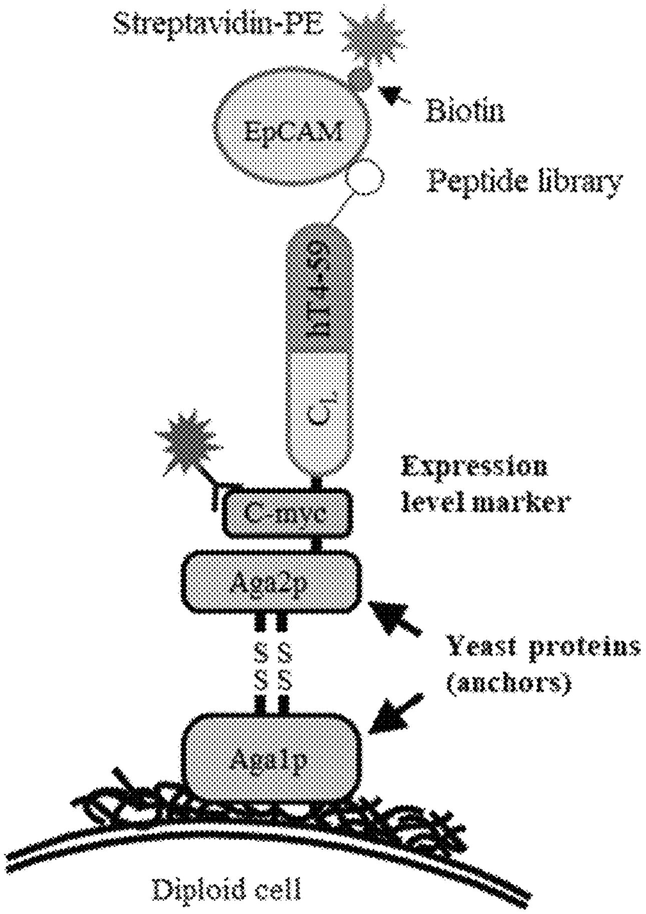

FIG. 9A: Schematic diagram showing the strategy for the screening of a Ep133-based cyclic peptide library. Mutations were introduced into the amino acid residues of cyclic peptide sequences (top). Biotinylated human recombinant EpCAM antigen was used to screen a library of cyclic peptides fused to VL (hT4-ep59 MG VL) and expressed on yeast cells. Yeast expressing the library binding to EpCAM was reacted with streptavidin prior to MACS sorting.

Figure 9B:
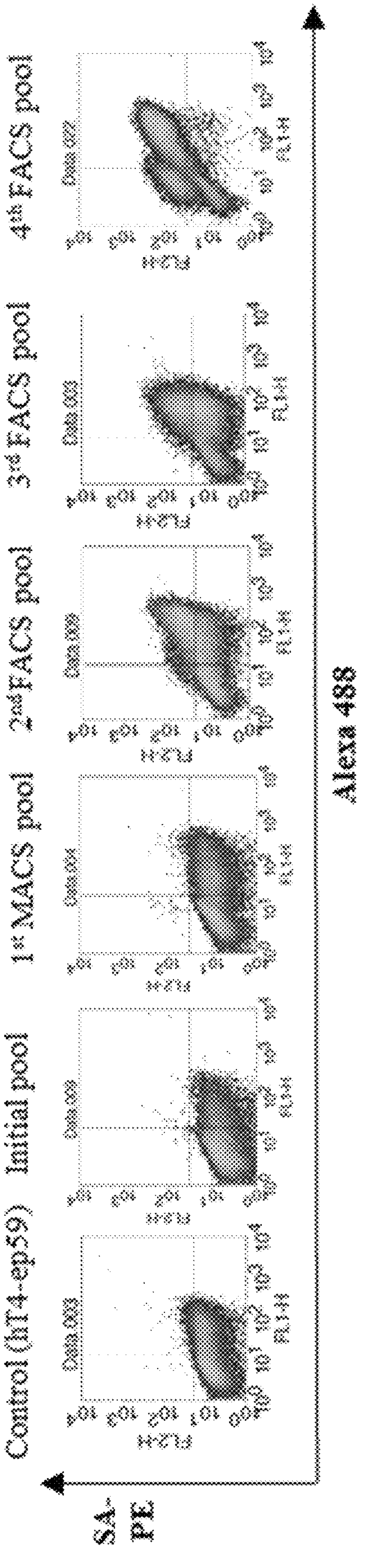

FIG. 9B: FACS analysis of the binding ability of the yeast in each step of the screening process for obtaining high specific affinity to EpCAM under a condition of 100 nM EpCAM. Streptavidin-R-phycoerythrin conjugate (SA-PE) and Alexa-488 are plotted for magnetic activated cell sorting (MACS) and fluorescence activated cell sorting (FACS) pools.

Figure 9C:
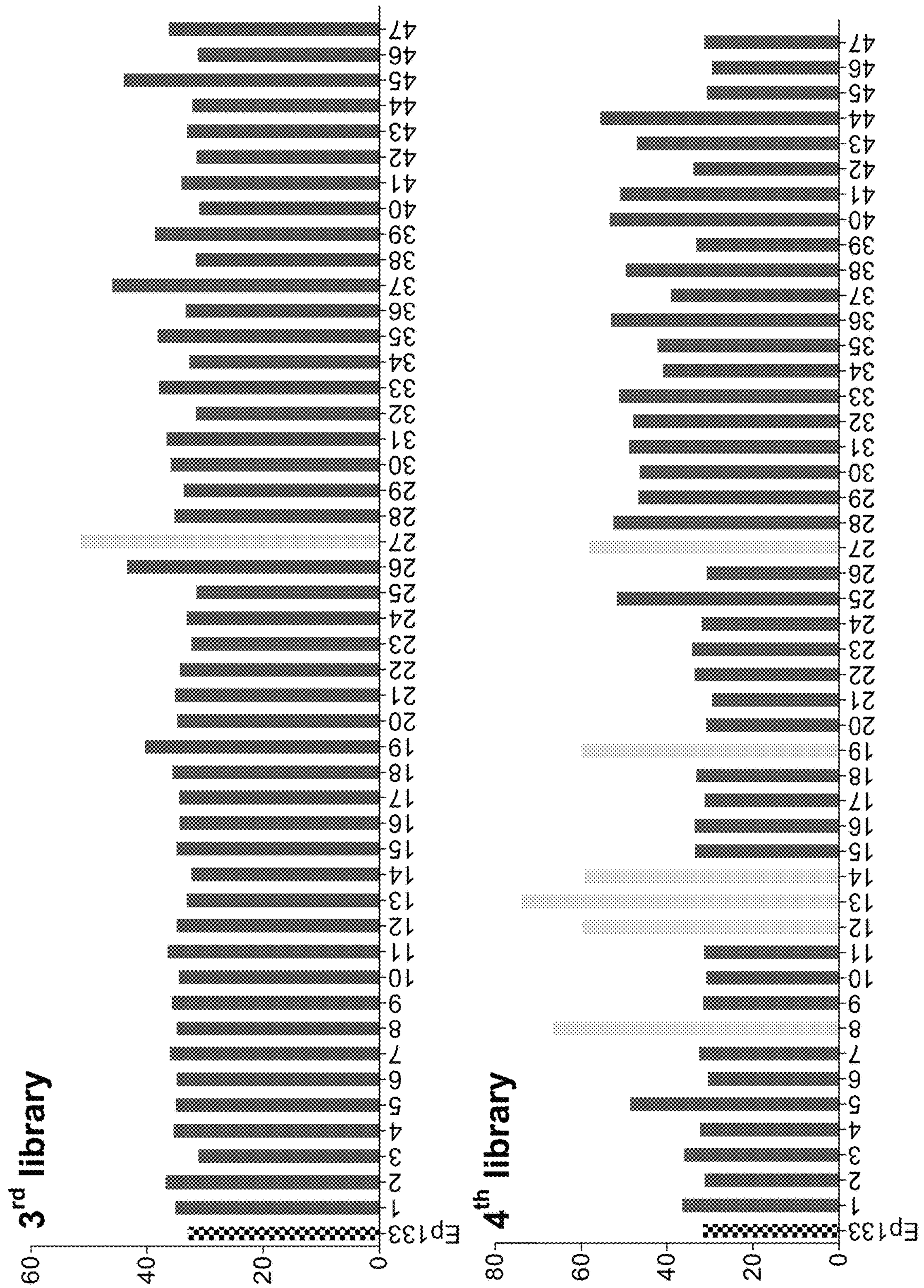

FIG. 9C: Results of FACS analysis on binding ability to EpCAM 100 nM for the analysis of the antigen binding ability for any of 47 individual clones among libraries sorted by the 3rd and 4th FACS.

Figure 10:
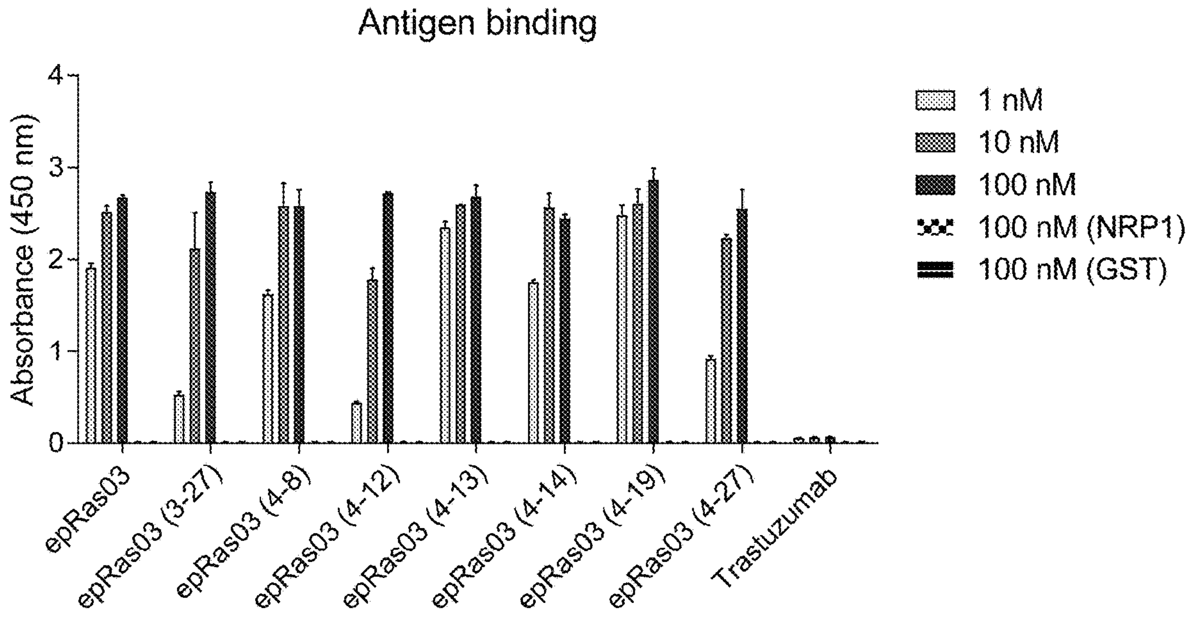

FIG. 10: ELISA analysis on binding ability between each of 1, 10, and 100 nM cyclic peptide-fused anti-Ras•GTP iMab and human recombinant EpCAM protein in order to confirm the specific binding of the affinity-enhanced EpCAM target cyclic peptide-fused anti-Ras•GTP iMabs.

Figure 11:
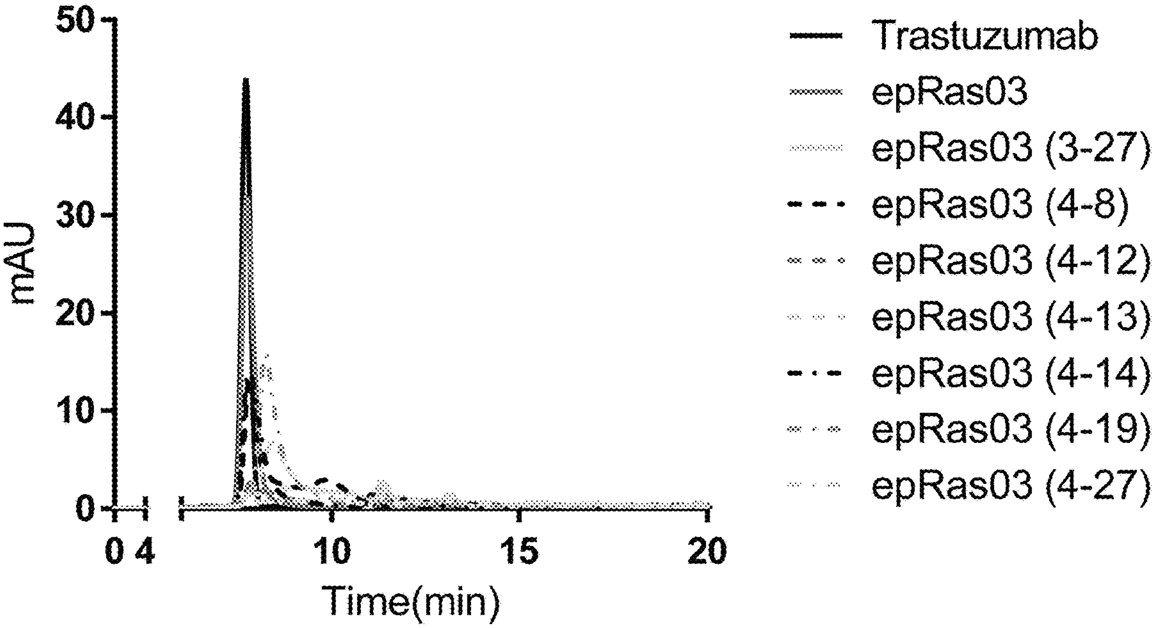

FIG. 11: Graph of illustrating the results of Zenix SEC-300 column analysis on 7 kinds of the affinity-enhanced EpCAM target cyclic peptide-fused anti-Ras•GTP iMabs constructed in Example 19, in which the results are mAU values at 280 nm obtained by Zenix SEC-300 column analysis which can evaluate the hydrophobicity of proteins using a high performance liquid chromatography.

Figure 12A:
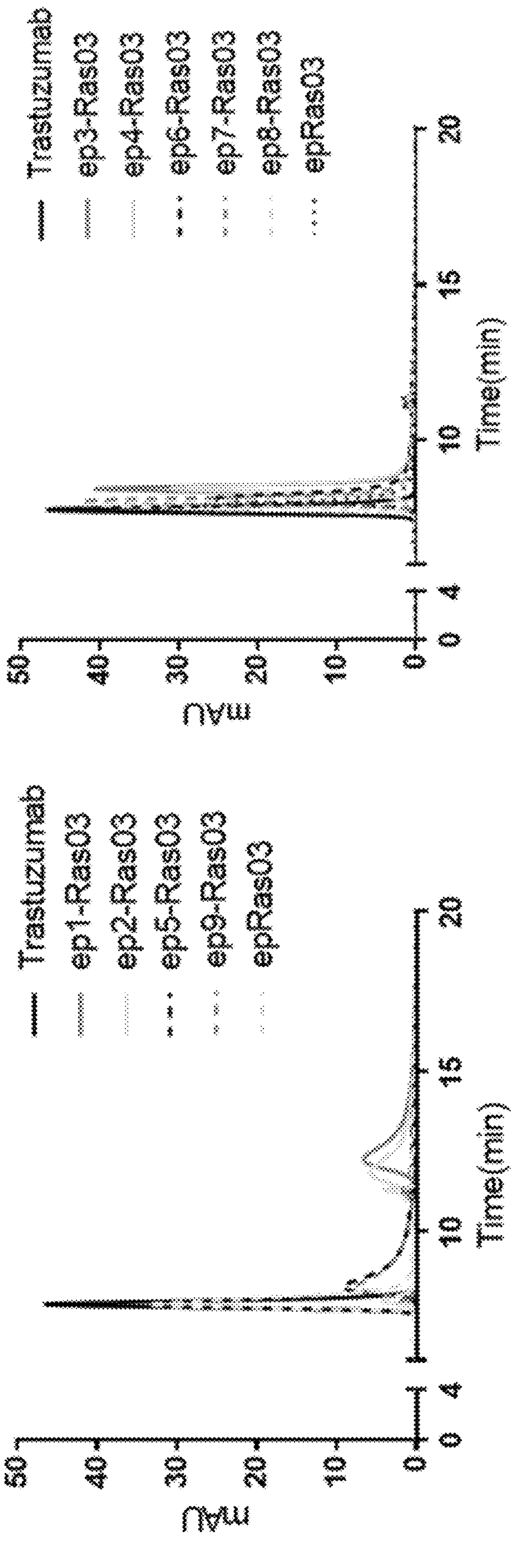

FIG. 12A: Results of Zenix SEC-300 column analysis on the affinity-enhanced EpCAM-targeting cyclic peptide-fused anti-Ras•GTP iMabs. Results are mAU values at 280 nm obtained by Zenix SEC-300 column analysis to evaluate the hydrophobicity of proteins.

Figure 12B:
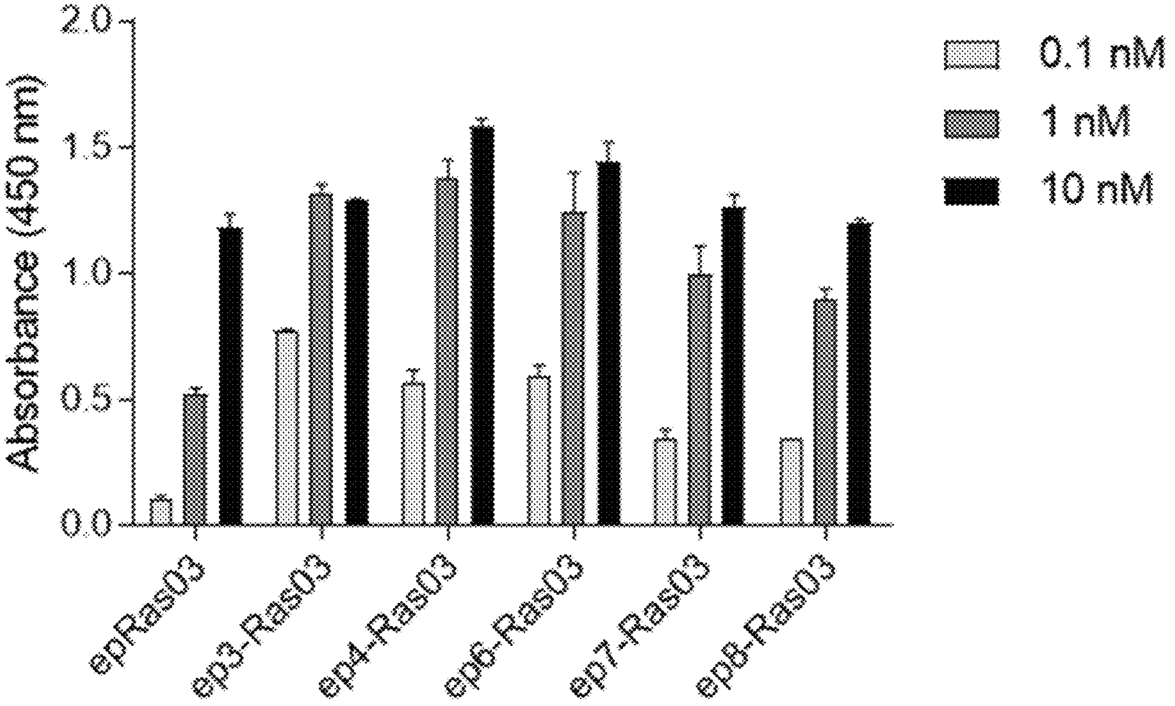

FIG. 12B: ELISA analysis of binding ability between each of 0.1, 1, and 10 nM cyclic peptide-fused anti-Ras•GTP iMab and human recombinant EpCAM protein.

Figure 12C:
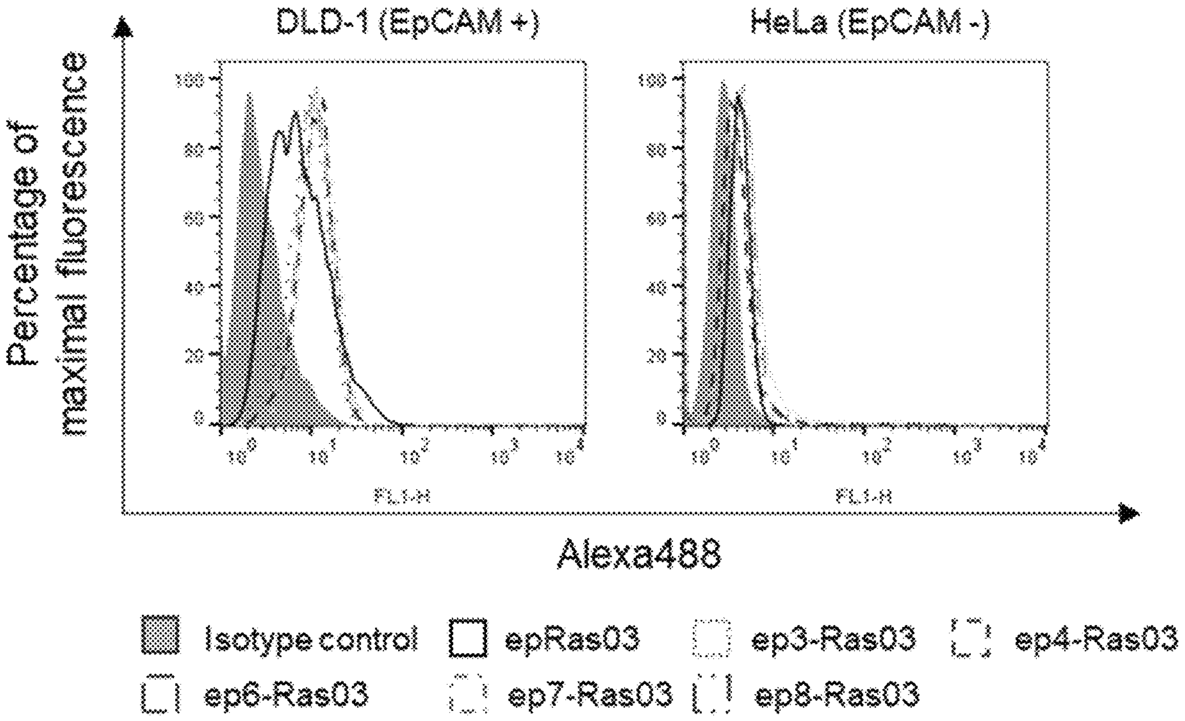

FIG. 12C: FACS analysis on the binding ability of the physical property- and affinity-enhanced EpCAM-targeting cyclic peptide-fused anti-Ras•GTP iMabs to EpCAM of the cell surface in the human colon cancer cell line DLD-1 and the human cervical cancer cell line HeLa.

Figure 13:
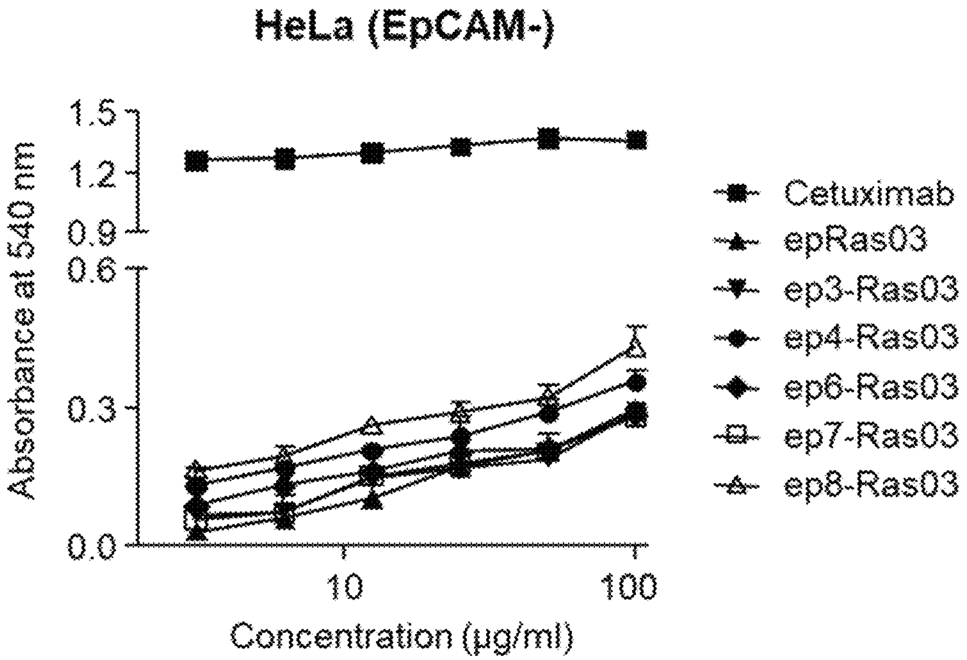

FIG. 13: ELISA analysis of non-specific cell surface binding in the HeLa cell line to confirm the non-specific binding of the physical property- and affinity-enhanced EpCAM-targeting cyclic peptide-fused anti-Ras•GTP iMab.

Figure 14:
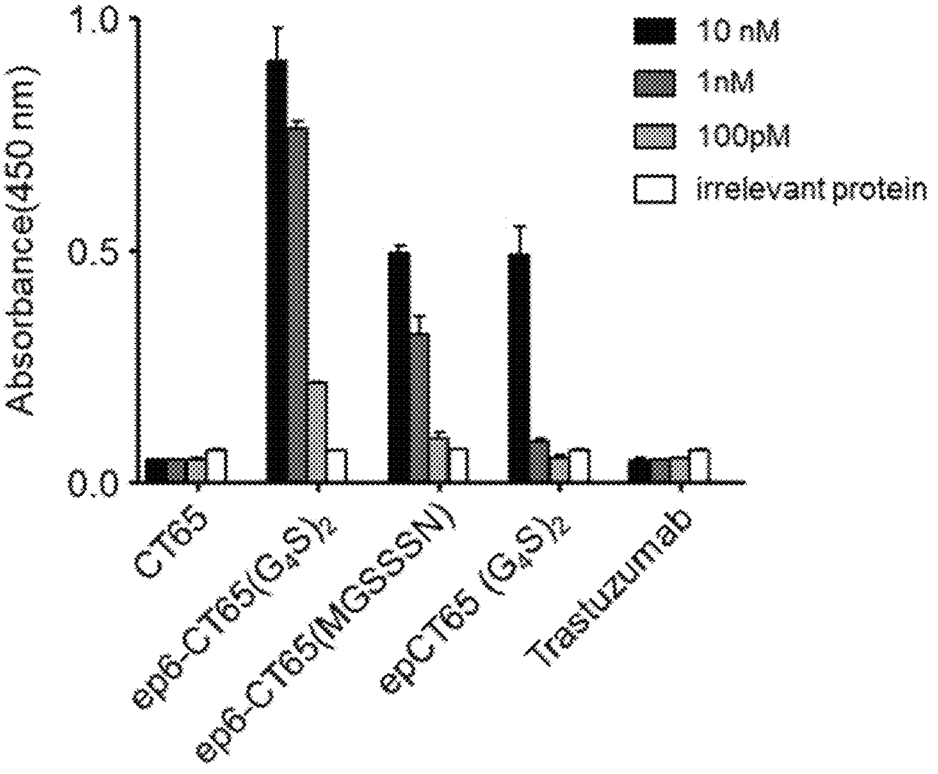

FIG. 14: ELISA analysis of binding ability between each of 0.1, 1, and 10 nM cyclic peptide-fused anti-Ras•GTP iMabs and human recombinant EpCAM protein in order to confirm the specific binding of ep6 cyclic peptide-fused cytoplasm-penetrating antibody to EpCAM.

Figure 15A:
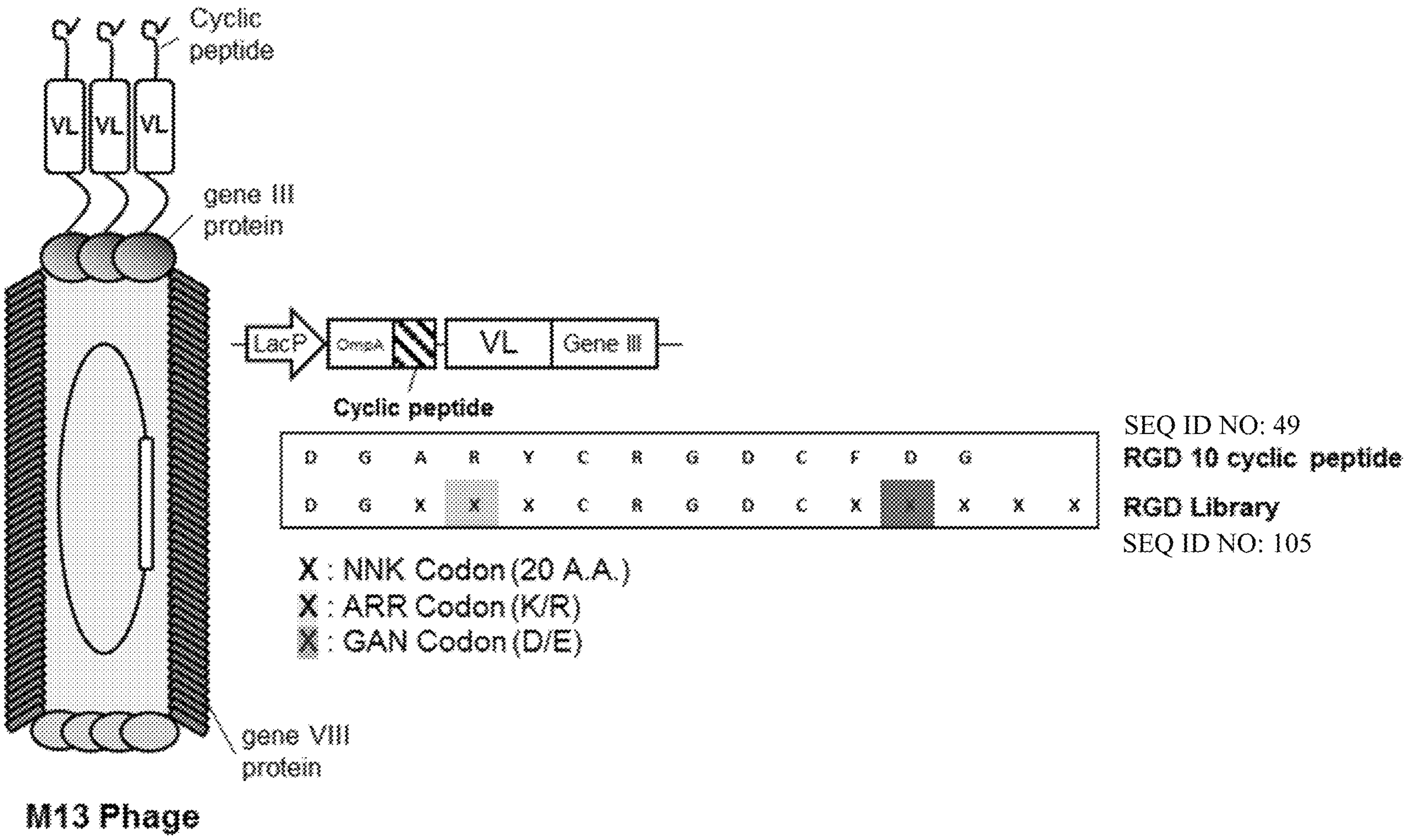

FIG. 15A: Schematic diagram illustrating a construction of an integrin αvβ5 affinity-enhanced library after the fused form of the RGD10 cyclic peptide and the light chain variable region of the cell-penetrating antibody are displayed on the M13 phage surface.

FIG. 15B: Panning procedure for screening, using a phage library, peptides specific for human integrin αvβ5 that are known to be overexpressed in tumor epithelial cells.

Figure 15C:
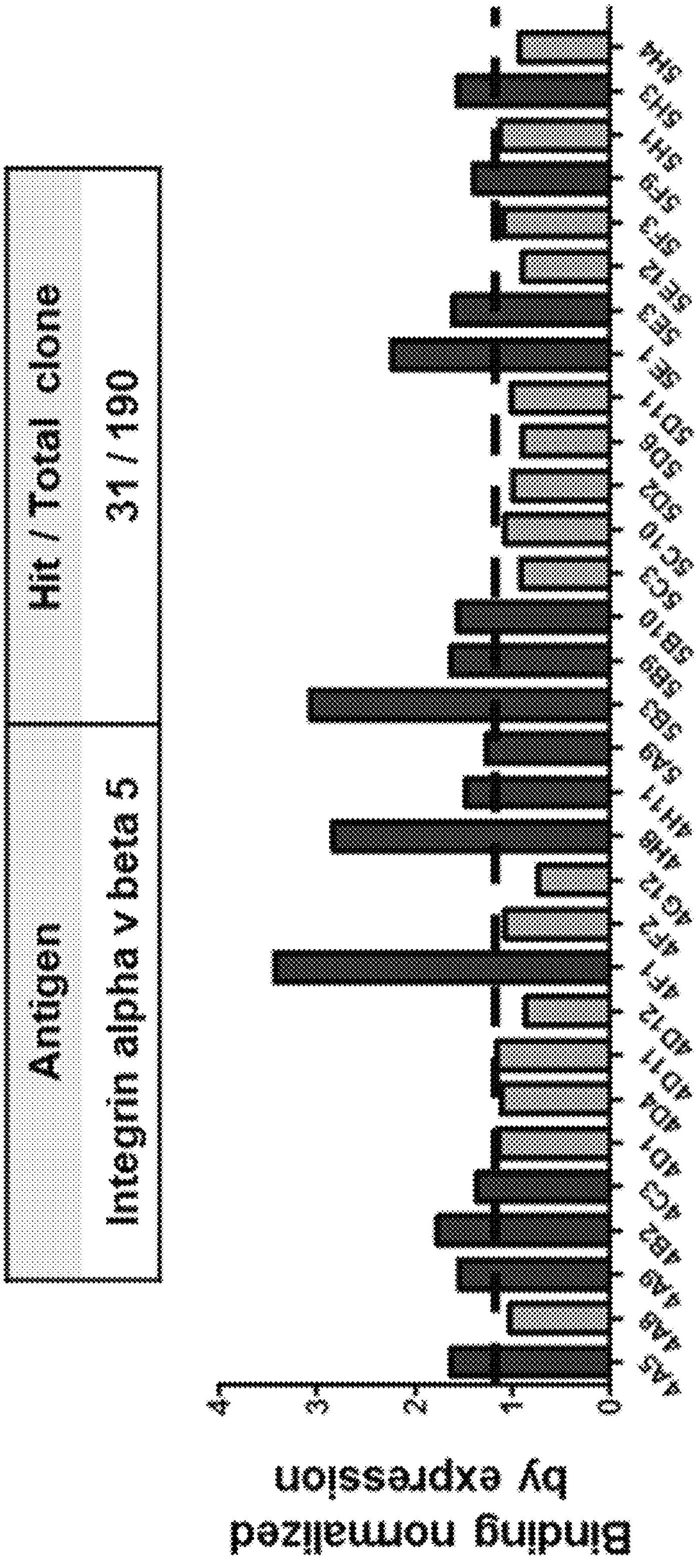

FIG. 15C: ELISA analysis of the binding ability of individual clones showing 31 binding abilities in the library up to 5th panning in FIG. 15B to the human integrin αvβ5.

Figure 16A:
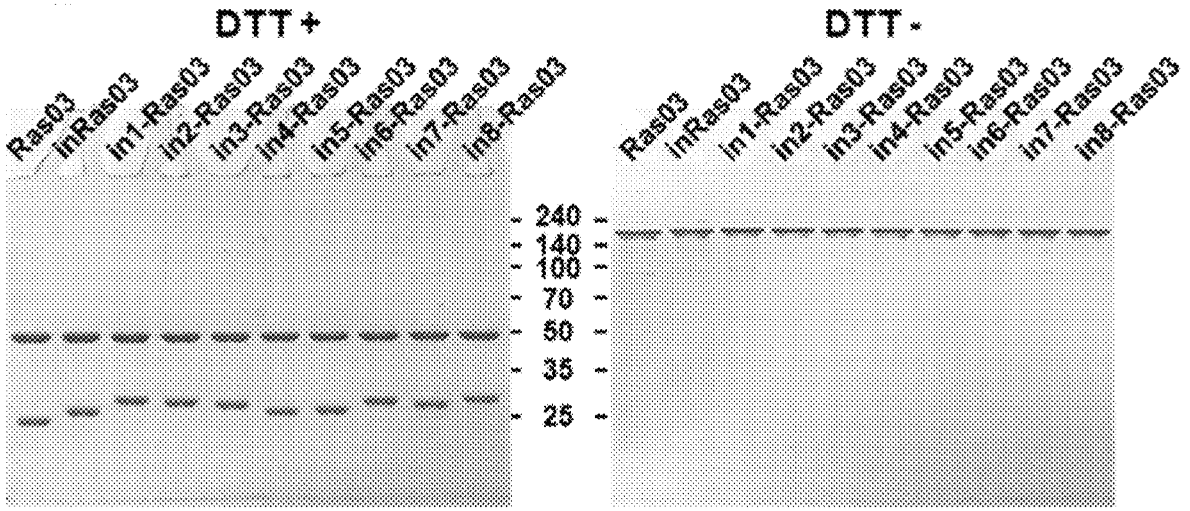

FIG. 16A: Results of 12% SDS-PAGE analysis of antibodies under reducing or non-reducing conditions. Antibodies are obtained by purifying IgG-type anti-Ras•GTP iMab antibodies, in which the affinity-enhanced cyclic peptide for the integrin αvβ5 is selected from the phage library is fused to N-terminus of the light chain.

Figure 16B:
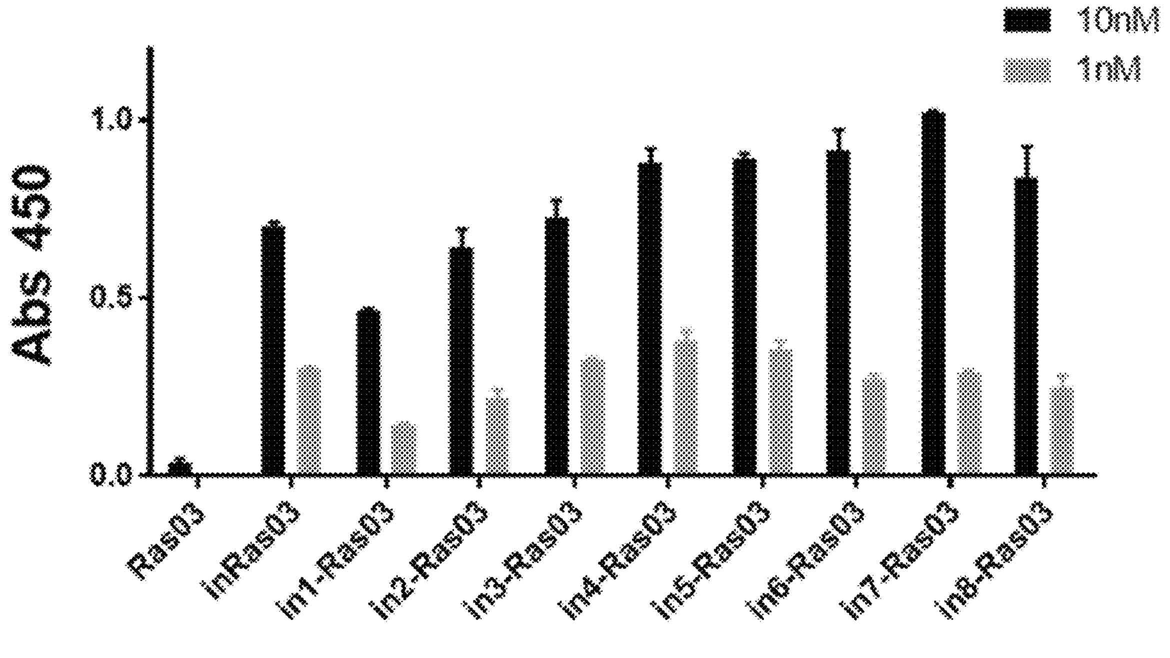

FIG. 16B: Results of ELISA analysis of the binding ability of IgG-type anti-Ras•GTP iMab antibodies, in which the affinity-enhanced cyclic peptide for the integrin αvβ5 selected from the phage library is fused to N-terminus of the light chain, to 1 nM or 10 nM of the activated integrin αvβ5.

Figure 16C:
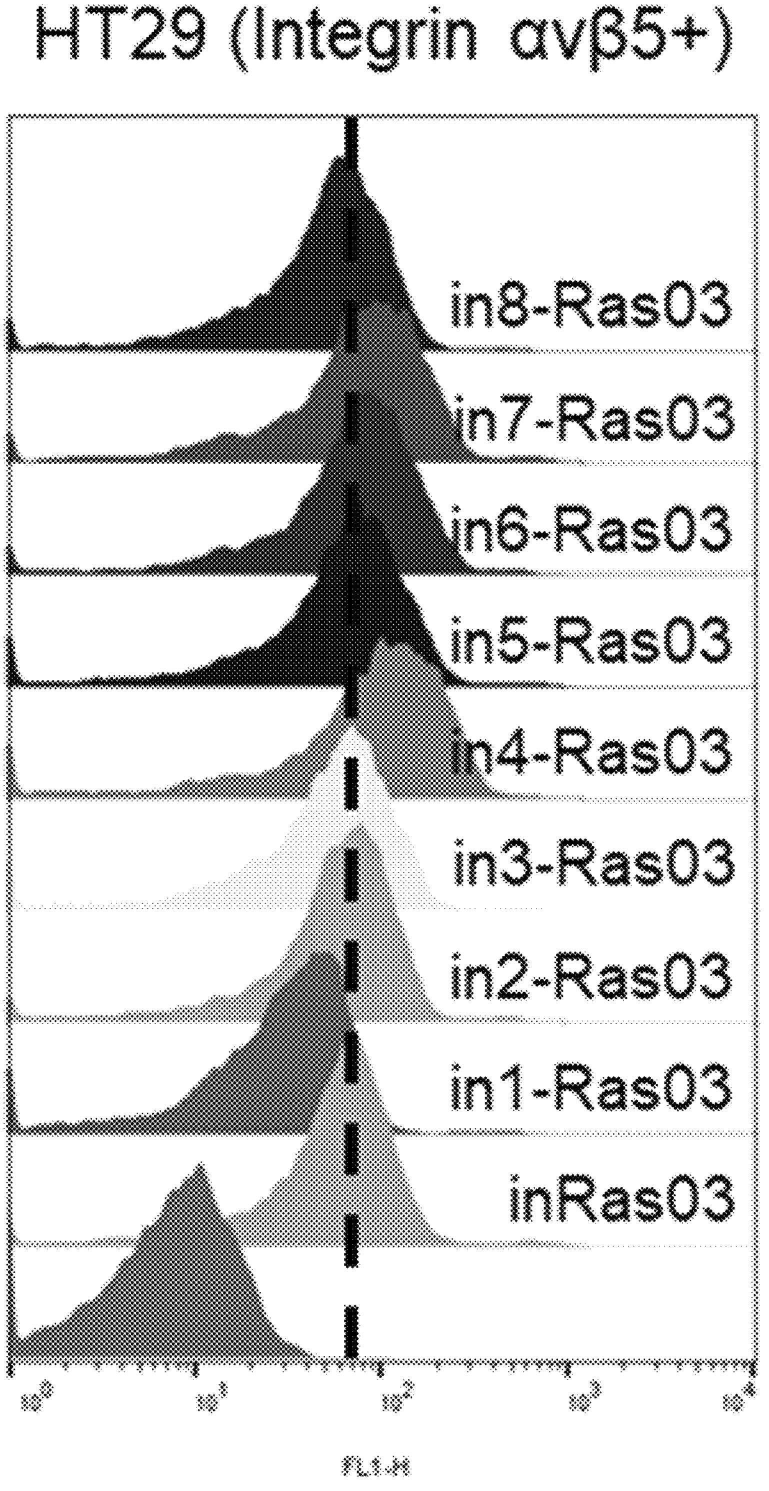

FIG. 16C: Confirmation of the binding ability of IgG-type anti-Ras•GTP iMab antibodies, in which the affinity-enhanced cyclic peptide to the integrin αvβ5 selected from the phage library is fused to N-terminus of the light chain, to the integrin αvβ5 expressed on the cell surface.

Figure 16D:
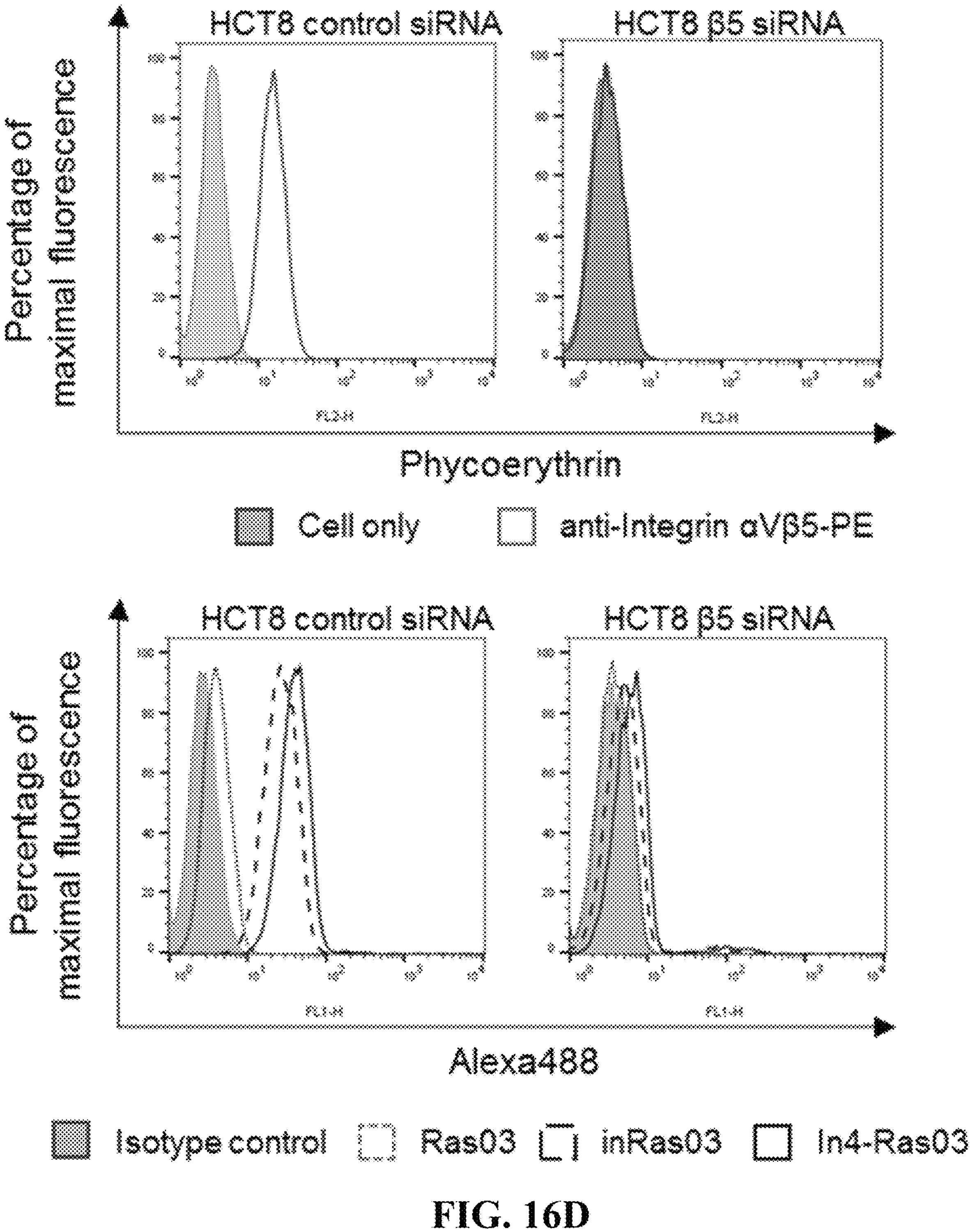

FIG. 16D: Analysis of the binding ability of each antibody, treated with short interfering RNAs (siRNAs) as a control or integrin β5 siRNAs using colorectal cancer cell line HCT8 overexpressing the integrin αvβ5 in order to confirm whether in4 cyclic peptide-fused IgG-type anti-Ras•GTP iMab antibodies specifically bind to the integrin αvβ5.

Figure 17:
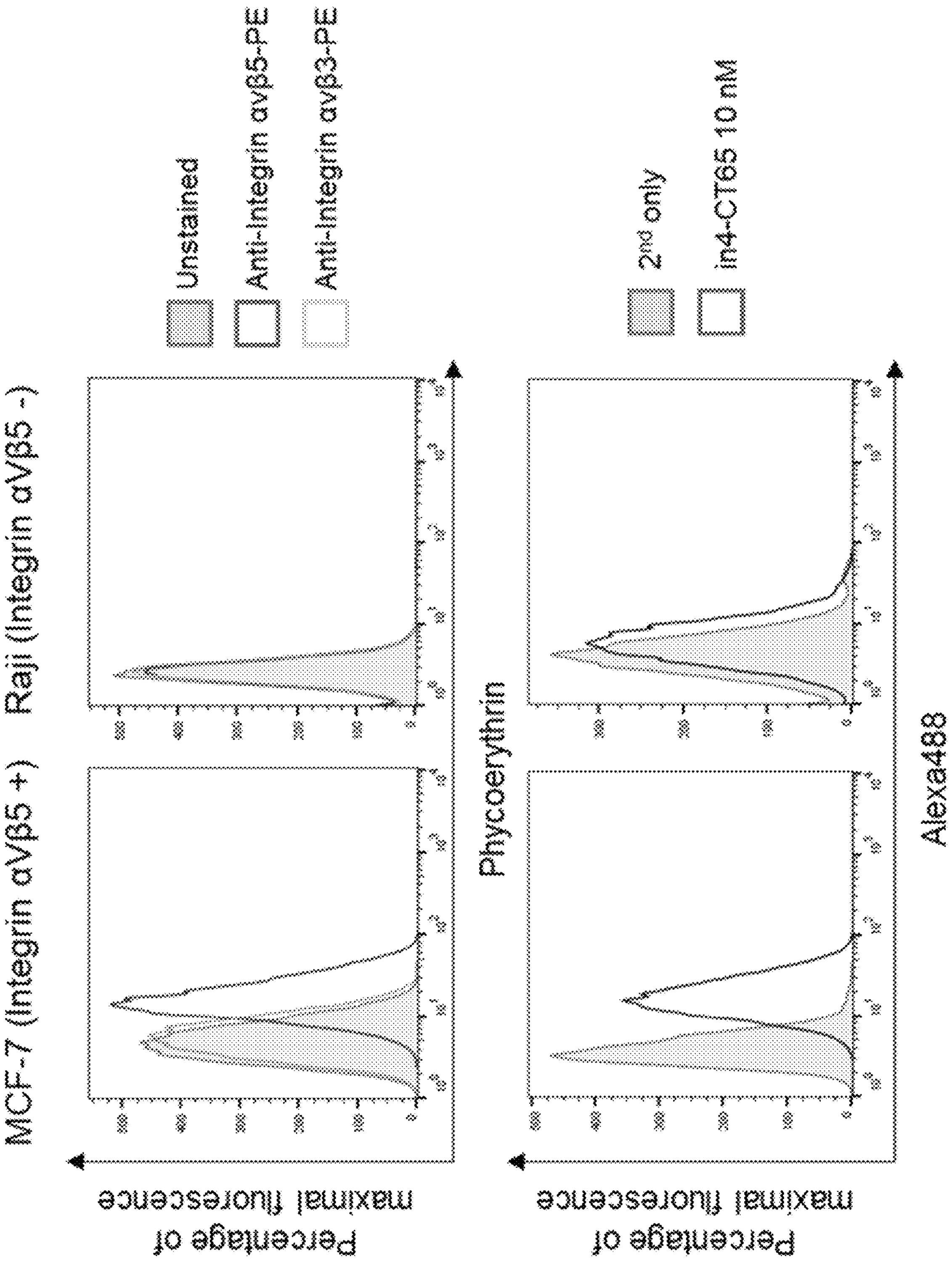

FIG. 17: Results of flow cytometry (FACS) analysis on cells obtained by treating MCF-7, a breast cancer cell line, (overexpressing integrin αvβ5) and Raji Burkitt's lymphoma cell line, (non-expressing integrin αvβ5) with 10 nM the antibody, in order to confirm the binding ability of in4 cyclic peptide-fused IgG-type cell-penetrating antibody to the integrin αvβ5 expressed on the cell.

Figure 18A:
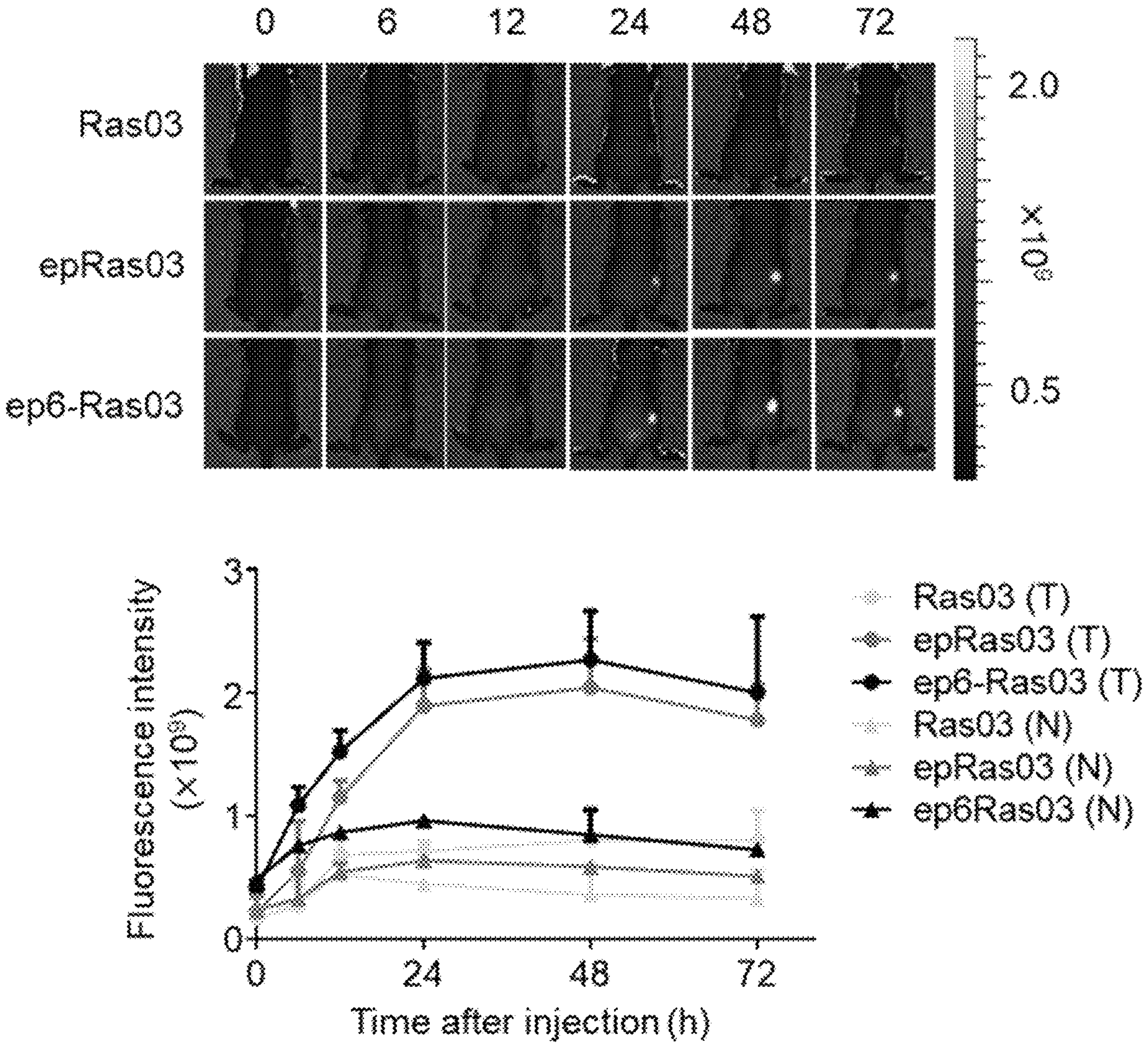

FIG. 18A: Images confirming mouse biodistribution of anti-Ras•GTP iMab ep6-RasO3 fused with the affinity-enhanced EpCAM-targeting cyclic peptide Ep6 for improving the tumor tissue targeting ability and a graph of quantifying the fluorescence of the tumor and the whole body.

Figure 18B:
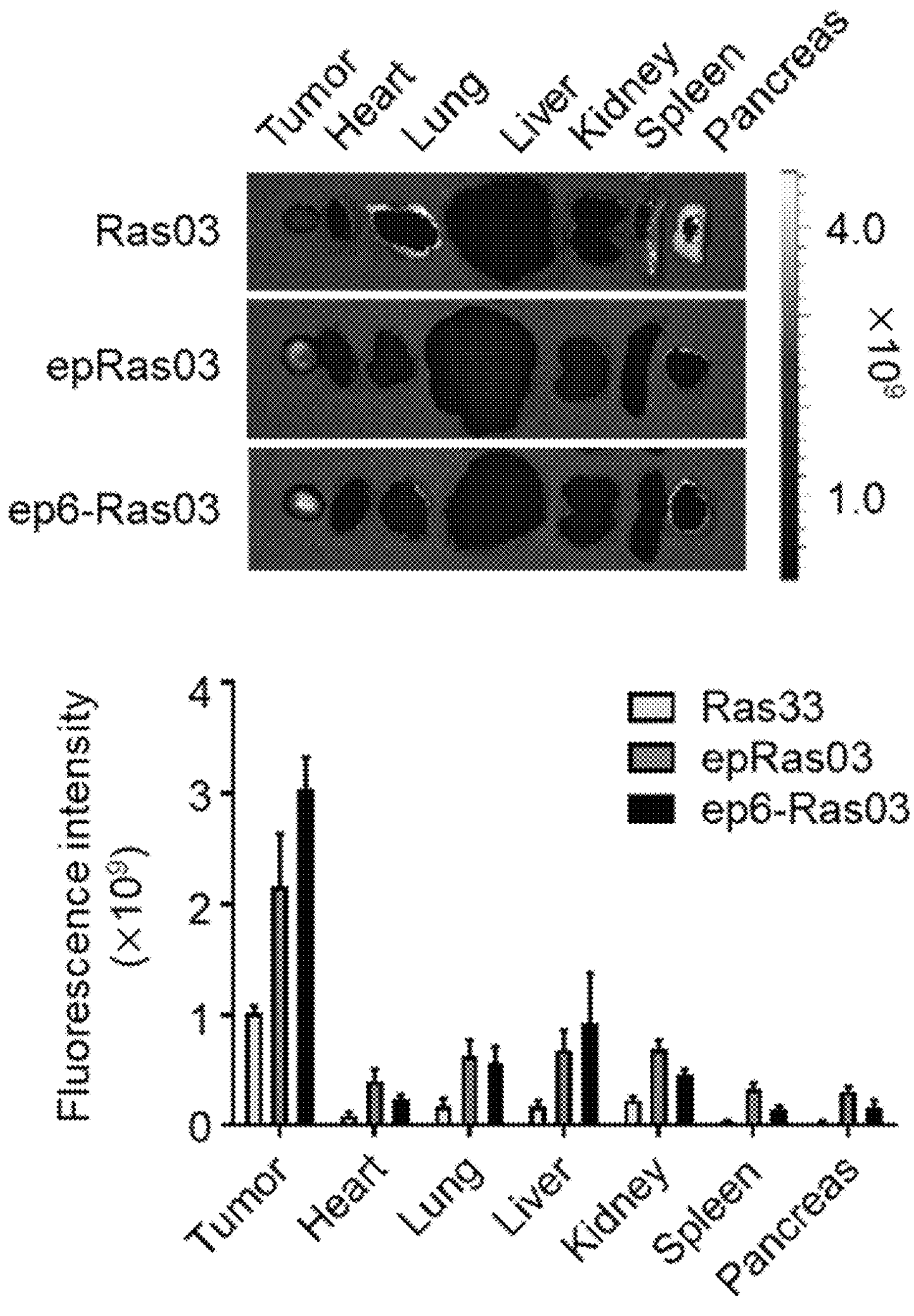

FIG. 18B: Images confirming mouse biodistribution of anti-Ras•GTP iMab ep6-RasO3 fused with the affinity-enhanced EpCAM-targeting cyclic peptide Ep6 for improving the tumor tissue targeting ability (left). Graph quantifying the fluorescence from extracted organs (right).

Figure 18C:
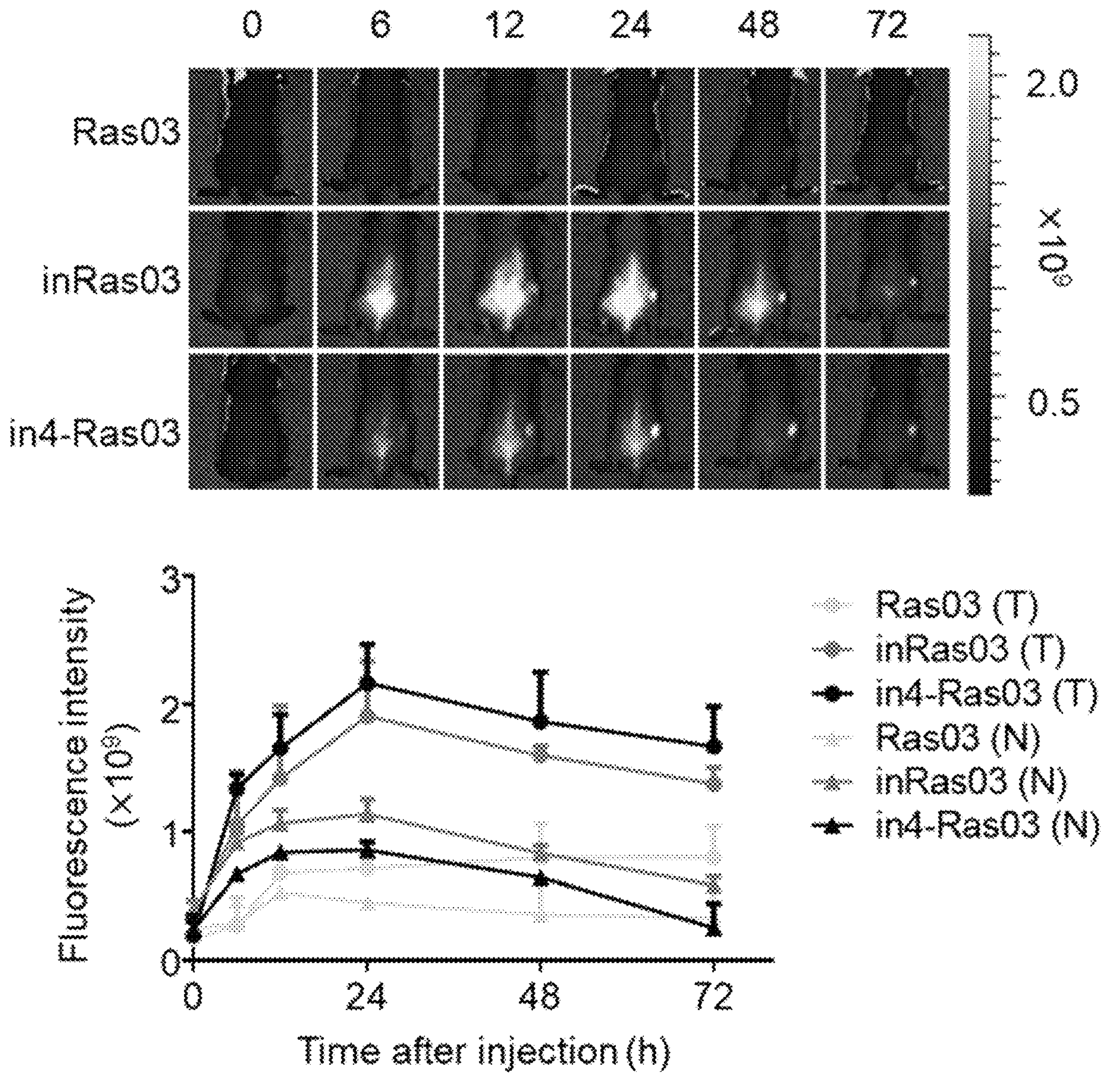

FIG. 18C: Images confirming mouse biodistribution of anti-Ras•GTP iMab in4-RasO3 fused with the affinity-enhanced integrin αvβ-target cyclic peptide in4 for improving the tumor tissue targeting ability (left). Graph quantifying the fluorescence of the tumor and the whole body (right).

Figure 18D:
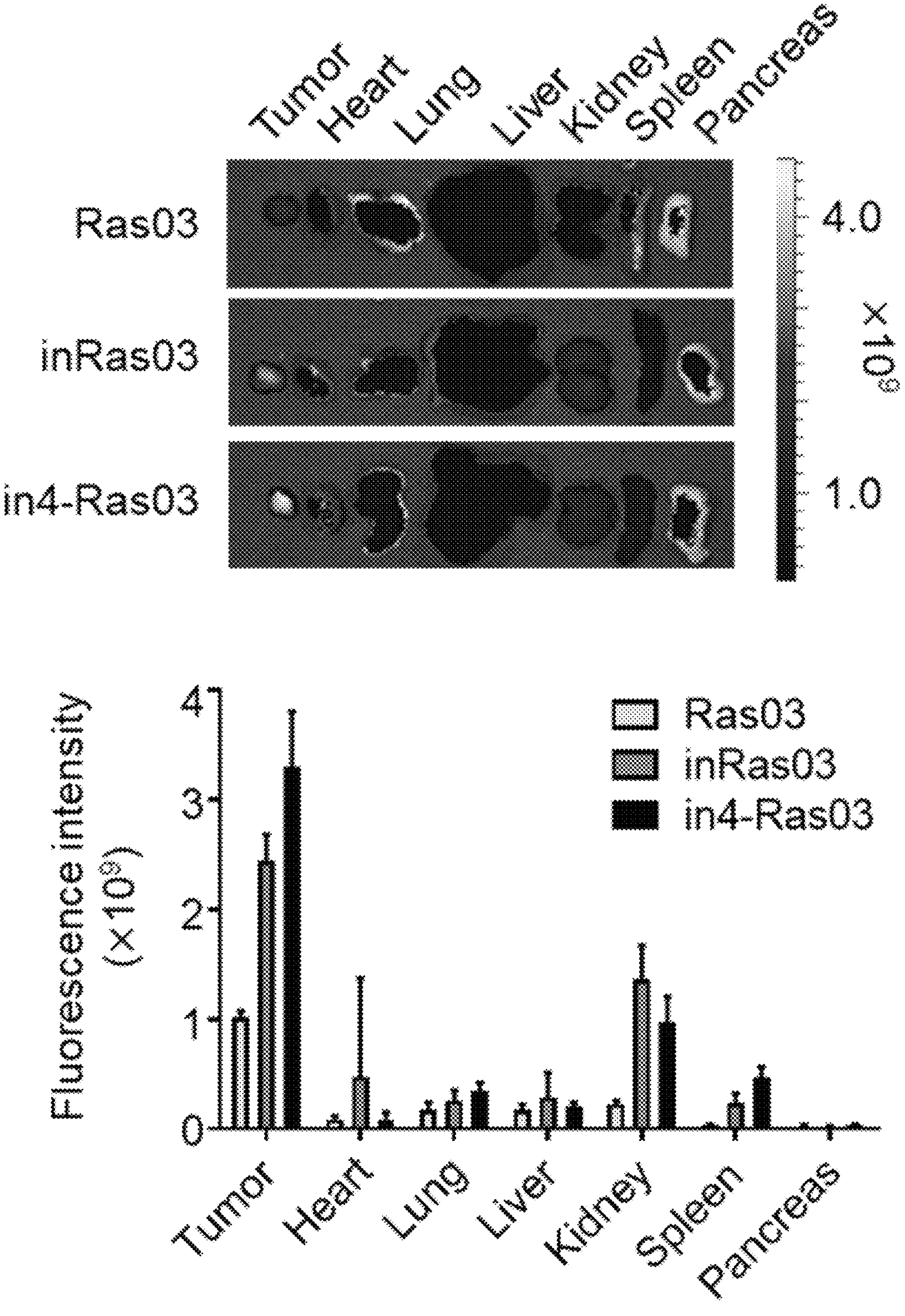

FIG. 18D: Images confirming mouse biodistribution of anti-Ras•GTP iMab in4-RasO3 fused with the affinity-enhanced integrin αvβ-targeting cyclic peptide in4 for improving the tumor tissue targeting ability (left). Graph quantifying the fluorescence from extracted organ (right).

Figure 19:
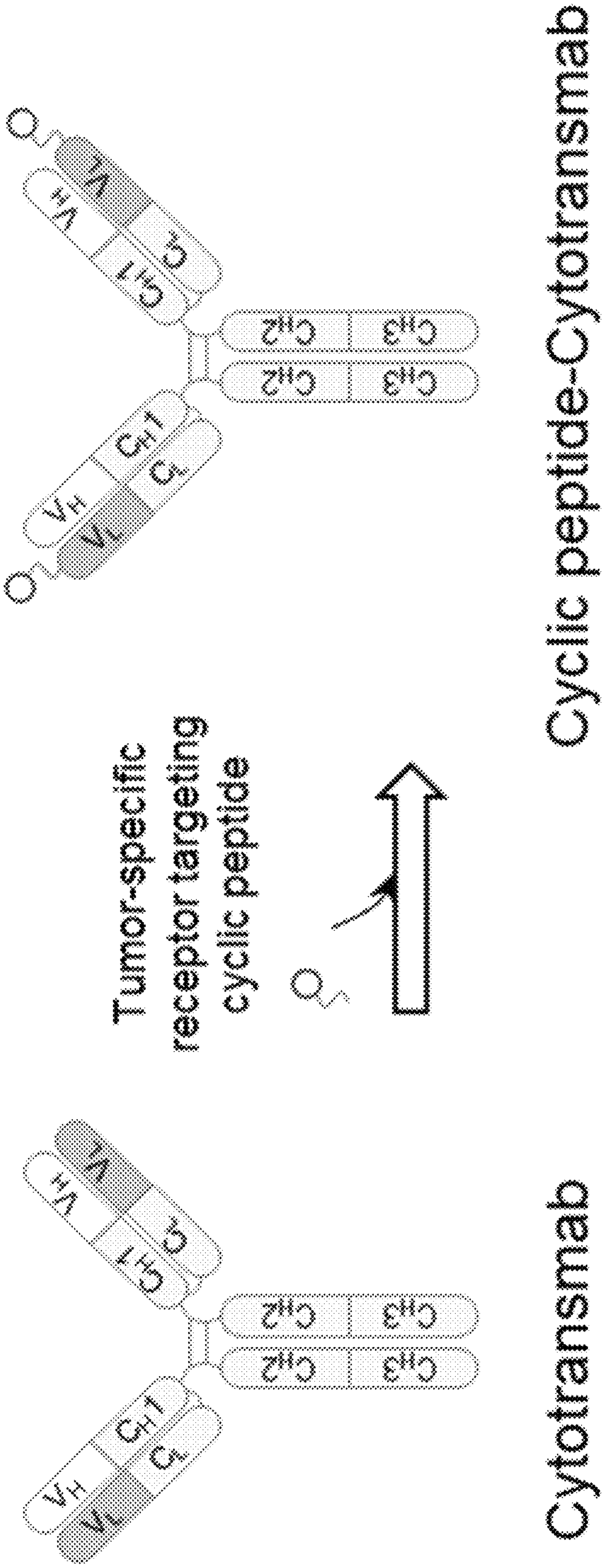

FIG. 19: Schematic diagram illustrating the structure of an antibody having a cell/tissue-specific penetrating ability by fusing the cyclic peptide to the light chain variable region (VL) of the antibody.

Figure 20:
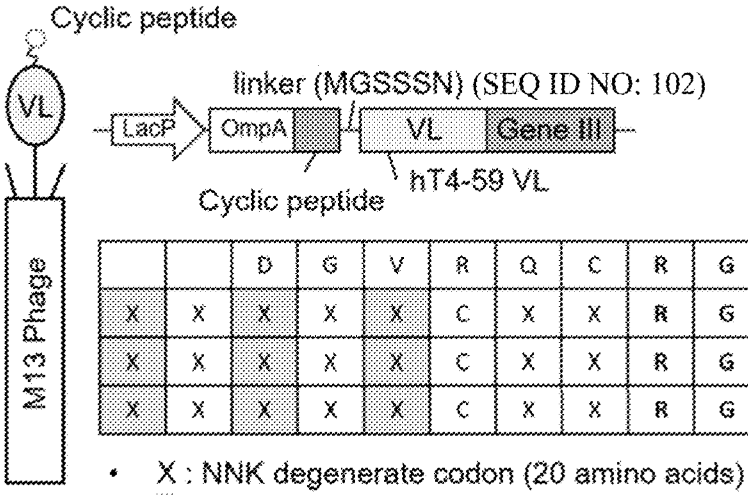

FIG. 20: Schematic representation of the in4 cyclic peptide that targets integrin αvβ5, fused to the N-terminus of the VL of the cell-penetrating antibody and displayed on the surface peptide III of M13 bacteriophage. Based on this display format, libraries were designed to screen cyclic peptides with maturated affinity for integrin αvβ5 (5#1 and 5#2 Library) and integrin αvβ6 (6# Library).

Figure 21A:
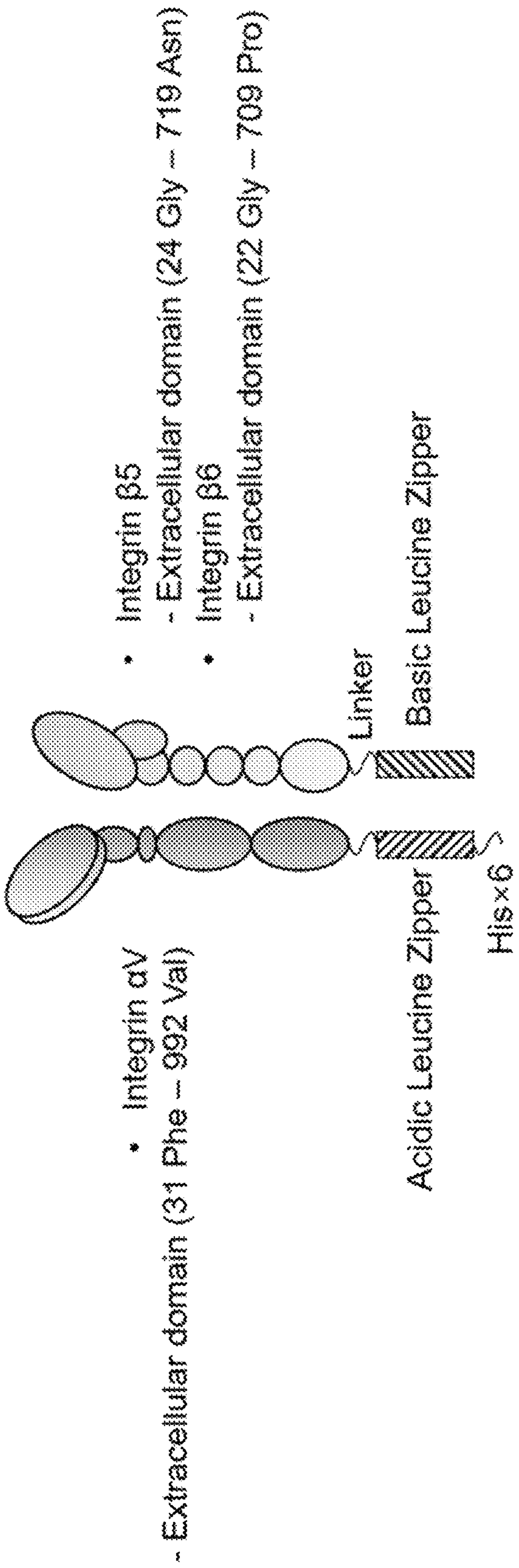

FIG. 21A: Schematic representation of a recombinant protein constructed to express integrin αvβ5 and integrin αvβ6, known to be overexpressed in tumors, in the form of heterodimers of the α chain and the β chain.

Figure 21B:
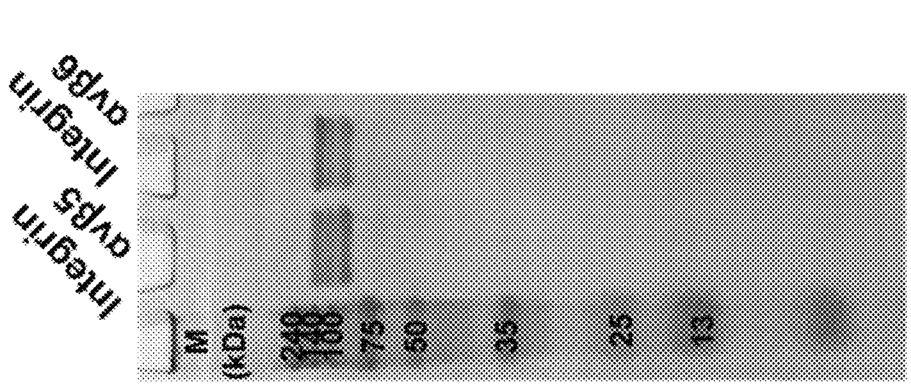

FIG. 21B: SDS-PAGE gel analysis result of the expressed human recombinant integrin antigens in 12% SDS-PAGE gel under reducing conditions.

Figure 21C:
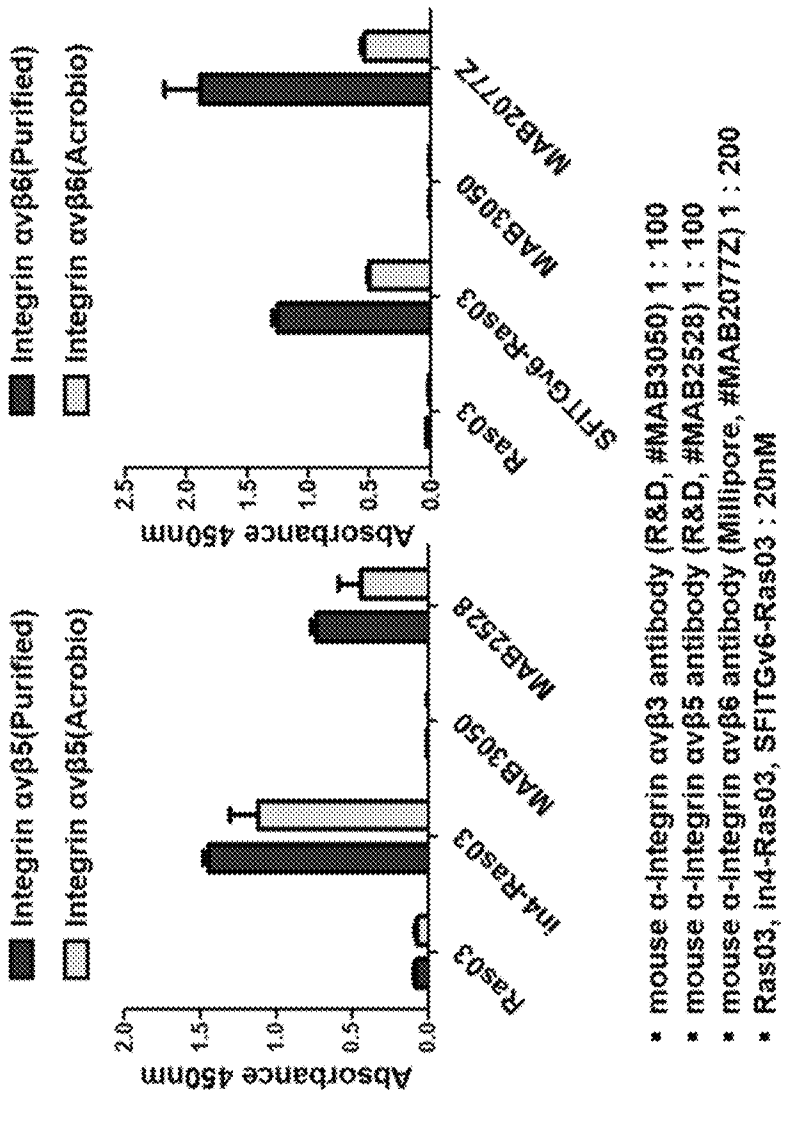

FIG. 21C: ELISA analysis of the quality of the expressed human recombinant integrin antigens, confirming the binding of the recombinant integrins to antibodies and cyclic peptides that are known to bind to human integrin αvβ5 and integrin αvβ6.

Figure 22A:
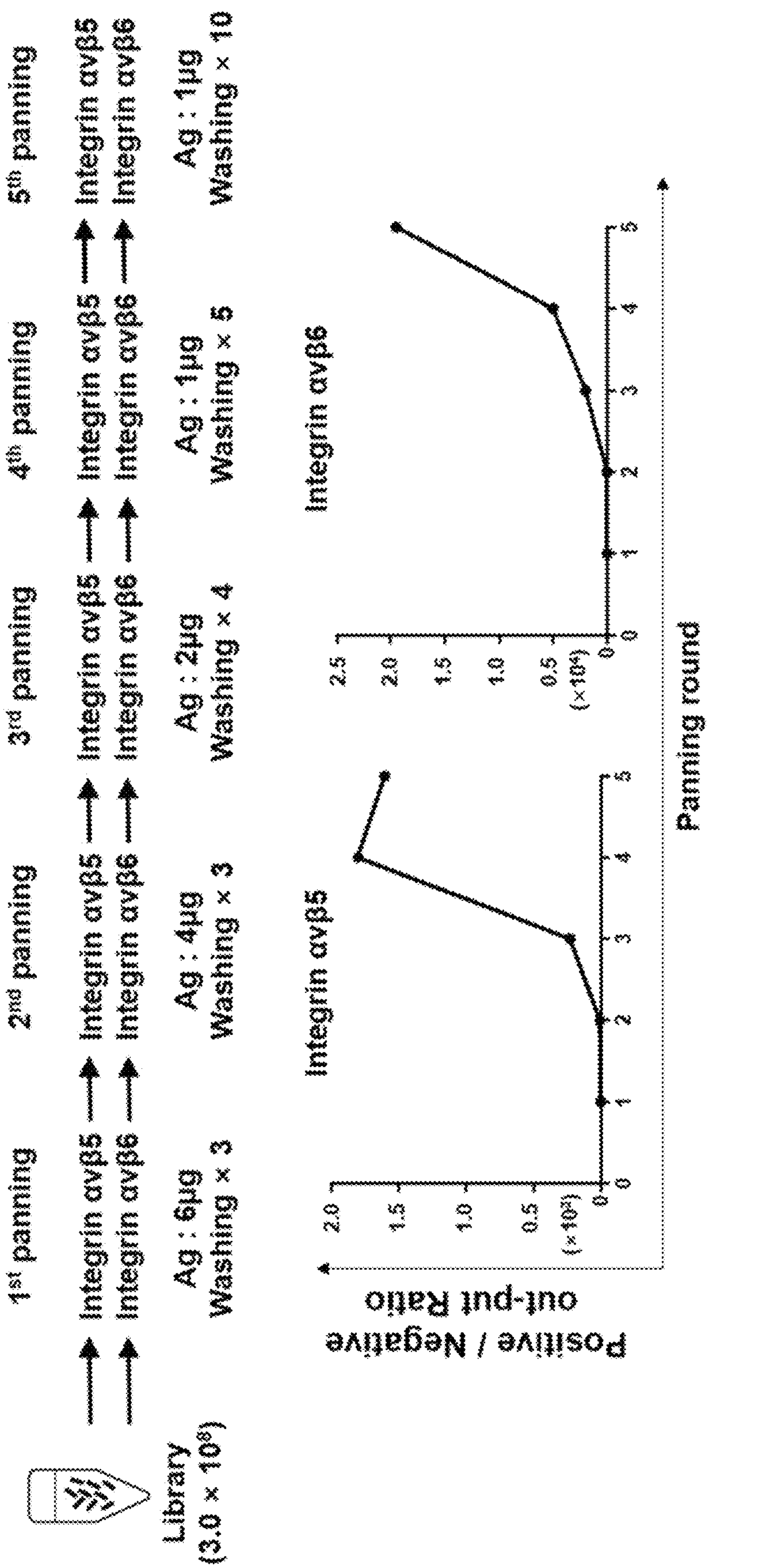

FIG. 22A: Schematic representation of panning procedure for screening of the library constructed in FIG. 20 for integrins αvβ5 and αvβ6. For each panning round, the output of bacteriophage is compared with the output of bacteriophage bound to the empty tube without antigen, and after the $5^{th}$ round of panning, phages that binds to integrins have been enriched.

Figure 22B:
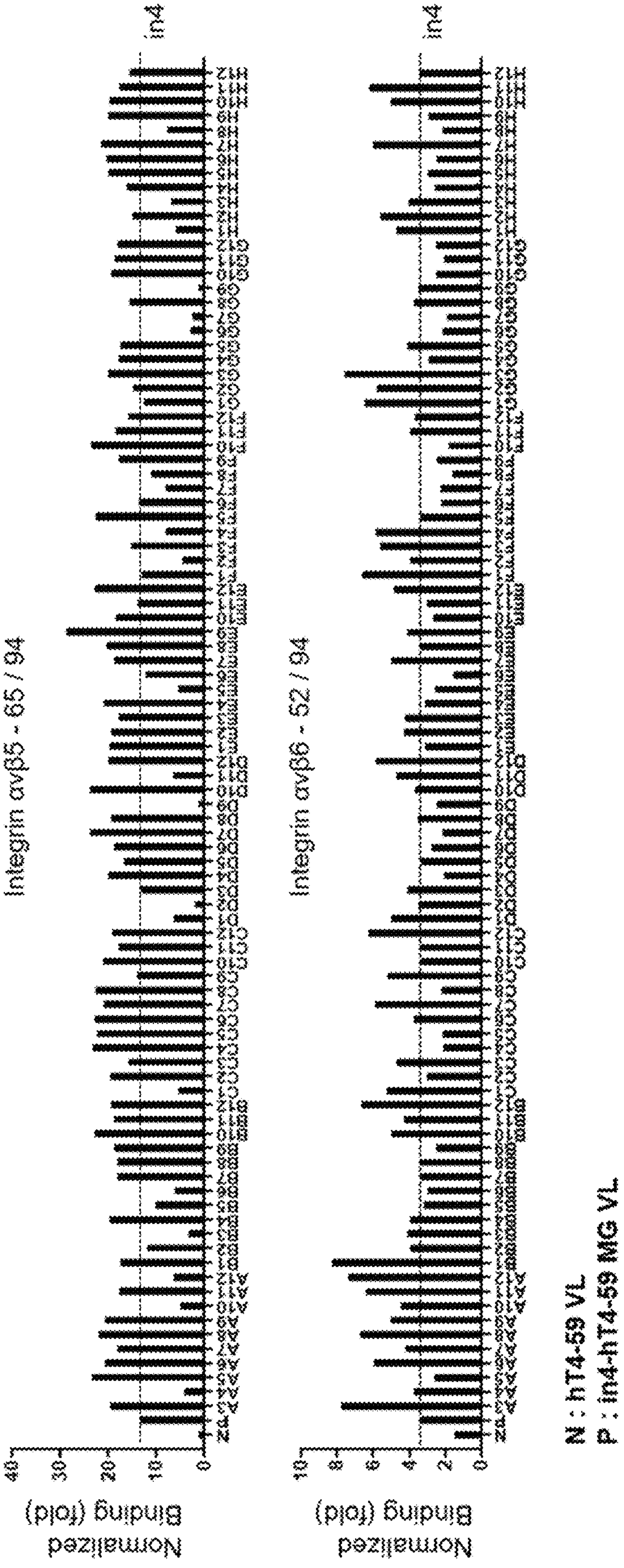

FIG. 22B: ELISA analysis showing the results of single clone study measuring the affinity of individual clones of the library to recombinant human integrin αvβ5 and αvβ6, after five rounds of panning as shown in FIG. 22A.

Figure 23:
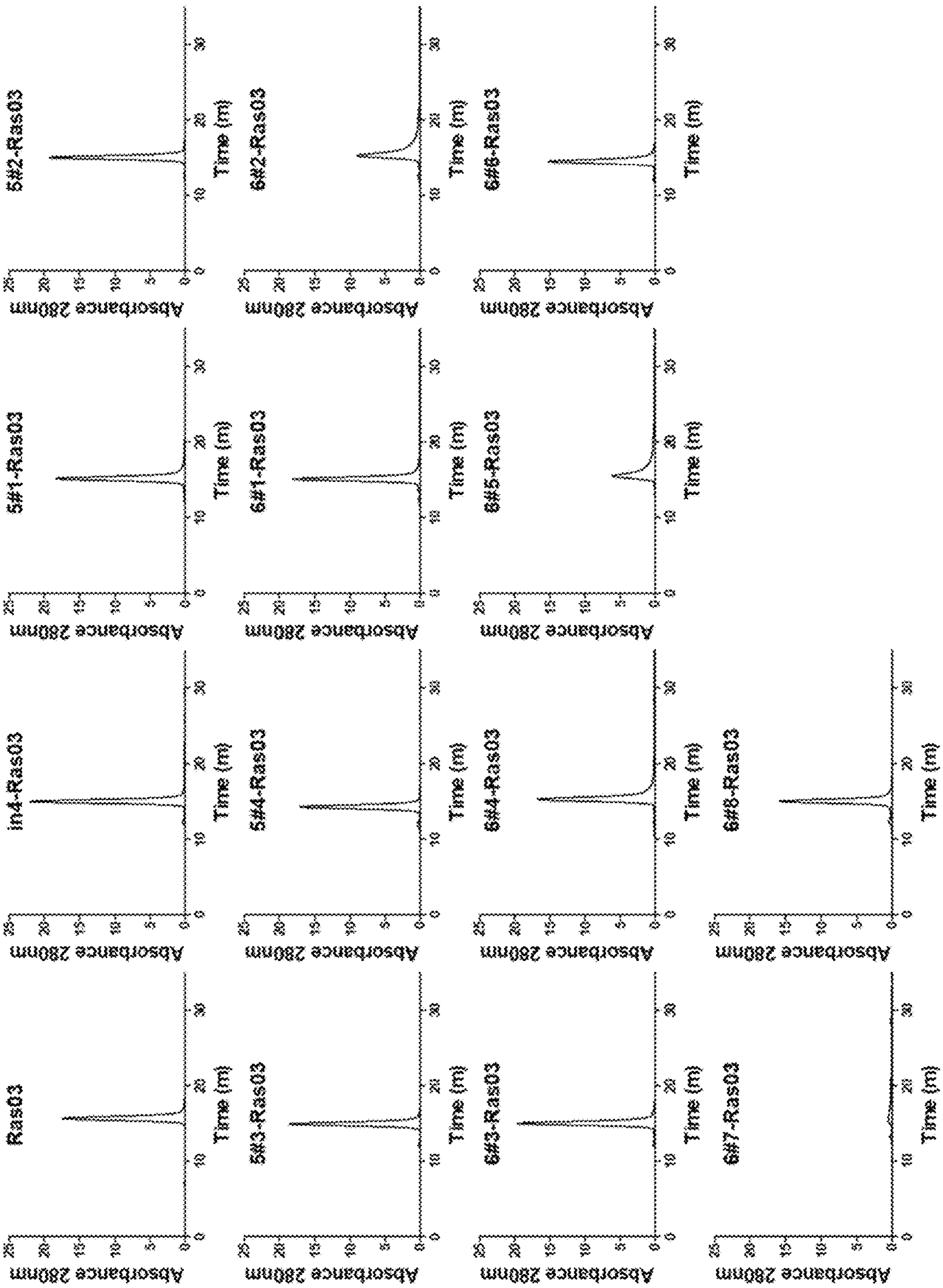

FIG. 23: Results of high performance liquid chromatography (HPLC) analysis showing SEC elution profiles on a Superdex column to confirm the presence of a monomeric cell penetrating antibody in which affinity maturated cyclic peptides selected from phage library to target integrin αvβ5 and αvβ6 were fused to light chain N-terminus of IgG-type anti-Ras•GTP iMab Ras03. The purified antibodies fused with cyclic peptides were injected in 10 μL sample volume at 1.0 mg/mL concentration, and were monitored at 280 nm.

Figure 24:
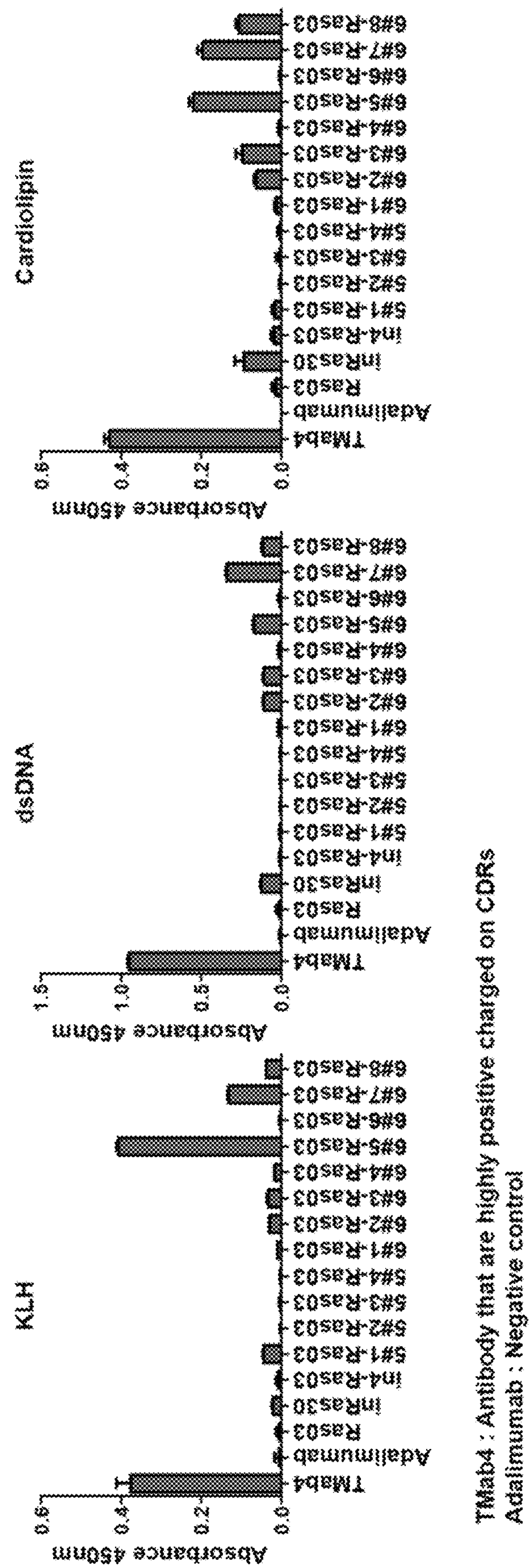

FIG. 24: ELISA analysis measuring non-specific binding of IgG-type anti-Ras-GTP iMab antibodies fused with affinity maturated integrin αvβ5 and αvβ6-targeting cyclic peptides against three antigens (dsDNA, cardiolipin, KLH) at a concentration of 500 nM.

Figure 25:
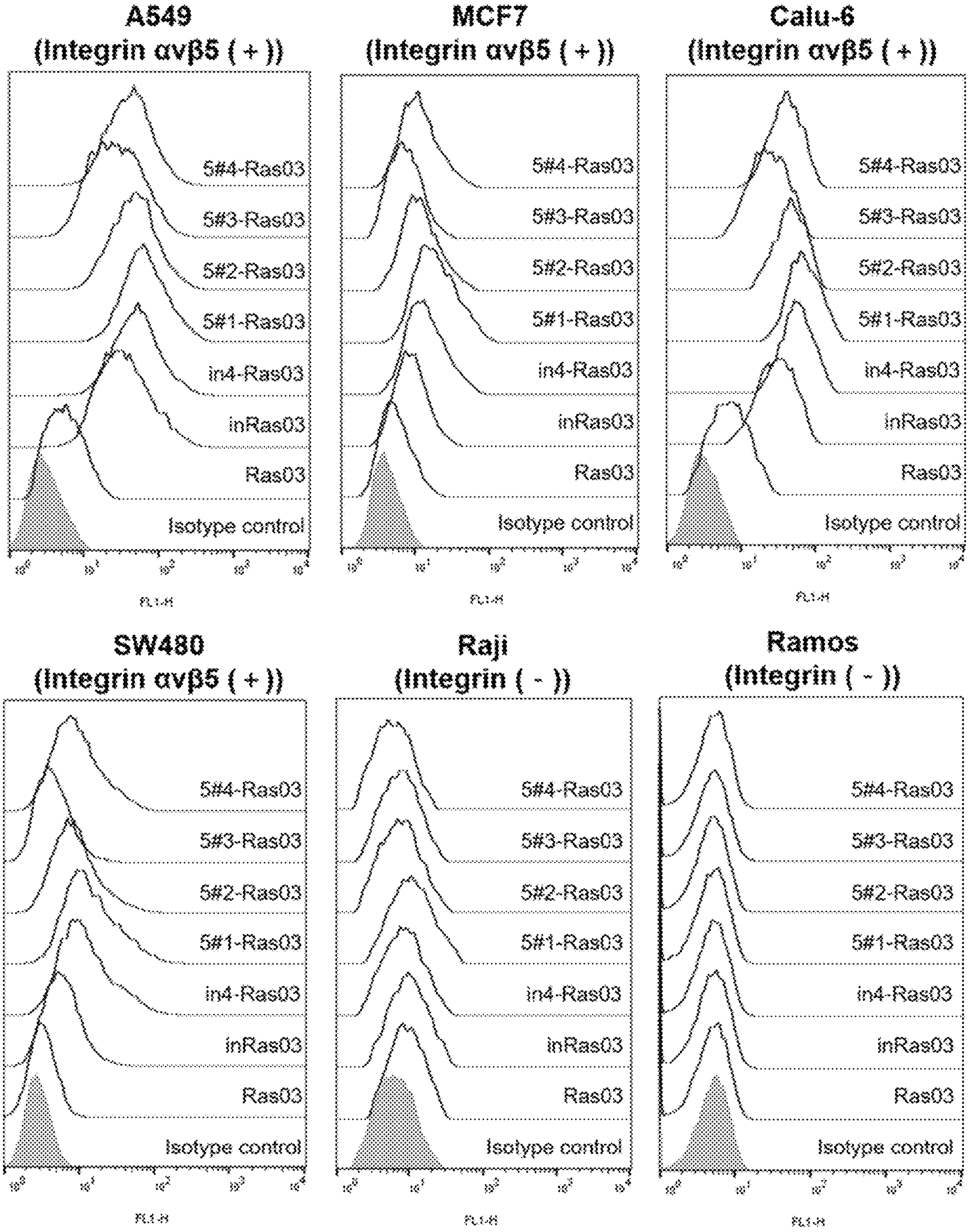

FIG. 25: FACS analysis measuring the binding ability of affinity maturated integrin αvβ5-targeting cyclic peptides fused with anti-Ras-GTP iMab, at a concentration of 20 nM, against four types of cell lines (A549, MCF7, Calu-6) that overexpress integrin αvβ5 and against two types of cell lines (Raji, Ramos) that do not express integrin.

Figure 26A:
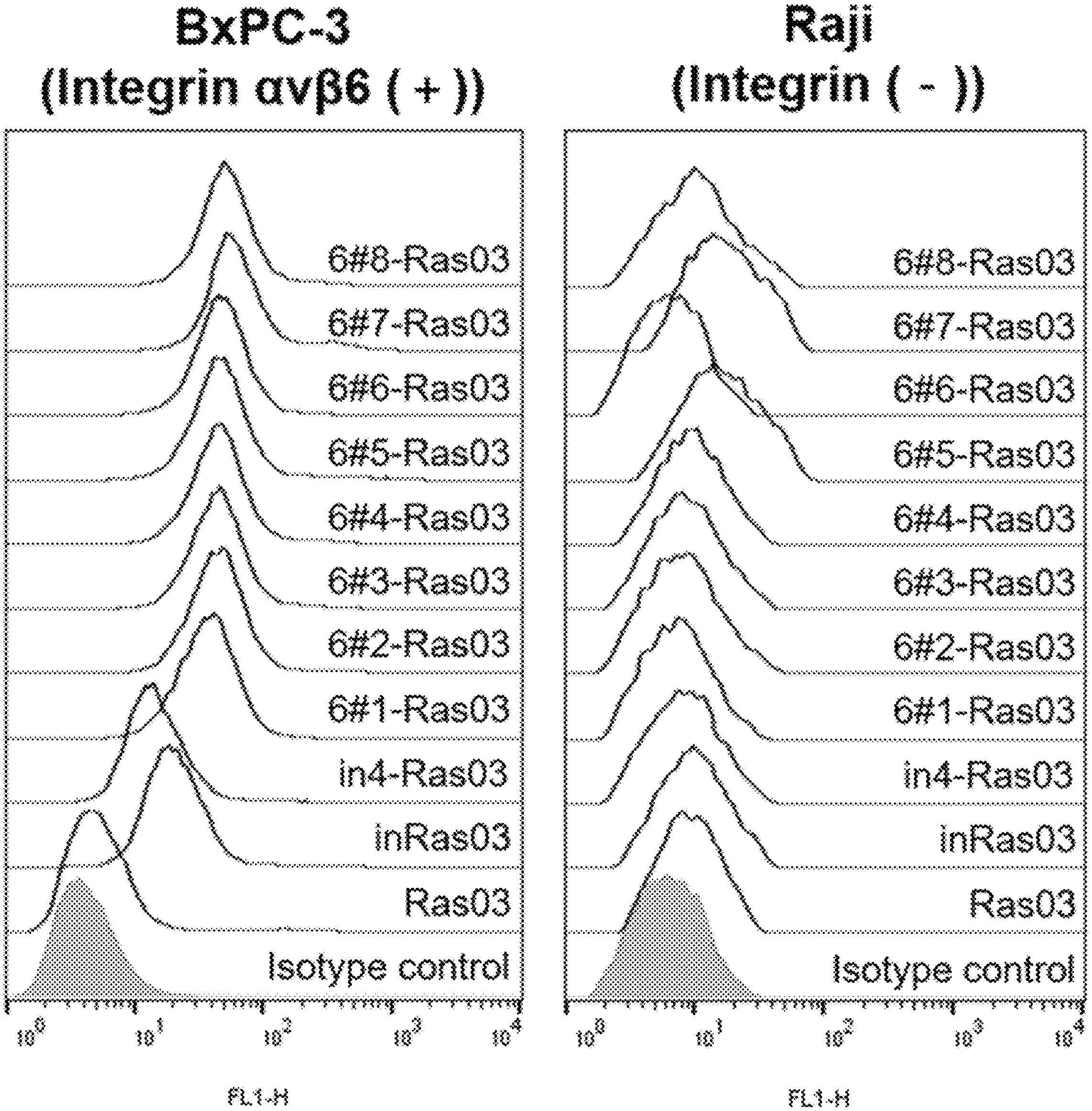

FIG. 26A: FACS analysis measuring the binding ability of affinity maturated integrin αvβ6-targeting cyclic peptides fused with anti-Ras GTP iMab, at a concentration of 20 nM, against the BxPC-3 cell line that overexpresses integrin αvβ6 and the Raji cell line that does not express integrin.

Figure 26B:
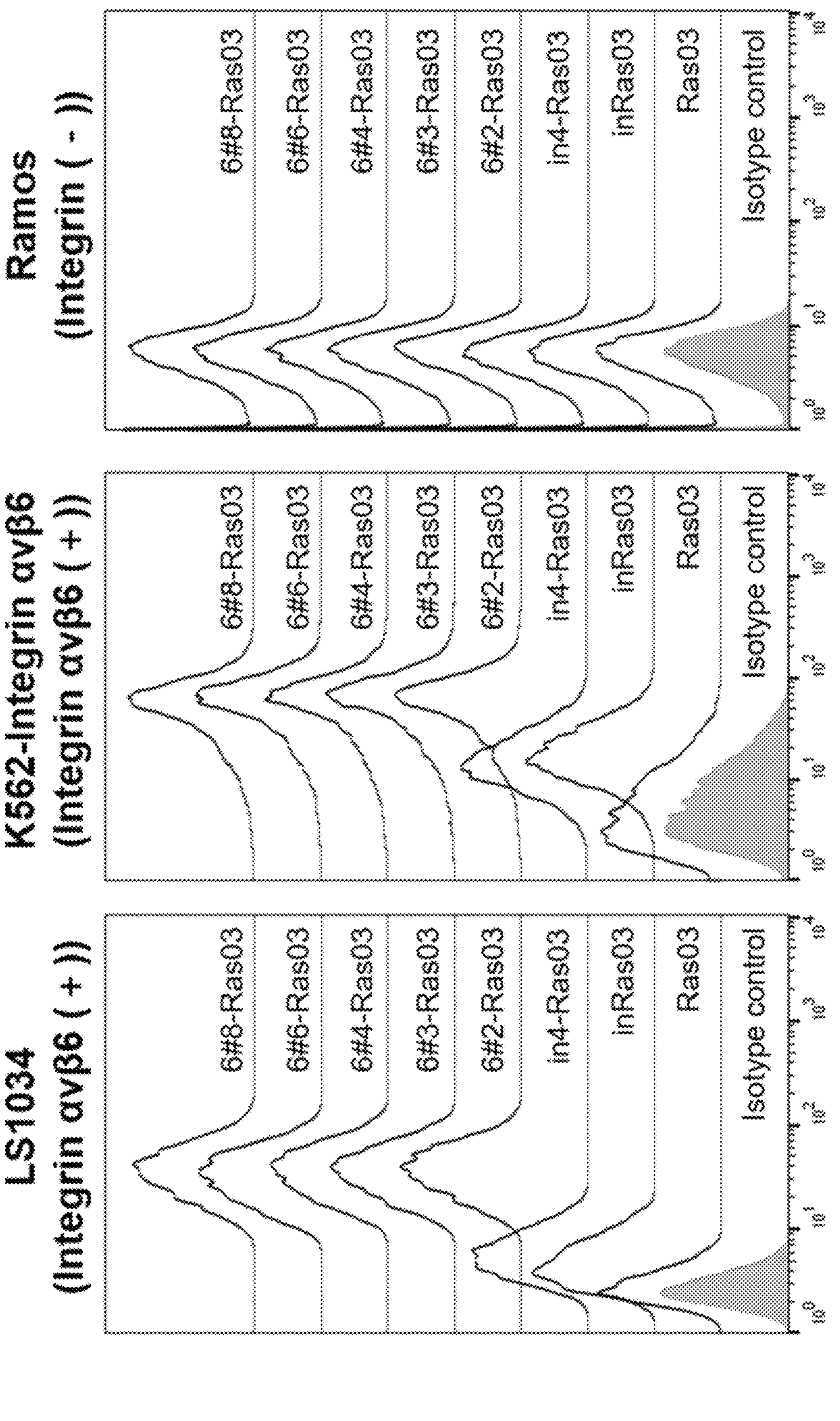

FIG. 26B: FACS analysis measuring the binding ability of five affinity maturated integrin αvβ6-targeting cyclic peptides, excluding one cyclic peptide predicted to have low binding affinity to integrin αvβ6 (6#1) and two cyclic peptides predicted to have non-specific binding (6#5, 6#7), fused with anti-Ras•GTP iMab, at a concentration of 20 nM, against LS1034 cell line that overexpresses integrin αvβ6, K562 cell line that stably overexpresses integrin αvβ6, and Ramos cell line that does not express integrin.

Figure 27:
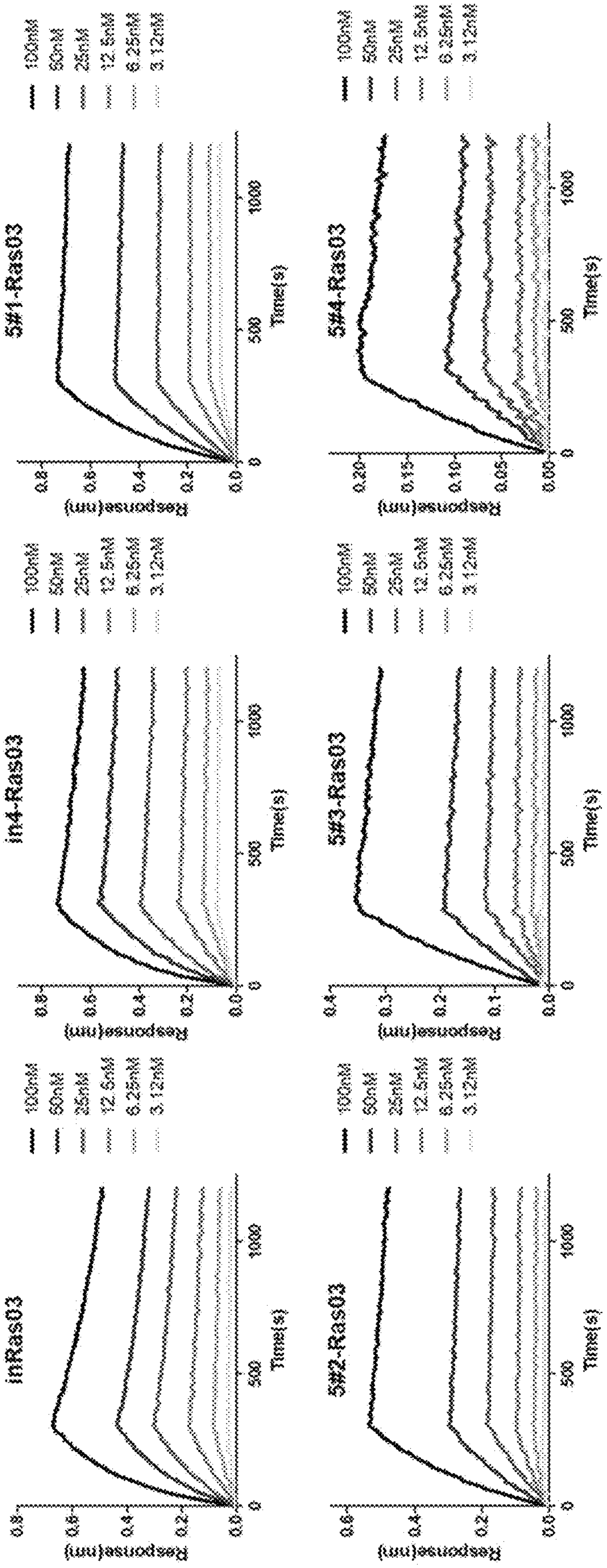

FIG. 27: Bio-layer interferometry experiment measuring the binding affinity against human recombinant integrin αvβ5 for: anti-Ras GTP iMab fused with the parental cyclic peptide clones (RGD10, in4), and anti-Ras GTP iMab fused with affinity maturated integrin αvβ5-targeting cyclic peptides (5#1, 5#2, 5#3, 5#4).

Figure 28:
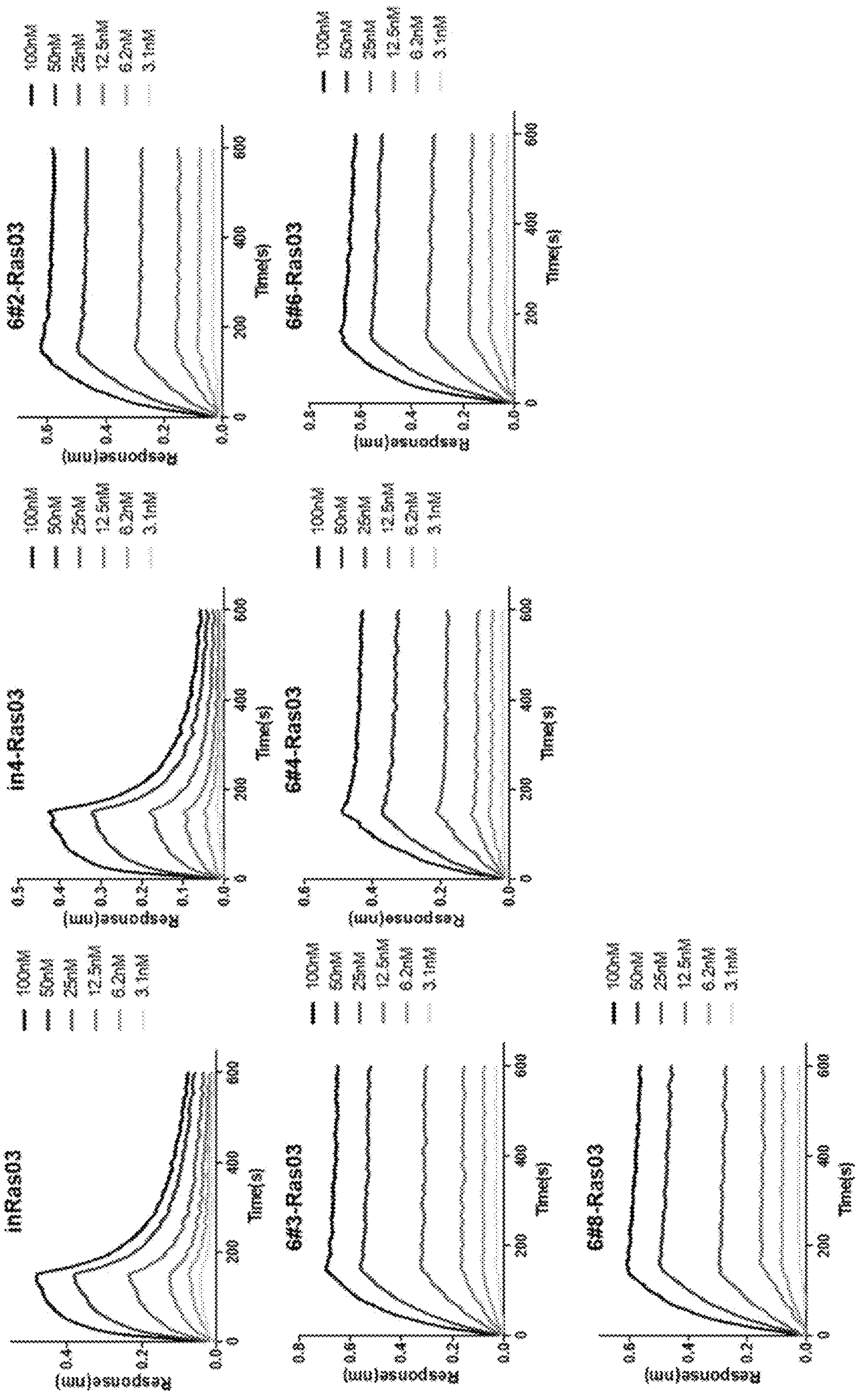

FIG. 28: Bio-layer interferometry experiment measuring the binding affinity against human recombinant integrin αvβ6 for: anti-Ras GTP iMab fused with the parental cyclic peptide clones (RGD10, in4), and anti-Ras GTP iMab fused with affinity maturated integrin αvβ5-targeting cyclic peptides (6#2, 6#3, 6#4, 6#6, 6#8).

Figure 29A:
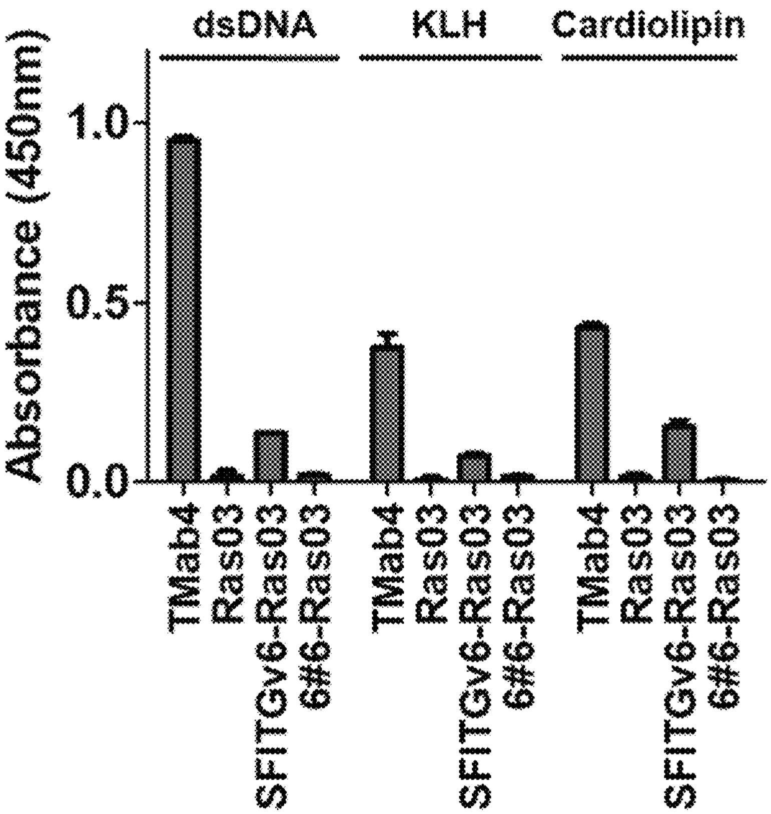

FIG. 29A: ELISA analysis of non-specific binding against three antigens (dsDNA, cardiolipin, KLH). Anti-Ras-GTP iMab fused with SFITGv6, a cyclic peptide known to have high affinity for integrin αvβ6 (SFITGv6-Ras03), and anti-Ras GTP iMab fused with 6#6, an affinity maturated αvβ6-targeting cyclic peptides selected from phage library screening in this study (6#6-Ras03), were tested at a concentration of 500 nM.

Figure 29B:
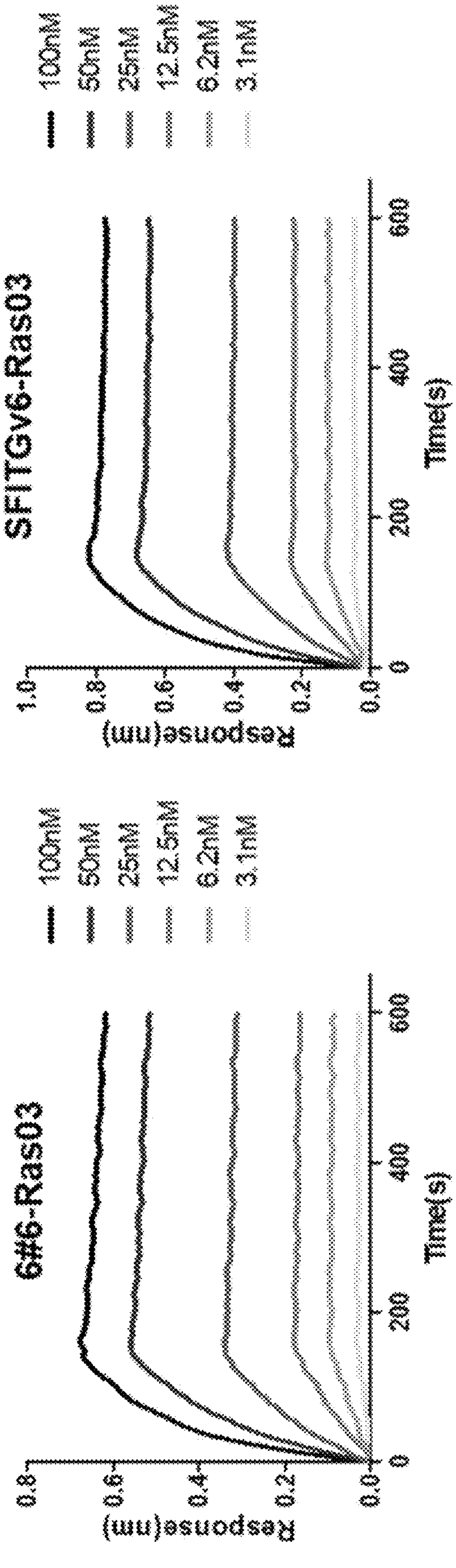

FIG. 29B: Bio-layer interferometry experiment measuring the binding affinity against human recombinant integrin αvβ6 for: Anti-Ras GTP iMab fused with SFITGv6, a cyclic peptide known to have high affinity for integrin αvβ6 (SFITGv6-Ras03), and anti-Ras GTP iMab fused with 6#6, an affinity maturated αvβ6-targeting cyclic peptides selected from phage library screening in this study (6#6-Ras03).

5. DETAILED DESCRIPTION

5.1 Terminology and Abbreviations

It is noted that technical terms used in the present invention are used to describe a specific embodiment and do not intend to limit the present invention. Further, if the technical terms used in the present invention are not particularly defined as other meanings in the present invention, the technical terms should be appreciated as meanings generally appreciated by those skilled in the art and should not be appreciated as excessively comprehensive meanings or excessively reduced meanings. In addition, a general term used in the present invention should be interpreted as defined in a dictionary or contextually and should not be interpreted as an excessively reduced meaning.

In addition, singular expressions used in the present invention include plurals expressions unless they have definitely opposite meanings. Terms including ordinal numbers, such as 'first' and 'second,' used in the present invention can be used to describe various components, but the components should not be limited by the terms. The above terms are used only to discriminate one component from the other components. For example, a first component may be named a second component and similarly, the second component may also be named the first component, without departing from the scope of the present invention.

Further, in the following description, a detailed explanation of known related technologies may be omitted to avoid unnecessarily obscuring the subject matter of the present invention. It is noted that the accompanying drawings are only for easily understanding the spirit of the present invention and it should not be interpreted that the spirit of the present invention is limited by the accompanying drawings. Hereinafter, the present invention is described in detail with accompanying Examples. However, these Examples are only for illustrative purposes and the scope of the present invention is not limited by these Examples.

Terms such as "cell/tissue specific" or "cell/tissue-specific" as used herein in the context of binding to, or targeting, refer to a selective or preferential binding to, or targeting by, an agent, for example, a polypeptide, to a cell/tissue at a higher level than to non-targeted cells/tissues. In some embodiments, an agent, for example, a polypeptide, exhibits an increased interaction with proteins or polypeptides on specific cells/tissues and/or localization to specific cells/tissues. In certain embodiments, the preferential binding or targeting is to an abnormal or diseased cell or tissue, e.g., a cell or tissue of cancer, immunological disease, or neurological disease, relative to the binding or targeting to the normal or non-diseased counterpart of the cell or tissue.

The term "interact" as used herein is meant to include interactions between molecules, such as can be detected using, for example, a yeast two hybrid assay. The term interact is also meant to include "binding" interactions between molecules (e.g., proteins, nucleic acids, protein fusions, peptides, glycoproteins, etc.).

The term "fusion protein" or "fusion polypeptide" as used herein refers to two or more separate amino acid sequences linked via a peptide bond or via a linker.

The term "linker" or "linker region" as used herein refers to a linker inserted between a first amino acid sequence and a second amino acid sequence. In some embodiments, the linker is a peptide linker. In one embodiment, linkers are not antigenic and do not elicit an immune response.

The term "antibody" is a well-known term of art, and, as used herein refers to an immunoglobulin molecule that recognizes and specifically binds to an antigen, such as, for example, a protein, polypeptide, peptide, carbohydrate, polynucleotide, lipid, or a combination of any of the foregoing, through at least one antigen-binding site wherein the antigen-binding site is usually within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single-chain Fv (scFv) antibodies, multispecific antibodies, bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site (e.g., dual variable domain immunoglobulin molecules). In certain embodiments, an antibody can comprise a constant domain. In particular embodiments, such an antibody can belong to any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. In particular embodiments, such an antibody can belong to any of the two major classes of light chain immunoglobulins λ and κ. Antibodies can be naked or conjugated to other molecules, including but not limited to, toxins and radioisotopes.

The term "intact immunoglobulin format" or "full-length immunoglobulin format" as used herein means an antibody that has a structure with two full-length light chains and two full-length heavy chains, with each light chain linked to each heavy chain by a disulfide bond (SS-bond). In certain embodiments, a constant region of the antibody is divided into a heavy-chain constant region and a light-chain constant region, and the heavy-chain constant region has γ, μ, α, δ, and ε types, and γ1, γ2, γ3, γ4, α1 and α2 subclasses while the light-chain constant region has κ and λ types.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single-chain antibodies, and multispecific antibodies formed from antibody fragments. "Antibody fragment" as used herein comprises an antigen-binding site or epitope-binding site.

The term "variable region" of an antibody refers to the variable region of an antibody light chain, or the variable region of an antibody heavy chain, either alone or in combination. Generally, the variable region of heavy and light chains each consist of four framework regions (FR) and three complementarity determining regions (CDRs), also known as "hypervariable regions". The CDRs in each chain are held together in close proximity by the framework regions and, with the CDRs from the other chain, contribute to the formation of the antigen-binding sites of the antibody. There are at least two techniques for determining CDRs: (1) an approach based on cross-species sequence variability, (Kabat, Wu, Foeller, Perry, & Gottesman, 1991)), and (2) an approach based on crystallographic studies of antigen-antibody complexes (Al-Lazikani, Lesk, & Chothia, 1997). In addition, combinations of these two approaches are sometimes used in the art to determine CDRs.

The term "monoclonal antibody" as used herein refers to a homogenous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (e.g., Fab, Fab', F(ab')2, Fv), single-chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage selection, recombinant expression, and transgenic animals.

The terms "selectively binds" or "specifically binds" mean that a polypeptide or molecule interacts more frequently, more rapidly, with greater duration, with greater affinity, or with some combination of the above to the epitope, protein, or target molecule than with alternative substances, including related and unrelated proteins. In certain embodiments "specifically binds" means, for instance, that a polypeptide or molecule binds a protein or target with a KD of about 0.1 mM or less, but more usually less than about 1 M. In certain embodiments, "specifically binds" means that a polypeptide or molecule binds a target with a KD of at least about 0.1 M or less, at least about 0.01 M or less, or at least about 1 nM or less. Because of the sequence identity between homologous proteins in different species, specific binding can include a polypeptide or molecule that recognizes a protein or target in more than one species. Likewise, because of homology within certain regions of polypeptide sequences of different proteins, specific binding can include a polypeptide or molecule that recognizes more than one protein or target. It is understood that, in certain embodiments, a polypeptide or molecule that specifically binds a first target may or may not specifically bind a second target. As such, "specific binding" does not necessarily require (although it can include) exclusive binding, i.e., binding to a single target. Thus, a polypeptide or molecule may, in certain embodiments, specifically bind more than one target. In certain embodiments, multiple targets may be bound by the same antigen-binding site on the polypeptide or molecule. For example, an antibody may, in certain instances, comprise two identical antigen-binding sites, each of which specifically binds the same epitope on two or more proteins. In certain alternative embodiments, an antibody may be bispecific and comprise at least two antigen-binding sites with differing specificities. Generally, but not necessarily, reference to "binding" means "specific binding".

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the amino acid sequences that is at least about 10 residues, at least about 20 residues, at least about 40-60 residues, at least about 60-80 residues in length or any integral value there between. In some embodiments, identity exists over a longer region than 60-80 residues, such as at least about 80-100 residues, and in some embodiments the sequences are substantially identical over the full length of the sequences being compared, such as the coding region of a target protein or an antibody. In some embodiments, identity exists over a region of the nucleotide sequences that is at least about 10 bases, at least about 20 bases, at least about 40-60 bases, at least about 60-80 bases in length or any integral value there between. In some embodiments, identity exists over a longer region than 60-80 bases, such as at least about 80-1000 bases or more, and in some embodiments the sequences are substantially identical over the full length of the sequences being compared, such as a nucleotide sequence encoding a protein of interest.

A "conservative amino acid substitution" is one in which one amino acid residue is replaced with another amino acid residue having a side chain with similar chemical characteristics. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Generally, conservative substitutions in the sequences of the polypeptides, soluble proteins, and/or antibodies of the invention do not abrogate the binding of the polypeptide, soluble protein, or antibody containing the amino acid sequence, to the target binding site. Methods of identifying amino acid conservative substitutions which do not eliminate binding are well-known in the art.

The term "heavy chain" as used herein can include a full-length heavy chain including variable region domain VH including an amino acid sequence having a variable region sequence sufficient to confer antigen-specificity and three constant region domains CH1, CH2 and CH3, and a fragment thereof. Also, the term "light chain" as used herein can include a full-length light chain including a variable region domain VL including an amino acid sequence having a variable region sequence sufficient to confer antigen-specificity and a constant region domain CL, and a fragment thereof.

A polypeptide, soluble protein, antibody, polynucleotide, vector, cell, or composition which is "isolated" is a polypeptide, soluble protein, antibody, polynucleotide, vector, cell, or composition which is in a form not found in nature. Isolated polypeptides, soluble proteins, antibodies, polynucleotides, vectors, cells, or compositions include those which have been purified to a degree that they are no longer in a form in which they are found in nature. In some embodiments, a polypeptide, soluble protein, antibody, polynucleotide, vector, cell, or composition which is isolated is substantially pure.

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a substance approved or approvable by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one agent of the present disclosure, and which does not destroy the pharmacological activity thereof and is nontoxic when administered in doses sufficient to deliver a therapeutic effect. In general, those of skill in the art and the U.S. FDA consider a pharmaceutically acceptable excipient, carrier, or adjuvant to be an inactive ingredient of any formulation.

The terms "effective amount" or "therapeutically effective amount" or "therapeutic effect" refer to an amount of a polypeptide or molecule described herein (e.g., a fusion protein, a soluble ligand, an antibody, a polypeptide, a polynucleotide, a small organic molecule, or other drug) effective to "treat" a disease or disorder in a subject such as, a mammal. In the case of cancer or a tumor, the therapeutically effective amount of a polypeptide or molecule (e.g., polypeptide, soluble protein, or antibody) has a therapeutic effect and as such can boost the immune response, boost the anti-tumor response, increase cytolytic activity of immune cells, increase killing of tumor cells by immune cells, reduce the number of tumor cells; decrease tumorigenicity, tumorigenic frequency or tumorigenic capacity; reduce the number or frequency of cancer stem cells; reduce the tumor size; reduce the cancer cell population; inhibit or stop cancer cell infiltration into peripheral organs including, for example, the spread of cancer into soft tissue and bone; inhibit and stop tumor or cancer cell metastasis; inhibit and stop tumor or cancer cell growth; relieve to some extent one or more of the symptoms associated with the cancer; reduce morbidity and mortality; improve quality of life; or a combination of such effects.

The terms "treating" or "to treat" refer to suppressing, eliminating, reducing, and/or ameliorating a symptom, the severity of the symptom, and/or the frequency of the symptom of the disease being treated.

5.2 Cyclic Peptides

The present disclosure is based at least in part on the recognition that cyclic peptides are capable of selectively targeting specific proteins. When attached to an agent, for example, a small molecule or a polypeptide, e.g., an antibody, such cyclic peptides are able to more selectively target the agent, for example, polypeptide, e.g. antibody, to certain cells/tissues. The present disclosure is based in part on the generation of cyclic peptides able to selectively target cell membrane proteins in a cell-specific and tissue-specific manner. In some embodiments, a cyclic peptide disclosed herein targets a cell membrane protein (e.g., EpCAM, integrin αvβ5, etc.), thereby selectively targeting cells/tissues exhibiting, e.g., expressing or overexpressing, the cell membrane protein. In some embodiments, a cyclic peptide disclosed herein targets a cell membrane protein (e.g., EpCAM) on cells exhibiting, (e.g., expressing or overexpressing) the cell membrane protein and does not target cells that do not exhibit (e.g., express or overexpress) the membrane protein, or exhibit or express the membrane protein at lower levels, thereby selectively targeting specific cells/tissues. In some embodiments, a cyclic peptide disclosed herein does not selectively target (e.g., has a low affinity for) a cell membrane protein that is not specific to a cell-type or tissue type (e.g., a cell or tissue of cancer, immunological disease, or neurological disease). As a non-limiting example, a cyclic peptide disclosed herein can have a lower affinity for a non-specific, broadly expressed protein (e.g., HSPG).

The present disclosure is based at least in part on the recognition that the cyclic peptide ep133 exhibits reduced in vivo affinity for EpCAM expressed on the surface of cells compared to its in vitro affinity towards purified EpCAM (see Example 17). In some embodiments, provided herein are methods of screening (e.g., mutagenically screening) cyclic peptides in order to identify cyclic peptides with one or more desirable properties, e.g., higher in vivo affinity. In some embodiments, an agent disclosed herein (e.g., a cyclic peptide) can selectively target cells/tissues (e.g., efficient tumor tissue-specificity for enhancing the EpCAM-targeting affinity). In some embodiments, cyclic peptides provided herein are identified in a mutagenesis screen and exhibit enhanced and/or improved binding affinity for a target (e.g., a protein or an extracellular domain of a protein).

In certain embodiments, a cyclic peptide described herein is attached to an agent, for example, a polypeptide (e.g., an antibody), and is fused to the agent. In a particular embodiment, the cyclic peptide is directed fused to the agent via a peptide bond. In another particular embodiment, the cyclic peptide is fused to the agent via a linker, for example, a peptide linker, e.g., a MGSSSN linker (SEQ ID NO: 102), a $(G_4S)_2$ linker (SEQ ID NO: 101). In certain embodiments, a cyclic peptide described herein that is attached to an agent, for example, a polypeptide, e.g., an antibody, is conjugated to the agent. In a particular embodiment, the cyclic peptide is directed conjugated to the agent directly. In another particular embodiment, the cyclic peptide is conjugated to the agent via a linker.

In some embodiments, provided herein is a cyclic peptide wherein the amino acid sequence of the cyclic peptide comprises: X1-X2-Leu3-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile.

In some embodiments, provided herein is a cyclic peptide wherein the amino acid sequence of the cyclic peptide comprises: X1-X2-Leu3-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser.

In certain embodiments, provided herein is a cyclic peptide wherein the amino acid sequence of the cyclic peptide comprises: X1-X2-Leu3-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile; and wherein cyclic peptide comprises a disulfide bond between Cys5 and Cys10.

In certain embodiments, provided herein is a cyclic peptide wherein the amino acid sequence of the cyclic peptide comprises: X1-X2-Leu3-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser, and wherein cyclic peptide comprises a disulfide bond between Cys5 and Cys10.

Further, in some embodiments, provided herein is a cyclic peptide wherein the amino acid sequence of the cyclic peptide comprises: X1-X2-Leu3-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln and Arg; X6 is any one of Leu and Ile; X8 is any one of Ser and Asn; and X9 is any one of Leu and Ile; and wherein the amino acid sequence of the cyclic peptide is selected from the group consisting of SEQ ID NOs: 29 to 37.

In some embodiments, provided herein is a cyclic peptide wherein the amino acid sequence of the cyclic peptide comprises: X1-X2-Leu3-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser; and wherein the amino acid sequence of the cyclic peptide is selected from the group consisting of SEQ ID NOs: 29 to 37.

In some embodiments, provided herein is a cyclic peptide wherein the amino acid sequence of the cyclic peptide comprises: X1-X2-Leu3-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile; and wherein cyclic peptide comprises a disulfide bond between Cys5 and Cys10; and wherein the amino acid sequence of the cyclic peptide is selected from the group consisting of SEQ ID NOs: 29 to 37.

In some embodiments, provided herein is a cyclic peptide wherein the amino acid sequence of the cyclic peptide comprises: X1-X2-Leu3-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser; and wherein cyclic peptide comprises a disulfide bond between Cys5 and Cys10; and wherein the amino acid sequence of the cyclic peptide is selected from the group consisting of SEQ ID NOs: 29 to 37.

In certain embodiments, provided herein is a cyclic peptide wherein the amino acid sequence of the cyclic peptide comprises: X1-X2-Leu3-X4-Cys5-X6-Gly-X8-X9-Cys10-Trp-Ser (SEQ ID NO: 99); wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile; and wherein cyclic peptide comprises a disulfide bond between Cys5 and Cys10; and wherein the amino acid sequence of the cyclic peptide is selected from the group consisting of SEQ ID NOs: 29 to 37; and wherein the amino acid sequence of the cyclic peptide fused or conjugated to the light chain is selected from the group consisting of SEQ ID NOs: 9, 21, and 38 to 48.

In certain embodiments, provided herein is a cyclic peptide wherein the amino acid sequence of the cyclic peptide comprises: X1-X2-Leu3-X4-Cys5-X6-Gly-X8-X9-Cys10-Trp-X12 (SEQ ID NO: 110); wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser; and wherein cyclic peptide comprises a disulfide bond between Cys5 and Cys10; and wherein the amino acid sequence of the cyclic peptide is selected from the group consisting of SEQ ID NOs: 29 to 37; and wherein the amino acid sequence of the cyclic peptide fused or conjugated to the light chain is selected from the group consisting of SEQ ID NOs: 9, 21, and 38 to 48.

In some embodiments, provided herein is a cyclic peptide wherein the amino acid sequence of the cyclic peptide comprises: Asp-Gly-X3-X4-X5-Cys6-Arg-Gly-Asp-Cys10-X11-X12-X13-X14-X15 (SEQ ID NO: 100); wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser.

In some embodiments, provided herein is a cyclic peptide wherein the amino acid sequence of the cyclic peptide comprises: Asp-Gly-X3-X4-X5-Cys6-Arg-Gly-Asp-Cys10-X11-X12-X13-X14-X15 (SEQ ID NO: 100); wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser; and wherein the cyclic peptide comprises a disulfide bond between Cys6 and Cys10.

Further, in certain embodiments, provided herein is a cyclic peptide wherein the amino acid sequence of the cyclic peptide comprises: Asp-Gly-X3-X4-X5-Cys6-Arg-Gly-Asp-Cys10-X11-X12-X13-X14-X15 (SEQ ID NO: 100); wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser; and wherein the amino acid sequence of the cyclic peptide is selected from the group consisting of SEQ ID NOs: 50 to 57.

In some embodiments, a cyclic peptide described herein comprises SEQ ID NO: 13, 14, 15, 16, 17, 18, 219, or 20.

In some embodiments, a cyclic peptide disclosed herein comprises a disulfide bond. In some embodiments, a cyclic peptide disclosed herein has been modified to change the cyclic peptide's affinity for one or more proteins (e.g., to increase or decrease affinity). In some embodiments, a cyclic peptide disclosed herein has been modified to change the cyclic peptide's targeting of one or more proteins. In some embodiments, a cyclic peptide disclosed herein has been modified to change the cyclic peptide's aggregation in certain environments (e.g., inside a cell). In some embodiments, a cyclic peptide disclosed herein has been modified to change the cyclic peptide's hydrophobicity in certain environments (e.g., inside a cell). In some embodiments, a cyclic peptide disclosed herein has been modified to change the cyclic peptide's conformation in certain environments (e.g., inside a cell, inside an endosome, and/or inside the cytosol, etc.). In some embodiments, a cyclic peptide disclosed herein has been modified to change the cyclic peptide's resistance to one or more proteolytic enzymes in certain environments (e.g., inside a cell, inside an endosome, and/or inside the cytosol, etc.). In some embodiments, a cyclic peptide disclosed herein has been modified to change the cyclic peptide's structural stability in certain environments (e.g., inside a cell, inside an endosome, and/or inside the cytosol, etc.).

In some embodiments, a cyclic peptide disclosed herein is modified such that it exhibits a desired change in its affinity for more than one protein (e.g., a decrease in binding to HSPG and an increase in binding to EpCAM).

In certain aspects, provided herein are methods of targeting specific cells and/or tissues with a cyclic peptide disclosed herein in order to treat a disease, such as cancer, immunological disease, or neurological disease. In some embodiments, a cyclic peptide disclosed herein targets a cell surface protein on a cell or tissue of cancer, immunological disease, or neurological disease.

5.3 Cell/Tissue Specificity

5.3.1 Cell Specificity

In some embodiments, a cyclic peptide disclosed herein targets one or more specific molecules, for example, receptors (e.g., proteins, peptides, molecules, and/or glycoproteins) on a cell surface. In some embodiments, a cyclic peptide disclosed herein does not interact with and/or target cells that do not exhibit, e.g., express or overexpress, the one or more specific molecules, for example, receptors (e.g., proteins, peptides, molecules, and/or glycoproteins) on a cell surface. In certain embodiments, the molecule, e.g., receptor, is a cell membrane protein, for example, an integral membrane protein (IMP), lipid-anchored protein (LAP), or peripheral membrane protein (PMP), depending on how the protein is distributed in the membrane. Cell-specific molecules, for example, receptors, within target cells and/or target tissues can readily be identified using methods known in the art such as, for example, immunohistochemical analyses, e.g., immunohistochemical analyses of tumor biopsies.

As a non-limiting example, in some embodiments, a cyclic peptide disclosed herein can preferentially or selectively target cells within a tumor (e.g., cells expressing or overexpressing a tumor-associated antigen on the cell surface) by interacting with a tumor-associated cell surface antigen (TAA), relative to non-tumor cells not exhibiting, or exhibiting or expressing lower amounts of, a tumor-associated antigen on the cell surface. In certain embodiments, a specific receptor is selectively expressed or overexpressed in the target cells compared to the non-target cells. In certain embodiments, the specific receptor is not expressed or expressed at lower levels in the non-target cells compared to the target cells.

As another non-limiting example, a cyclic peptide disclosed herein can specifically target an immune cell by interacting with a cell surface molecule present on the immune cell. As a non-limiting example, such an immune cell can, for example, be a dendritic cell and can, for example, exhibit, e.g., express or overexpress, such cell surface molecules as, for example, DEC-205 (Lymphocyte antigen 75, CD205), DC-SIGN (dendritic cell-specific intercellular adhesion molecule-3-grabbing non-integrin, CD209), BDCA-2 (CLEC4C DC-specific type II C-type lectin), Langerin (CD207), CLEC9A (group V C-type lectin-like receptor).

In another non-limiting example, a cyclic peptide disclosed herein can selectively target an immune cell by interacting with a cell surface molecule present on the immune cell, wherein the immune cell is a T cell that, for example, exhibits, e.g., expresses or overexpresses, such cell surface molecules as, for example, a checkpoint inhibitor molecule, including for example, programmed cell death protein 1 (PD1), TIM3, LAG3, VISTA, or PDL1, CD3, or a T cell receptor (TCR). In yet another non-limiting example, a cyclic peptide disclosed herein can specifically target an immune cell by interacting with a cell surface molecule present on the immune cell, wherein the immune cell is a B cell that, for example, exhibits, e.g., expresses or overexpresses, such cell surface molecules as, for example, CD19 or CD20.

In still another non-limiting example, a cyclic peptide disclosed herein can specifically target an immune cell by interacting with a cell surface molecule present on the immune cell, wherein the immune cell is an innate immune cell that, for example, exhibits, e.g., expresses or overexpresses, such cell surface molecules as, for example, a pathogen recognition receptor (PRR) such as a Toll-like receptor (TLR), or a C-type lectin receptor (CLR).

In certain embodiments, as a non-limiting example, a cyclic peptide described herein binds to epithelial cell adhesion molecule (EpCAM), which is known to be a targeted marker expressed on the surface of cancer cells. In another specific non-limiting example, a cyclic peptide described herein binds to an integrin comprising a heterodimer of a subunit and 3 subunit, which is present on the surface of a cell, and which plays a role in mediating cell-to-cell and/or cell-to-extracellular matrix interactions. In a non-limiting example, such an integrin can be integrin αvβ5 or integrin αvβ3. In certain embodiments, a cyclic peptide described herein binds to epidermal growth factor receptor (EGFR). In certain embodiments, as a further non-limiting example, a cyclic peptide described herein that binds to any such cell surface molecule is fused to an antibody, for example, a cell/tissue specific or cell-penetrating antibody, as described herein.

5.3.2 Cell-Type Specificity and Microenvironment Specificity

In certain embodiments, a cyclic peptide disclosed herein can target specific types of cells (e.g., cardiac cells, endothelial cells, dendritic cells, etc.). In some embodiments, a cyclic peptide disclosed herein can target specific receptors on cells within a target microenvironment. In certain embodiments, the target microenvironment can be a tumor microenvironment (TME). For example, cancer tissues are composed of cancer cells and the surrounding stromal cells (e.g., fibroblasts, vascular endothelial cells, and immune cells), in addition to the extracellular matrix. In some embodiments, a cyclic peptide disclosed herein target specific receptors on cells within a tumor microenvironment. Non-limiting examples of target microenvironment components that can be specifically targeted by a cyclic peptide disclosed herein is tumor vasculature (e.g., the extra domain B of fibronectin) or cancer-associated fibroblasts (CAFs). In some embodiments, a cyclic peptide disclosed herein can target specific receptors within a target microenvironment that are not cancer-associated fibroblasts (CAFs).

5.3.3 Tissue Specificity

Further provided herein are cyclic peptides that exhibit tissue specificity. In some embodiments, a cyclic peptide disclosed herein targets one or more specific receptors (e.g., proteins, peptides, molecules, and/or glycoproteins) on the surface of cells within a targeted tissue. In some embodiments, a cyclic peptide disclosed herein does not interact with and/or target one or more specific receptors (e.g., proteins, peptides, molecules, and/or glycoproteins) on a the surface of cells within a non-targeted tissue. As a non-limiting example, in some embodiments, a cyclic peptide disclosed herein can preferentially or selectively target cells within a tumor tissue (e.g., cells expressing a tumor-associated antigen on the cell surface) by interacting with the tumor-associated antigen relative to non-tumor cells not exhibiting, or exhibiting or expressing lower amounts of, a tumor-associated antigen on the cell surface. In another non-limiting example, in some embodiments, a cyclic peptide disclosed herein can specifically target cells within a tumor (e.g., cells expressing a tumor-associated antigen on the cell surface) by interacting with the tumor-associated antigen, while the cyclic peptide does not target non-tumor cells. In certain embodiments, the specific receptor is selectively expressed or overexpressed in the target cells compared to the non-target cells. In certain embodiments, the specific receptor is not expressed or expressed at lower levels in the non-target cells compared to the target cells.

5.3.4 Tumor Tissue-Specific Membrane Proteins

Tumor tissue-specific membrane proteins refer to membrane proteins that are preferentially present on tumor cells or tissues. In one example, such proteins may not be expressed in normal (e.g. non-tumor) tissues or cells. In another example, such proteins can be overexpressed in tumor tissue or tumor cells relative to normal tissue or cells. In certain embodiments, for example, such proteins can be expressed at 2-fold, 5-fold, 10-fold, 20-fold, 50-fold, 100-fold or higher levels relative to non-tumor tissues or cells. Thus, when antibodies or drugs are delivered by targeting them, the adverse effect induced by the drug delivery to normal tissues may be significantly reduced. Non-limiting examples of tumor cells or tissues include cells or tissues of solid cancers such as, for example, stomach cancer, colon cancer and pancreatic cancer, or cells of blood cancers such as, for example, lymphomas or myelomas.

In certain embodiments, non-limiting examples of proteins which are overexpressed or expressed on the surface of solid tumor cells and/or tissues and can be targeted by a cyclic peptide disclosed herein include epithelial cell adhesion protein (EpCAM), integrin αvβ5, integrin αvβ6, integrin αvβ3, an epidermal growth factor receptor (EGFR), human epidermal growth factor receptor 2 (Her2), vascular endothelial growth factor receptor 2 (VEGFR2), fibroblast growth factor receptor (FGFR), hepatocyte growth factor receptor (c-Met), neuropilin (NRP) (HGFR), Mesothelin, insulin-like growth factor I receptor (IGF1R), programmed cell death protein ligand 1 (PD-L1), cytotoxic T lymphocyte protein 4 (CTLA4), disialoganglioside (GD2), platelet-derived growth factor receptor-α (PDGFRc), cancer testes antigen family, carcinoembryonic antigen (CEA), or NY-ESO-1.

In some embodiments, a non-limiting list of membrane proteins which are overexpressed on the cell surface of blood tumors such as leukemia and lymphoma and can be targeting by a cyclic peptide disclosed herein include cluster of differentiation 19 (CD 19), CD20, CD22, CD30, CD33, CD38, or CC-chemokine receptor 4 (CCR4).

5.4 Cyclic Peptide-Fused Antibodies

In certain embodiments, provided herein is a cell/tissue-specific cell-penetrating antibody comprising a light chain comprising a light chain variable region ("VL"), a heavy chain comprising a heavy chain variable region ("VH"), and a cyclic peptide that specifically binds to a cell surface molecule.

In some embodiments, an agent described herein, e.g., a cell/tissue-specific cell-penetrating antibody, comprises one or more endosome escape motifs. In some embodiments, upon binding of the cyclic peptide fused with an antibody of intact full-length immunoglobulin format to targeted cell membrane protein receptors, the cyclic peptide-fused antibody is internalized into cells via endosomes through an endocytic pathway, and once inside the cell, the cyclic peptide-fused antibody exploits one or more endosome escape motifs to reach the cytosol.

In some embodiments, a cell/tissue-specific cell-penetrating antibody described herein comprises a light chain comprising a light chain variable region (VL) and a heavy chain comprising a heavy chain variable region (VH). In some embodiments, a cell/tissue-specific cell-penetrating antibody described herein specifically binds to a cell surface molecule. In some embodiments, a cell/tissue-specific cell-penetrating antibody described herein comprises a light chain and a heavy chain wherein the light chain and the heavy chain are separate molecules. In some embodiments, a cell/tissue-specific cell-penetrating antibody described herein comprises a light chain and a heavy chain wherein the light chain and the heavy chain are part of the same molecule.

In some embodiments, a cell/tissue-specific cell-penetrating antibody described herein comprises a cyclic peptide fused to an antibody. In some embodiments, a cell/tissue-specific cell-penetrating antibody described herein comprises a cyclic peptide is directed fused to an antibody. In some embodiments, a cell/tissue-specific cell-penetrating antibody described herein comprises a cyclic peptide is fused to an antibody via a peptide linker. In some embodiments, a cell/tissue-specific cell-penetrating antibody described herein comprises a cyclic peptide is directed conjugated to the antibody. In some embodiments, a cell/tissue-specific cell-penetrating antibody described herein comprises a cyclic peptide is conjugated to the antibody via a linker.

In some embodiments, an antibody disclosed herein comprises a cyclic peptide fused to the light chain or heavy chain of the antibody. In some embodiments, an antibody disclosed herein comprises a cyclic peptide fused to the N-terminus or the C-terminus of the light chain of the antibody. In some embodiments, an antibody disclosed herein comprises a cyclic peptide fused to the light chain or heavy chain of the antibody. In some embodiments, an antibody disclosed herein comprises a cyclic peptide fused to the N-terminus or the C-terminus of the heavy chain of the antibody. In some embodiments, an antibody disclosed herein comprises a cyclic peptide fused to the light chain and a cyclic peptide fused to the heavy chain of the antibody. In some embodiments, an antibody disclosed herein comprises a cyclic peptide fused to the N terminus of the light chain and the heavy chain of the antibody.

In some embodiments, an antibody disclosed herein comprises a cyclic peptide fused to the C-terminus of the light chain and the heavy chain of the antibody. In some embodiments, an antibody disclosed herein comprises a cyclic peptide fused to the C-terminus of the light chain or the heavy chain of the antibody. In some embodiments, an antibody disclosed herein comprises a cyclic peptide fused to the N-terminus of the light chain or the heavy chain of the antibody. In some embodiments, an antibody disclosed herein comprises a cyclic peptide fused to the C-terminus of the light chain or the heavy chain of the antibody.

In some embodiments, a cell/tissue-specific cell-penetrating antibody disclosed herein specifically binds to a cell surface molecule, wherein the cell surface molecule is a membrane protein selectively expressed on the surface of a cell or tissue. In some embodiments, a cell/tissue-specific cell-penetrating antibody disclosed herein specifically binds to a cell surface molecule, wherein the cell surface molecule is a membrane protein selectively expressed on the surface of a cell. In some embodiments, a cell/tissue-specific cell-penetrating antibody disclosed herein specifically binds to a cell surface molecule, wherein the cell surface molecule is a membrane protein selectively expressed on the surface of a tissue.

In some embodiments, a cell/tissue-specific cell-penetrating antibody disclosed herein specifically binds to a cell surface molecule, wherein the cell surface molecule is selected from the group consisting of cell membrane protein epithelial cell adhesion molecule (EpCAM), integrin $\alpha v\beta 5$, integrin $\alpha$ $v\beta 3$, and epidermal growth factor receptor (EGFR).

In some embodiments, a cell/tissue-specific cell-penetrating antibody disclosed herein comprises a cyclic peptide that comprises a disulfide bond.

In some embodiments, a cyclic peptide disclosed herein comprises an amino acid sequence X1-X2-Leu3-X4-Cys5-X6-Gly-X8-X9-Cys10-Trp-Ser (SEQ ID NO: 99), wherein X1 is any one of Glu, His, Asp and Lys; X2 is any one of His and Asn; X4 is any one of His, Leu, Gln, and Arg; X6 is any one of Leu and Ile; X8 is any one of Ser and Asn; and X9 is any one of Leu and Ile.

In some embodiments, a cyclic peptide disclosed herein comprises an amino acid sequence X1-X2-Leu3-X4-Cys5-X6-Gly-X8-X9-Cys10-Trp-X12 (SEQ ID NO: 110), wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser.

In some embodiments, a cyclic peptide disclosed herein comprises a disulfide bond between Cys5 and Cys10.

In some embodiments, a cyclic peptide disclosed herein is selected from the group consisting of SEQ ID NOs: 29 to 37. In some embodiments, a cell/tissue-specific cell-penetrating antibody disclosed herein comprises a cyclic peptide that is selected from the group consisting of SEQ ID NOs: 29 to 37.

In some embodiments, the amino acid sequence of the cyclic peptide fused or conjugated to the light chain of an antibody disclosed herein is selected from the group consisting of SEQ ID NOs: 9, 21, and 38 to 48. In some embodiments, the amino acid sequence of a cyclic peptide disclosed herein comprises Asp-Gly-X3-X4-X5-Cys6-Arg-Gly-Asp-Cys10-X11-X12-X13-X14-X15 (SEQ ID NO: 100), wherein X3 is any one of Glu, Val, Gly, Gin, and Asp; X4 is any one of Arg and Lys; X5 is any one of Asn, Ser, Ala, Gin, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser.

In some embodiments, the amino acid sequence of the cyclic peptide fused or conjugated to the light chain of an antibody disclosed herein is selected from the group consisting of SEQ ID NOs: 9, 21, and 38 to 48. In some embodiments, the amino acid sequence of a cyclic peptide disclosed herein comprises Asp-Gly-X3-X4-X5-Cys6-Arg-Gly-Asp-Cys10-X11-X12-X13-X14-X15 (SEQ ID NO: 100), wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the cyclic peptide comprises a disulfide bond between Cys6 and Cys10.

In some embodiments, the amino acid sequence of the cyclic peptide fused or conjugated to the light chain of an antibody disclosed herein is selected from the group consisting of SEQ ID NOs: 9, 21, and 38 to 48. In some embodiments, the amino acid sequence of a cyclic peptide disclosed herein comprises Asp-Gly-X3-X4-X5-Cys6-Arg-Gly-Asp-Cys10-X11-X12-X13-X14-X15 (SEQ ID NO: 100), wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the amino acid sequence of the cyclic peptide is selected from the group consisting of SEQ ID NOs: 50 to 57.

In some embodiments, the amino acid sequence of the cyclic peptide fused or conjugated to the light chain of an antibody disclosed herein is selected from the group consisting of SEQ ID NOs: 9, 21, and 38 to 48. In some embodiments, the amino acid sequence of a cyclic peptide disclosed herein comprises Asp-Gly-X3-X4-X5-Cys6-Arg-Gly-Asp-Cys10-X11-X12-X13-X14-X15 (SEQ ID NO: 100), wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the cyclic peptide comprises a disulfide bond between Cys6 and Cys10, and wherein the amino acid sequence of the cyclic peptide is selected from the group consisting of SEQ ID NOs: 50 to 57.

In some embodiments, the amino acid sequence of the cyclic peptide fused or conjugated to the light chain of an antibody disclosed herein is selected from the group consisting of SEQ ID NOs: 9, 21, and 38 to 48. In some embodiments, the amino acid sequence of a cyclic peptide disclosed herein comprises Asp-Gly-X3-X4-X5-Cys6-Arg-Gly-Asp-Cys10-X11-X12-X13-X14-X15 (SEQ ID NO: 100), wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the amino acid sequence of the cyclic peptide is selected from the group consisting of SEQ ID NOs: 50 to 57, and wherein the amino acid sequence of the cyclic peptide fused or conjugated to the light chain is selected from the group consisting of SEQ ID NOs: 58 to 66.

In some embodiments, the amino acid sequence of the cyclic peptide fused or conjugated to the light chain of an antibody disclosed herein is selected from the group consisting of SEQ ID NOs: 9, 21, and 38 to 48. In some embodiments, the amino acid sequence of a cyclic peptide disclosed herein comprises Asp-Gly-X3-X4-X5-Cys6-Arg-Gly-Asp-Cys10-X11-X12-X13-X14-X15 (SEQ ID NO: 100), wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the cyclic peptide comprises a disulfide bond between Cys6 and Cys10, and wherein the amino acid sequence of the cyclic peptide is selected from the group consisting of SEQ ID NOs: 50 to 57, and wherein the amino acid sequence of the cyclic peptide fused or conjugated to the light chain is selected from the group consisting of SEQ ID NOs: 58 to 66.

In some aspect, an antibody disclosed herein comprises a light chain constant region (CL) and the heavy chain comprises a heavy chain constant region (CH). In some aspect, an antibody disclosed herein is of IgG1 subtype. In some embodiments, an antibody disclosed herein is of IgG2 subtype. In some embodiments, an antibody disclosed herein is of IgG3 subtype. In some embodiments, an antibody disclosed herein is of IgG4 subtype. In some embodiments, an antibody disclosed herein is of IgG4 subtype. In some embodiments, an antibody disclosed herein is of lambda subtype. In some embodiments, an antibody disclosed herein is of kappa subtype. In some embodiments, an antibody disclosed herein is of kappa subtype. In some embodiments, an antibody disclosed herein is of a full-length immunoglobulin format.

In some aspect, an antibody of full-length immunoglobulin format has a structure with two full-length light chains and two full-length heavy chains, and each light chain is linked to each heavy chain by a disulfide bond (SS-bond). In some embodiments, a constant region of the antibody is divided into a heavy-chain constant region and a light-chain constant region, and the heavy-chain constant region has $\gamma$, $\mu$, $\alpha$, $\delta$, and $\varepsilon$ types, and $\gamma1$, $\gamma2$, $\gamma3$, $\gamma4$, $\alpha1$ and $\alpha2$ subclasses. In some embodiments, the light-chain constant region is of type K or X.

In some embodiments, an agent presented herein is an antibody, for example an intact immunoglobulin type antibody, having endosomal escape ability in its light chain variable region (VL) and/or heavy chain variable region (VH), in which the cyclic peptide is fused to N-terminus of its light chain variable region (VL) and/or heavy chain variable region (VH), and has target cell/tissue-penetrating ability.

The endosomal escape ability of an antibody is influenced by structural changes in the endosomal escape motif within the light chain variable region and/or the heavy chain variable region of the antibody. In certain embodiments a complementarity-determining region 3 (CDR3) of the VL and/or VH of an antibody disclosed herein comprises a WYWX (SEQ ID NO: 69) sequence motif in which X is selected from the group consisting of methionine (M), isoleucine (I), and leucine (L); and the first amino acid in the light chain variable region (VL) and/or the heavy chain variable region (VH) being aspartic acid (D) or glutamic acid (E).

In certain embodiments, an antibody disclosed herein is fused to a cyclic peptide using a linker. In some embodiments, the linker is a polypeptide comprising the amino acid sequence MGSSSN (SEQ ID NO: 102) and/or GGGGS (SEQ ID NO: 103).

In certain embodiments, the light chain variable region (VL) of the antibody exhibits reduced or no binding ability to heparan sulfate proteoglycan (HSPG) of the target cell.

In some embodiments, provided herein is a method for preparing a vector comprising a light chain variable region (VL) and/or a heavy chain variable region (VH) of a human antibody. In some embodiments a VL and/or VH disclosed herein has been modified using methods known in the art. As non-limiting examples, in some embodiments, a VL and/or a VH disclosed herein has been mutated (e.g., point mutations insertions, deletions, etc.), fused to a heterologous sequence, glycoengineered (e.g., glycosylated or de-glycosylated), etc. In specific embodiments, a VL and/or a VH disclosed herein has been fused to one or more peptide sequences (e.g., a cyclic peptide sequence). In some embodiments, a VL and/or a VH produced using the methods disclosed herein and comprise a cyclic peptide sequence. In some embodiments, a cyclic peptide sequence is fused to the N-terminus of the light chain variable region (VL). In some embodiments, a cyclic peptide sequence is fused to the N-terminus of the heavy chain variable region (VH). In some embodiments, a cyclic peptide sequence is fused to the N-terminus of the light chain variable region (VL) and a cyclic peptide sequence is fused to the N-terminus of the heavy chain variable region (VH). In some embodiments, an agent, e.g., a cytotransmab (CT) and/or an antibody disclosed herein comprises one or more cyclic peptide sequences. In some embodiments a CT disclosed herein comprises two cyclic peptide sequences.

In certain embodiments, provided herein are cyclic-peptide fused antibodies wherein the antibody has been modified such that a functional motif (e.g., an endosomal escape motif) has been removed, added, or modified on the antibody. In some embodiments, a cyclic peptide disclosed herein is fused to a modified antibody or fragment thereof. Typically, grafting of a protein-binding continuous sequence motif has been executed to transfer binding specificity and affinity to another protein with a similar structural scaffold (Lee, et al., 2011). The representative example includes grafting of the antigen-recognizing CDR loops to the corresponding regions of another antibody's FR during antibody humanization (Ewert, Honegger, & Pluckthun, 2004) (Kim & Bae, 2015)

In certain embodiments, provided herein are cyclic peptide-fused antibodies wherein an endosomal escape motif (e.g., composed of a pH-sensing pair and/or a membrane-binding motif) is modified. In some embodiments, provided herein are methods for modifying the two-dimensional amino acid sequence that constitute a motif (e.g., an endosomal escape motif) in an agent (e.g., an antibody, polypeptide, CT) disclosed herein. In some embodiments, provided herein are methods for modifying the two-dimensional amino acid sequence in order to modify a three-dimensional structural fold in the agent (e.g. antibody and/or antibody fragment, polypeptide). In certain embodiments, provided herein are methods of modifying an antibody, and/or antibody fragment by grafting amino acid sequences from the same antibody, an exogenous antibody, or a heterologous sequence onto the antibody and/or antibody fragment. In some embodiments, the modified regions are highly homologous motifs from one region of an antibody (e.g., VL) to another (e.g., VH). In some embodiments one or more regions (e.g., functional motifs) of an antibody and/or antibody fusion disclosed herein is modified to alter functional motifs within the antibody and/or antibody fusion. In some embodiments, the fusion proteins, antibodies, antibody-cyclic peptide fusions, antibody fragments, and any agents disclosed herein may be modified in order to alter certain properties (e.g., protein targeting, protein affinity, aggregation, hydrophobicity, disulfide bonding, conformation, etc.)

In some aspects, the amino acid sequence of the cyclic peptide fused or conjugated to the light chain of an antibody disclosed herein is selected from the group consisting of SEQ ID NOs: 50 to 57. In some embodiments, the amino acid sequence of the cyclic peptide fused or conjugated to the light chain of an antibody disclosed herein is selected from the group consisting of SEQ ID NOs: 58 to 66.

In some embodiments, a cell/tissue-specific cell-penetrating antibody disclosed herein comprises a light chain constant region (CL) and the heavy chain comprises a heavy chain constant region (CH). In some embodiments, a cell/tissue-specific cell-penetrating antibody disclosed herein is of the IgG1 isotype. In some embodiments, a cell/tissue-specific cell-penetrating antibody disclosed herein is of the IgG2 isotype. In some embodiments, a cell/tissue-specific cell-penetrating antibody disclosed herein is of the IgG3 isotype. In some embodiments, a cell/tissue-specific cell-penetrating antibody disclosed herein is of the IgG4 isotype. In some embodiments, a cell/tissue-specific cell-penetrating antibody disclosed herein comprises a light chain of the lambda subtype. In some embodiments, a cell/tissue-specific cell-penetrating antibody disclosed herein comprises a light chain of the kappa subtype.

In some embodiments, a cell/tissue-specific cell-penetrating antibody disclosed herein is of full-length immunoglobulin format. In some embodiments, a cell/tissue-specific cell-penetrating antibody disclosed herein comprises an endosomal escape motif in the light chain variable region (VL) and/or the heavy chain variable region (VH) of the antibody. In some embodiments, a cell/tissue-specific cell-penetrating antibody disclosed herein comprises an endosomal escape motif in the light chain variable region (VL) of the antibody. In some embodiments, a cell/tissue-specific cell-penetrating antibody disclosed herein comprises an endosomal escape motif in the heavy chain variable region (VH) of the antibody. In some embodiments, a cell/tissue-specific cell-penetrating antibody disclosed herein comprises an endosomal escape motif in the light chain variable region (VL) and the heavy chain variable region (VH) of the antibody.

In some embodiments, a cell/tissue-specific cell-penetrating antibody disclosed herein comprises an endosomal escape motif that comprises the amino acid sequence 1) WYWX (SEQ ID NO:69) in the complementarity-determining region 3 (CDR3) of the light chain variable region (VL) and/or the heavy chain variable region (VH), wherein W is tryptophan, Y is tyrosine, and X is selected from the group consisting of methionine (M), isoleucine (I), and leucine (L); and 2) aspartic acid (Asp or D) or glutamic acid (Glu or E) as the first amino acid in the light chain variable region (VL) and/or the heavy chain variable region (VH), wherein the endosomal escape motif induces penetration of the antibody into the cytosol of the cell.

In some embodiments, a cell/tissue-specific cell-penetrating antibody disclosed herein comprises a VL region wherein the binding ability to heparan sulfate proteoglycan (HSPG) is reduced or abolished. In some embodiments, a cell/tissue-specific cell-penetrating antibody disclosed herein comprises a VL region selected from the group consisting of SEQ ID NOs: 2 to 8. In some embodiments, a cell/tissue-specific cell-penetrating antibody disclosed herein comprises a VL region selected from the group consisting of SEQ ID NOs: 11 and 12. In some embodiments, a cell/tissue-specific cell-penetrating antibody disclosed herein comprises a VL region represented by SEQ ID NO: 8 and a VH region represented by SEQ ID NO: 12.

5.4.1 Cyclic Peptide Fused to Full-Length Immunoglobulin Format Antibody

Full-length IgG antibodies cannot cross cell membranes of living cells, limiting their use for direct targeting of cytosolic proteins. Full-length immunoglobulin G (IgG) antibodies have primarily been developed to target proteins expressed on the cell-surface and some secreted proteins. Provided herein are methods for targeting full-length format antibodies to intracellular proteins.

Further, full-length format antibodies generally cannot cross intact cellular or subcellular membranes in living cells due to their large size and hydrophilicity. Provided herein are methods of fusing full-length format antibodies to cyclic peptides, where the hydrophobicity of the cyclic peptide-fused full-length format antibody is modified.

In some embodiments, provided herein are methods for fusing a full-length format antibody, wherein the full-length antibody can penetrate a cell membrane. In some embodiments, provided herein are cyclic peptides that can be fused to a full-length format antibody, wherein the full-length antibody can be selectively targeted to a cell/tissue, wherein the antibody is active.

The term "heavy chain" as used herein may be interpreted to include a full-length heavy chain including variable region domain VH including an amino acid sequence having a variable region sequence sufficient to confer antigen-specificity and three constant region domains CH1, CH2 and CH3, and a fragment thereof. Also, the term "light chain" as used herein may be interpreted to include a full-length light chain including a variable region domain VL including an amino acid sequence having a variable region sequence sufficient to confer antigen-specificity and a constant region domain CL, and a fragment thereof.

In the present invention, an intact immunoglobulin-type antibody has a structure with two full-length light chains and two full-length heavy chains, and each light chain is linked to each heavy chain by a disulfide bond (SS-bond). A constant region of the antibody is divided into a heavy-chain constant region and a light-chain constant region, and the heavy-chain constant region has γ, μ, α, δ, and ε types, and γ1, γ2, γ3, γ4, α1 and α2 subclasses. The light-chain constant region has κ and λ types.

In some embodiments, disclosed herein are cyclic peptides that can be linked to any antibody or antibody fragment. In some embodiments, further provided herein are agents, for example, a polypeptide such as an antibody, e.g., a cell-penetrating antibody, that are biologically active (e.g., functional) in the cytosol of a cell. In some embodiments, an agent described herein that is cell-penetrating, e.g., a full-length format antibody, can target cytosolic proteins. Non-limiting examples of a full-length format antibodies that can be selectively targeted to a cell/tissue using the methods disclosed herein are adalimumab (Humira®) and bevacizumab (Avastin®). (Choi, Bae, Shin, Shin, & Kim, 2014).

In some embodiments, a cyclic peptide disclosed herein can be attached to an agent, for example, an antibody comprising a clinically-approved antibody (e.g., adalimumab or bevacizumab). In some embodiments, a cyclic peptide disclosed herein can be attached to an agent, for example, an antibody comprising a clinically-approved antibody or a fragment thereof (e.g., 2 HCs of adalimumab or bevacizumab).

In some embodiments, a cytosol-penetrating antibody disclosed herein (e.g., a 'cytotransmab', or CT), comprises a full-length IgG. In some embodiments, a cytosol-penetrating antibody disclosed herein (e.g., a 'cytotransmab', or CT), comprises a full-length IgG by incorporating a cytosol-penetrating VL into light chains (LCs) and then co-expressing the LCs with the heavy chains (HCs).

In some embodiments, a cytosol-penetrating antibody disclosed herein (e.g., a 'cytotransmab', or CT), comprises a Ras antibody. In some embodiments, a cytosol-penetrating antibody disclosed herein is a full-length Ras antibody. Intracellular targeting of oncogenic Ras has been previously described (Shin, et al., 2017) (Korean Patent Application No. 10-2017-0152998). In some embodiments, an agent disclosed herein (e.g. a cytosol-penetrating antibodies, 'cytotransmab', or CT) comprises an antibody or an antibody fragment that can target Ras, e.g., oncogeneic Ras including K-Ras, N-Ras, and H-Ras. In some embodiments, an agent disclosed herein (e.g. a cytosol-penetrating antibody, 'cytotransmab', or CT) comprises a full-length immunoglobulin format anti-Ras antibody. In some embodiments, an anti-Ras antibody or fragment thereof can be fused or conjugated to a cyclic peptide. In some embodiments, a cyclic peptide disclosed herein, targeting a cell membrane protein (e.g., EpCAM, integrin cαvβ5, etc.) thereby selectively targeting cells/tissues exhibiting (e.g., expressing or overexpressing) the cell membrane protein, can be fused to a Ras antibody (e.g., a full-length antibody or fragment thereof.)

As a non-limiting example, a Ras antibody can be fused to an EpCAM-targeting cyclic peptide (see Example 20). In some embodiments, a cyclic-peptide fused Ras antibody can selectively target cells/tissues. In some embodiments, a cyclic-peptide fused Ras antibody can penetrate into a targeted cell.

5.4.2 Linkers

As described herein, the antibody with the cell-penetrating ability and cyclic peptides are fused by the genetic engineering method using MGSSSN linker (SEQ ID NO: 102) and G4S (Gly-Gly-Gly-Gly-Ser) (SEQ ID NO: 103) or $(G_4S)_2$ linker (SEQ ID NO: 101), and they are cloned into an animal expression vector. The linker has been conventionally used for fusing antibodies and peptides. The linker is selected and used for fusing antibodies and peptides described herein because it provides its structural flexibility and spatial arrangement to maintain the original function of the proteins before and behind the linker. However, as used herein, a linker for fusing antibodies and cyclic peptides is not limited by the antibody as described above. Any linker can be applicable as used herein as long as the linker provides the structural flexibility and spatial distance, which is suitable for genetic engineering fusion in the art.

In some embodiments, the linker is a polypeptide linker of about 1 to about 20 residues in length. In some embodiments the linker is a polypeptide linker of about 1 to about 5 residues, about 6 to about 10 residues, about 10 to about 15 residues, or about 15 to about 20 residues. In some embodiments, the linker comprises the amino acid sequence MGSSSN (SEQ ID NO: 102). In certain embodiments the linker comprises the amino acid sequence GGGS (SEQ ID NO: 109).

5.4.3 Cytotransmabs

In general, antibodies do not penetrate directly into living cells due to their large size and hydrophilic nature. However, the development of cell-penetrating antibodies, referred to as cytotransmabs (CTs), was recently reported (Choi, Bae, Shin, Shin, & Kim, 2014). Cytotransmabs are full-length IgG antibodies, which are able to penetrate into living cells through endocytic internalization and localization to the cytosol. Without wishing to be bound by theory or mechanism, after the cell internalization (endocytosis), they are dissociated from the membrane protein in the endosome. Then, the endosomal escape ability causes the antibody to escape from the endosome into the cytoplasm, so that the antibody is located in the cytoplasm. In other words, the cytosolic localization of a cytotransmab takes place through the following three sequential steps: i) cellular internalization by receptor-mediated endocytosis, ii) dissociation from the endosomal lumen, and iii) escape from the endosomal lumen to the cytosol.

In certain embodiments, a CT binds to HSPG, a cell membrane receptor, but HSPG is not a cell membrane receptor specifically expressed in only target cells. Thus, in certain embodiments, presented herein are antibodies with lower HSPG binding ability, which can contribute to or increase the cell/tissue-specificity cell of the cyclic peptide-containing antibodies presented herein.

The initial version of cytotransmab, TMab4 and TMab4-WYW, showed cell-penetrating activity in a variety of tumor cells due to its cellular uptake through heparan sulfate proteoglycan (HSPG), a ubiquitously expressed receptor (Choi, Bae, Shin, Shin, & Kim, 2014); (Kim, et al., 2016). HSPG, a receptor for cytotransmab, is generally expressed in most animal tissues (Perrimon & Bernfield, 2000). The nonspecific cytosol-penetration activity of earlier cytotransmab is undesirable because it can lead to off-target effects and/or an accelerated clearance rate due to nonspecific tissue binding after systemic administration.

Previously reported cytotransmabs, such as TMab4 and TMab4-WYW localize to the cytosol of cells after receptor-mediated endocytosis via cell surface-expressed heparan sulfate proteoglycan (HSPG), and are subsequent released from endosomes into the cytosol. Generally, endocytosed molecules are first transported to early endosomes (EEs; pH 5.5-6.5) and then usually to late endosomes (pH 4.5-5.5), and subsequently to lysosomes (pH<5.0) for degradation (Kim, et al., 2016). However, rather than being routed to degradative lysosomes, CTs, including TMab4-WYW, are dissociated from HSPG in acidified EEs, allowing them to escape into the cytosol from the lumen of EEs (Kim, et al., 2016).

The endosomal escape motif of TMab4-WYW resides in the light chain variable domain (VL) and is composed of a pH-sensing pair [AspL1 (where L=light chain with Kabat numbering) (Kabat, Wu, Foeller, Perry, & Gottesman, 1991) in the framework region (FR) and MetL95 in the third complementarity-determining region of the VL (VL-CDR3)] and a membrane-binding motif of 92WYW94 (TrpL92, TyrL93, and TrpL94) in VL-CDR3. At the mildly acidified pH of early endosomes, the carboxyl group of the negatively charged Asp (or Glu) residues become more protonated and therefore more hydrophobic, facilitating new hydrophobic interactions with MetL95 and shortening the distance between AspL1 and MetL95 from ~6.5 to ~3-4 Å. This AspL1-MetL95 interaction subsequently triggers local structural rearrangement of the MetL95-neighboring residues of 92WYW94, forcing the side chains to become upright in a favorable conformation to interact with the endosomal membrane. This interaction causes membrane lipid flip-flop, leading to the formation of membrane toroidal pores composed of the cytotransmab and a phospholipid for the endosomal escape of the cytotransmab into the cytosol. Consequently, the endocytosed cytotransmab escapes into the cytosol from endosomes.

In some embodiments, a CT provided herein comprises an intact immunoglobulin. In some embodiments, a CT disclosed herein is bioengineered to have a reduction in the interaction with one or more cell membrane proteins (e.g., ubiquitously expressed proteins such as HSPG), such that the CT will not exhibit non-specific interactions with non-targeted cells and/or tissues. In some embodiments a CT disclosed herein comprises amino acid substitutions (and/or other mutations) in one or more domains (e.g. a VL domain) that result in reduced non-specific interaction with one or more cell surface proteins. In some embodiments, a CT disclosed herein exhibits improved biophysical properties. Optimization of protein physical properties is well-known in the art, and non-limiting examples of physical properties of a CT disclosed herein are reduced protein aggregation, higher stability, reduced degradation, and reduced hydrophobicity.

In certain embodiments, the CTs described herein exhibit improved properties, such as improved expression level, colloidal stability, and manufacturability.

5.5 Methods of Making

5.5.1 Vectors, Cloning, and Mutagenesis

Provided herein are methods of preparing a cyclic peptide, cyclic peptide fusion, CT, cyclic-peptide-CT fusion, or any agents disclosed herein. In some embodiments, provided herein is a method for preparing a vector comprising a light chain variable region (VL) and/or a heavy chain variable region (VH) of a human antibody.

5.5.2 Transfections, Cell Culture, Purification

In some embodiments, a CT disclosed herein is made by transfecting an animal cell with a VL and/or a VH of an antibody disclosed herein with prepared heavy chain and light chain expression vectors, thereby expressing an antibody fused with an intact immunoglobulin-type cell-penetrating antibody and a cyclic peptide specifically binding to a cell membrane surface protein; and purifying and recovering the expressed antibody.

In some embodiments, the method can produce an intact immunoglobulin-type antibody having a cell-penetrating ability by expressing a light chain expression vector and a heavy chain expression vector. In some embodiments, the light chain expression vector and the heavy chain expression vector may be introduced into the host cell by co-transformation. In certain embodiments, the vector-introduced host cell is cultured to express an intact IgG-type cell-penetrating antibody, and then the antibody is purified and recovered from the supernatant.

In certain embodiments, the host cell can be any host cell known in the art. Non-limiting examples of host cells include, for example, *E. coli* JM109, *E. coli* BL21, *E. coli* RR1, *E. coli* LE392, *E. coli* B, *E. coli* X 1776, *E. coli* W3110, *Bacillus* sp. strains such as *Bacillus thuringiensis* and *Bacillus subtilis*, intestinal bacteria or strains such as *Salmonella typhimurium, Serratia marcescens*, and various *Pseudomonas* species. In some embodiments, the host cells for transforming eukaryotic cells include, as non-limiting examples, yeast (*Saccharomyce cerevisiae*), an insect cell, a plant cell or an animal cell such as SP2/0, CHO (Chinese hamster ovary) K1, CHO DG44, PER.C6, W138, BHK, COS-7, 293, HepG2, Huh7, 3T3, RIN and MDCK cell lines.

In certain embodiments, also disclosed herein are methods for making a cell/tissue-specific cell-penetrating antibody disclosed herein. In some embodiments, methods for making a cell/tissue-specific cell-penetrating antibody disclosed herein comprise introducing a vector into a host cell; expressing the vector in the host cell; and recovering the expressed antibody. In certain embodiments, further disclosed herein are methods for making a cell/tissue-specific cell-penetrating antibody disclosed herein. In some embodiments, methods for making a cell/tissue-specific cell-penetrating antibody disclosed herein comprise introducing a vector into a host cell; expressing the vector in the host cell; and recovering the expressed antibody.

In some embodiments, also disclosed herein are methods of making an antibody disclosed herein comprising introducing into a host cell a vector comprising a polynucleotide encoding a polynucleotides encoding a light chain variable region (VL) and/or a heavy chain variable region (VH) of an antibody comprising an endosome escape motif, a polynucleotide encoding the light chain variable region (VL) with reduced or abolished HSPG binding ability, and a polynucleotide encoding a cyclic peptide that specifically binds to a cell surface molecule fused at the N-terminus of the light chain variable region (VL) and/or the heavy chain variable region (VH); expressing the vector in the host cell; and recovering the expressed antibody.

In some embodiments, further disclosed herein are polynucleotides encoding a cell/tissue-specific cell-penetrating antibody disclosed herein. In some embodiments, disclosed herein are vectors comprising polynucleotides disclosed herein. In some embodiments, also provided herein are cells comprising vectors disclosed herein.

In some embodiments, further provided herein are pharmaceutical compositions comprising the cell/tissue-specific cell-penetrating antibody according disclosed herein as an active ingredient and a pharmaceutically acceptable carrier. In some embodiments, a pharmaceutical composition disclosed herein can be used in treating a disease or condition in a subject. In some embodiments, a pharmaceutical composition disclosed herein can be used in treating cancer. In some embodiments, a pharmaceutical composition disclosed herein can be used in treating an immune disease. In some embodiments, a pharmaceutical composition disclosed herein can be used in treating a neurological disease.

5.6 Therapeutic Methods of Use

In some embodiments, a cell/tissue-specific cell-penetrating antibody described herein can be useful for therapeutic agents which target cancer to which the fused cyclic peptide may specifically bind.

Further, in some embodiments, the tissue-specific cell-penetrating antibody can be genetically fused or chemically conjugated with payload such as a toxin, an enzyme, a protein, a peptide, an siRNA (small interfering RNA), and/or an antisense RNA, as a sole substance without cell-penetrating ability, so that it can be used as medium of delivering the payload to the cytoplasm.

Further, in certain embodiments, the properties of cell/tissue-specific cell-penetrating antibody of the present invention can be used to develop the antibody therapeutic agent in which the target disease and tissue are specified to increase the therapeutic effect and to lower the side effects (e.g., toxicity) by no distribution or little distribution of the antibody therapeutic agent in the normal tissue.

In some embodiments, provided herein are methods of preventing or treating a disease or condition in a subject comprising administering a therapeutically effective amount of an agent, e.g., a cell/tissue-specific cell-penetrating antibody and/or cyclic peptide disclosed herein to the subject.

In some embodiments, further provided herein are methods of preventing or treating a disease or condition in a subject comprising administering a therapeutically effective amount of the cell/tissue-specific cell-penetrating antibody or the cyclic peptide disclosed herein to the subject, wherein the disease or condition is a cancer. In some embodiments, further provided herein are methods of preventing or treating a disease or condition in a subject comprising administering a therapeutically effective amount of the cell/tissue-specific cell-penetrating antibody or the cyclic peptide disclosed herein to the subject, wherein the disease or condition is an immune disease.

6. EXAMPLES

6.1 Example 1. Design of Light Chain Variable Region (VL) Variants with Reduced HSPG Binding Ability A cell-penetrating, human IgG1 antibody TMab4-WYW, generally referred to as a cytotransmab (CT), has been previously described (WIPO Publication Nos: WO2016013870A1 and WO2017204606A1 and Korean Patent Application No: 10-2017-0152998). Cell-penetrating antibodies can penetrate into the cytoplasm through a mechanism whereby the antibody's light chain variable region (VL) binds to cell surface heparan sulfate proteoglycan (HSPG) receptors, which mediate endocytosis. However, due to the ubiquitous expression of HSPG receptors, CT targets cells non-specifically. In order to improve the specificity of CT cell targeting, a next-generation CT was designed in which HSPG binding ability is reduced.

Previous studies have revealed that a unique cationic patch sequence composed of Arg27f, Arg29, and Lys30 in the complementarity-determining region 1 (CDR1) of the cytotransmab hT4-WYW antibody's light chain variable region (VL-CDR1) is critical for HSPG binding (Choi, Bae, Shin, Shin, & Kim, 2014). In order to reduce the binding of CT to HSPG, the VL-CDR1 region was targeted for mutagenesis. Variants were generated by replacing the cationic patch sequence of CDR1 and adjacent amino acids with the CDR1 sequence of Vκ2-40 subtype, which has the same number of amino acids of CDR1 among human germline derived sequences. In this example, amino acids known to be important for the stability of the conventional light chain variable region were conserved.

In order to maintain a low HSPG binding ability, phenylalanine residue of 27c, which was thought to affect the loop structure formation of the light chain variable region CDR1 of hT4-WYW VL, was mutated with leucine conserved in the light chain variable region, which had the reduced HSPG binding ability. Further, residues at 27f to 30, which were located at the tip of the CDR1 loop structure in a region expected to expose the side chain, were also mutated. Variants were generated using hT4-WYW VL as a template. In variant CT03a VL (hT4-34 VL; Korean Patent Application No. 10-2017-0152998), residue 27c, which was thought to affect the loop structure formation in the light chain variable region CDR1, was point-mutated. In generating variant CT03b VL (hT4-35 VL; Korean Patent Application No. 10-2017-0152998), threonine, arginine, lysine, and asparagine residues of 28, 29, 30, and 31, respectively, were replaced with aspartate, glycine, asparagine, and threonine. To generate variant CT03c VL (hT4-36 VL; Korean Patent Application No. 10-2017-0152998), arginine, threonine, lysine, and asparagine residues 27f, 28, 30, and 31, respectively, were replaced with aspartate, aspartate, asparagine, and threonine. To create variant CT03d VL (hT4-38 VL; Korean Patent Application No. 10-2017-0152998), arginine and asparagine residues of 29 and 31, respectively, were replaced with glycine and threonine. In the case of CT03e VL (hT4-39 VL; Korean Patent Application No. 10-2017-0152998), threonine and arginine residues of 28 and 29, respectively, were replaced with aspartate and glycine. Amino acids are numbered according to the Kabat numbering scheme.

Table 1 shows sequences of light chain variable regions (VL) containing mutations for reducing HSPG binding ability.

6.1.1

TABLE 1

| Names of light chain variable regions | Amino acid sequence | SEQ ID NO: |
|---|---|---|
| hT4-WYW VL | 1 10 20 abcdef 30 40 50<br>DLVMTQSPSSLSASVGDRVTITCKSSQSLFNSRTRKNYLAWYQQKPGKAPKLLIYW<br>60 70 80 90 100<br>ASTRESGVPSRFSGSGSGTDFTLTISSLQPEDFATYYCQQYWYWMYTFGQGTKVEIKR | 1 |
| CT03a VL (hT4-34 VL) | 1 10 20 abcdef 30 40 50<br>DLVMTQSPSSLSASVGDRVTITCKSSQSLLNSRTRKNYLAWYQQKPGKAPKLLIYW<br>60 70 80 90 100<br>ASTRESGVPSRFSGSGSGTDFTLTISSLQPEDFATYFCQQYWYWMYTFGQGTKVEIKR | 2 |
| CT03b VL (hT4-35 VL) | 1 10 20 abcdef 30 40 50<br>DLVMTQSPSSLSASVGDRVTITCKSSQSLLNSRDGNTYLAWYQQKPGKAPKLLIYW<br>60 70 80 90 100<br>LSYRASGVPSRFSGSGSGTDFTLTISSLQPEDFATYFCQQYWYWMYTFGQGTKVEIKR | 3 |
| CT03c VL (hT4-36 VL) | 1 10 20 abcdef 30 40 50<br>DLVMTQSPSSLSASVGDRVTITCKSSQSLLNSDDRNTYLAWYQQKPGKAPKLLIYW<br>60 70 80 90 100<br>LSYRASGVPSRFSGSGSGTDFTLTISSLQPEDFATYFCQQYWYWMYTFGQGTKVEIKR | 4 |
| CT03d VL (hT4-38 VL) | 1 10 20 abcdef 30 40 50<br>DLVMTQSPSSLSASVGDRVTITCKSSQSLLNSRTGKTYLAWYQQKPGKAPKLLIYW<br>60 70 80 90 100<br>ASTRESGVPSRFSGSGSGTDFTLTISSLQPEDFATYFCQQYWYWMYTFGQGTKVEIKR | 5 |
| CT03e VL (hT4-39 VL) | 1 10 20 abcdef 30 40 50<br>DLVMTQSPSSLSASVGDRVTITCKSSQSLLNSRDGKNYLAWYQQKPGKAPKLLIYW<br>60 70 80 90 100<br>ASTRESGVPSRFSGSGSGTDFTLTISSLQPEDFATYFCQQYWYWMYTFGQGTKVEIKR | 6 |

6.2 Example 2. Expression and Purification

In order to construct a heavy chain expression vector for producing a monoclonal antibody in the form of an intact IgG, DNA encoding the heavy chain fused with DNA encoding the secretion signal peptide at the 5'-terminus were cloned into NotI/HindIII of pcDNA3.4 (Invitrogen) vector. Heavy chain sequences included the heavy chain variable region (humanized HT0 VH: SEQ ID NO: 10) and the heavy chain constant region (CH1-hinge-CH2-CH3) of the antibody.

In order to construct a light chain expression vector, DNA encoding the light chain, fused with DNA encoding the secretion signal peptide at the 5'-terminus were cloned into NotI/HindIII of pcDNA3.4 (Invitrogen) vector. Light chain sequences included the cell-penetrating light chain variable region (hT4-WYW, CT03a, CT03b, CT03c, CT03d, CT03e VL) and the light chain constant region (CL).

The light and heavy chain expression vectors were transiently transfected to express and purify proteins. In a shaking flask, HEK293-F cells (Invitrogen) suspended-growing in serum-free FreeStyle 293 expression medium (Invitrogen) were transfected with a mixture of plasmid and polyethylenimine (PEI) (Polyscience). Following 200 mL transfection in a shaking flask (Corning), HEK293-F cells were seeded in 100 ml of the medium at a density of $2\times10^6$ cells/ml and cultured at 150 rpm and 8% $CO_2$. In order to produce each monoclonal antibody, suitable heavy and light chain plasmids were diluted in 10 ml of FreeStyle 293 expression medium (Invitrogen) so as to yield 125 μg of the heavy chain and 125 μg of light chain for a total of 250 μg (2.5 μg/ml). These were mixed with 10 ml of culture medium, which was diluted with 750 μg of PEI (7.5 μg/ml), and the mixture was incubated at room temperature for 10 minutes. Then, the reacted mixture medium was added to 100 ml of seeded cells. The obtained mixture was cultured for 4 hours at 150 rpm and 8% $CO_2$. The remaining 100 ml of FreeStyle 293 expression medium was further added thereto, and the obtained mixture was cultured for 6 days. Cell culture supernatant was collected and the protein was purified from the supernatant using standard protocols. Antibodies were applied to Protein A Sepharose column (GE healthcare), washed with PBS (pH 7.4), and eluted with 0.1 M glycine buffer at pH 3.0. Then, the sample was immediately neutralized with 1 M Tris buffer. The eluted antibody fractions were concentrated by dialysis while the buffer was exchanged with PBS (pH 7.4). The purified protein was quantified at 280 nm wavelength using absorbance and absorption coefficient.

6.3 Example 3. HSPG Binding Ability

The effect of light chain variable region (VL) mutation on HSPG binding was analyzed. HSPG binding of VL variants CT03a, CT03b, CT03c, CT03d, and CT03e was compared to binding for TMab4-WYW, which is the parent hT4-

WYW light chain of TMab4. VL binding to HSPG was detected by confocal microscopy.

FIG. 1A illustrates whether the HSPG binding ability and cell-penetrating ability of the antibody are reduced in the CT VL variants. HeLa cells were treated with 1 μM the antibody at 37° C. for 6 hours and the cellular localization of CT antibodies was observed by confocal microscopy. The experiment revealed that the order of fluorescence intensity of cell-penetrating antibodies located in the cytoplasm via HSPG was as follows: TMab4-WYW (100%), CT03a (40.1%), CT03c (31.8%), CT03d (26.3%), CT03e (19.6%), and CT03b (12.4%).

A HeLa cell line expressing HSPG was placed in 0.5 ml of a medium containing 10% FBS, at a density of $2\times10^4$ cells per well in a 24-well plate and cultured at 37° C. in a 5% $CO_2$ for 5 hours. When the cells were stabilized, 1 μM of PBS, TMab4-WYW, CT03a, CT03b, CT03c, CT03d, and CT03e, respectively, was cultured at 37° C. for 6 hours. Then, the medium was removed, and the remnants were washed with PBS. Then, proteins attached to the cell surface were removed with a mild-acidic solution (200 mM glycine, 150 mM NaCl pH 2.5). After washing with PBS, 4% paraformaldehyde was added thereto. Then, the cells were fixed at 25° C. for 10 minutes. Then, the cells were washed with PBS and cultured with a buffer solution which was PBS containing 0.1% saponin, 0.1% sodium azide, and 1% BSA at 25° C. for 10 minutes, thereby forming holes in the cell membrane. After washing with PBS again, the reaction was carried out at 25° C. for 1 hour with a buffer solution (PBS containing 2% BSA) to suppress non-specific binding. Each antibody was stained with a Alexa-488-conjugated secondary antibody that specifically recognizes human Fc (green fluorescence). The nuclei were stained (blue fluorescence) using Hoechst 33342.

6.4 Example 4. Physical Properties of VL Variants

For therapeutic proteins, aggregates are a significant risk factor for deleterious immune responses in patients. Controlling protein aggregation and degradation is essential for enabling improved design of therapeutic protein stability, ligand binding, targeting, and activity in vivo. Evaluation of protein hydrophobicity is an efficient parameter for indirectly confirming protein physical properties. Proteins with high hydrophobicity are likely to aggregate due to nonspecific interactions between protein molecules. Thus, during the drug development process, screening candidates with poor physical properties due to high hydrophobicity is critical for the success of new drug development.

To assess the biophysical properties of the CT variants at an early stage of construction, they were analyzed on the Zenix SEC-300 HPLC column (Sepax technologies) to evaluate the hydrophobicity of proteins by high-performance liquid chromatography.

80 μl of TMab4-WYW, CT03b, CT03c, CT03d, and CT03e at a 1 mg/ml concentration was prepared. CT03a, which showed the least reduction in HSPG binding in Example 3, was not analyzed. For the Zenix SEC-300 size-exclusion chromatography column, a buffer of 150 mM $Na_3PO_4$ and 137 mM NaCl at pH 7.0 flowed at a flow rate of 1.0 ml/min. Then, the chromatography column was set when the pressure and the mAU at 280 nm were stabilized. The purified antibodies were injected at 1.0 mg/mL and 30 μL sample volume and were monitored at 280 nm for 30 min.

HPLC results reveal that CT03e showed a peak at a time similar to that of the Trastuzumab control monoclonal antibody (FIG. 1B). However, CT03b, CT03c, and CT03d showed peaks at a later time compared to the control. Further, the peaks' widths were abnormally broad. Based on the results of analysis HSPG binding and protein hydrophobicity, VL variant CT03e was chosen for further development. CT03 showed significantly lower HSPG binding ability (FIG. 1A) and the least protein aggregation (FIG. 1B).

6.5 Example 5. Design of New CT03e VL Variant with Improved Physical Properties The results demonstrated that CT03e had better physical properties than other variant, but showed more aggregation than the control trastuzumab antibody (FIG. 1B). Among the mutants, variant CT03e was eluted with the earliest retention time but showed an asymmetric elution peak (FIG. 1B). To further improve the biophysical properties of CT03e, we investigated other replaceable regions and residues in the VL domain of CT03e.

A residue at L50 of VL-CDR2 of CT03e is tryptophan. A hydrophobic and bulky Trp residue at this position is known to cause more aggregation than negatively charged residues (Dudgeon, et al., 2012) and can negatively affect VH-VL interactions (Choi, Bae, Shin, Shin, & Kim, 2014). Therefore, studies have searched for clinically-approved antibodies that have a CDR2 sequence in which a negatively charged amino acid, particularly, aspartate or glutamate, is located at this 50th residue rather than tryptophan (Dudgeon, et al., 2012).

An endosomal escape motif was previously introduced into the light chain variable region of various clinically-approved antibodies to develop a new light chain variable region with endosomal escape ability (WIPO Publication No. WO2017204606A1). Among the clinically-approved antibodies, panitumumab-WYW VL has an aspartate at the 50th residue. Therefore, the sequences of CT03e VL and panitumumab-WYW VL were combined to construct a novel light chain variable region sequence. The VL-CDR2 ($^{50}$WASTERS$^{56}$) of CT03e was replaced with ($^{50}$DASNLET$^{56}$) derived from panitumumab (Vectibix®) to generate CT05 VL. Table 2 shows sequences of light chain variable regions (VL) containing mutations for improving protein aggregation.

6.5.1

TABLE 2

| Names of light chain variable regions | Amino acid sequence | SEQ ID NO: |
|---|---|---|
| CT03e VL (hT4-39 VL) | 1 10 20 abcdef 30 40 50<br>DLVMTQSPSSLSASVGDRVTITCKSSQSLLNSRDGKNYLAWYQQKPGKAPKLLIYW<br>60 70 80 90 100<br>ASTRESGVPSRFSGSGSGTDFTLTISSLQPEDFATYFCQQYWYWMYTFGQGTKVEIKR | 6 |

TABLE 2-continued

| Names of light chain variable regions | Amino acid sequence | SEQ ID NO: |
|---|---|---|
| Panitumumab-WYW VL | 1 10 20 abcd 40 50<br>DIQMTQSPSSLSASVGDRVTITCQASQDISNYLNWYQQKPGKAPKLLIYD<br>60 70 80 90 100<br>ASNLETGVPSRFSGSGSGTDFTFTISSLQPEDIATYFCQQYWYWMYTFGGGTKVEIKR | 7 |
| CT05 VL | 1 10 20 abcdef 30 40 50<br>DIQMTQSPSSLSASVGDRVTITCKSSQSLLNSRDGKNYLAWYQQKPGKAPKLLIYD<br>60 70 80 90 100<br>ASNLETGVPSRFSGSGSGTDFTFTISSLQPEDIATYFCQQYWYWMYTFGGGTKVEIKR | 8 |

The light chain variable region was designed in the same method as described in Example 2. The VL was cloned into a light chain expression vector, and they were transiently co-transfected into HEK293F cells along with a cell-penetrating humanized heavy chain expression vector. Proteins were purified by the same method as in Example 2.

6.6 Example 6. Improved Physical Properties of the CT05 VL Variant

To test the physical properties of the newly generated CT05 variant using high-performance liquid chromatography, Zenix SEC-300 column analysis was conducted, in which the results are mAU values at 280 nm obtained by Zenix SEC-300 column analysis which can evaluate the protein hydrophobicity using a high-performance liquid chromatography.

80 μl of TMab4-WYW, CT03e, and CT05, were prepared at a concentration of 1 mg/ml as described in Example 4. For the Zenix SEC-300 size-exclusion chromatography column, a buffer of 150 mM $Na_3PO4$ and 137 mM NaCl at pH 7.0 flowed at a flow rate of 1.0 ml/min. Then, the chromatography column was set when the pressure and the mAU at 280 nm were stabilized. Thereafter, 30 μl of the prepared samples were loaded at the same flow rate thereof, and the mAU values had been measured at 280 nm for 30 min.

CT05 showed a sharp symmetric peak with a retention time similar to that of Trastuzumab (Herceptin®) (FIG. 2A). Thus, the VL-CDR2 variant CT05 was determined to have better physical properties (e.g., protein aggregation and hydrophobicity) than CT03e. CT05 was selected for further characterization and development.

6.7 Example 7. HSPG Binding Ability of the CT05 VL Variant

Confocal microscopy was performed for detection of internalized antibodies in cultured cells, as described in Example 5. Confocal microscopy was used to compare the HSPG binding and cell internalization ability of CT05 and the parent TMab4-WYW.

A HeLa cell line expressing HSPG was placed in 0.5 ml of a medium containing 10% FBS, at a density of $2\times10^4$ cells per well in a 24-well plate and cultured at 37° C. in 5% $CO_2$ for 12 hours. Cells were treated with 1 μM of TMab4-WYW, 1 μM CT05, or PBS control and cultured at 37° C. for 6 hours. After two washes with PBS, the cells were washed two times for 30 s at room temperature with a mildly acidic glycine buffer (200 mM glycine, 150 mM NaCl, pH 2.5), followed by two additional washes with PBS to remove non-internalized and nonspecifically surface-bound antibodies. After fixation with 4% paraformaldehyde in PBS for 10 min at room temperature, permeabilization with PERM-buffer (0.1% saponin, 0.1% sodium azide, and 1% BSA in PBS) for 10 min at 25° C., and then blocking with 2% BSA in PBS for 1 h at room temperature, the internalized antibody was detected with an Alexa Fluor 488-conjugated goat anti-human IgG antibody (Invitrogen, A-11013) for 2 h at room temperature. The nuclei were stained with Hoechst 33342 for 5 min in PBS. After mounting the coverslips onto glass slides with the Perma Fluor aqueous mounting medium (Thermo Scientific, TA-030-FM), we obtained center-focused single z-section images on a Zeiss LSM710 system with the ZEN software (Carl Zeiss).

The experiment revealed that the fluorescence intensity of CT05 was only 17.3% that of TMab4-WYW, indicating a five-fold decrease in cellular internalization for the CT05 variant compared to the parent antibody (FIG. 2B). Thus, the VL-CDR variant CT05 maintains the desired reduction in HSPG binding ability of CT03e (FIG. 1A, lower left) compared to the parent antibody.

6.8 Example 8. Endosomal Escape Ability

Previous studies have revealed that endosomal escape ability is due to a cell membrane-binding motif located in CDR3 as well as a pH-sensitive interaction between a residue in the framework region and a residue in CDR3, but it was not dependent on sequences within CDR1 and CDR2 (Kim, et al., 2016). The newly constructed CT05 variant includes the same pH-sensing pair and cell membrane-binding motif sequences as the parental antibody, hT4-WYW VL. Thus, its endosomal escape ability is expected to be similarly maintained. To test whether CT05 retains the endosomal escape ability of TMab4-WYW, we assessed the uptake of trypan blue dye by a nonadherent cell line that lacks HSPG expression (Ramos human Burkitt's lymphoma cells). As a negative control, a CT05-AAA mutant was created, harboring a $^{92}$AAA$^{94}$ substitution of the membrane-binding motif $^{92}$WYW$^{94}$ in VL-CDR3, wherein the 92nd to 94th amino acids responsible for the endosomal escape ability and located in the existing light chain variable region, was replaced with consecutive three alanines.

In order to adhere Ramos cells to cell culture plates, 24-well plates were first coated with poly-L-lysine. 200 μl of 0.01% poly-L-lysine was added to the 24-well plate, and they were reacted at 25° C. for 20 min. After washing with PBS, Ramos cells adhered to the plate at $5\times10^4$ cells per well. After confirming the cell adhesion, 1 μM of TMab4-WYW, CT05, or CT05-AAA, was added to 200 μl of buffers at two pHs. Buffer alone was used as a negative control. pH 7.4 buffer (HBSS (Welgene), 50 mM HEPES pH 7.4) is similar to the cytoplasmic pH. pH 5.5 buffer (HBSS (Welgene), 50 mM MES pH 5.5) is similar to initial endosomal pH. Cells were cultured at 37° C. for 2 hours. After carefully washing with PBS, 10 µl of trypan blue was mixed with 190 µl of PBS, and 200 µl of the mixture was dispensed in each well. Then, they were observed by a microscope.

Antibody that retains endosomal escape ability will be expected to facilitate uptake of the dye at pH 5.5, which is the endosomal acidic pH condition, but not at pH 7.4, which is the cytosolic pH (FIG. 2C, top). CT05 facilitated cellular uptake of the trypan blue dye at pH 5.5 (endosomal acidic pH condition), but not at pH 7.4 (FIG. 2D). CT05 showed trypan blue uptake ability similar to that of TMab4-WYW which has the same endosomal escape motif. On the other hand, cells incubated with the CT05-AAA variant lacking the membrane-binding motif showed little trypan blue uptake ability (FIG. 2D, bottom right). The Ramos cells maintained intact morphology without lysis, confirming that the endosomal escape of CTs proceeds through formation of membrane toroidal pores rather than via membrane lysis (FIG. 2D).

The percentage of blue-stained cells at each pH condition was also quantitated, showing strikingly similar endosomal escape ability between CT05 and TMab4-WYW (FIG. 2C, bottom graph). These results revealed that CT05 was successfully engineered to have minimal HSPG-mediated cellular internalization while retaining the pH-dependent membrane pore formation ability of TMab4-WYW through preservation of the endosomal escape motif.

6.9 Example 9. Design and Purification of epCT05, a Cyclic Peptide-Fused CT05 Variant Capable of Tumor Tissue-Specific Targeting CT05 has maintains its endosomal escape ability, while maintaining a dramatically reduced HSPG binding ability. These combined features can confer the ability to selectively target specific receptors within tumors for the tumor tissue-specific cellular internalization and cytoplasmic penetration. EpCAM (epithelial cell adhesion molecule) was selected as a potential target receptor for tumor tissue-specific targeting by CT05. EpCAM is a glycosylated type I transmembrane protein involved in cell adhesion. It is overexpressed in many solid tumors, such as colon cancer, with limited expression in normal epithelial tissues (Went, et al., 2006) (Munz, Baeuerle, & Gires, 2009) and has been validated as a target for tumor tissue-specific delivery of cancer therapeutics (Simon, Stefan, Pluckthun, & Zangemeister-Wittke, 2013) (Di Paolo, et al., 2003) (Singh, et al., 2016).

To generate a tumor tissue-specificity cell-penetrating antibody, CT05, which has been engineered to have reduced HSPG-binding, was targeted to EpCAM receptors. The twelve residue cyclic peptide Ep133 (amino acid sequence EHLHCLGSLCWP (SEQ ID NO: 13)), which binds specifically to the EpCAM receptor, was employed to direct CT05 targeting. This cyclic peptide is described in U.S. Pat. No. 9,815,866B2, "Peptides that bind to epithelial cell adhesion molecule." To selectively target CT05 to EpCAM receptors on EpCAM-expressing tumor tissues, Ep133 was fused at the N-terminus of the CT05 light chain variable region (VL) via a $(G_4S)_2$ linker (SEQ ID NO: 101), thereby generating epCT05 (FIG. 3A). The resulting epCT05 antibody contains a bivalent EpCAM-binding peptide moiety.

For the mammalian cell expression of the cell-penetrating antibody fused with the EpCAM targeting cyclic peptide (epCT05), DNAs encoding the light chain including the cyclic peptide-fused CT05 light chain variable region and the light chain constant region (CL) were cloned into pcDNA3.4 vector fused with DNA encoding the secretion signal peptide at the 5'-terminus as described in Example 2. Light chain expression constructs were transiently co-transfected into HEK293F cells along with a cell-penetrating humanized heavy chain expression vector, thereby expressing individual clones. They were purified by the same method as in Example 2. Table 3 depicts the sequences and names of light chain variable regions (VL) fused with tumor-specific cyclic peptides.

6.9.1

TABLE 3

| Names of light chain variable regions | Amino acid sequence | SEQ ID NO: |
|---|---|---|
| CT05 VL | 1 10 20 abcdef 30 40 50<br>DIQMTQSPSSLSASVGDRVTITCKSSQSLLNSRDGKNYLAWYQQKPGKAPKLLIYD<br>60 70 80 90 100<br>ASNLETGVPSRFSGSGSGTDFTFTISSLQPEDIATYFCQQYWYWMYTFGGGTKVEIKR | 8 |
| epCT05 $(G_4S)_2$ VL | 1 10 20 30 40 50<br>EHLHCLGSLCWPGGGGSGGGGSDIQMTQSPSSLSASVGDRVTITCKSSQSLLNSR<br>60 70 80 90 100 110<br>DGKNYLAWYQQKPGKAPKLLIYDASNLETGVPSRFSGSGSGTDFTFTISSLQPED<br>120 130<br>IATYFCQQYWYWMYTFGGGTKVEIKR | 9 |

6.10 Example 10. Selective Targeting of epCT05 to EpCAM-Expressing Cells

The EpCAM-binding peptide-fused epCT05 was incubated with three cell lines in order to assay tissue-specific binding. HCT116 (human colon cancer cell line) and SW480 (colon adenocarcinoma cell line) cells are EpCAM positive, and HeLa (cervical carcinoma cell line) cells are EpCAM negative.

To detect cell-surface expression of EpCAM on the human tumor cells, $1\times10^5$ cells of HCT116, SW480, and HeLa were prepared for the respective samples. The anti-EpCAM antibody was diluted and placed at 1:200 and cultured at 4° C. for 1 hour. Then, the primary antibody anti-EpCAM antibody was reacted with Alexa Fluor 488-labeled anti-EpCAM antibody specific for rat Fc (green fluorescence), at 4° C. for 30 min. After washing with PBS, the cells were analyzed by flow cytometry. The results revealed that anti-EpCAM antibodies bound to HCT116 and SW480 cells, but not to HeLa cells (FIG. 3B, top panels).

To test for epCT05 targeting to cell surface EpCAM receptors, the cells were cultured in PBSF (PBS buffer, 2% BSA) with 100 nM of CT05 or epCT05 at 4° C. for 1 hour. Then, each antibody was reacted with antibodies specific for human Fc to which Alexa488 (green fluorescence) was linked, at 4° C. for 30 min. After washing with PBS, the cells were analyzed by flow cytometry.

Flow cytometric analysis revealed that epCT05, but not CT05, selectively bound to EpCAM-positive HCT116 and SW480 cells with little binding to EpCAM-negative HeLa cells (FIG. 3B). Therefore, epCT05 antibodies were able to specifically target EpCAM-expressing cancer cells.

6.11 Example 11. Cellular Internalization and Endosomal Escape Ability of epCT05

It was demonstrated that epCT05, the cell-penetrating antibody containing an EpCAM-targeting cyclic peptide, can specifically bind to EpCAM-expressing tumor tissue. Experiments were carried out to confirm whether the in addition to binding to cell surface EpCAM, epCT05 is internalized into tumor cells.

SW480 and HeLa cells were treated with 1 μM of the epCT05 antibody, 1 μM TMab4-WYW, or buffer at 37° C. for 6 hours. Cells were grown in 0.5 ml of a medium containing 10% FBS in a 24-well plate at a density of $2\times10^4$ cells/well. The cells were cultured at 37° C. in 5% $CO_2$ for 12 hours. When the cells were stabilized, 1 μM TMab4-WYW, 1 μM epCT05 or PBS was added and cells were cultured at 37° C. for 6 hours. Then, the cells were washed with PBS and a mild-acidic solution as described in Example 3 and then subjected to cell fixation, cell perforation, and blocking. Each antibody was stained with an antibody that specifically recognizes human Fc to which Alexa-488 (green fluorescence) was conjugated. The nuclei were stained (blue fluorescence) using Hoechst 33342.

The epCAM-expressing SW480 cells were able to internalize both the epCT05 antibody and TMab4-WYW (FIG. 4A, upper panel). On the other hand, the EpCAM negative Hela cell line could only internalize the TMab4-WYW antibody (FIG. 4A, bottom panel). This specificity indicates that cellular internalization of epCT05 through endocytosis is mediated by cell surface-expressed EpCAM rather than by an HSPG. Therefore, the reduced HSPG binding activity of epCT05 coupled with the EpCAM-specific targeting activity conferred by the Ep133 cyclic peptide, enable epCT05 antibodies to selectively bind to EpCAM-expressing tumor cells and penetrate into the cytosol.

The EpCAM-targeting Ep133 cyclic peptide is a cyclic peptide which is formed by a disulfide bond. When the disulfide bond is cleaved due to the reducing conditions of the endosome, the peptide's affinity to EpCAM is significantly reduced (U.S. Pat. No. 9,815,866B2, "Peptides that bind to epithelial cell adhesion molecule"). Accordingly, following cellular internalization of epCT05, the Ep133 disulfide bond is cleaved inside the endosome, and the Ep133 cyclic peptide is expected to dissociate from EpCAM. Dissociation of Ep133 from EpCAM, would free the epCT05 within the endosome, allowing it to escape into the cytoplasm. In order to verify this hypothesis, the cell penetrating antibody CT05 was fused at the N-terminus with Ep114 peptide (U.S. Pat. No. 9,815,866B2, "Peptides that bind to epithelial cell adhesion molecule"). Ep114 is a linear peptide-type which specifically binds to EpCAM.

To examine escape of internalized antibodies from endosomes, a calcein leakage assay was performed. Cells are incubated with antibody and calcein and calcein is internalized into endosomes only when antibodies are internalized (FIG. 4B, top left). If the antibody is not capable of endosomal escape, calcein remains in the endosomes, resulting in punctuate fluorescence (FIG. 4B, top middle). However, if internalized antibodies are capable of endosomal escape, calcein is also released into the cytosol, resulting in diffusive fluorescence (FIG. 4B, top right).

The HCT116 cell line was prepared as described in Example 3, and 1 μM of cytotransmab, Ep133-fused cytotransmab, or Ep114-fused cytotransmab were incubated with the cells at 37° C. for 6 hours. After 4 hours, the wells containing the antibody were treated with 150 μM calcein, and the cells were cultured at 37° C. for 2 hours. After washing with PBS and mild-acidic solution as described in Example 3, the cells were fixed. The nuclei were stained (blue fluorescence) using Hoechst 33342, and they were observed by confocal microscopy.

The cells treated with the linear peptide Ep114-fused cytotransmab showed almost no release of calcein fluorescence into the cytosol (FIG. 4C, bottom right). However, the cells treated with Ep133-fused cytotransmab (epCT05) showed green calcein fluorescence throughout the cytoplasm, which was concentration-dependent in the cell. Therefore, the Ep114-fused cytotransmab showed no cell-penetrating ability, but the Ep133-fused cytotransmab showed cell-penetrating ability. The linear peptide Ep114-fused cytotransmab was able to bind to EpCAM and travel to the endosomes, but the antibody maintained binding to EpCAM. It remained bound to EpCAM in the endosome and ultimately migrated to the lysosome to be destroyed. On the other hand, the cytotransmab fused with cyclic peptide Ep133 was internalized into the cell via EpCAM, and then the disulfide bond of the Ep133 cyclic peptide was cleaved in the endosome. The affinity of the antibody to EpCAM decreased, and the antibody was dissociated from EpCAM. Then, the cell-penetrating antibody was free in the endosome. Then the condition of mild-acidic endosome led to a structural change, resulting in the endosomal escape. These results demonstrated that unlike linear peptides, cyclic peptides were suitable for binding to the target membrane protein in order to impart the tissue-specificity or cell-specificity to the cell penetrating antibody.

6.12 Example 12. Cellular Localization of epCT05

In order to directly demonstrate that epCT05 is located in the cytoplasm, an enhanced split green fluorescent protein (GFP) complementation assay was conducted as described in Korean Patent No. 10-1790669, "Enhanced split-GFP complementation system, and its application thereof.". Complemented GFP fluorescence can be observed only when an extracellularly added IgG-GFP11-SBP2 antibody (IgG antibody fused with a GFP11 fragment and a streptavidin-binding peptide 2, SBP2, at the C terminus of HC) is internalized by cells via receptor-mediated endocytosis, escapes from endosomes into the cytosol, and then is assembled with a streptavidin (SA)-fused GFP1-10 fragment expressed in the cytosol of SW480 cells (FIG. 4C, top). When both fragments are in close proximity, fluorescence is restored (Kim, et al., 2016).

The GFP1-10 fragments were expressed in the cytoplasm, and the GFP11 fragment was fused to the C-terminus of the heavy chain of the cell-penetrating antibodies TMab4-WYW or epCT05. EpCAM-targeting cyclic peptide-fused light chain expression vector and GFP11-SBP2-fused cell-penetrating humanized heavy chain expression vector constructed as described (Korean Patent No. 10-1790669). Constructs were transiently co-transfected into a HEK293F protein expression cell. They were purified as described in Example 2.

The transformed SW480 cell line stably expressing SA-GFP1-10 was placed in 0.5 ml of medium containing 10% FBS at $2\times10^4$ cells/well in a 24-well plate and was cultured at 37° C. in 5% $CO_2$ for 12 hours. When cells were stabilized, 0.2, 0.8, and 3.2 μM TMab4-WYW-GFP11-SBP2, epCT05-GFP11-SBP2 or PBS were incubated with cells at 37° C. for 6 hours. After washing with PBS and mild-acidic solution as described in Example 2, the cells were fixed. The nuclei were stained (blue fluorescence) using Hoechst 33342 to be observed by confocal microscopy. Image J software (National Institutes of Health, USA) was used to select 20 cells in each condition. Then, the mean values of fluorescence obtained were calculated.

epCT05-GFP11-SBP2 showed concentration-dependent complemented GFP fluorescence in the cytosol at the levels comparable to those of TMab4-WYW-GFP11-SBP2 (FIG. 4C, bottom left). These data pointed to the cell-penetrating activity of epCT05 after EpCAM-mediated endocytosis.

The endosomal escape efficiency of epCT05 was determined using a method previously reported (Kim, et al., 2016) and as described in Example 16. To determine the endosomal escape efficiency of epCT05, the amount of epCT05 detected in the cytosol is divided by the total cellular internalized amount estimated by quantitative western blotting. epCT05 showed a concentration-dependent increase in endosomal escape efficiency (FIG. 4C, bottom right), with approximately 9.5% endosomal escape efficiency at the extracellular concentration of 1 μM (Table 5). This was similar to the concentration-dependent cellular escape efficiency for TMab4-WYW-GFP11-SBP2 (data not shown). These results indicate that epCT05 was successfully engineered to reach the cytosol of cells via EpCAM-mediated endocytosis and endosomal escape.

6.13 Example 13. Generation of a CT with a VH-Mediated Endosomal Escape Activity The endosomal escape activity of CTs such as TMab4-WYW and epCT05 reside in the VL. Although the VH and VL share low sequence similarity, their folding topology is the similar, with quite high similarity of tertiary structural in the framework backbone structure (Ewert, Honegger, & Pluckthun, 2004), comprising a beta-pleated sheet and three CDRs with a loop structure in common (FIG. 5A, left).

The endosomal escape motif of VL comprises the pH-sensing pair AspL1-MetL95 (FIG. 5A, right) and the membrane-binding motif $^{92}$WYW$^{94}$ in VL-CDR3. It was hypothesized that due to their similar structure, the endosomal escape motifs (i.e., the pH-sensing interaction and the cell membrane-binding motif) could be grafted onto the VH as well. The resulting CT will acquire the ability to access the cytosol through VH-mediated endosomal escape.

The VH-CDR3 was designed to impart endosomal escape activity, and appropriate acceptor human VH FR was selected based on the following criteria: 1) a negatively charged residue at H1 (the first residue of VH); 2) a hydrophobic residue in VH-CDR3 within a distance of ~5-6 Å threshold from the H1 residue for a pH-sensing pair; and 3) an FR compatible with the designed length of VH-CDR3 carrying the membrane-binding motif WYW.

Four heavy chain variable region mutants were previously designed, in which the endosomal escape motif was introduced into the humanized heavy chain variable region containing all of these elements (WIPO publication No. WO2017204606A1). Among them, CT01 VH (SEQ ID NO. 11) was selected for further development (HT0-01 VH; WIPO Publication No. WO2017204606A1).

The number of amino acids in HT0 VH (SEQ ID NO. 10) of the CT was 11, and the center portion of the CDR loop structure was exposed to the surface. Thus, it was determined that these structural features would not be conducive to pH-sensitivity. Therefore, the number of amino acids in CDR3 was reduced to 7 or 8 while retaining a partial sequence. Further, it was determined that residue 102 of VH-CDR3 was located at a suitable distance to GluH1, suggesting that these residues may interact at the initial endosome condition of pH 5.5. Thus, the residue was substituted with leucine (FIG. 5A, middle).

In order to introduce the CDR3 sequence containing the endosomal escape motif, the number of amino acids in CDR3 of the heavy chain variable region HT0 VH (SEQ ID NO. 10) of the CT was significantly reduced from 11 to 7. It was determined that these alterations may affect the overall stability of the heavy chain variable region. Thus, a new heavy chain variable region ws selected that can appropriately receive CDR3 containing the endosomal escape motif with 7 amino acids. Since the CDR3 of the RT22 VH of the anti-Ras•GTP iMab previously described (Korean Patent Application No. 10-2017-0152998) has 6 amino acids, and its first residue is the negatively charged glutamate residue, it was determined to be suitable for introducing the endosomal escape motif in VH-CDR3 of CT01 VH (SEQ ID NO. 11). The heavy chain variable region including the CDR3 sequence containing the endosomal escape motif in RT22 VH was named CT60 VH (SEQ ID NO. 12) (CT10 VH; WIPO publication number WO2017204606A1).

Table 4 shows the sequences of the heavy chain variable region (VH) containing the endosomal escape motif.

6.13.1

TABLE 4

| Names of heavy chain variable regions | Amino acid sequence | SEQ ID NO: |
|---|---|---|
| HT0 VH | 1 10 20 30 40 50<br>EVQLVESGGGLVQPGGSLRLSCAASGYTFTSYVMHWVRQAPGKGLEWVSAINPYNDGNYY<br>60 70 80 90 110<br>ADSVKGRFTISRDNSRKTLYLQMNSLRAEDTAVYYCARGAYKRGYAMDYWGQGTTVTVSS | 10 |
| CT01 VH (HT0-01 VH) | 1 10 20 30 40 50<br>EVQLVESGGGLVQPGGSLRLSCAASGYTFTSYVMHWVRQAPGKGLEWVSAINPYNDGNYY<br>60 70 80 90 110<br>ADSVKGRFTISRDNSRKTLYLQMNSLRAEDTAVYYCARGWYWMDLWGQGTTVTVSS | 11 |

TABLE 4-continued

| Names of heavy chain variable regions | Amino acid sequence | SEQ ID NO: |
|---|---|---|
| CT60 VH (CT10 VH) | 1 10 20 30 40 50 52a<br>EVQLVESGGGLVQPGGSLRLSCAASGFTFSDFSMSWVRQAPGKGLEWVSYISRTSHTTY<br>60 70 80 82a 90 100a 110<br>YADSVKGRFTISRDNSKNTLYLQMNSLRAEDTAVYYCARGWYWMDLWGQGTLVTVSS | 12 |

Similarity-based structure modeling (ABodyBuilder) (Leem, Dunbar, Georges, Shi, & Deane, 2016), was used to generate the structure of the light chain variable region and the heavy chain variable region with the endosomal escape motifs. The superimposing method was used to compare the distance between the pH sensing pairs located at the framework and CDR3 and the location of the cell membrane binding motif located in CDR3. The distance between the pH sensing pairs was 5.1 Å in the heavy chain variable region, which was similar to 5.8 Å in the light chain variable region. The shape of the CDR3 loop structure and the location of the cell membrane binding motif of the heavy chain variable region were also similar to those of the light chain variable region (FIG. 5A).

FIG. 5B illustrates the construction of epCT65-AAA, a CT with the endosomal escape motifs/residues removed from the VL and introduced into the VH. The endosomal escape VH region was cloned into a heavy chain expression vector as described in Example 2. In order to evaluate the VH-dependent endosomal escape ability, residues $^{92}$WYW$^{94}$, which are responsible for the endosomal escape ability and located in the existing VL, were replaced with AAA (consecutive three alanines), thereby eliminating the ability (FIG. 5B, left). To generate epCT65-AAA, the heavy chain including VH region with the endosomal escape motif and the light chain including the VL variant lacking endosomal escape ability (epCT105-AAA) were expressed and purified in HEK293K cell lines.

6.14 Example 14. cpCT65-AAA Exhibits VH-Mediated Endosomal Escape

Endosomal escape ability was examined in epCT05, epCT05-AAA and epCT65-AAA using trypan blue in Ramos cells adhered to the plate as described in Example 8. 1 μM of epCT05, epCT05-AAA, and epCT65-AAA, was placed in 200 μl of pH 7.4 buffer (HBSS (Welgene), 50 mM HEPES pH 7.4), or pH 5.5 buffer (HBSS (Welgene), 50 mM MES pH 5.5), and they were cultured at 37° C. for 2 hours. After carefully washing with PBS, 10 μl of trypan blue was mixed with 190 μl of PBS, and 200 μl of the mixture was dispensed in each well. Then, they were observed by a microscope. The number of cells that had acquired trypan blue among all cells was counted to be shown in a percentage. A total of more than 400 cells were counted, and the mean value was plotted. The number of the trypan blue acquired by epCT65-AAA was about half of that of TMab4-3.

The percentage of blue-stained cells at each pH condition was also quantitated, revealing that epCT65-AAA, but not epCT05-AAA, showed pH-dependent membrane pore formation ability only at pH 5.5 (FIG. 6A, left). These results revealed that epCT65-AAA was successfully engineered to exhibit VH-mediated minimal endosomal escape. The Ramos cells maintained intact morphology without lysis, confirming that the endosomal escape of CTs proceeds through formation of membrane toroidal pores rather than via membrane lysis (FIG. 6A, right).

To validate the endosomal escape activity of epCT65-AAA, we monitored epCT65-AAA-mediated cytosolic release of coincubated calcein, a membrane-nonpenetrating green fluorophore, in SW480 cells. The cytosolic diffusion of coincubated calcein is detected only when it escapes into the cytosol from the endosomal lumen through CT-induced endosomal pores after passive endocytic uptake. As expected, epCT05-AAA showed a punctuate fluorescence of calcein, indicative of endosomal entrapment without a cytosolic release (FIG. 6B, left). On the other hand, epCT65-AAA yielded a diffusive fluorescence signal area throughout the cytosolic region of cells in a dose-dependent manner (FIG. 6B, left). Median fluorescent intensity (MFI) of calcein in the cytoplasm of cells as compared were quantitated, confirming uptake of calcein in the presence of epCT65-AAA is dose-dependent (FIG. 6B, right).

Complemented GFP fluorescence assay was conducted to further verify with the format of epCT65-AAA-GFP11-SBP2 revealed concentration-dependent cytosolic localization in SW480-SA-GFP10 cells (FIG. 3F). The transformed SW480 cell line stably expressing SA-GFP1-10 was prepared in the same method as in Example 12. When the cells were stabilized, 0.2, 0.4, 0.8, 1.6, and 3.2 μM of epCT05-AAA-GFP11-SBP2, epCT65-AAA-GFP11-SBP2, respectively, were cultured at 37° C. for 6 hours. After washing with PBS and mild-acidic solution in the same method as in Example 3, the cells were fixed. The nuclei were stained (blue fluorescence) using Hoechst 33342, and they were observed by a confocal microscope. The cells treated with epCT05-AAA-GFP11-SBP2 showed almost no GFP fluorescence, whereas the cells treated with epCT65-AAA-GFP11-SBP2 showed green GFP fluorescence, which was concentration-dependent in the cell.

The cells treated with epCT05-AAA-GFP11-SBP2 showed almost no spread-type fluorescence (FIG. 6C, top panels), whereas the cells treated with epCT65-AAA-GFP11-SBP2 showed green fluorescence spread in the cytoplasm, which was concentration-dependent in the cell (FIG. 6C, bottom panels). GFP fluorescence was quantitated as described in Example 12, confirming that GFP fluorescence was concentration-dependent in the epCT65-AAA treated cells (FIG. 6C, bottom). Taken together, these result indicate that the epCT65-AAA exhibited cell-penetrating activity dependent on the engineered VH endosomal escape motif.

6.15 Example 15. Generation of epCT65, a CT with an Endosomal Escape Motif in Both the VH and VL To generate a CT with a high endosomal escape activity, the HC of epCT65-AAA and the LC of epCT05, both of which have endosomal escape motifs, were co-expressed.

The resulting intact IgG-type CT, epCT65, comprises a total of four endosomal escape motifs, and fused EpCAM-targeting cyclic peptide (FIG. 7A).

To produce epCT65, the endosomal escape humanized heavy chain expression vector containing the heavy chain variable region with the endosomal escape motif and the light chain expression vector containing the tumor-specific light chain variable region fused with the EpCAM target cyclic peptide were transiently co-transfected into HEK293F cells to express individual clones. They were purified by the same method as in Example 2.

SEC analysis on a Superdex column verified that epCT65 was in the correctly assembled monomeric form without non-native oligomers, (FIG. 7B). 80 μl of epCT05 and epCT65, were prepared at a concentration of 1 mg/ml and then placed in an insert to prepare samples. For the Superdex size-exclusion chromatography column, the buffer of PBS pH 7.4 flowed at a flow rate of 1.0 ml/min. Then, the chromatography column was set when the pressure and the mAU at 280 nm were stabilized. Thereafter, 30 μl of the prepared samples were loaded at the same flow rate thereof, and the mAU values had been measured at 280 nm for 30 min. Beta amylase (200 kDa) and albumin (66 kDa) were used as a protein size marker. One peak was measured in epCT05 and epCT65 as well as trastuzumab (150 kDa) as a control, indicating that they existed as a monomer (FIG. 7B).

Zenix SEC-300 column-based SMAC analysis revealed the elution of epCT65 in a symmetric Gaussian-shaped peak in the absence of any heterogeneous species but with somewhat longer retention time compared to that of trastuzumab (FIG. 7C). 80 μl of epCT05 and epCT65 were prepared at a concentration of 1 mg/ml, and then they were placed into an insert to prepare samples. For the Zenix SEC-300 size-exclusion chromatography column, the buffer of 150 mM $Na_3PO_4$ and 137 mM NaCl at pH 7.0 flowed at a flow rate of 1.0 ml/min. Then, the chromatography column was set when the pressure and the mAU at 280 nm were stabilized. 30 μl of the prepared samples were loaded at the same flow rate thereof, and the mAU values had been measured at 280 nm for 30 min.

epCT05 and epCT65 showed the peak at the time similar to that of Trastuzumab as the control monoclonal antibody. The widths of the peaks were normally narrow (FIG. 7C).

6.16 Example 16. Endosomal Escape Ability and Cytosol-Penetration of epCT65

Endosomal escape ability was assessed by measuring the uptake of trypan blue dye by a nonadherent cell line that lacks HSPG expression as described in Example 8. Briefly, Ramos cells adhered to the plate in the same method as in Example 8. Then, 0.5 and 1 μM of epCT05, epCT65, or buffer were placed in 200 μl of pH 7.4 buffer (HBSS (Welgene), 50 mM HEPES pH 7.4), which is the same to the cytoplasm's pH, and pH 5.5 buffer (HBSS (Welgene), 50 mM MES pH 5.5), which is the same to initial endosomal pH, and they were cultured at 37° C. for 2 hours. After carefully washing with PBS, 10 μl of trypan blue was mixed with 190 μl of PBS, and 200 μl of the mixture was dispensed in each well. Then, they were observed by a microscope. The percent of cells acquiring trypan blue is shown (FIG. 8A). A total of more than 400 cells were counted, and the mean value was plotted. Results indicate that epCT65 acquired more trypan blue than epCT05, indicating enhanced endosomal escape. The Ramos cells maintained intact morphology and cytosolic trypan blue was visible in EpCT65 treated cells (FIG. 8A, right).

In order to further demonstrate that epCT05 is located in the cytoplasm, an enhanced split green fluorescent protein (GFP) complementation assay was conducted as described in Korean Patent No. 10-1790669 and herein. Briefly, the transformed SW480 cell line stably expressing SA-GFP1-10 was prepared in the same method as in Example 12. When the cells were stabilized, 0.1, 0.2, 0.4, 0.8, and 1.6 μM of epCT05-GFP11-SBP2 and epCT65-GFP11-SBP2, respectively, were cultured at 37° C. for 6 hours. After washing with PBS and mild-acidic solution in the same method as in Example 3, the cells were fixed. The nuclei were stained (blue fluorescence) using Hoechst 33342, and they were observed by a confocal microscope. The cells treated with epCT65-GFP11-SBP2 showed concentration-dependently intense green GFP fluorescence in the cells compared with the cells treated with epCT05-GFP11-SBP2 (FIG. 8B).

The results revealed that epCT65, which bears endosomal escape motifs in both VL and VH, showed improved endosomal escape ability and localization to the cytoplasm compared to epCT05, which has endosomal escape motifs in VL alone (FIG. 7A).

Table 5 shows the cytosolic concentration and the endosomal escape efficiency of the intact IgG-type cell-penetrating antibody fused with GFP11-SBP2 and the endosomal escape ability-increased cell-penetrating antibody. The cytosolic concentrations of epCT65 were ~1.8-fold higher than those of epCT05, being ~20, 141, and 377 nM after 6 h of extracellular treatment of SW480-SA-GFP1-10 cells with 0.1, 0.5, or 1 μM epCT65, for treatment concentrations of 0.1, 0.5 and 1 μM, respectively (Table 5, top). In contrast, the internalized amounts of epCT65, estimated by quantitative western blotting, were similar to those of epCT05 in SW480 cells (Table 5 and FIG. 8B, right). This is due to the fact that the two CTs have the same bivalent EpCAM-binding peptide moiety at the N terminus of the LC for EpCAM-mediated endocytosis. Therefore, even though epCT65 was internalized at levels similar to those of epCT05, the ~1.8-fold higher cytosolic access (amount) of epCT65 than epCT05 yielded much higher endosomal escape efficiency (~17.5%) than that of epCT05 (~9.5%) at 1 μM (Table 1). These results indicated that the endosomal escape activity of epCT65 was substantially higher because of the presence of an endosomal escape motif in both the VH and VL, as compared with epCT05 having this motif in the VL only.

6.17

TABLE 5

| Parameters | Cytotransmabs | Treated concentrations (μM) 0.1 | 0.5 | 1 |
|---|---|---|---|---|
| Cytosolic concentration (nM)[c] | epCT05 | 13 ± 4 | 97 ± 5 | 215 ± 16 |
| | epCT65 | 20 ± 6 | 141 ± 10 | 377 ± 20 |
| Endosomal escape efficiency (%)[d] | epCT05 | 2.50 ± 0.3 | 6.66 ± 0.4 | 9.53 ± 0.6 |
| | epCT65 | 5.00 ± 0.4 | 10.1 ± 1.1 | 17.5 ± 1.3 |

Table 5.

[c]The cytosolic molar concentration was estimated by dividing the cytosolic amount by the cytosolic volume of SW480 cells and cell numbers in each well, as described in detail (Kim, et al., 2015);

[d]The endosomal escape efficiency was estimated by dividing the cytosolic amount with the internalized amount of antibodies, as described in detail previously (Kim, et al., 2015).

6.18 Example 17. Generation of Biotinylated EpCAM Protein for Selection of Targeting Peptides In order to construct tumor-specific cell-penetrating antibodies, Ep133 cyclic peptide was used to target EpCAM.

Ep133 binds to EpCAM target but shows relatively low binding ability considering the binding ability to EpCAM expressed on the cell surface. Thus, in order to generate efficient tumor tissue-specificity for enhancing the EpCAM target affinity, an EpCAM target cyclic peptide library was constructed at the N-terminus of the light chain variable region to select a cyclic peptide with the improved EpCAM target affinity.

First, a human recombinant EpCAM antigens was constructed for the library selection. Briefly, PCR was performed using GSG linker to construct DNA fused with 6×His tag and the Avi-tag at N-terminus and the extracellular domain (residues 1 to 265) except for the intracellular domain and the C-terminal transmembrane domain in the EpCAM protein. These were cloned into pcDNA3.4 vector for animal cell expression using NotI/HindIII restriction enzymes. Then, the constructed pcDNA3.4 EpCAM antigen vector was transiently transfected to express the protein in a similar manner as in Example 2. The cell culture supernatant was collected using standard protocol in the art and was purified using Ni-NTA resin that specifically purified the protein fused with His tag. After washing with 50 ml of wash buffer (20 mM Tris, pH 7.4, 300 mM NaCl, 20 mM imidazole) to remove Ni-NTA resin, the proteins were eluted by the lysis buffer (20 mM Tris, pH 7.4, 300 mM NaCl, 250 mM imidazole). The eluted protein was buffered with the preservative buffer (50 mM Tris-HCl, pH 8.0) using a dialysis method. The purified protein was quantified using absorbance and absorption coefficient at 280 nm wavelength. The purified human recombinant EpCAM protein was biotinylated for the library screening (EZ-LINK™ Sulfo-NHS-LC-Biotinylation kit, Pierce Inc., USA).

6.19 Example 18. Construction of EpCAM-Targeting Cyclic Peptide Library

FIG. 9A illustrates the library screening strategy for using a Ep133-based cyclic peptide library for improving affinity to EpCAM. The cyclic peptide library for improving affinity to EpCAM was based on Ep133 cyclic peptide and the light chain variable region fragment.

Specifically, the light chain variable region used in the screening of EP133 cyclic peptide-based affinity-enhanced EpCAM target cyclic peptide was the hT4-ep59 MG light chain variable region described (Korean Patent Application No. 10-2017-0152998, “Antibody which internalize into the cytosol of cells and binds to inhibit activated Ras and use thereof”). Several EpCAM target cyclic peptide sequences described in the art were analyzed, and random mutations were introduced into the amino acid residues which were predicted to play a critical role in antigen binding. A degenerated codon capable of including several amino acid sequences was used for the residues 1, 2, 4, 6 to 9, and 12. VRK was used for the residues 1 and 2 so that amino acid sequence having a polarity such as aspartate, glutamate, histidine, lysine, asparagine, glutamine, arginine, and serine can be located at the position. BNK was used for the residue 4 so that all amino acid sequences except for isoleucine, lysine, asparagine, methionine, and threonine can be located at the position. The residues 6 to 9 were located inside the disulfide bond and were thought to play a critical role in antigen binding. Thus, NNK containing all amino acids was used for the position. YCA encoding Pro and Ser, which was maintained in the conventional patent (WIPO Publication No. WO2014042209A1), was used for the residue 12 (FIG. 9A).

DNAs encoding the designed library were amplified by PCR, and then concentrated by the ethanol precipitation method. Yeast surface expression vector (C-aga2) expressing aga2 protein at C-terminus for homologous recombination was treated with NheI/BamHI restriction enzyme. The result was purified by the agarose gel extraction method and concentrated by the ethanol precipitation method. Each 12 μg of DNA encoding library was transformed by electroporation using yeast surface expression yeast Jar200 with 5 μg of vector treated with restriction enzymes (Baek, Liss, Clancy, Chesnut, & Katzen, 2014). The serial dilution was carried out to calculate the number of colonies grown on selective medium SDU-CAA (20 g/L glucose, 6.7 g/L yeast nitrogen base without amino acids, 5.4 g/L $Na_2HPO_4$, 8.6 g/L $NaH_2PO_4$, 5 g/L casamino acids, final concentration 0.002% Uracil) to confirm the library size.

6.20 Example 19. Identification of Affinity-Enhanced EpCAM-Targeting Cyclic Peptides The biotinylated human recombinant EpCAM antigen prepared in Example 17 was used to screen EP133 peptide-based affinity-enhanced EpCAM-targeting cyclic peptide library constructed in Example 18.

Using SGU-CAA media (20 g/L galactose, 6.7 g/L yeast nitrogen base without amino acids, 5.4 g/L $Na_2HPO_4$, 8.6 g/L $NaH_2PO_4$, 5 g/L casamino acids, final concentration 0.002% Uracil), 1 μM of purified EpCAM was reacted with yeast at room temperature for 1 hour, inducing the cell surface expression of the light chain variable region fused at the N-terminus with the cyclic peptide library (FIG. 9A). Then, the yeast expressing the library binding to EpCAM was reacted with streptavidin Microbead™ (Miltenyi Biotec) at 4° C. for 20 minutes. Then, the yeast expressing the cyclic peptide with high affinity to EpCAM was suspended using a magnetic activated cell sorting (MACS). The yeast expressing the selected library was cultured in selective medium SDU-CAA (20 g/L glucose, 6.7 g/L yeast nitrogen base without amino acids, 5.4 g/L $Na_2HPO_4$, 8.6 g/L $NaH_2PO_4$, 5 g/L casamino acids, final concentration 0.002% Uracil) and SGU-CAA to induce the library expression. Then, for the 1 st FACS screening, about 100 nM of EpCAM antigen was reacted with the library-expressed yeast at room temperature for 1 hour. Then, the result was reacted with PE-conjugated streptavidin (Streptavidin-R-phycoerythrin conjugate (SA-PE) Invitrogen) to be suspended through fluorescence activated cell sorting (FACS Caliber) (BD biosciences). Then, the 2nd FACS screening was performed using 100 nM EpCAM antigen in the same method as the 1st screening. Then, the 3rd FACS and the 4th FACS screening were performed using 10 nM EpCAM antigen.

Each step of the screen for high affinity EpCAM-targeting peptides was plotted following dual parameter flow cytometry (FACS) (FIG. 9B). The binding ability of the yeast in each step of the screening process described above under a condition of 100 nM EpCAM was analyzed. The results indicated that the high-speed screening process selected clones having a high affinity for human recombinant EpCAM compared with Ep133.

FIG. 9C illustrates the results of FACS analysis on the binding ability of 47 clones sorted in the 3$^{rd}$ FACS pool (FIG. 9C, top) and the 4th FACS pool (FIG. 9C, bottom) to EpCAM 100 nM. Mean fluorescence intensities (y-axis) are plotted for the 47 individual clones are shown. The analysis of the binding ability of individual clones allowed the selection of 7 unique clones with high affinity and high specificity binding to EpCAM. (FIG. 9C, red bars). The 7 unique clones were identified as: 3-27, 4-8, 4-12, 4-13, 4-14, 4-19, and 4-27 (SEQ ID NO. 13-20, respectively).

Table 6 shows the selected 7 cyclic peptide sequences having the high binding ability to EpCAM.

6.20.1

TABLE 6

| Names of cyclic peptide | Target receptor | Amino acid sequence | SEQ ID NO: |
|---|---|---|---|
| EP133 | EpCAM | 1 10<br>EHLHCLGSLCWP | 13 |
| 3-27 | | 1 10<br>RGLRCLGRLCWP | 14 |
| 4-8 | | 1 10<br>RNLLCIGNLCWP | 15 |
| 4-12 | | 1 10<br>RNLLCLRRICWP | 16 |
| 4-13 | | 1 10<br>RNLQCIRNICWS | 17 |
| 4-14 | | 1 10<br>RNLHCIGNLCWP | 18 |
| 4-19 | | 1 10<br>RNLRCIGNICWS | 19 |
| 4-27 | | 1 10<br>RHLWCLGRLCWP | 20 |

6.21 Example 20. Analysis of Antigen Binding Ability of Affinity-Enhanced EpCAM Target Cyclic Peptide The affinity-enhanced EpCAM target cyclic peptides, which were selected by the same method described in Example 2, were fused to the N-terminus of the light chain of the cell-penetrating humanized light chain hT4-59 using the MGSSSN linker (SEQ ID NO: 102), and then were cloned into the mammalian expression vector.

Table 7 shows sequences of light chain variable regions (VL) fused with the selected affinity-enhanced EpCAM target cyclic peptides.

6.21.1

TABLE 7

| Names of light chain variable regions | Amino acid sequence | SEQ ID NO: |
|---|---|---|
| hT4-ep59 MG VL | 1 10 20 30 40 50 60<br>EHLHCLGSLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 21 |
| hT4-ep59 (3-27) MG VL | 1 10 20 30 40 50 60<br>RGLRCLGRLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 22 |
| hT4-ep59 (4-8) MG VL | 1 10 20 30 40 50 60<br>RNLLCIGNLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 23 |
| hT4-ep59 (4-12) MG VL | 1 10 20 30 40 50 60<br>RNLLCLRRICWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 24 |
| hT4-ep59 (4-13) MG VL | 1 10 20 30 40 50 60<br>RNLQCIRNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 25 |
| hT4-ep59 (4-14) MG VL | 1 10 20 30 40 50 60<br>RNLHCIGNLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 26 |
| hT4-ep59 (4-19) MG VL | 1 10 20 30 40 50 60<br>RNLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 27 |
| hT4-ep59 (4-27) MG VL | 1 10 20 30 40 50 60<br>RHLWCLGRLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 28 |

RT22 heavy chain expression vector was described in (Korean Patent Application No. 10-2017-0152998, "Antibody which internalize into the cytosol of cells and binds to inhibit activated Ras and use thereof"). The EpCAM-targeting cyclic peptide-fused cell-penetrating humanized light chain expression constructs were transiently co-transfected into HEK293F cells to express affinity-enhanced EpCAM-targeting cyclic peptide-fused anti-Ras•GTP iMab individual clones. Then, they were purified by the same method as in Example 2. The purified antibodies were named epRas03, epRas03 (3-27), epRas03 (4-8), epRas03 (4-12), epRas03 (4-13), epRas03 (4-14), epRas03 (4-19) and epRas03 (4-27).

In order to confirm the specific binding of these cyclic peptide-fused antibodies to EpCAM, the interaction was assayed by ELISA (enzyme-linked immunosorbent assay). The human recombinant EpCAM was bound to each well of a 96-well EIA/RIA plate at a concentration of 5 μg/ml at room temperature for 1 hour. Then, they were washed with 0.1% PBST (PBS pH 7.4, 137 mM NaCl, 2.7 mM KCl, 0.1% Tween 20) for 10 minutes 3 times. Then, they were bound with 4% PBSB (PBS pH 7.4, 137 mM NaCl, 2.7 mM KCl 4% BSA) for 1 hour, and then washed with 0.1% PBST for 10 minutes 3 times. The affinity-enhanced EpCAM target cyclic peptide-fused anti-Ras•GTP iMab (epRas03, epRas03 (3-27), epRas03 (4-8), epRas03 (4-12), epRas03 (4-13), epRas03 (4-14), epRas03 (4-19) and epRas03 (4-27)) were diluted with 4% PBSB and bound at various concentrations of 100 nM, 10 nM and 1 nM at room temperature for 1 hour. Then, they were washed with 0.1% PBST for 10 minutes 3 times. Labeled antibodies were used for the conjugation to produce HRP-conjugated anti-his mAb. The results were reacted with TMB ELISA solution, quantifying the absorbance at 450 nm.

The ELISA analysis indicated that the epRas03 (4-13) and epRas03 (4-19) showed higher antigen binding ability compared with epRas03 (FIG. 10).

Surface plasmon resonance (SPR) was carried out using Biacore 2000 instrument in order to more quantitatively analyze the binding ability of the 7 affinity-enhanced cyclic peptide clones with the human recombinant EpCAM. The human recombinant EpCAM antigen was diluted with 10 mM NaAc buffer (pH 4.0) at a concentration of 20 μl/ml. The diluted antigen was fixed on a CM5 sensor chip (GE healthcare) in about 211 response units (RU). Then, the analysis was performed using HBS-EP buffer at a flow rate of 30 μl/min. The EpCAM target cyclic peptide-fused anti-Ras•GTP iMab was analyzed at a concentration of 6.25 nM from 100 nM. After the binding and disassociation analysis, the CM5 chip was regenerated by flowing a buffer (20 mM NaOH, 1 M NaCl, pH 10.0) at a flow rate of 30 μl/min for 1 minute. Each sensorgram obtained at 3 minutes of binding and at 3 minutes of dissociation was compared with a blank cell for normalization, and affinity was calculated.

Table 8 shows the results of the affinity analysis of EpCAM and EpCAM target cyclic peptide-fused anti-Ras•GTP iMab using SPR (BIACORE 2000).

6.22

TABLE 8

| EpCAM | $k_a$ ($M^{-1}s^{-1}$) | $k_d$ ($s^{-1}$) | $K_D$ (M) |
|---|---|---|---|
| epRas03 | $1.36 \times 10^5$ | $2.89 \times 10^{-3}$ | $2.13 \times 10^{-5}$ |
| epRas03 (3-27), | $2.96 \times 10^4$ | $1.71 \times 10^{-3}$ | $5.78 \times 10^{-5}$ |
| epRas03 (4-8) | $7.37 \times 10^5$ | $2.24 \times 10^{-3}$ | $3.04 \times 10^{-5}$ |
| epRas03 (4-12) | $6.64 \times 10^4$ | $1.17 \times 10^{-3}$ | $1.77 \times 10^{-5}$ |

TABLE 8-continued

| EpCAM | $k_a$ ($M^{-1}s^{-1}$) | $k_d$ ($s^{-1}$) | $K_D$ (M) |
|---|---|---|---|
| epRas03 (4-13) | $5.69 \times 10^6$ | $1.05 \times 10^{-3}$ | $1.85 \times 10^{-10}$ |
| epRas03 (4-14) | $1.12 \times 10^4$ | $2.05 \times 10^{-3}$ | $1.83 \times 10^{-7}$ |
| epRas03 (4-19) | $5.38 \times 10^6$ | $1.68 \times 10^{-3}$ | $3.13 \times 10^{-10}$ |
| epRas03 (4-27) | $4..24 \times 10^5$ | $4.21 \times 10^{-3}$ | $9.94 \times 10^{-9}$ |

6.23 Example 21. Physical Properties of Affinity-Enhanced EpCAM-Targeting Cyclic Peptide-Fused Anti-Ras•GTP iMab Zenix SEC-300 column analysis was conducted to evaluate the hydrophobicity of the 7 EpCAM-targeting cyclic peptide-fused anti-Ras•GTP iMabs constructed in Example 19. 80 μl of each antibody was prepared at a concentration of 1 mg/ml, and then they were placed into an insert to prepare samples. For the Zenix SEC-300 size-exclusion chromatography column, the buffer of 20 mM $Na_3PO_4$ at pH 7.0 flowed at a flow rate of 1.0 ml/min. Then, the chromatography column was set when the pressure and the mAU values at 280 nm were stabilized. 10 μl of the prepared samples were loaded at the same flow rate, and the mAU values were measured at 280 nm for 30 min.

Ep133 cyclic peptide-fused anti-Ras•GTP iMab (epRas03) had a similar peak to the control trastuzumab (FIG. 11). Peaks for all 7 affinity-enhanced EpCAM target cyclic peptide-fused anti-Ras•GTP iMabs were abnormal (FIG. 11, epRas03, epRas03 (3-27), epRas03 (4-8), epRas03 (4-12), epRas03 (4-13), epRas03 (4-14), epRas03 (4-19) and epRas03 (4-27)).

6.24 Example 22. Rational Design for Improving the Physical Properties of Affinity-Enhanced EpCAM-Targeting Cyclic Peptide-Fused Anti-Ras•GTP iMab As confirmed in Example 21, the affinity-enhanced EpCAM-targeting cyclic peptide-fused anti-Ras•GTP iMabs exhibit high affinity to EpCAM, however, they have inferior physical properties than the Ep133 cyclic peptide from which they were derived. Thus, novel cyclic peptides were designed wherein the physical properties (e.g., low aggregation, hydrophobicity) are improved while maintaining the enhanced affinity exhibited by the cyclic peptide clones.

The first residue of the cyclic peptide is thought to be an important factor in determining physical properties of the cyclic peptides. The first residue of Ep133 (SEQ ID NO. 13) was glutamic acid, whereas all 7 cyclic peptide clones (SEQ ID NO. 14-20) had arginine, which tend to be non-specific, as the first residue. The first residue of cyclic peptides was thus changed to polar and charged amino acid residues such as glutamate, lysine, histidine, asparagine and aspartate. Used for the second residue were histidine from the parental peptide Ep133, and asparagine, the most frequently found residue among the 7 cyclic peptide clones. For the 4th and 12th residues, residues frequently found in the cyclic peptide clones with higher affinity, such as leucine, glutamine ($4^{th}$) and serine ($12^{th}$) were used. For the 6th to 9th residues, isoleucine, glycine, asparagine and leucine, the amino acid residues showing the highest frequency of occurrence at the respective position among the 7 cyclic peptide clones, were sequentially used. Based on the above logic, 9 new variants of cyclic peptides were rationally designed.

Table 9 lists the amino acid sequences of the 9 rationally designed cyclic peptides with improved physical properties. They were constructed using the overlapping PCR method.

6.25

TABLE 9

| Names of cyclic peptides | Target receptor | Amino acid sequence | SEQ ID NO: |
|---|---|---|---|
| EP133 | EpCAM | 1 10<br>EHLHCLGSLCWP | 13 |
| Ep1 | | 1 10<br>ENLLCIGNLCWS | 29 |
| Ep2 | | 1 10<br>EHLLCIGNLCWS | 30 |
| Ep3 | | 1 10<br>ENLQCIGNLCWS | 31 |
| Ep4 | | 1 10<br>EHLHCLGSLCWS | 32 |
| Ep5 | | 1 10<br>HNLRCIGNICWS | 33 |
| Ep6 | | 1 10<br>NNLRCIGNICWS | 34 |

TABLE 9-continued

| Names of cyclic peptides | Target receptor | Amino acid sequence | SEQ ID NO: |
|---|---|---|---|
| Ep7 | | 1 10<br>DNLRCIGNICWS | 35 |
| Ep8 | | 1 10<br>ENLRCIGNICWS | 36 |
| Ep9 | | 1 10<br>KNLRCIGNICWS | 37 |

6.26 Example 23. Physical Properties of Rationally-Designed EpCAM-Targeting Cyclic Peptide In order to improve the physical properties of the affinity-enhanced cyclic peptides, rationally-designed cyclic peptides (SEQ ID NO. 29-37) were fused to the N-terminus of the light chain of the cell-penetrating humanized light chain hT4-59 via the MGSSSN linker (SEQ ID NO: 102). They were then cloned into the mammalian expression vector using methods described in Example 2 above. Table 10 shows sequences of the rationally-designed cyclic peptides fused to light chain variable regions (VL) for improving physical properties (SEQ ID NO. 21-46).

6.26.1

TABLE 10

| Names of light chain variable regions | Amino acid sequence | SEQ ID NO: |
|---|---|---|
| hT4-ep59 MG VL | 1 10 20 30 40 50 60<br>EHLHCLGSLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 21 |
| hT4-ep59 (ep1) MG VL | 1 10 20 30 40 50 60<br>ENLLCIGNLCWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 38 |
| hT4-ep59 (ep2) MG VL | 1 10 20 30 40 50 60<br>EHLLCIGNLCWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 39 |
| hT4-ep59 (ep3) MG VL | 1 10 20 30 40 50 60<br>ENLQCIGNLCWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 40 |
| hT4-ep59 (ep4) MG VL | 1 10 20 30 40 50 60<br>EHLHCLGSLCWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 41 |
| hT4-ep59 (ep5) MG VL | 1 10 20 30 40 50 60<br>HNLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 42 |
| hT4-ep59 (ep6) MG VL | 1 10 20 30 40 50 60<br>NNLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 43 |

TABLE 10-continued

| Names of light chain variable regions | Amino acid sequence | SEQ ID NO: |
|---|---|---|
| hT4-ep59 (ep7) MG VL | 1 10 20 30 40 50 60<br>DNLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 44 |
| hT4-ep59 (ep8) MG VL | 1 10 20 30 40 50 60<br>ENLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 45 |
| hT4-ep59 (ep5) MG VL | 1 10 20 30 40 50 60<br>KNLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 46 |

The anti-Ras•GTP RT22 heavy chain expression vector and the EpCAM-targeting cyclic peptide-fused cell-penetrating humanized light chain expression vectors were transiently co-transfected into HEK293F cells, thereby expressing affinity-enhanced EpCAM-targeting cyclic peptide-fused anti-Ras•GTP iMab individual clones. Antibodies were purified by the same method as described in Example 2 above. The purified antibodies were named epRas03, ep1-Ras03, ep2-Ras03, ep3-Ras03, ep4-Ras03, ep5-Ras03, ep6-Ras03, ep7-Ras03, ep8-Ras03 and ep9-Ras03.

To test if the rationally-designed cyclic peptides exhibited improved physical properties, fused antibodies were evaluated for hydrophobicity using high-performance liquid chromatography (Zenix SEC-300 column analysis). Specifically, 80 μl of each antibody was prepared at a concentration of 1 mg/ml, and then placed into an insert to prepare samples. For the Zenix SEC-300 size-exclusion chromatography column, the buffer of 20 mM $Na_3PO_4$ at pH 7.0 flowed at a flow rate of 1.0 ml/min. Then, the chromatography column was set when the pressure and the mAU values at 280 nm were stabilized. 10 μl of the prepared samples were loaded at the same flow rate, and the mAU values were measured at 280 nm for 30 min.

epRas03, ep3-Ras03, ep4-Ras03, ep6-Ras03, ep7-Ras03 and ep8-Ras03 cyclic peptide-fused anti-Ras•GTP iMab behaved similarly to the control trastuzumab (FIG. 12A, right), whereas ep1-Ras03, ep2-Ras03, ep5-Ras03 and ep9-Ras03 cyclic peptide-fused anti-Ras•GTP iMab showed abnormal, broad peaks (FIG. 12A, left).

Rational design of cyclic peptides resulted in improved physical properties for ep3-Ras03, ep4-Ras03, ep6-Ras03, ep7-Ras03 and ep8-Ras03.

6.27 Example 24. Antigen Binding Ability of Rationally-Designed Cyclic Peptide with Improved Physical Properties It was confirmed that the EpCAM-targeting cyclic peptides described in Example 22 had improved physical properties as desired. Further experiments were conducted to confirm whether the improved affinity of the cyclic peptides for EpCAM described in Example 20 was maintained.

FIG. 12B illustrates the results of ELISA analysis of binding ability between indicated cyclic peptide-fused anti-Ras•GTP iMabs (0.1, 1, and 10 nM) and human recombinant EpCAM protein. The human recombinant EpCAM was bound to each well of a 96-well EIA/RIA plate at a concentration of 5 μg/ml at room temperature for 1 hour. Then, they were washed with 0.1% PBST (PBS pH 7.4, 137 mM NaCl, 2.7 mM KCl, 0.1% Tween 20) for 10 minutes 3 times. Then, they were bound with 4% PBSB (PBS pH 7.4, 137 mM NaCl, 2.7 mM KCl 4% BSA) for 1 hour, and then washed with 0.1% PBST for 10 minutes 3 times. ep3-Ras03, ep4-Ras03, ep6-Ras03, ep7-Ras03 and ep8-Ras03 were diluted with 4% PBSB and bound at various concentrations of 10 nM, 1 nM and 0.1 nM at room temperature for 1 hour. Then, they were washed with 0.1% PBST for 10 minutes 3 times. The labeled antibodies were used for the conjugation so as to produce HRP-conjugated anti-his mAb. The results were reacted with TMB ELISA solution, thereby quantifying the absorbance at 450 nm.

The ELISA analysis indicated that the ep3-Ras03, ep4-Ras03, ep6-Ras03, ep7-Ras03 and ep8-Ras03 showed higher antigen binding ability compared with epRas-3 (FIG. 12B).

Surface plasmon resonance (SPR) was carried out using Biacore 2000 instrument in order to more quantitatively analyze the binding ability of the human recombinant EpCAM and the affinity-enhanced EpCAM-targeting cyclic peptide-fused anti-Ras•GTP iMabs. Specifically, the human recombinant EpCAM antigen was diluted with 10 mM NaAc buffer (pH 4.0) at a concentration of 20 μl/ml. The dilute was fixed on a CM5 sensor chip (GE healthcare) in about 367 response units (RU). Then, the analysis was performed using HBS-EP buffer at a flow rate of 30 μl/min. The ep3-Ras03, ep4-Ras03, ep6-Ras03, ep7-Ras03 and ep8-Ras03 were analyzed at a concentration of 6.25 nM from 100 nM. After the binding and disassociation analysis, the CM5 chip was regenerated by flowing a buffer (20 mM NaOH, 1 M NaCl, pH 10.0) at a flow rate of 30 μl/min for 1 minute. Each sensorgram obtained at 3 minutes of binding and at 3 minutes of dissociation was compared with a blank cell to be normalized and subtracted, thereby calculating the affinity.

Table 11 shows the results of the SPR affinity analysis (BIACORE 2000) of EpCAM and the EpCAM-targeting cyclic peptide-fused anti-Ras•GTP iMabs variants that displayed both improved affinity and physical properties.

6.28

TABLE 11

| EpCAM | $k_a$ ($M^{-1}s^{-1}$) | $k_d$ ($s^{-1}$) | $K_D$ (M) |
|---|---|---|---|
| epRas03 | $9.06 \times 10^4$ | $1.94 \times 10^{-3}$ | $2.14 \times 10^{-8}$ |
| ep3-Ras03 | $1.7 \times 10^6$ | $3.6 \times 10^{-3}$ | $2.11 \times 10^{-9}$ |
| ep4-Ras03 | $7.28 \times 10^5$ | $9.05 \times 10^{-3}$ | $1.24 \times 10^{-8}$ |
| ep6-Ras03 | $3.02 \times 10^6$ | $3.02 \times 10^6$ | $1.86 \times 10^{-9}$ |
| ep7-Ras03 | $1.36 \times 10^6$ | $1.36 \times 10^6$ | $4.35 \times 10^{-9}$ |
| ep8-Ras03 | $1.67 \times 10^6$ | $1.67 \times 10^6$ | $2.39 \times 10^{-9}$ |

The binding of the cyclic peptide variants to EpCAM on the cell surface in the human colon cancer cell line DLD-1 and the human cervical cancer cell line HeLa was analyzed by FACS. Specifically, DLD-1 cells (which express EpCAM) and HeLa cells (which do not express EpCAM) were prepared at $1\times10^5$ cells per sample. The cells were cultured with 100 nM of ep3-Ras03, ep4-Ras03, ep6-Ras03, ep7-Ras03 or ep8-Ras03, in PBSF (PBS buffer, 2% BSA) at 4° C. for 1 hour. Then, each sample was incubated with Alexa488-linked secondary antibodies specific for human Fc at 4° C. for 30 minutes. After washing with PBS, the samples were analyzed by flow cytometry. The results indicated that all variants, ep3-Ras03, ep4-Ras03, ep6-Ras03, ep7-Ras03 and ep8-Ras03, showed an improved binding to EpCAM compared with epRas03 in the EpCAM positive cell line (DLD-1) (FIG. 12C, left), whereas there was almost no binding observed in the EpCAM negative cell line (HeLa) (FIG. 12C, right).

6.29 Example 25. Analysis of Non-Specific Binding of Affinity-Enhanced EpCAM-Targeting Cyclic Peptides FIG. 13 illustrates the results of ELISA analysis of non-specific cell surface binding in the HeLa cell line (which does not express EpCAM) in order to assay the non-specific binding of the EpCAM-targeting cyclic peptide-fused anti-Ras•GTP iMabs. Specifically, the HeLa cell line was cultured in a 96-well plate so that cells were filled in the whole bottom of the well, and then washed 3 times with a wash buffer (HBSS buffer, 50 mM HEPES). Then, they were cultured with epRas03, ep3-Ras03, ep4-Ras03, ep6-Ras03, ep7-Ras03 and ep8-Ras03 in a blocking buffer (HBSS buffer, 50 mM HEPES, 1% BSA) at a concentration of 100, 50, 25, 12.5, 6.25, and 3.125 ng/ml at 4° C. for 2 hours. After washing 3 times with a wash buffer, the labeled antibodies were used to produce HRP-conjugated anti-His mAb. The results were reacted with TMB ELISA solution, quantifying the absorbance at 450 nm.

The results indicated that ep4-Ras03 and ep8-Ras03 showed greater nonspecific cell surface binding compared with epRas03 (FIG. 13). Ep6-Ras03 cyclic peptides exhibited no increase in nonspecific cell surface binding compared with ep-Ras03. Thus, Ep6 (SEQ ID NO. 34) was selected as the final EpCAM target cyclic peptides.

6.30 Example 26. Ep-Ras03, a CT with Enhanced Physical Properties and Enhanced, Selective EpCAM The newly selected cyclic peptide ep-Ras03 was fused to the light chain variable region of the cell-penetrating antibody CT05 in order to impart the CTs with tumor cell/tissue-specificity. Ep6 cyclic peptide (SEQ ID NO. 34) was fused to the N-terminus of epCT05 (G4S) 2 VL constructed in Example 9 instead of Ep133. In this Example, two linkers $(G_4S)_2$ and MGSSSN were used for fusing the Ep6 cyclic peptide.

The following Table 12 shows light chain variable region sequences of the physical property- and affinity-enhanced EpCAM target cyclic peptide-fused cell-penetrating antibody.

6.30.1

TABLE 12

| Names of light chain variable regions | Amino acid sequence | SEQ ID NO: |
|---|---|---|
| hT4-ep59 MG VL | 1 10 20 30 40 50 60<br>EHLHCLGSLCWPMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 21 |
| hT4-ep59 (ep6) MG VL | 1 10 20 30 40 50 60<br>NNLRCIGNICWSMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 43 |
| epCT05 $(G_4S)_2$ VL | 1 10 20 30 40 50 60<br>EHLHCLGSLCWPGGGGSGGGGSDIQMTQSPSSLSASVGDRVTITCKSSQSLLNSRDGKNYLAWYQ<br>70 80 90 100 110 120 130<br>QKPGKAPKLLIYDASNLETGVPSRFSGSGSGTDFTFTISSLQPEDIATYFCQQYWYWMYTFGGGT<br>KVEIKR | 9 |
| ep6-CT05 MG VL | 1 10 20 30 40 50 60<br>NNLRCIGNICWSMGSSSNDIQMTQSPSSLSASVGDRVTITCKSSQSLLNSRDGKNYLAWYQQKPG<br>70 80 90 100 110 120 130<br>KAPKLLIYDASNLETGVPSRFSGSGSGTDFTFTISSLQPEDIATYFCQQYWYWMYTFGGGTKVEIKR | 47 |
| ep6-CT05 $(G_4S)_2$ VL | 1 10 20 30 40 50 60<br>NNLRCIGNICWSGGGGSGGGGSDIQMTQSPSSLSASVGDRVTITCKSSQSLLNSRDGKNYLAWYQ<br>70 80 90 100 110 120 130<br>QKPGKAPKLLIYDASNLETGVPSRFSGSGSGTDFTFTISSLQPEDIATYFCQQYWYWMYTFGGGT<br>KVEIKR | 48 |

Ep6 was cloned into the light chain mammalian expression vector as described in Example 2. It was transiently co-transfected with the heavy chain expression vector containing the heavy chain variable region containing the endosomal escape motif into HEK293F cells, thereby expressing individual clones. They were purified by the same method as described in Example 2. The purified antibodies were named ep6-CT65$(G_4S)_2$ and ep6-CT65 MG.

FIG. 14 illustrates the results of ELISA analysis of binding ability between each of 0.1, 1, and 10 nM cyclic peptide-fused anti-Ras•GTP iMabs and human recombinant EpCAM protein in order to confirm the specific binding of the ep6 cyclic peptide-fused cell-penetrating antibody to EpCAM.

The human recombinant EpCAM was bound to each well of a 96-well EIA/RIA plate at a concentration of 5 μg/ml at room temperature for 1 hour in the same method as in Example 24. Then, they were washed with 0.1% PBST (PBS pH 7.4, 137 mM NaCl, 2.7 mM KCl, 0.1% Tween 20) for 10 minutes 3 times. Then, they were bound with 4% PBSB (PBS pH 7.4, 137 mM NaCl, 2.7 mM KCl, 4% BSA) for 1 hour, and then washed with 0.1% PBST for 10 minutes 3 times. The indicated EpCAM-targeting cyclic peptides were diluted in 4% PBSB and bound at various concentrations of 10 nM, 1 nM and 0.1 nM at room temperature for 1 hour. Then, they were washed with 0.1% PBST for 10 minutes 3 times. The labeled antibodies were used for the conjugation so as to produce HRP-conjugated anti-His mAb. The results were reacted with TMB ELISA solution, thereby quantifying the absorbance at 450 nm.

The ELISA analysis indicated that the Ep6 cyclic peptide-fused ep6-CT65$(G_4S)_2$ and ep6-CT65 MG showed higher antigen binding ability compared with the conventional Ep133 cyclic peptide-fused epCT65 (FIG. 14). Further, EpCAM binding ability varied depending on linkers fusing Ep6.

6.31 Example 27. Construction of Integrin-Targeting Peptide RGD10-Based High-Diversity Peptide Library and Screening of Peptide with Enhanced Affinity Specific for Integrin αvβ5

A search was conducted for a novel tumor tissue-specific receptor capable of the cellular internalization rather than EpCAM. RGD10 was selected due to its property of specifically binding to integrin (e.g., integrin αvβ3 and integrin αvβ5) which is overexpressed in neovascular cells and various tumors (DGARYCRGDCFDG (SEQ ID NO: 49)) (Holig, et al., 2004).

The RGD10 peptide show binding ability to integrin αvβ3 and integrin αvβ5. Integrin αvβ3 is a receptor overexpressed in neovascular cells, making it suitable for targeting neovascular cells in tumor tissues, but is rarely expressed in tumor cells, into which antibodies should actually penetrate. Thus, the present work sought to increase the affinity for integrin αvβ5, which is known to be overexpressed in tumor tissues.

FIG. 15A is a schematic diagram illustrating a construction of an integrin αvβ5 affinity-enhanced library after the fused form of the RGD10 cyclic peptide, and the light chain variable region of the cell-penetrating antibody are displayed on the M13 phage surface;

Specifically, the RGD10 cyclic peptide was fused with the MGSSSN linker (SEQ ID NO: 102) at the N-terminus of the hT4-59 light chain variable region (VL) so as to construct a template for the phage library. The complex structure of the RGD peptide and the integrin revealed that the C-terminus of the RGD peptide interacted with the beta chain of the integrin (Xiong, et al., 2002). Thus, two additional amino acids were added at the C-terminal direction of the RGD10 cyclic peptide so as to construct the cyclic peptide library consisting of 15 amino acids in total. Cysteine was fixed at the 6th and 10th residue, such that cysteine forms disulfide bonds with arginine, glycine and aspartate, respectively, which are the 7th to 9th residues an known to bind directly to integrin. The NNK degenerate codon, which can encode all amino acids, was introduced at residues 3, 5, 11, 13, 14 and 15 that are positioned outside the cyclic peptide. The 4th and 12th residues are expected to be responsible for binding to the integrin. For the 4th and 12th residues, respectively, the ARR degenerate codon was used to encode arginine and lysine that are positively charged amino acids so as to encode amino acids similar in nature to the wild-type peptide RGD10, and the GAN degenerate codon was used to encode aspartate and glutamate which are negatively charged amino acids.

Specifically, the DNAs encoding the designed library were amplified using the PCR and then concentrated using ethanol precipitation to obtain genes. After cleaving with SfiI restriction enzyme, they were ligated into pComb3X vector (Barbas, Burton, Scott, & Silverman, 2007) cleaved with the same restriction enzyme. Then, they were transformed into XL-1 Blue *E. coli*., which were cultured in a medium containing ampicillin, thereby obtaining a library having a size of $4\times10^8$.

FIG. 15B illustrates a panning procedure for screening, using a phage library, peptides specific for human integrin αvβ5 that are known to be overexpressed in tumor epithelial cells.

Specifically, 5 μg of recombinant human integrin αvβ5 protein (R&D systems, 2528-AV-050) was added to the immunotube to allow the protein to adhere onto the surface of the tube for 1 hour. Then, 5% powdered milk containing divalent cations (1 mM $MnCl_2$, 1 mM $MgCl_2$ and 2 mM $CaCl_2$) was added to the tube to prepare a condition for activating the integrin while shielding the surface on which the integrin αvβ5 protein did not adhere. Then, the phage library of $10^{11}$ CFU diluted was placed in a solution of the powdered milk containing divalent cations (1 mM $MnCl_2$, 1 mM $MgCl_2$ and 2 mM $CaCl_2$) so as to bind to the integrin. After washing with a TBST (Tris Buffered Saline-Tween 20) solution containing divalent cations (1 mM $MnCl_2$, 1 mM $MgCl_2$ and 2 mM $CaCl_2$) in order to wash the non-specifically bound phages, the remaining phages were eluted with glycine solution (pH 2.2). The eluted phages were neutralized with an 1M Tris-HCl solution (pH 9.0), and they were transfected into XL-1 Blue *E. coli*. at 37° C. for 1 hour. Then, the transfected *E. coli* was suspended in SB (Super Broth) containing ampicillin and cultured at 37° C. When the absorbance of the 600 nm light of the culture solution became 0.5, $10^{12}$ PFU (plaque-forming unit) VSCM helper phage was added thereto. Then, while the mixture was slowly stirred, they were cultured at 37° C. for 1 hour. Kanamycin was added thereto, and the mixture was cultured overnight. The next day, the culture was centrifuged, and the supernatant containing the phage particles was completely isolated from the *E. coli*. Then, 4% PEG and 3% NaCl were added to concentrate the phage. The phage was then dissolved in TBS and stored. They were used for subsequent panning. The panning conditions were set so that the amount of antigen decreased and the number of washing increased as the number of times increased, thereby linking only stronger binding clones. At the 1st to 5th panning orders, the content of antigens was decreased to 5, 3, 2, 1, and 1 μg, respectively, and the number of washes was increased to 3, 5, 10, 15, and 25, respectively.

FIG. 15C illustrates the results of ELISA analysis of the binding ability of individual clones showing 31 binding abilities in the library up to 5th panning in FIG. 15B to the human integrin αvβ5.

Specifically, after the 5th panning, the *E. coli* containing the antibody gene was applied to an LB agar medium containing ampicillin so as to obtain a single colony. The colony was inoculated and cultured in 200 μl SB-ampicillin medium. IPTG induced the expression of cyclic peptide-light chain variable region proteins in the periplasm. After culturing at 20° C. overnight, the periplasm was extracted using a TES solution. ELISA was conducted on the periplasm to confirm its binding ability to the integrin αvβ5 antigen.

Specifically, the respective integrin αvβ5 proteins adhered to 96-well EIA/RIA plates at a concentration of 1 μg/ml at room temperature for 1 hour. Then, 3% solution of powdered milk containing divalent cations (1 mM $MnCl_2$, 1 mM $MgCl_2$ and 2 mM $CaCl_2$) was added to the wells so as to shield the surface to which the integrin αvβ5 protein did not adhere. Then, they were washed with TBST solution containing divalent cations 3 times. The extracted periplasm solution bound for 1 hour. They were washed with TBST solution containing divalent cations 3 times. The labeled antibodies were used for the conjugation so as to produce HRP-conjugated anti-his mAb. The results were reacted with TMB ELISA solution, thereby quantifying the absorbance at 450 nm. Then, they were compared with the wild-type peptide RGD10.

The ELISA analysis revealed that 31 clones of 190 individual clones showed the higher binding ability to integrin αvβ5 than the conventional cyclic peptides. A further test was conducted on these 31 individual clones. The results demonstrated that 15 individual clones showed repeated experimental results. Among these, clones with three or more positively charged amino acids expected to exhibit nonspecific binding were excluded.

The following Table 13 shows sequences for 8 individual clones targeting integrin αvβ5 selected through the phage library.

6.31.1

TABLE 13

| Names of cyclic peptides | Target receptor | Amino acid sequence | SEQ ID NO: |
|---|---|---|---|
| RGD10 | Integrin αVβ3, Integrin αVβ5 | 1 10<br>DGARYCRGDCFDG | 49 |
| in1 | | 1 10<br>DGEKNCRGDCIEDQP | 50 |
| in2 | | 1 10<br>DGEKSCRGDCFDPSQ | 51 |
| in3 | | 1 10<br>DGVRACRGDCFDVQD | 52 |
| in4 | | 1 10<br>DGVRQCRGDCFDGPL | 53 |
| in5 | | 1 10<br>DGGRLCRGDCFDAQQ | 54 |
| in6 | | 1 10<br>DGERQCRGDCFDAPV | 55 |
| in7 | | 1 10<br>DGQRTCRGDCFDPPS | 56 |
| in8 | | 1 10<br>DGDKQCRGDCFDPAP | 57 |

6.32 Example 28. Expression and Purification of Affinity-Enhanced Integrin αvβ5-Targeting Cyclic Peptide-Fused iMabs In order to evaluate the cyclic peptides specific for the selected human integrin αvβ5, each cyclic peptide-fused intact IgG-type anti-Ras•GTP iMab was produced to perform the experiment.

Using the same method as described in Example 2 above, the selected affinity-enhanced integrin αvβ5 target cyclic peptides were fused, by a genetic engineering method, at the N-terminus of the light chain of the cell-penetrating humanized light chain hT4-59 using an MGSSSN linker. Then, they were cloned into an animal expression vector.

The following Table 14 shows sequences of light chain variable regions (VL) fused with affinity-enhanced integrin αvβ5 target cyclic peptides.

6.32.1

TABLE 14

| Names of light chain variable regions | Amino acid sequence | SEQ ID NO: |
|---|---|---|
| hT4-i59 MG VL | 1 10 20 30 40 50 60<br>DGARYCRGDCFDGMGSSSNDIQMTQSPSSLSASVGDRVTITCKSSQSLLNSRDGKNYLAWYQQKP<br>70 80 90 100 110 120 130<br>GKAPKLLIYWASTRESGVPSRFSGSGSGTDFTLTISSLQPEDFATYFCQQYWYWMYTFGQGTKVEIKR | 58 |
| hT4-i59 (int1) MG VL | 1 10 20 30 40 50 60<br>DGEKNCRGDCIEDQPMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 59 |
| hT4-i59 (in2) MG VL | 1 10 20 30 40 50 60<br>DGEKSCRGDCFDPSQMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 60 |

TABLE 14-continued

| Names of light chain vari-able regions | Amino acid sequence | SEQ ID NO: |
|---|---|---|
| hT4-i59 (in3) MG VL | 1 10 20 30 40 50 60<br>DGVRACRGDCFDVQDMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 61 |
| hT4-i59 (in4) MG VL | 1 10 20 30 40 50 60<br>DGVRQCRGDCFDGPLMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 62 |
| hT4-i59 (in5) MG VL | 1 10 20 30 40 50 60<br>DGGRLCRGDCFDAQQMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 63 |
| hT4-i59 (in6) MG VL | 1 10 20 30 40 50 60<br>DGERQCRGDCFDAPVMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 64 |
| hT4-i59 (in7) MG VL | 1 10 20 30 40 50 60<br>DGQRTCRGDCFDPPSMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 65 |
| hT4-i59 (in8) MG VL | 1 10 20 30 40 50 60<br>DGDKQCRGDCFDPAPMGSSSNDIQMTQSPSSLSASVGDRVTITCKSSQSLLNSRDGKNYLAWYQQKPGK<br>70 80 90 100 110 120 130<br>APKLLIYWASTRESGVPSRFSGSGSGTDFTLTISSLQPEDFATYFCQQYWYWMYTFGQGTKVEIKR | 66 |

The heavy chain expression vector of RT22, which is an anti-Ras•GTP iMab, and the HEK293F protein expression cell were transiently co-transfected to express individual clones. They were purified in the same manner as in Example 2. The purified antibodies were named inRas03, in1-Ras03, in2-Ras03, in3-Ras03, in4-Ras03, in5-Ras03, in6-Ras03, in7-Ras03 and in8-Ras03.

FIG. 16A illustrates the results of 12% SDS-PAGE analysis of antibodies under reducing or non-reducing condition, in which the antibodies are obtained after purifying IgG-type anti-Ras•GTP iMab antibodies in which the affinity-enhanced cyclic peptide for the integrin αvβ5 selected from the phage library is fused to N-terminus of the light chain.

The results showed a molecular weight of about 150 kDa under non-reducing conditions (DTT−) and a molecular weight of 50 kDa for the heavy chain and 25 kDa for the light chain under reducing conditions (DTT+). These results indicated that the expressed and purified individual clones were present as a monomer in a solution state and did not generate a dimer or oligomer through a non-natural disulfide bond.

6.33 Example 29. Analysis of Binding Ability of Affinity-Enhanced Integrin αvβ5 Target Cyclic Peptide-Fused iMab to Human Integrin αvβ5

In order to analyze the binding ability of the anti-Ras•GTP iMab fused with the cyclic peptide having enhanced affinity to the integrin αvβ5 for the human integrin αvβ5, ELISA and flow cytometry (FACS) were conducted on the binding ability of the activated integrin αvβ5 fixed on the plate and the activated integrin αvβ5 expressed in cells. FIG. 16B illustrates the results of ELISA analysis of the binding ability of IgG-type anti-Ras•GTP iMab antibodies, in which the affinity-enhanced cyclic peptide for the integrin αvβ5 selected from the phage library is fused to N-terminus of the light chain, to 1 nM or 10 nM of the activated integrin αvβ5.

The respective integrin αvβ5 proteins adhered to 96-well EIA/RIA plates at a concentration of 1 μg/ml at room temperature for 1 hour. Then, 3% solution of powdered milk containing divalent cations (1 mM $MnCl_2$, 1 mM $MgCl_2$ and 2 mM $CaCl_2$) was added to the wells so as to transform activated integrin during shielding the surface to which the integrin αvβ5 protein did not adhere. Then, they were washed with a TBS-T solution containing divalent cations 3 times. They had bound to inRas03, in1-Ras03, in2-Ras03, in3-Ras03, in4-Ras03, in5-Ras03, in6-Ras03, in7-Ras03 and in8-Ras03 diluted with TBS containing divalent cations for 1 hour. Then, they were washed 3 times with TBST solution containing divalent cations (1 mM $MnCl_2$, 1 mM $MgCl_2$ and 2 mM $CaCl_2$). The labeled antibodies were used for the conjugation so as to produce HRP-conjugated anti-Fc mAb. The results were reacted with TMB ELISA solution, thereby quantifying the absorbance at 450 nm. Then, they were compared with the antibodies fused with the wild-type peptide RGD10 as a control.

The ELISA analysis revealed that 5 peptides (in4-8) among 8 kinds of cyclic peptides selected showed the higher binding ability to integrin αvβ5 compared with the conventional RGD10-fused antibody. FIG. 16C illustrates the results of confirming the binding ability of IgG-type anti-Ras•GTP iMab antibodies in which the affinity-enhanced cyclic peptide to the integrin αvβ5 selected from the phage library is fused to N-terminus of the light chain to the integrin αvβ5 expressed on the cell surface.

Specifically, HT29 (integrin αvβ5+) was prepared at $1\times10^5$ cells per sample. The cells were cultured with 100 nM of inRas03, in1-Ras03, in2-Ras03, in3-Ras03, in4-Ras03, in5-Ras03, in6-Ras03, in7-Ras03 and in8-Ras03, respectively, in TBSF (TBS buffer, 2% BSA) containing divalent cations (1 mM $MnCl_2$, 1 mM $MnCl_2$ and 2 mM $CaCl_2$) at 4° C. for 1 hour. Then, each antibody was reacted with antibodies specific for human Fc to which Alexa488 (green fluorescence) was linked at 4° C. for 30 minutes. After they were washed with TBS containing divalent cations (1 mM $MnCl_2$, 1 mM $MgCl_2$, 2 mM $CaCl_2$), the cells were analyzed by flow cytometry. The results demonstrated that in4-Ras03, in6-Ras03 and in7-Ras03 showed the high intensity of fluorescence for binding to the cells compared with inRas03.

The results showed the stronger binding ability than RGD10 in the ELISA and the strongest binding to cell surface integrin αvβ5. Further experiments were performed using in4 cyclic peptide.

FIG. 16D illustrates the results of analyzing the binding ability of each antibody, which is treated with short interfering RNAs (siRNAs) as a control or integrin β5 siRNAs using colorectal cancer cell line HCT8 overexpressing the integrin αvβ5 in order to confirm whether in4 cyclic peptide-fused IgG-type anti-Ras•GTP iMab antibodies specifically bind to the integrin αvβ5.

Specifically, $2\times10^5$ cells of HCT8 were placed in 4 ml medium containing 10% FBS in a 60-pi culture dish, and they were cultured in a condition of 5% $CO_2$ at 37° C. for 12 hours. After culturing for 24 hours, siRNA was transiently transfected. 100 nM the control siRNA having no targeting ability for the transient transfection and siRNA targeting inhibition of integrin β5 expression, respectively, were reacted with 1 ml Opti-MEM media (Gibco) and 3.5 μl Lipofectamine 2000 (Invitrogen, USA) for 10 min at room temperature, and then they were added to each well. Further, 1 ml DMEM media without antibiotics was added thereto. The mixtures were cultured in 5% $CO_2$ at 37° C. for 6 hours. Thereafter, their medium was changed to 4 ml DMEM medium containing 10% FBS, and then the cells were cultured for 48 hours.

The results showed that expression of integrin αvβ5 of HCT8 was inhibited by 35 siRNA. Further, when treating with the control siRNA, in4-Ras03 showed the stronger binding ability to integrin αvβ5 than wild-type peptide (RGD10). On the other hand, in HCT8, which did not express integrin αvβ5 by treating with β5 siRNA treatment, both antibodies showed no binding ability and exhibited a binding ability similar to that of Ras03. This indicated that in4-Ras03 binds specifically to integrin αvβ5.

6.34 Example 30. Analysis of the Binding Ability of Cell-Penetrating Antibody Fused with Affinity-Enhanced Integrin αvβ5 Target Cyclic Peptide to Cell Surface Integrin αvβ5

A cell-penetrating antibody has been developed can be applied to various tumor tissues by fusing cyclic peptides targeting integrin αvβ5 as well as EpCAM to cell-penetrating antibodies as well as anti-Ras•GTP iMabs. Thus, RGD10 and in4 cyclic peptides, instead of Ep133, were fused to the N-terminus of epCT05 $(G_4S)_2$ VL constructed in Example 9. In this Example, MGSSSN was used as a linker for fusing RGD10 and in4 cyclic peptides.

The following Table 15 shows sequences of the light chain variable region of cell-penetrating antibodies fused with wild-type and affinity-enhanced integrin αvβ5 target cyclic peptides.

6.34.1

TABLE 15

| Names of light chain variable regions | Amino acid sequence | SEQ ID NO: |
|---|---|---|
| hT4-i59 MG VL | 1 10 20 30 40 50 60<br>DGARYCRGDCFDGMGSSSNDIQMTQSPSSLSASVGDRVTITCKSSQSLLNSRDGKNYLAWYQQKPGKA<br>70 80 90 100 110 120 130<br>PKLLIYWASTRESGVPSRFSGSGSGTDFTLTISSLQPEDFATYFCQQYWYWMYTFGQGTKVEIKR | 58 |
| hT4-i59 (in4) MG VL | 1 10 20 30 40 50 60<br>DGVRQCRGDCFDGPLMGSSSNDIQMTQSPSSLSASVGDRVTITCKSSQSLLNSRDGKNYLAWYQQKPG<br>70 80 90 100 110 120 130<br>KAPKLLIYWASTRESGVPSRFSGSGSGTDFTLTISSLQPEDFATYFCQQYWYWMYTFGQGTKVEIKR | 62 |
| inCT05 MG VL | 1 10 20 30 40 50 60<br>DGARYCRGDCFDGMGSSSNDIQMTQSPSSLSASVGDRVTITCKSSQSLLNSRDGKNYLAWYQQKPGKA<br>70 80 90 100 110 120 130<br>PKLLIYDASNLETGVPSRFSGSGSGTDFTFTISSLQPEDIATYFCQQYWYWMYTFGGGTKVEIKR | 67 |
| in4-CT05 MG VL | 1 10 20 30 40 50 60<br>DGVRQCRGDCFDGPLMGSSSNDIQMTQSPSSLSASVGDRVTITCKSSQSLLNSRDGKNYLAWYQQKPG<br>70 80 90 100 110 120 130<br>KAPKLLIYDASNLETGVPSRFSGSGSGTDFTFTISSLQPEDIATYFCQQYWYWMYTFGGGTKVEIKR | 68 |

The light chain variable region fused with the affinity-enhanced integrin αvβ5 target cyclic peptide was cloned into a light chain animal expression vector in the same manner as in Example 2. Then, they were transiently co-transfected into the heavy chain expression vector containing the heavy chain variable region with the endosomal escape motif and the HEK293F protein expression cell so as to express individual clones. They were purified in the same manner as in Example 2. They were named inCT65 and in4-CT65, respectively. Further experiments were performed with in4-CT65 fused with affinity-enhanced in4 cyclic peptides.

FIG. 17 illustrates the results of flow cytometry (FACS) analysis on cells obtained by treating MCF-7, a breast cancer cell line, overexpressing the integrin αvβ5 and Raji, bucket lymphoma cell line, non-expressing the integrin αvβ5 with 10 nM the antibody, in order to confirm the binding ability of in4 cyclic peptide-fused IgG-type cell-penetrating antibody to the integrin αvβ5 expressed on the cell.

Specifically, $1\times10^5$ cells of MCF-7 (integrin αvβ5+) and Raji (integrin αvβ5−), respectively, were prepared for each sample. The cells were cultured with 10 mM in4-CT65 in TBSF (TBS buffer, 2% BSA) containing divalent cations (1 mM $MnCl_2$, 1 mM $MnCl_2$ and 2 mM $CaCl_2$)) at 4° C. for 1 hour. Then, each sample was incubated with antibodies specific for human Fc to which Alexa488 (green fluorescence) was linked at 4° C. for 30 minutes. After washing with TBS containing divalent cations, they were analyzed by a flow cytometer. The results indicated that the cell-penetrating antibody comprising the affinity-enhanced cyclic peptides showed binding to the MCF-7 cell line expressing integrin αvβ5, but not to the Raji cell line not expressing integrin αvβ5 showed no binding ability.

The results showed that the antibody, in which the affinity-enhanced integrin αvβ5 target cyclic peptide in4 was fused at N-terminus of the light chain of the cell-penetrating antibody, which was a different kind of an antibody, showed specific binding ability to the integrin αvβ5.

6.35 Example 31. Confirmation of Enhancement of Tumor Tissue Targeting Ability of Affinity-Enhanced EpCAM or Integrin αvβ5 Target Cyclic Peptide FIG. 18A includes images of confirming the mouse's biodistribution of anti-Ras•GTP iMab ep6-RasO3 fused with the affinity-enhanced EpCAM target cyclic peptide Ep6 for improving the tumor tissue targeting ability and a graph of quantifying the fluorescence of the tumor tissue (T) and the normal tissue (N) of whole body.

Specifically, 20 μg of DyLight fluorescence-labeled anti-Ras•GTP iMab Ras03, epRas03, and ep6-Ras03, respectively, were injected into human colorectal LoVo tumor xenografted BALB/c nude mice. The fluorescence emitted from the whole body of mice were observed by IVIS Lumina XRMS Series III (Perkin Elmer) at 0, 6, 12, 24, 48 and 72-hours, respectively. In this Example, the mice were anesthetized using 1.5% to 2.5% isoflurane (Piramal Critical Care). Each image was analyzed by Living Image software (Perkin Elmer) so as to quantify fluorescence values of the whole body.

As illustrated in FIG. 18A, epRas03 and ep6-Ras03 showed a large number of antibodies in tumor tissues than those of Ras03 not fused with EpCAM target peptide. Further, ep6-Ras03 showed a large number of antibodies in tumor tissues than those of epRas03 over time after injecting the antibodies. FIG. 18B includes images of confirming the mouse's biodistribution of anti-Ras•GTP iMab ep6-RasO3 fused with the affinity-enhanced EpCAM target cyclic peptide Ep6 for improving the tumor tissue targeting ability and a graph of quantifying the fluorescence from extracted organs.

After the experiments as described above, the mice were euthanized 72 hours after the antibody injection. Then, the tumor as well as the heart, lung, liver, kidney, pancreas and spleen were excised, and the fluorescence in the organs was quantified by living image software (Perkin Elmer).

As illustrated in FIG. 18B, epRas03 and ep6-Ras03 were present in larger numbers in the tumor tissue and in lesser numbers in other organs compared to Ras03 not fused with EpCAM target peptide. The amounts of antibodies located in tumor tissues were in the order of ep6-Ras03, epRas03, and Ras03.

FIG. 18C includes images of confirming the mouse's biodistribution of anti-Ras•GTP iMab in4-RasO3 fused with the affinity-enhanced integrin αvβ5 target cyclic peptide in4 for improving the tumor tissue targeting ability and a graph of quantifying the fluorescence of the tumor and the whole body.

Specifically, 20 μg of DyLight fluorescence-labeled anti-Ras•GTP iMab Ras03, inRas03, and in4-Ras03, respectively, were injected into human colorectal LoVo tumor xenografted BALB/c nude mice. The fluorescence emitted from the whole body of mice were observed by IVIS Lumina XRMS Series III (Perkin Elmer) at 0, 6, 12, 24, 48 and 72-hours, respectively. In this Example, the mice were anesthetized using 1.5% to 2.5% isoflurane (Piramal Critical Care). Each image was analyzed by Living Image software (Perkin Elmer) so as to quantify fluorescence values of the whole body.

As illustrated in FIG. 18C, inRas03 and in4-Ras03 showed larger number of antibodies in tumor tissues than those of Ras03 not fused with integrin αvβ5 target peptide. Further, in4-Ras03 showed more significant number of antibodies in tumor tissues than those of inRas03 overtime after the antibody injection. FIG. 18D includes images of confirming the mouse's biodistribution of anti-Ras•GTP iMab in4-RasO3 fused with the affinity-enhanced integrin αvβ5 target cyclic peptide in4 for improving the tumor tissue targeting ability and a graph of quantifying the fluorescence from the extracted organ.

Specifically, after the experiments as described above, the mice were euthanized 72 hours after the antibody injection. Then, the tumor and the heart, lung, liver, kidney, pancreas and spleen were excised, and the fluorescence in the organs was quantified by living image software (Perkin Elmer).

As illustrated in FIG. 18D, inRas03 and in4-Ras03 showed larger number of antibodies present in the tumor tissue and lesser number of antibodies present in other organs than those of Ras03 not fused with integrin αvβ5 target peptide. The amounts of antibodies located in tumor tissues were in the order of in4-Ras03, inRas03 and Ras03.

6.36 Example 32. Construction of Additional Phage Libraries Based on In4 Cyclic Peptide Integrin αvβ5 and integrin αvβ6 are overexpressed by cells of several tumors. The in4 cyclic peptide, having high affinity to integrin αvβ5, has been selected as described in Example 27 above. To screen for additional peptides that can bind to integrin αvβ5 and integrin αvβ6 with high affinity, additional phage libraries were constructed.

FIG. 20 is a schematic drawing of a library constructed based on an in4 cyclic peptide by displaying a cyclic peptide fused to the N-terminus of a light chain variable region on the surface of M13 bacteriophage.

The RGD motif of the in4 cyclic peptide is immediately flanked by single cysteine on both sides. The loop structure of the cyclic peptide was made wider by expanding the number of amino acids between these two cysteine residues. In particular, between the cysteines at positions 6 and 10, two amino acids were added N-terminal to the RGD motif, and four amino acids were added C-terminal to the RGD motif. As a result, the cyclic peptide forms a loop structure of 9 amino acids between the two cysteines. The overall length of the cyclic peptide was then increased by adding four amino acids N-terminal to the cysteine at position 6 and four amino acids C-terminal to the cysteine at position 10. To generate a cyclic peptide library, the NHB degenerate codon, which can encode phenylalanine, isoleucine, leucine, methionine, valine, serine, proline, threonine, alanine, tyrosine, histidine, glutamine, asparagine, lysine, aspartic acid, and glutamic acid, was introduced at residues 1, 3, 5 and 18 of the peptide. The NNK degenerate codon, which can encode all 20 amino acids, was introduced in the 2nd, 4th, 7th, 8th, 14th, 15th, 17th, and 19th residues. The 5#1 and 5#2 libraries, created to target integrin αvβ5, were designed to have serine (5#1) or threonine (5#2) as the 12th amino acid immediately following the RGD motif and phenylalanine as the 13th amino acid (both), because, in proteins having an affinity for integrin αvβ5, the first amino acid after RGD was often serine or threonine and the second amino acid after RGD was often phenylalanine (Rubtsov, Syrkina et al. 2016). To generate the 6# cyclic peptide library, designed to target integrin αvβ6, leucine was used as the 12th amino acid immediately following the RGD motif and phenylalanine was used as the 13th amino acid. MTH degenerate codon encoding leucine or isoleucine were introduced at the 15th amino acid. The 6# library was designed this way because it was known that proteins with ability to bind integrin αvβ6 generally have an LXXL or LXXI motif after the RGD motif (Rubtsov, Syrkina et al. 2016).

The DNA encoding each of the designed libraries was amplified using PCR. The 5#1, 5#2, and 6# libraries were amplified individually, and then combined and concentrated using ethanol precipitation. The resulting DNA was cleaved with restriction enzymes EcoRI and NheI to form sticky ends, and then the phage display vector pComb3X vector was linearized with the same restriction enzymes. The restriction enzyme-cleaved insert gene and the linearized vector gene were ligated by T4 ligase. The library DNA was transformed into XL1-blue competent cells via electroporation. The library was cultured in a medium containing ampicillin to finally generate a library with a size of $3\times10^8$ phage molecules.

FIG. 21A is a schematic view of the construction of integrin αvβ5 and integrin αvβ6, which are antigens used in selecting cyclic peptides from the constructed library.

Specifically, the extracellular domain portion of integrin αv chain (31 Phe-992 Val), the extracellular domain portion of integrin β5 chain (24 Gly-719 Asn), and the extracellular domain portion of integrin β6 chain (22 Gly-709 Pro) were used as antigens. The integrin is a heterodimer composed of a chain and β chain. To replicate this, the α chain was fused at the C-terminus of the extracellular domain with a negatively charged leucine zipper of integrin via a linker consisting of 10 amino acids in HPGGGSGGGS sequence (SEQ ID NO: 104), and the leucine zipper was fused at the C-terminus with a 6×His tag for purification. The β chain was fused at the C-terminus of the extracellular domain with a positively charged leucine zipper via the same linker as was used for the α chain. The integrin DNA was constructed by PCR and cloned into the animal cell expression vector pcDNA3.4 vector using restriction enzymes NotI and BamHI. The resulting a chain vector and β chain vector were simultaneously transfected transiently into HEK293F protein-expressing cells and expressed for 6 days, and proteins present in the supernatant were purified using Ni-NTA Agarose resin.

FIG. 21B shows the result of an SDS-PAGE analysis of purified integrin αvβ5 and integrin αvβ6 on 12% SDS-PAGE under the reducing condition.

Specifically, it was shown that α chain and β chain exist at a molecular weight of 100 to 155 kDa under the reducing condition, indicating that the proteins expressed as both the α chain and β chain are purely present as a heterodimer.

FIG. 21C shows ELISA experiment results confirming whether expressed and purified integrin αvβ5 and integrin αvβ6 are equivalent to commercially available recombinant integrins.

Specifically, integrin αvβ5 and integrin αvβ6 purified using above methods and commercially available integrin αvβ5 and integrin αvβ6 were fixed on 96-well EIA/RIA plates. Recombinant human integrin αvβ5 (ACRO Biosystems, IT5-H52W5) and integrin αvβ6 (ACRO Biosystems, IT6-H52E1) were used for the commercially available recombinant human integrins. The antigens were fixed at a concentration of 2 μg/mL for 1 hour at room temperature. 3% skim milk solution containing divalent cations (1 mM $MnCl_2$, 1 mM $MgCl_2$, 2 mM $CaCl_2$) was added to the wells to shield the non-adsorbed side of the antigen. Thereafter, the wells were washed 3 times for 10 minutes with a TBS-T (TBS with 0.05% Tween20) solution containing divalent cations. As the negative control for integrin αvβ5 and integrin αvβ6, anti-Ras•GTP iMab not fused with cyclic peptide was used at a concentration of 20 nM. Commercially available mouse anti-integrin αvβ3 antibody (R&D, MAB3050) was diluted 1:100 and processed. For validation of each integrin αvβ5, commercially available mouse anti-Integrin αvβ5 antibody (R&D, MAB2528, diluted 1:100) and anti-Ras iGTP iMab fused with cyclic peptide in4 with improved affinity for integrin αvβ5 were used at a concentration of 20 nM. For validation of each integrin αvβ6, anti-Ras•GTP iMab fused with cyclic peptide SFITGv6, known to specifically bind to integrin αvβ6 (Altmann, Sauter et al. 2017), and commercially available mouse anti-integrin αvβ6 antibody (Millipore, MAB2077Z, diluted 1:200), were used at a concentration of 20 nM. All antibody incubations were for 1 hour at room temperature. After washing 3 times for 10 minutes in the same manner as described above, HRP-conjugated anti-human antibody (HRP-conjugated anti-human mAb) and anti-mouse antibody (HRP-conjugated anti-mouse maAb) were added for 30 minutes at room temperature. Subsequently, the wells were washed 3 times for 10 minutes, and treated with TMB ELISA solution, and the absorbance at 450 nm was quantified.

The above-described ELISA experiments show that human recombinant integrin αvβ5 and αvβ6 expressed and purified according to the above methods are equivalent to commercially available recombinant integrin αvβ5 and αvβ6. For further experiments, human recombinant integrins that were expressed and purified according to the above method were used.

Table 16 below shows the protein sequences of human recombinant integrin αv, β5, and β6 chains used to produce human recombinant integrin αvβ5 and αvβ6.

TABLE 16

| Antigen Names | Amino acid sequence | SEQ ID NO: |
|---|---|---|
| Integrin αV Extra-cellular domain-Acidic Leucine zipper-Hisx6 | 1 10 20 30 40 50 60<br>FNLDVDSPAEYSGPEGSYFGFAVDFFVPSASSRMFLLVGAPKANTTQPGIVEGGQVLKCD<br>70 80 90 100 110 120<br>WSSTRRCQPIEFDATGNRDYAKDDPLEFKSHQWFGASVRSKQDKILACAPLYHWRTEMKQ<br>130 140 150 160 170 180<br>EREPVGTCFLQDGTKTVEYAPCRSQDIDADGQGFCQGGFSIDFTKADRVLLGGPGSFYWQ<br>190 200 210 220 230 240<br>GQLISDQVAEIVSKYDPNVYSIKYNNQLATRTAQAIFDDSYLGYSVAVGDFNGDGIDDFV<br>250 260 270 280 290 300<br>SGVPRAARTLGMVYIYDGKNMSSLYNFTGEQMAAYFGFSVAATDINGDDYADVFIGAPLF<br>310 320 330 340 350 360<br>MDRGSDGKLQEVGQVSVSLQRASGDFQTTKLNGFEVFARFGSAIAPLGDLDQDGFNDIAI<br>370 380 390 400 410 420<br>AAPYGGEDKKGIVYIFNGRSTGLNAVPSQILEGQWAARSMPPSFGYSMKGATDIDKNGYP<br>430 440 450 460 470 480<br>DLIVGAFGVDRAILYRARPVITVNAGLEVYPSILNQDNKTCSLPGTALKVSCFNVRFCLK<br>490 500 510 520 530 540<br>ADGKGVLPRKLNFQVELLLDKLKQKGAIRRALFLYSRSPSHSKNMTISRGGLMQCEELIA<br>550 560 570 580 590 600<br>YLRDESEFRDKLTPITIFMEYRLDYRTAADTTGLQPILNQFTPANISRQAHILLDCGEDN<br>610 620 630 640 650 660<br>VCKPKLEVSVDSDQKKIYIGDDNPLTLIVKAQNQGEGAYEAELIVSIPLQADFIGVVRNN<br>670 680 690 700 710 720<br>EALARLSCAFKTENQTRQVVCDLGNPMKAGTQLLAGLRFSVHQQSEMDTSVKFDLQIQSS<br>730 740 750 760 770 780<br>NLFDKVSPVVSHKVDLAVLAAVEIRGVSSPDHVFLPIPNWEHKENPETEEDVGPVVQHIY<br>790 800 810 820 830 840<br>ELRNNGPSSFSKAMLHLQWPYKYNNNTLLYILHYDIDGPMNCTSDMEINPLRIKISSLQT<br>850 860 870 880 890 900<br>TEKNDTVAGQGERDHLITKRDLALSEGDIHTLGCGVAQCLKIVCQVGRLDRGKSAILYVK<br>910 920 930 940 950 960<br>SLLWTETFMNKENQNHSYSLKSSASFNVIEFPYKNLPIEDITNSTLVTTNVTWGIQPAPM<br>970 980 990 1000 1010<br>PVHPGGGSGGGSGGSAQLEKELQALEKENAQLEWELQALEKELAQGATHHHHHH | 70 |
| Integrin β5 Extra-cellular domain-Basic Leucine zipper | 1 10 20 30 40 50 60<br>GLNICTSGSATSCEECLLIHPKCAWCSKEDFGSPRSITSRCDLRANLVKNGCGGEIESPA<br>70 80 90 100 110 120<br>SSFHVLRSLPLSSKGSGSAGWDVIQMTPQEIAVNLRPGDKTTFQLQVRQVEDYPVDLYYL<br>130 140 150 160 170 180<br>MDLSLSMKDDLDNIRSLGTKLAEEMRKLTSNFRLGFGSFVDKDISPFSYTAPRYQTNPCI<br>190 200 210 220 230 240<br>GYKLFPNCVPSFGFRHLLPLTDRVDSFNEEVRKQRVSRNRDAPEGGFDAVLQAAVCKEKI<br>250 260 270 280 290 300<br>GWRKDALHLLVFTTDDVPHIALDGKLGGLVQPHDGQCHLNEANEYTASNQMDYPSLALLG<br>310 320 330 340 350 360<br>EKLAENNINLIFAVTKNHYMLYKNFTALIPGTTVEILDGDSKNIIQLIINAYNSIRSKVE<br>370 380 390 400 410 420<br>LSVWDQPEDLNLFFTATCQDGVSYPGQRKCEGLKIGDTASFEVSLEARSCPSRHTEHVFA<br>430 440 450 460 470 480<br>LRPVGFRDSLEVGVTYNCTCGCSVGLEPNSARCNGSGTYVCGLCECSPGYLGTRCECQDG<br>490 500 510 520 530 540<br>ENQSVYQNLCREAEGKPLCSGRGDCSCNQCSCFESEFGKIYGPFCECDNFSCARNKGVLC<br>550 560 570 580 590 600<br>SGHGECHCGECKCHAGYIGDNCNCSTDISTCRGRDGQICSERGHCLCGQCQCTEPGAFGE<br>610 620 630 640 650 660<br>MCEKCPTCPDACSTKRDCVECLLLHSGKPDNQTCHSLCRDEVITWVDTIVKDDQEAVLCF<br>670 680 690 700 710 720<br>YKTAKDCVMMFTYVELPSGKSNLTVLREPECGNTPNHPGGGSGGGSGGSAQLKKKLQALK<br>730 740<br>KKNAQLKWKLQALKKKLAQGAT | 71 |
| Integrin β6 Extra-cellular domain-Basic Leucine zipper | 1 10 20 30 40 50 60<br>GCALGGAETCEDCLLIGPQCAWCAQENFTHPSGVGERCDTPANLLAKGCQLNFIENPVSQ<br>70 80 90 100 110 120<br>VEILKNKPLSVGRQKNSSDIVQIAPQSLILKLRPGGAQTLQVHVRQTEDYPVDLYYLMDL<br>130 140 150 160 170 180<br>SASMDDDLNTIKELGSRLSKEMSKLTSNFRLGFGSFVEKPVSPFVKTTPEEIANPCSSIP<br>190 200 210 220 230 240<br>YFCLPTFGFKHILPLTNDAERFNEIVKNQKISANIDTPEGGFDAIMQAAVCKEKIGWRND<br>250 260 270 280 290 300<br>SLHLLVFVSDADSHFGMDSKLAGIVIPNDGLCHLDSKNEYSMSTVLEYPTIGQLIDKLVQ<br>310 320 330 340 350 360<br>NNVLLIFAVTQEQVHLYENYAKLIPGATVGLLQKDSGNILQLIISAYEELRSEVELEVLG<br>370 380 390 400 410 420<br>DTEGLNLSFTAICNNGTLFQHQKKCSHMKVGDTASFSVTVNIPHCERRSRHIIIKPVGLG | 72 |

TABLE 16-continued

| Antigen Names | Amino acid sequence | SEQ ID NO: |
|---|---|---|
| | 430 440 450 460 470 480<br>DALELLVSPECNCDCQKEVEVNSSKCHHGNGSFQCGVCACHPGHMGPRCECGEDMLSTDS<br>490 500 510 520 530 540<br>CKEAPDHPSCSGRGDCYCGQCICHLSPYGNIYGPYCQCDNFSCVRHKGLLCGGNGDCDCG<br>550 560 570 580 590 600<br>ECVCRSGWTGEYCNCTTSTDSCVSEDGVLCSGRGDCVCGKCVCTNPGASGPTCERCPTCG<br>610 620 630 640 650 660<br>DPCNSKRSCIECHLSAAGQAREECVDKCKLAGATISEEEDFSKDGSVSCSLQGENECLIT<br>670 680 690 700 710 720<br>FLITTDNEGKTIIHSINEKDCPKPPNIPHPGGGSGGGSGGSAQLKKKLQALKKKNAQLKW<br>730<br>KLQALKKKLAQGAT | |

FIG. 22A shows a panning process for screening cyclic peptides specific for integrin αvβ5 and integrin αvβ6, which are known to be overexpressed on tumor epithelial cells, using the phage library prepared in FIG. 20.

Specifically, the human recombinant integrin αvβ5 and αvβ6 expressed and purified in FIG. 21 were added to an immunotube in an integrin activation buffer (TBS, pH 7.4, 1 mM $MnCl_2$, 1 mM $MgCl_2$ and 2 mM $CaCl_2$)). After allowing the antigen to be adsorbed onto the surface of the immunotube, 3% skim milk solution containing divalent cations (1 mM $MnCl_2$, 1 mM $MgCl_2$, 2 mM $CaCl_2$)) was added to the immunotube to block the surface to which the antigen was not adsorbed. To wash the non-specifically bound phages, the imunotube was washed with TBS-T washing buffer containing divalent cations 3 times for 10 minutes each. The phages that specifically bound to the integrin were eluted with glycine buffer (pH 2.2). The eluted phages were neutralized with 1M Tris-HCl solution (pH 9.0), and then used to infect XL1-blue *E. coli* at 37° C. for 1 hour. The infected *E. coli* was suspended in SB (Super Broth) containing ampicillin, and cultured at 37° C. When the absorbance of the light at 600 nm of the culture reached 0.5, VCSM13 helper phage of $10^{12}$ PFU (plaque forming unit) was added and cultured at 37° C. for 1 hour. After infection with helper phage, kanamycin was added and the culture was incubated overnight. The next day, the supernatant containing the generated phage particles was completely separated from the *E. coli* by centrifugation, and 4% PEG and 3% NaCl were added to concentrate the phage, which was then dissolved in TBS and used for panning. The panning progressed from the first to the fifth round, each round reducing the amounts of antigens and increasing the number of washing cycles, while maintaining the clones with stronger binding affinity. For each successive round of panning, the amount of antigens adsorbed was 6, 4, 2, 1, and 1 μg human recombinant integrin, and the frequency of washing steps was 3, 3, 4, 5, and 10 times, respectively. During the panning process, the output of bacteriophage calculated for each round of panning was quantified by serial dilution, and the eluted phages were used to infect XL 1-blue *E. coli*, which were then spread on LB agar plate containing ampicillin. The degree of bacteriophage enrichment for integrin αvβ5 and integrin αvβ6 was determined by adding the same amount of bacteriophage to the immunotube adsorbed with the recombinant integrin, and to the immunotube without adsorbing antigens. It was confirmed that, as the panning was repeated, phages with stronger binding affinity to the integrins were enriched.

FIG. 22B shows the results of an ELISA analysis of the ability of individual clones to bind to integrin αvβ5 and integrin αvβ6, after the bacteriophage library was subjected to the 5th round of panning for recombinant human integrin αvβ5 and recombinant human integrin αvβ6.

Specifically, the bacteriophages obtained after the 5th round of panning were used to infect XL1-blue *E. coli*, which were then plated on LB agar plate containing ampicillin to obtain a single colony. The colony was then inoculated in 200 μL SB-ampicillin medium and incubated at 37° C. for 2 hours and induced to express the protein fused with the cyclic peptide-VL with IPTG in the periplasmic space. After incubation at 30° C. overnight, the periplasmic extract was obtained by osmotic shock to *E. coli* using periplasmic extraction solution (200 mM Tris-HCl, pH 8.0, 500 mM Sucrose). Divalent cations (1 mM $MnCl_2$, 1 mM $MgCl_2$, 2 mM $CaCl_2$)) were added to the extract of this periplasm, and ELISA was used to analyze the ability of individual clones to bind human recombinant integrin αvβ5 and αvβ6.

Specifically, 96-well EIA/RIA plates were used to adsorb integrin αvβ5 and integrin αvβ6 at a concentration of 2 g/mL and a buffer only, containing no antigen, in a off-target analysis for 1 hour at room temperature. 3% skim milk solution containing divalent cations (1 mM $MnCl_2$, 1 mM $MgCl_2$, 2 mM $CaCl_2$)) was added to the wells to block the surface on which the antigen was not adsorbed. The periplasmic extracts containing the divalent cations obtained from the individual clones were placed in each well, bound at room temperature for 1 hour, and washed with TBS-T containing divalent cations for 3 times for 10 minutes. Each phage particles were labeled with HRP-conjugated secondary antibody that specifically recognizes the human influenza hemagglutinin(HA) tag. TMB-ELISA solution was used to determine the absorbance at 450 nm. The absorbance of the off-target wells was used to normalize the binding signal, and the normalized signal of each clone was compared with that of the parental cyclic peptide in4.

Through the above ELISA analysis, it has been confirmed that 65 out of 94 of individual clones obtained from a library panned using recombinant human integrin αvβ5 showed higher binding affinity for integrin αvβ5 than parental cyclic peptide in4. And 52 out of 94 individual clones obtained from a library panned using recombinant human integrin αvβ6 showed higher binding affinity for integrin αvβ6 than the parental cyclic peptide in4.

Table 17 below shows the amino acid sequences of 12 individual clones capable of binding to integrin αvβ5 or integrin αvβ6 selected via the phage library panning and the cyclic peptide SFTIGv6 reported to have the ability to bind strongly to integrin αvβ6.

TABLE 17

| Names of cyclic peptides | Target receptor | Amino acid sequence | SEQ ID NO: |
|---|---|---|---|
| 5#1 | Integrin αvβ5 | 1 10<br>LPSGACVVRGDTFQCVSVG | 73 |
| 5#2 | | 1 10<br>ASYNDCQSRGDTFCVAD | 74 |
| 5#3 | | 1 10<br>SRDETCTPRGDTFAIC | 75 |
| 5#4 | | 1 10<br>EHATNCTTRGDTFVVLCGLG | 76 |
| SFITGv6 | Integrin αvβ6 | 1 10<br>GRCTFRGDLMQLCYPD | 77 |
| 6#1 | | 1 10<br>NENPDCPRRGDLFHICLKWP | 78 |
| 6#2 | | 1 10<br>HVEFPCTRRGDLFVLCEGS | 79 |
| 6#3 | | 1 10<br>TAIEPCKNRGDLFMLCSA | 80 |
| 6#4 | | 1 10<br>ESFRPCQYRGDLFVLCFPSD | 81 |
| 6#5 | | 1 10<br>TLIKACHRRGDTFVLCEHYS | 82 |
| 6#6 | | 1 10<br>LGPLPCQTRGDLFSLCHY | 83 |

TABLE 17-continued

| Names of cyclic peptides | Target receptor | Amino acid sequence | SEQ ID NO: |
|---|---|---|---|
| 6#7 | | 1 10<br>DRDRHCNKRGDLFSLCALRS | 84 |
| 6#8 | | 1 10<br>FPNNQCQHRGDLFALCAD | 85 |

6.37 Example 33. Expression and Purification of iMab Fused Cyclic Peptide with Improved Affinity for Integrin αvβ5 and Integrin αvβ6

In order to evaluate four cyclic peptides selected from the above phage library that were expected to have the ability to bind integrin αvβ5, and eight cyclic peptides expected to have the ability to bind integrin αvβ6, each cyclic peptide was genetically fused at the N-terminus of the light chain using an MGSSSN linker (SEQ ID NO: 102) to produce the full IgG form of the anti-Ras•GTP iMab for further experiments.

Specifically, in the same manner as described in Example 2 above, the selected integrin targeting cyclic peptide was genetically fused to the N-terminus of the cell penetrating human light chain hT4-59 light chain. An animal cell expression vector pcDNA3.4 vector was cloned using restriction enzymes NotI and BamHI.

Table 18 below shows the sequences of light chain variable region (VL) fused with affinity maturated integrin αvβ5 and integrin αvβ6-targeting cyclic peptides.

TABLE 18

| Names of light chain variable regions | Amino acid sequence | SEQ ID NO: |
|---|---|---|
| hT4-i59 (5#1) MG VL | 1 10 20 30 40 50<br>LPSGACVVRGDTFQCVSVGMGSSSNDIQMTQSPSSLSASVGDRVTITCKSSQSLL<br>60 70 80 90 100<br>NSRDGKNYLAWYQQKPGKAPKLLIYWASTRESGVPSRFSGSGSGTDFTLTISSL<br>110 120 130<br>QPEDFATYFCQQYWYWMYTFGQGTKVEIKR | 86 |
| hT4-i59 (5#2) MG VL | 1 10 20 30 40 50<br>ASYNDCQSRGDTFCVADMGSSSNDIQMTQSPSSLSASVGDRVTITCKSSQSLL<br>60 70 80 90 100<br>NSRDGKNYLAWYQQKPGKAPKLLIYWASTRESGVPSRFSGSGSGTDFTLTISSL<br>110 120 130<br>QPEDFATYFCQQYWYWMYTFGQGTKVEIKR | 87 |
| hT4-i59 (5#3) MG VL | 1 10 20 30 40 50<br>SRDETCTPRGDTFAICMGSSSNDIQMTQSPSSLSASVGDRVTITCKSSQSLL<br>60 70 80 90 100<br>NSRDGKNYLAWYQQKPGKAPKLLIYWASTRESGVPSRFSGSGSGTDFTLTISSL<br>110 120 130<br>QPEDFATYFCQQYWYWMYTFGQGTKVEIKR | 88 |
| hT4-i59 (5#4) MG VL | 1 10 20 30 40 50<br>EHATNCTTRGDTFVVLCGLGMGSSSNDIQMTQSPSSLSASVGDRVTITCKSSQSLL<br>60 70 80 90 100 110<br>NSRDGKNYLAWYQQKPGKAPKLLIYWASTRESGVPSRFSGSGSGTDFTLTISSL<br>120 130 140<br>QPEDFATYFCQQYWYWMYTFGQGTKVEIKR | 89 |

TABLE 18-continued

| Names of light chain variable regions | Amino acid sequence | SEQ ID NO: |
|---|---|---|
| hT4-i59 (SFITGv6) MG VL | 1 10 20 30 40 50<br>GRCTFRGDLMQLCYPDMGSSSNDIQMTQSPSSLSASVGDRVTITCKSSQSLLNSR<br>60 70 80 90 100 110<br>DGKNYLAWYQQKPGKAPKLLIYWASTRESGVPSRFSGSGSGTDFTLTISSLQPED<br>120 130<br>FATYFCQQYWYWMYTFGQGTKVEIKR | 90 |
| hT4-i59 (6#1) MG VL | 1 10 20 30 40 50<br>NENPDCPRRGDLFHICLKWPMGSSSNDIQMTQSPSSLSASVGDRVTITCKSSQSL<br>60 70 80 90 100 110<br>LNSRDGKNYLAWYQQKPGKAPKLLIYWASTRESGVPSRFSGSGSGTDFTLTISSL<br>120 130<br>QPEDFATYFCQQYWYWMYTFGQGTKVEIKR | 91 |
| hT4-i59 (6#2) MG VL | 1 10 20 30 40 50<br>HVEFPCTRRGDLFVLCEGSMGSSSNDIQMTQSPSSLSASVGDRVTITCKSSQSLL<br>60 70 80 90 100 110<br>NSRDGKNYLAWYQQKPGKAPKLLIYWASTRESGVPSRFSGSGSGTDFTLTISSLQP<br>120 130<br>EDFATYFCQQYWYWMYTFGQGTKVEIKR | 92 |
| hT4-i59 (6#3) MG VL | 1 10 20 30 40 50<br>TAIEPCKNRGDLFMLCSAMGSSSNDIQMTQSPSSLSASVGDRVTITCKSSQSLLN<br>60 70 80 90 100 110<br>SRDGKNYLAWYQQKPGKAPKLLIYWASTRESGVPSRFSGSGSGTDFTLTISSLQP<br>120 130<br>EDFATYFCQQYWYWMYTFGQGTKVEIKR | 93 |
| hT4-i59 (6#4) MG VL | 1 10 20 30 40 50<br>ESFRPCQYRGDLFVLCFPSDMGSSSNDIQMTQSPSSLSASVGDRVTITCKSSQSL<br>60 70 80 90 100 110<br>LNSRDGKNYLAWYQQKPGKAPKLLIYWASTRESGVPSRFSGSGSGTDFTLTISSL<br>120 130 140<br>QPEDFATYFCQQYWYWMYTFGQGTKVEIKR | 94 |
| hT4-i59 (6#5) MG VL | 1 10 20 30 40 50<br>TLIKACHRRGDTFVLCEHYSMGSSSNDIQMTQSPSSLSASVGDRVTITCKSSQSL<br>60 70 80 90 100 110<br>LNSRDGKNYLAWYQQKPGKAPKLLIYWASTRESGVPSRFSGSGSGTDFTLTISSL<br>120 130 140<br>QPEDFATYFCQQYWYWMYTFGQGTKVEIKR | 95 |
| hT4-i59 (6#6) MG VL | 1 10 20 30 40 50<br>LGPLPCQTRGDLFSLCHYMGSSSNDIQMTQSPSSLSASVGDRVTITCKSSQSLLN<br>60 70 80 90 100 110<br>SRDGKNYLAWYQQKPGKAPKLLIYWASTRESGVPSRFSGSGSGTDFTLTISSLQP<br>120 130<br>EDFATYFCQQYWYWMYTFGQGTKVEIKR | 96 |
| hT4-i59 (6#7) MG VL | 1 10 20 30 40 50<br>DRDRHCNKRGDLFSLCALRSMGSSSNDIQMTQSPSSLSASVGDRVTITCKSSQSL<br>60 70 80 90 100 110<br>LNSRDGKNYLAWYQQKPGKAPKLLIYWASTRESGVPSRFSGSGSGTDFTLTISSL<br>120 130 140<br>QPEDFATYFCQQYWYWMYTFGQGTKVEIKR | 97 |
| hT4-i59 (6#8) MG VL | 1 10 20 30 40 50<br>FPNNQCQHRGDLFALCADMGSSSNDIQMTQSPSSLSASVGDRVTITCKSSQSLLN<br>60 70 80 90 100 110<br>SRDGKNYLAWYQQKPGKAPKLLIYWASTRESGVPSRFSGSGSGTDFTLTISSLQP<br>120 130<br>EDFATYFCQQYWYWMYTFGQGTKVEIKR | 98 |

The RT22 heavy chain expression vector is described in Korean Patent Application No. 10-2017-0152998, "Antibody which internalize into the cytosol of cells and binds to inhibit activated Ras and use thereof"). The Integrin αvβ5 and integrin αvβ6 targeting cyclic peptide-fused anti-Ras•GTP iMab expression constructs were transiently co-transfection into HEK293F protein-expressing cells. Individual clones were expressed as full IgG and purified as described in Example 2 above.

FIG. 23 shows the quality of the anti-Ras•GTP iMab antibody fused with cyclic peptide candidates with affinity maturated for integrin αvβ5 and integrin αvβ6 using high performance liquid chromatography (HPLC). The graph shows mAU values at 280 nm analyzed using a Superdex column that can determine whether a protein is monomer in a liquid phase.

Specifically, each of anti-Ras•GTP iMab antibody fused with cyclic peptides affinity maturated for integrin αvβ5 or integrin αvβ6 was prepared in 25 μL at a concentration of 1 mg/mL, and then placed in the insert before the sample was added. In the case of a Superdex size exclusion chromatography column, PBS (pH 7.4) buffer was flowed at a flow rate of 0.75 mL/min. After pressure and mAU values had stabilized, the analysis was started. The preparation sample was then loaded with 10 μL at the same flow rate and the mAU value at 280 nm for 35 minutes was measured using high performance liquid chromatography.

Most of the clones were similar to the Ras03 antibody used as the control, which is not fused with the cyclic peptide, in that they were present as a monomer in a liquid phase. However, among the cyclic peptides targeting the integrin αvβ6, Ras03 fused with the 6#2 and 6#5 cyclic peptides exhibited abnormal peaks, and no peaks were observed with antibodies fused with the 6#7 cyclic peptide. This is because the proportion of positively charged amino acids in the amino acid sequence of the three cyclic peptides is large, and it is likely that the peak is not correctly observed due to nonspecific binding to the resin in the column.

6.38 Example 34. Identification of Non-Specific Binding of Affinity Maturated Cyclic Peptides Fused Anti-Ras•GTP iMab In order to analyze non-specific binding ability of the anti-Ras•GTP iMab fused with the cyclic peptide candidates targeting integrin αvβ5 and integrin αvβ6, which were affinity maturated as described in the above Example 33, (Jain, Sun et al. 2017), ELISA was carried out using 3 kinds of antigens, dsDNA, keyhole limpet hemocyanin (KLH), and cardiolipin, which can confirm nonspecific binding of the antibody.

FIG. 24 shows that anti-Ras•GTP iMabs fused with cyclic peptides binding to these three antigens were identified by ELISA as non-specific.

Specifically, 1 μg/mL of dsDNA (Sigma, D4522), 5 μg/mL of Keyhole limpet hemocyanin (Sigma, H8283), and 10 μg/mL of cardiolipin (Sigma, C0563), were added to 96-well EIA/RIA plate, diluted with PBS, and adsorbed to the plate surface at room temperature for 1 hour. Then, 3% skim milk in PBS was added to the wells to block the non-adsorbed side of the antigen. Subsequently, the plates were washed three times for 10 minutes with PBS-T solution containing 0.05% Tween 20 with PBS, and each antibody was diluted with the blocking solution to a concentration of 500 nM and incubated at room temperature for 1 hour. TMab4 was used as a positive control. TMab4 is an antibody having a large amount of amino acids with a cation in CDR-L1, and is known to bind nonspecifically with HSPG. As a negative control, Ras03, an anti-Ras•GTP iMab without cyclic peptide, and adalimumab were used. After washing with PBS-T for 3 times for 10 minutes, HRP-conjugated anti-human mAb (HRP conjugated anti-human mAb) was added to the plate for 1 hour at room temperature, and the plates were then reacted with TMB ELISA solution and absorbance at 450 nm was quantified.

It was determined from the above experiment that there is non-specific binding when the absorbance at 450 nm is more than 0.05 for at least one of the three antigens. Thus, it was confirmed that cyclic peptide candidates 6#2, 6#3, 6#5, 6#7, and 6#8 have non-specific binding ability.

6.39 Example 35. Binding Ability Analysis of Anti-Ras•GTP iMab Fused with Affinity Maturated Cyclic Peptides Targeting Human Integrin αvβ5 or Human Integrin αvβ6

The binding ability of anti-Ras•GTP iMab fused with affinity maturated cyclic peptides targeting human integrin αvβ5 or human integrin αvβ6, expressed and purified as described in Example 33 above, was determined using Flow cytometry (FACS) against cells expressing integrin αvβ5 or integrin αvβ6 on the surface. To quantify the affinity, the kinetics were measured by Octet instrument (ForteBio) based on the principle of BLI (Bio-Layer Interferometry).

FIG. 25 shows the results of FACS data to determine the degree of integrin binding ability of anti-Ras•GTP iMab fused with integrin αvβ5-targeting cyclic peptide candidates, measured against four cell lines expressing integrin αvβ5 (A549, MCF7, Calu-6, SW480) and two cell lines not expressing integrin (Raji, Ramos).

Specifically, $1\times10^5$ cells were prepared for each sample. The cells were incubated with inRas03 and in4-Ras03 (anti-Ras•GTP iMab fused with parental cyclic peptides, RGD10 and in4, respectively), and anti-Ras•GTP iMabs fused with the four cyclic peptides selected through the phage library (5#1, 5#2, 5#3, 5#4) at a concentration of 20 nM for 1 hour at 4° C. Each sample was then incubated with an antibody conjugated with Alexa488 (green fluorescence) label specifically recognizing human Fc at 4° C. for 30 minutes. After washing with TBSF solution containing divalent cations (1 mM $MnCl_2$, 1 mM $MgCl_2$, 2 mM $CaCl_2$), the fluorescence value of each cell was analyzed using a flow cytometer.

It was confirmed from the above experiment that anti-Ras•GTP iMab fused with 5#1 cyclic peptide showed stronger binding ability to cells expressing integrin αvβ5 than anti-Ras•GTP iMab fused with parental in4 cyclic peptide. The anti-Ras•GTP iMab fused with the 5#1 cyclic peptide showed the same degree of binding in the four cell lines expressing integrin αvβ5, and in those four cell lines, anti-Ras•GTP iMab fused with the 5#1 cyclic peptide showed stronger binding than anti-Ras•GTP iMab fused with parental cyclic peptide in4. The non-specific binding was determined by using Raji and Ramos cell line that does not express integrin. None of the four clones bound to Raji or Ramos cell, indicating that none of the four clones has non-specific binding ability.

FIG. 26A is a histogram showing the results of FACS analysis to determine the degree of binding ability of anti-Ras•GTP iMabs fused with integrin αvβ6-targeting cyclic peptide candidates with improved affinity. Cell lines BxPC-3 (expressing integrin αvβ6) and Raji (not expressing integrin) were used for the experiment.

Specifically, each sample was prepared in the same manner as shown in FIG. 25, and was incubated with inRas03 and in4-Ras03 (anti-Ras•GTP iMab fused with parental cyclic peptides), and anti-Ras•GTP iMabs fused with 8 peptides selected through the phage library (6#1, 6#2, 6#3, 6#4, 6#5, 6#6, 6#7, 6#8) at 20 nM for hour at 4° C. Thereafter, an antibody conjugated with Alexa488 (green fluorescence) label specifically recognizing human Fc was added at 4° C. for 30 minutes. After washing with TBSF solution containing divalent cations (1 mM $MnCl_2$, 1 mM $MgCl_2$, 2 mM $CaCl_2$), the fluorescence value of each cell was analyzed using a flow cytometer.

It was confirmed from the above experiment that the anti-Ras•GTP iMab fused with the cyclic peptides screened through the phage library (6#1, 6#2, 6#3, 6#4, 6#5, 6#6, 6#7, 6#8) exhibited higher binding ability to the integrin αvβ6 expressed on the cell surface than the anti-Ras•GTP iMab fused with the parental peptide (RGD10, in4). However, in the Raji cell line not expressing integrin, it was confirmed that the anti-Ras•GTP iMab fused with 6#5 and 6#7 cyclic peptides showed non-specific binding. Among the remaining cyclic peptides, anti-Ras•GTP iMab fused with 6#1 cyclic peptide exhibited the lowest binding ability to the BxPC-3 cell line expressing integrin αvβ6. Thus, only the anti-Ras•GTP iMabs fused with cyclic peptides 6#2, 6#3, 6#4, 6#6, 6#8 were used for further study.

FIG. 26B is a histogram showing the results of FACS to determine the binding ability of anti-Ras•GTP iMabs fused with cyclic peptide candidates targeting integrin αvβ6 selected as described in FIG. 27A above. The binding ability of the anti-Ras•GTP iMabs fused with cyclic peptides to the cell surface integrin was determined by flow cytometry (FACS) against LS1034 cell line expressing integrin αvβ6, K562 cell line stably expressing integrin αvβ6, and the Ramos cell line not expressing integrin.

Specifically, each sample was prepared in the same manner as described in FIG. 26A. inRas03 and in4-Ras03 (parental cyclic peptide fused anti-Ras•GTP iMab), and anti-Ras•GTP iMabs fused with 5 peptides selected in FIG. 26A (6#2, 6#3, 6#4, 6#6, 6#8) were incubated at 20 nM for 1 hour at 4° C. Thereafter, an antibody conjugated with Alexa488 (green fluorescence) specifically recognizing human Fc was added at 4° C. for 30 minutes. After washing with TBSF solution containing divalent cations (1 mM $MnCl_2$, 1 mM $MgCl_2$, 2 mM $CaCl_2$), the fluorescence value of each cell was analyzed using a flow cytometer.

As a result of the above experiment, it was confirmed that the anti-Ras•GTP iMabs fused with the five cyclic peptides targeting integrin αvβ6 exhibited almost the same binding affinity to the cell line expressing the integrin αvβ6. All the 5 cyclic peptides showed significantly higher binding ability than the parental cyclic peptide in4 fused anti-Ras•GTP iMab. And for Ramos cell lines that do not express integrin, none of the clones showed binding ability, indicating that none of the clones had non-specific binding ability.

FIG. 27 is a graph showing the results of kinetic analysis of the binding ability of human recombinant integrin αvβ5 and anti-Ras•GTP iMab fused with the integrin αvβ5 targeting cyclic peptides having improved affinity, using an Octet (ForteBio) instrument based on the principle of BLI (Bio-layer interferometry).

Specifically, anti-Ras•GTP iMab fused with an integrin αvβ5 target cyclic peptide having improved affinity was diluted with TBS containing a divalent cations (1 mM $MnCl_2$, 1 mM $MgCl_2$, 2 mM $CaCl_2$) and 0.02% Tween 20, at a concentration of 2 μg/mL to immobilize on the anti-human IgG Fc (AHC) biosensor. Subsequently, the recombinant human integrin αvβ5 protein was analyzed for association and dissociation at concentrations of 100 nM, 50 nM, 25 nM, 12.5 nM, 6.2 nM and 3.1 nM for 300 seconds and 900 seconds, respectively. After the analysis, immersion for 5 seconds in pH 2.2 glycine solution and pH 7.4 TBS solution for regeneration of AHC biosensor was repeated three times. The affinities were calculated by normalizing the results by excluding the results of blank spaces that did not contain integrin.

When the affinity was measured by the above-described method, anti-Ras•GTP iMab antibody fused with 5#1 cyclic peptide showed binding affinity similar to that against cell surface integrin αvβ5. The anti-Ras•GTP iMab fused with 5#1 cyclic peptide showed about 2-fold higher affinity than anti-Ras•GTP iMab fused with parental in4 cyclic peptide against recombinant human integrin αvβ5.

Table 19 shows the results of kinetic assay using Octet (ForteBio) between human recombinant integrin αvβ5 and anti-Ras•GTP iMabs fused with cyclic peptides targeting integrin αvβ5.

TABLE 19

| | $K_{on}$ (1/Ms) | $K_{off}$ (1/s) | $K_D$ (M) | $R^2$ |
|---|---|---|---|---|
| inRas03 | (7.88 ± 0.064) × $10^4$ | (3.56 ± 0.023) × $10^{-4}$ | (4.52 ± 0.047) × $10^{-9}$ | 0.9993 |
| in4-Ras03 | (8.06 ± 0.064) × $10^4$ | (1.66 ± 0.020) × $10^{-4}$ | (2.06 ± 0.030) × $10^{-9}$ | 0.9993 |
| 5#1-Ras03 | (5.67 ± 0.046) × $10^4$ | (6.39 ± 0. 162) × $10^{-5}$ | (1.13 ± 0.030) × $10^{-9}$ | 0.9996 |
| 5#2-Ras03 | (4.55 ± 0.055) × $10^4$ | (1.20 ± 0.022) × $10^{-4}$ | (2.63 ± 0.058) × $10^{-9}$ | 0.9994 |
| 5#3-Ras03 | (3.33 ± 0.069) × $10^4$ | (1.63 ± 0.030) × $10^{-4}$ | (4.88 ± 0.14) × $10^{-9}$ | 0.9989 |
| 5#4-Ras03 | (2.25 ± 0.083) × $10^4$ | (1.58 ± 0.037) × $10^{-4}$ | (7.01 ± 0.31) × $10^{-9}$ | 0.9983 |

FIG. 28 is a graph showing the results of kinetic analysis of the binding ability of recombinant human integrin αvβ6 and anti-Ras•GTP iMab fused with the integrin αvβ6 targeting cyclic peptides having improved affinity using an Octet (ForteBio) instrument based on the principle of BLI (Bio-layer interferometry).

Specifically, anti-Ras•GTP iMab fused with an integrin αvβ6 target cyclic peptide having improved affinity was diluted with TBS containing a divalent cations (1 mM $MnCl_2$, 1 mM $MgCl_2$, 2 mM $CaCl_2$) and 0.02% Tween 20 at a concentration of 2 g/mL to immobilize on the anti-human IgG Fc (AHC) biosensor. Subsequently, the recombinant human integrin αvβ6 protein was analyzed for association and dissociation at concentrations of 100 nM, 50 nM, 25 nM, 12.5 nM, 6.2 nM and 3.1 nM for 150 seconds and 450 seconds, respectively. After the analysis, immersing for 5 seconds in pH 2.2 glycine solution and pH 7.4 TBS solution for 5 seconds for regeneration of AHC biosensor was repeated 3 times. The affinities were calculated by normalizing the results by excluding the results of blank spaces that did not contain integrin.

When the affinity was measured by the above-described experimental method, it was confirmed that the anti-Ras•GTP iMab fused with the 6#6 cyclic peptide exhibited the highest binding affinity to the human recombinant integrin αvβ6, except for the cyclic peptides showing non-specific binding in Example 34. Compared with the anti-Ras•GTP iMab fused with parental cyclic peptide in4, the anti-Ras•GTP iMab fused with the 6#6 cyclic peptide exhibited about 12-fold higher binding affinity.

Table 20 shows the results of kinetic assay using Octet (ForteBio) between human recombinant integrin αvβ6 and anti-Ras•GTP iMabs fused with cyclic peptides targeting integrin αvβ6.

TABLE 20

| | $K_{on}$ (1/Ms) | $K_{off}$ (1/s) | $K_D$ (M) | $R^2$ |
|---|---|---|---|---|
| inRas03 | (6.05 ± 0.34) × $10^5$ | (5.83 ± 0.95) × $10^{-3}$ | (9.63 ± 0.56) × $10^{-9}$ | 0.9699 |
| in4-Ras03 | (5.83 ± 0.33) × $10^5$ | (7.03 ± 0.12) × $10^{-3}$ | (1.21 ± 0.07) × $10^{-8}$ | 0.9732 |
| 6#2-Ras03 | (2.12 ± 0.046) × $10^5$ | (1.53 ± 0.078) × $10^{-4}$ | (7.22 ± 0.38) × $10^{-10}$ | 0.9988 |
| 6#3-Ras03 | (2.08 ± 0.25) × $10^5$ | (1.29 ± 0.068) × $10^{-4}$ | (6.21 ± 0.33) × $10^{-10}$ | 0.9992 |
| 6#4-Ras03 | (1.75 ± 0.037) × $10^5$ | (2.65 ± 0.12) × $10^{-4}$ | (1.52 ± 0.074) × $10^{-9}$ | 0.9976 |
| 6#6-Ras03 | (2.16 ± 0.024) × $10^5$ | (1.82 ± 0.065) × $10^{-4}$ | (8.43 ± 0.31) × $10^{-10}$ | 0.9992 |
| 6#8-Ras03 | (1.84 ± 0.021) × $10^5$ | (1.75 ± 0.061) × $10^{-4}$ | (9.52 ± 0.35) × $10^{-10}$ | 0.9993 |

6.40 Example 36. Comparative Analysis of Cyclic Peptide 6#6 with Improved Affinity for Integrin αvβ6 and Cyclic Peptide SFITGv6 Known to Bind Integrin αvβ6 in Previous Studies The 6#6 cyclic peptide was the peptide with the highest binding affinity to human integrin αvβ6, without any non-specific binding through the above studies. Experiments were conducted to compare the 6#6 cyclic peptide with the cyclic peptide SFITGv6, which were studied to bind integrin αvβ6 with high affinity. The affinity analysis was carried out using non-specific ELISA and Octet (ForteBio), in the same manner as described in Example 34 for the non-specific ELISA and in Example 35 for the comparative analysis of binding ability.

FIG. 29A shows the result of an ELISA using three antigens, dsDNA, keyhole limpet hemocyanin (KLH), cardiolipin, which indicate non-specific binding of an antibody, to confirm whether anti-Ras-GTP iMabs fused with cyclic peptide, SFITGv6 and 6#6, show non-specific binding ability to these three antigens.

Specifically, the experiment was performed in the same manner as described in Example 34 above. 1 μg/mL of dsDNA (Sigma, D4522), 5 μg/mL of Keyhole limpet hemocyanin (Sigma, H8283), and 10 g/mL of cardiolipin (Sigma, C0563), were added to 96-well EIA/RIA plate diluted with PBS and adsorbed on the plate surface at room temperature for 1 hour. Then, 3% skim milk dissolved in PBS was added to the wells to block the non-adsorbed side of the antigen. Subsequently, the cells were washed three times for 10 minutes with PBS-T solution containing 0.05% Tween 20 with PBS, and each antibody was diluted with the blocking solution to a concentration of 500 nM and incubated at room temperature for 1 hour. TMab4 was used as a positive control. As a negative control, Ras03, an anti-Ras-GTP iMab without cyclic peptide was used. After washing with PBS-T three times for 10 minutes, HRP-conjugated anti-human mAb (HRP conjugated anti-human mAb) was added to the plate for 1 hour at room temperature, and the plates were then reacted with TMB ELISA solution and absorbance at 450 nm was quantified.

In the above experiment, anti-Ras•GTP iMab fused with affinity maturated cyclic peptide 6#6 targeting integrin αvβ6 showed no non-specific binding to any of the three antigens, while anti-Ras•GTP iMab fused with the SFITGv6 cyclic peptide, which has been reported to have strong binding ability to integrin αvβ6, showed non-specific binding to all three antigens.

FIG. 29B is a graph showing the results of kinetic analysis of the binding ability of recombinant human integrin αvβ6 and anti-Ras•GTP iMab fused with the integrin αvβ6 targeting cyclic peptides (6#6, SFITGv6) using an Octet (ForteBio) instrument based on the principle of BLI (Bio-layer interferometry).

Specifically, the experiment was performed in the same manner as described in Example 35 above. Anti-Ras•GTP iMab fused with an integrin αvβ6 target cyclic peptide 6#6 and SFITGv6 was diluted with TBS containing divalent cations (1 mM $MnCl_2$, 1 mM $MgCl_2$, 2 mM $CaCl_2$), 0.02% Tween 20 at a concentration of 2 μg/mL to immobilize on the anti-human IgG Fc (AHC) biosensor. Subsequently, the recombinant human integrin αvβ6 protein was analyzed for association and dissociation at concentrations of 100 nM, 50 nM, 25 nM, 12.5 nM, 6.2 nM and 3.1 nM for 150 seconds and 450 seconds, respectively. After the analysis, immersion for 5 seconds in pH 2.2 glycine solution and pH 7.4 TBS solution for 5 seconds for regeneration of AHC biosensor was repeated three times. The affinities were calculated by normalizing the results by excluding the results of blank spaces that did not contain integrin.

Through the above experiment, anti-Ras•GTP iMab fused with the cyclic peptide 6#6, affinity maturated to bind integrin αvβ6, and anti-Ras•GTP iMab fused with the cyclic peptide SFITGv6, previously reported to have strong binding ability to integrin αvβ6, were confirmed to bind human integrin αvβ6 with similar affinity.

Table 21 shows the results of kinetic assay using Octet (ForteBio) between human recombinant integrin αvβ6 and anti-Ras•GTP iMabs fused with 6#6 or SFITGv6 cyclic peptide targeting integrin αvβ6.

TABLE 21

| | $K_{on}$ (1/Ms) | $K_{off}$ (1/s) | $K_D$ (M) | $R^2$ |
|---|---|---|---|---|
| 6#6-Ras03 | (2.16 ± 0.024) × $10^5$ | (1.82 ± 0.065) × $10^{-4}$ | (8.43 ± 0.31) × $10^{-10}$ | 0.9992 |
| SFITGv6-Ras03 | (2.79 ± 0.041) × $10^5$ | (1.28 ± 0.009) × $10^{-4}$ | (4.57 ± 0.33) × $10^{-10}$ | 0.9983 |

Hereinabove, although the present invention is described by specific matters such as concrete components, and the like, embodiments, and drawings, they are provided only for assisting in the entire understanding of the present invention. Therefore, the present invention is not limited to the embodiments. Various modifications and changes may be made by those skilled in the art to which the present invention pertains from this description. Therefore, the spirit of the present invention should not be limited to the above-described embodiments, and the following claims as well as all modified equally or equivalently to the claims are intended to fall within the scope and spirit of the invention.

The entirety of each patent, patent application, publication and document referenced herein is hereby incorporated by reference for all purposes.

REFERENCES

Al-Lazikani, B., Lesk, A. M., & Chothia, C. (1997). Standard conformations for the canonical structures of immunoglobulins. *J Mol Biol,* 273(4), 927-48.

Baek, C. H., Liss, M., Clancy, K., Chesnut, J., & Katzen, F. (2014). DNA Assembly Tools and Strategies for the Generation of Plasmids. *Microbiol Spectr,* 2(5), 1-12.

Barbas, C. F., Burton, D. R., Scott, J. K., & Silverman, G. J. (2007). Quantitation of DNA and RNA. *Cold Spring Harb. Protoc.*

Choi, D. K., Bae, S. M., Shin, J. Y., Shin, S. K., & Kim, Y. S. (2014). A general strategy for generating intact, full-length IgG antibodies that penetrate into the cytosol of living cells. *mAbs,* 6(6), 1402-1414.

Di Paolo, C., Willuda, J., Kubetzko, S., Lauffer, I., Tschudi, D., Waibel, R., . . . Zangemeister-Wittke, U. (2003). A recombinant immunotoxin derived from a humanized epithelial cell adhesion molecule-specific single-chain antibody fragment has potent and selective antitumor activity. *Clin Cancer Res,* 9, 2837-2848.

Dohi, T., Rennert, P. D., Fujihashi, K., Kiyono, H., Shirai, Y., & Kawamura, Y. I. (2001). Elimination of colonic patches with lymphotoxin receptor-Ig prevents Th2 cell-type colitis. *The Journal of Immunology,* 167(5), 2781-2790.

Dudgeon, R., Rouet, I., Kokmeijer, P., Schofield, J., Stolp, D., Langley, D., . . . Christ, D. (2012). General strategy for the generation of human antibody variable domains with increased aggregation resistance. *Proc Natl Acad Sci USA,* 109, 10879-10884.

Edman, P. (1959). Chemistry of amino acids and peptides. *Annu Rev Biochem,* 28, 69-96.

Ewert, S., Honegger, A., & Pluckthun, A. (2004). Stability improvement of antibodies for extracellular and intracellular applications: CDR grafting to stable frameworks and structure-based framework engineering. *Methods,* 184-199.

Fernandes, M. T., Dejardin, E., & dos Santos, N. R. (2016). Context-dependent roles for lymphotoxin-β receptor signaling in cancer development. *Biochimica et Biophysica Acta,* 1865, 204-219.

Gouttefangeas, C., Walter, S., Welters, M. J., Ottensmeier, C., van der Burg, S. H., & Britten, C. M. (2014). Flow Cytometry in Cancer Immunotherapy: Applications, Quality Assurance, and Future. *Cancer Immunology,* 471-490.

Guidotti, G., Brambilla, L., & Rossi, D. (2017). Cell-Penetrating Peptides: From Basic Research to Clinics. *Trends in Pharmacological Sciences,* 38, 406-424.

Guillard, S., Minter, R. R., & Jackson, R. H. (2015). Engineering therapeutic proteins for cell entry: the natural approach. *Trends in biotechnology,* 33, 163-171.

Holig, P., Bach, M., Volkel, T., Nahde, T., Hoffmann, S., Muller, R., & Kontermann, R. E. (2004). Novel RGD lipopeptides for the targeting of liposomes to integrin-expressing endothelial and melanoma cells. *Prot Eng Des Sel,* 433-441.

Hollingshead, M. G. (2008). Antitumor Efficacy Testing in Rodents. *JNCI: Journal of the National Cancer Institute,* 100(21), 1500-1510.

Horton, D. A., Bourne, G. T., & Smythe, M. L. (2002). Exploring privileged structures: the combinatorial synthesis of cyclic peptides. *J Comput Aided Mol Des.,* 16, 5-6.

Imai, K., & Takaoka, A. (2006). Comparing antibody and small-molecule therapies for cancer. *Nat Rev Cancer,* 6(9), 714-727.

Kabat, E. A., Wu, T. T., Foeller, C., Perry, H. M., & Gottesman, K. S. (1991). *Sequences of Proteins of Immunological Interest* (5 ed.). Bethesda, Md.: National Institutes of Health.

Kai, I., & Takaoka, A. (2006). Comparing antibody and small-molecule therapies for cancer. *Nat Rev Cancer.,* 6(9), 714-27.

Kim, J. S., Choi, D. K., Park, W. W., Shin, S. M., Bae, J., Kim, D. M., . . . Kim, Y. S. (2015). Quantitative assessment of cellular uptake and cytosolic access of antibody in living cells by an enhanced split GFP complementation assay. *Biochemical and Biophysical Research Commun,* 771-777.

Kim, J. S., Choi, D. K., Shin, J. Y., Shin, S. M., Park, S. W., Cho, H. S., & Kim, Y. S. (2016). Endosomal acidic pH-induced conformational changes of a cytosol-penetrating antibody mediate endosomal escape. *J Control Release,* 235, 165-175.

Kim, Y. S., & Bae, D. S. (2015). Humanization of a phosphothreonine peptide-specific chicken antibody by combinatorial library optimization of the phosphoepitope-binding motif. *Biochemical and biophysical research communications,* 414-420.

Lee, C. H., Park, K. J., Kim, S. J., Kwon, O., Jeong, K. J., Kim, A., & Kim, Y. S. (2011). Generation of bivalent and bispecific kringle single domains by loop grafting as potent agonists against death receptors 4 and 5. *Journal of Molecular biology,* 210-219.

Leem, J., Dunbar, J., Georges, G., Shi, J., & Deane, C. M. (2016). ABodyBuilder: Automated antibody structure prediction with data-driven accuracy estimation. *mAbs,* 1259-1268.

Leshchiner, E. S., Parkhitko, A., Bird, G. H., Luccarelli, J., Bellairs, J. A., Escudero, S., . . . Walensky, L. D. (2015). Direct inhibition of oncogenic KRAS by hydrocarbon-stapled SOS1 helices. *Proc Natl Acad Sci USA.,* 112(6), 1761-6.

Mauri, D. N., Ebner, R., Montgomery, R. I., Kochel, K. D., Cheung, T. C., & Yu, G. L. (1998). LIGHT, a new member of the TNF superfamily, and lymphotoxin alpha are ligands. *Immunity,* 8, 21-30.

Munz, M., Baeuerle, P. A., & Gires, O. (2009). The emerging role of EpCAM in cancer and stem cell signaling. *Cancer Res,* 69, 5627-5629.

Patgiri, A., Yadav, K. K., & Bar-Sagi, D. (2011). An orthosteric inhibitor of the Ras-Sos interaction. *Nat Chem Biol,* 7(9), 585-7.

Perrimon, N., & Bernfield, M. (2000). Specificities of heparan sulphate proteoglycans in developmental processes. *Nature,* 72508.

Pimenta, E. M. (n.d.). Pimenta, E. M., & Barnes, B. J. (2014). Role of tertiary lymphoid structures (TLS) in antitumor immunity: Potential tumor-induced cytokines/chemokines that regulate TLS formation in epithelial-derived cancers. 6(2), 969-997.

Pimenta, E. M., & Barnes, B. J. (2014). Role of tertiary lymphoid structures (TLS) in antitumor immunity: Potential tumor-induced cytokines/chemokines that regulate TLS formation in epithelial-derived cancers. *Cancer,* 6(2), 969-997.

Rezai, T., Yu, B., Millhauser, G. L., Jacobson, M. P., & Lokey, R. S. (2006). Testing the conformational hypothesis of passive membrane permeability using synthetic cyclic peptide diastereomers. *J Am Chem Soc,* 128, 2510-2511.

Shin, S. M., Choi, D. K., Jung, K., J, B., Kim, J. S., Park, S. W., . . . Kim, Y. S. (2017). Antibody targeting intracellular oncogenic Ras mutants exerts anti-tumour effects after systemic administration. *Nature Communications,* 8, 15090.

Simon, M., Stefan, N., Pluckthun, A., & Zangemeister-Wittke, U. (2013). Epithelial cell adhesion molecule-targeted drug delivery for cancer therapy, Expert opinion on drug delivery. *Expert opinion on drug delivery,* 10, 451-468.

Singh, R., Setiady, Y. Y., Ponte, J., Kovtun, Y. V., Lai, K. C., Hong, E. E., . . . Widdison, W. C. (2016). A New Triglycyl Peptide Linker for Antibody-Drug Conjugates (ADCs) with Improved Targeted Killing of Cancer Cells. *Molecular Cancer Therapeutics,* 15, 1311-1320.

Sudhamsu, J., Yin, J., Chiang, E. Y., Starovasnik, M. A., Grogan, J. L., & Hymowitz, S. G. (2013). Dimerization of LTβR by LTα1β2 is necessary and sufficient for signal transduction. *Proc Natl Acad Sci USA,* 110(49), 19896-901.

Teicher, B. A. (2009). In vivo/ex vivo and in situ assays used in cancer research: a brief review. *Toxicol Pathol,* 37(1), 114-22.

Wang, J., Lo, J. C., Foster, A., Yu, P., Chen, H. M., Wang, Y., . . . Fu, Y. X. (2001). The regulation of T cell homeostasis and autoimmunity by T cell-derived LIGHT. *J Clin Invest,* 108, 1771-1780.

Weinstein A M, S. W. (2015). Lymphotoxin Therapeutic Lymphoid Organogenesis in the Tumor Microenvironment. *Adv Cancer Res.,* 128, 197-233.

Went, P., Vadei, M., Bubendorf, L., Terracciano, L., Tornillo, L., Riede, U., . . . Baeuerle, P. A. (2006). Frequent high-level expression of the immunotherapeutic target Ep-CAM in colon, stomach, prostate and lung cancers. *Br J Cancer,* 94(1), 128-135.

Xiong, J. P., Stehle, T., Zhang, R., Joachimiak, A., Frech, M., Goodman, S. L., & Arnaout, M. A. (2002). Crystal structure of the extracellular segment of integrin alpha Vbeta3 in complex with an Arg-Gly-Asp ligand. *Science,* 296, 151-5.

---

What is claimed:

1. A cyclic peptide comprising:

(SEQ ID NO: 110)
X1-X2-Leu3-X4-Cys5-X6-Gly-X8-X9-Cys10-Trp-X12 wherein X1 is any one of Glu, His, Asp, Lys, Asn, and Arg; X2 is any one of His, Asn, and Gly; X4 is any one of His, Leu, Gln, Arg, and Trp; X6 is any one of Leu and Ile; X8 is any one of Ser, Asn, and Arg; X9 is any one of Leu and Ile; and X12 is any one of Pro and Ser, wherein the cyclic peptide specifically binds to EpCAM.

2. The cyclic peptide of claim 1, wherein the amino acid sequence of the cyclic peptide is selected from the group consisting of SEQ ID NOs: 14 to 20 and 29 to 37.

3. A cyclic peptide comprising:

(SEQ ID NO: 100)
Asp-Gly-X3-X4-X5-Cys6-Arg-Gly-Asp-Cys10-X11-X12-
X13-X14-X15 wherein X3 is any one of Glu, Val, Gly, Gln, and Asp; X4 is any one of Arg and Lys; X5 is any one of Asn, Ser, Ala, Gln, Leu, and Thr; X11 is any one of Ile and Phe; X12 is any one of Asp and Glu; X13 is any one of Gly, Asp, Pro, Val and Ala; X14 is any one of Gln, Ser, Pro, and Ala; and X15 is any one of Pro, Gln, Asp, Leu, Val, and Ser, wherein the cyclic peptide specifically binds αvβ35 or αvβ33 integrin.

4. The cyclic peptide of claim 3, wherein the amino acid sequence of the cyclic peptide is selected from the group consisting of SEQ ID NOs: 50 to 57.

5. A cyclic peptide of the amino acid sequence selected from the group consisting of SEQ ID NOs: 73 to 76 and 78 to 85.

6. A polypeptide comprising the cyclic peptide of claim 1.

7. A polypeptide comprising the cyclic peptide of claim 3.

8. A polypeptide comprising the cyclic peptide of claim 5.

* * * * *

UNITED STATES PATENT AND TRADEMARK OFFICE
CERTIFICATE OF CORRECTION

PATENT NO. : 10,787,487 B2
APPLICATION NO. : 16/447804
DATED : September 29, 2020
INVENTOR(S) : Yong Sung Kim et al.

Page 1 of 1

It is certified that error appears in the above-identified patent and that said Letters Patent is hereby corrected as shown below:

In the Claims

In Column 179, Claim 1, Lines 16-17, replace:
"(SEQ ID NO: 110) X1-X2-Leu3-X4-Cys5-X6-Gly-X8-X9-Cys10-Trp-X12"
With:
--1-X2-Leu3-X4-Cys5-X6-Gly-X8-X9-Cys10-Trp-X12 (SEQ ID NO: 110)--

In Column 179, Claim 3, Lines 32-34, replace:
"(SEQ ID NO: 100) Asp-Gly-X3-X4-X5-Cys6-Arg-Gly-Asp-Cys10-X11-X12-X13-X14-X15"
With:
--Asp-Gly-X3-X4-X5-Cys6-Arg-Gly-Asp-Cys10-X11-X12-X13-X14-X15 (SEQ ID NO: 100)--

In Column 180, Claim 3, Line 22, replace:
"αvβ35 or αvβ33"
With:
--αvβ5 or αvβ3--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*